US011142580B2

United States Patent
Champion et al.

(10) Patent No.: US 11,142,580 B2
(45) Date of Patent: Oct. 12, 2021

(54) ONCOLYTIC VIRUS AND METHOD

(71) Applicant: PSIOXUS THERAPEUTICS LIMITED, Oxfordshire (GB)

(72) Inventors: Brian Champion, Oxfordshire (GB); Alice Claire Noel Bromley, Oxfordshire (GB); Matthieu Besneux, Oxfordshire (GB)

(73) Assignee: PSIOXUS THERAPEUTICS LIMITED, Abingdon (GB)

( * ) Notice: Subject to any disclaimer, the term of this patent is extended or adjusted under 35 U.S.C. 154(b) by 0 days.

(21) Appl. No.: 16/618,068

(22) PCT Filed: Jun. 1, 2018

(86) PCT No.: PCT/EP2018/064524
§ 371 (c)(1),
(2) Date: Nov. 27, 2019

(87) PCT Pub. No.: WO2018/220207
PCT Pub. Date: Dec. 6, 2018

(65) Prior Publication Data
US 2020/0140563 A1    May 7, 2020

(30) Foreign Application Priority Data

Jun. 1, 2017  (GB) ...................................... 1708778
Jun. 1, 2017  (GB) ...................................... 1708779

(51) Int. Cl.
*C07K 16/28*   (2006.01)
*A61K 35/761*  (2015.01)
*C12N 15/86*   (2006.01)

(52) U.S. Cl.
CPC ........ *C07K 16/2878* (2013.01); *A61K 35/761* (2013.01); *C12N 15/86* (2013.01); *C07K 2317/75* (2013.01); *C12N 2710/10332* (2013.01); *C12N 2710/10343* (2013.01); *C12N 2710/10371* (2013.01)

(58) Field of Classification Search
CPC ............ C07K 16/2878; C07K 2317/75; A61K 35/761; A61K 2039/505; C12N 15/86; C12N 2710/10332; C12N 2710/10343; C12N 2710/10371; Y02A 50/30
See application file for complete search history.

(56) References Cited

U.S. PATENT DOCUMENTS

2016/0319304 A1*  11/2016  Brown ................... A61P 35/00

FOREIGN PATENT DOCUMENTS

| CN | 101381742 A | 3/2009 |
| WO | 03/040170 A2 | 5/2003 |
| WO | 2015/059303 A1 | 4/2015 |
| WO | 2015/059465 A1 | 4/2015 |
| WO | 2016/174200 A1 | 11/2016 |
| WO | 2017/161360 A2 | 9/2017 |
| WO | 2018/075978 A1 | 4/2018 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*
Winkler K, Kramer A, Kuttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14.*
Kussie PH, Parhami-Seren B, Wysocki LJ, Margolies MN. A single engineered amino acid substitution changes antibody fine specificity. J Immunol. Jan. 1, 1994;152(1):146-52.*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714.*
Sela-Culang I, Kunik V, Ofran Y. The structural basis of antibody-antigen recognition. Front Immunol. Oct. 8, 2013;4:302.*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016.*
Collis AV, Brouwer AP, Martin AC. Analysis of the antigen combining site: correlations between length and sequence composition of the hypervariable loops and the nature of the antigen. J Mol Biol. Jan. 10, 2003;325(2):337-54.*
Bett AJ, Prevec L, Graham FL. Packaging capacity and stability of human adenovirus type 5 vectors. J Virol. Oct. 1993;67(10):5911-21.*
Goswami R, Subramanian G, Silayeva L, Newkirk I, Doctor D, Chawla K, Chattopadhyay S, Chandra D, Chilukuri N, Betapudi V. Gene Therapy Leaves a Vicious Cycle. Front Oncol. Apr. 24, 2019;9:297.*

(Continued)

*Primary Examiner* — Rachel B Gill
(74) *Attorney, Agent, or Firm* — Debora Plehn-Dujowich; Eckert Seamans Cherin & Mellott, LLC

(57) ABSTRACT

An oncolytic virus (for example a replication competent virus) comprising a transgene cassette encoding an anti-CD40 antibody or binding fragment thereof, wherein the transgene cassette comprises an amino acid sequence given in SEQ ID NO: 12 or a sequence at least 95% identical thereto (such as 96, 97, 98 or 99% identical thereto), in particular a cassette of SEQ ID NO: 12; pharmaceutical compositions comprising the same, methods of preparing said oncolytic virus and compositions and use of the oncolytic virus or composition in treatment, in particular in the treatment of cancer. Also provided is the treatment of a patient population characterised as having a cancer expressing CD40, in particular a cancer over expressing CD40, with a therapy according to the present disclosure.

18 Claims, 55 Drawing Sheets

Specification includes a Sequence Listing.

(56) References Cited

OTHER PUBLICATIONS

Nemunaitis, J., et al., Intravenous infusion of a replication-selective adenovirus (ONYX-015) in cancer patients: safety, feasibility and biological activity, Gene Therapy (2001) 8, 746-759.

Marino, N. et al, "Development of a versatile oncolytic virus platform for local intra-tumoural expression of therapeutic transgenes", PLOS ONE, vol. 12, No. 5, May 18, 2017 (May 18, 2017), p. 1-23.

Champion, B., et al, "Developing tumor-localized, combination immunotherapies", Jul. 1, 2016.

Fountzilas, C., et al, "Review: Oncolytic virotherapy, updates and future directions", ONCOTARGET, vol. 8, No. 60, May 31, 2017, pp. 102617-102639.

International Search Report, PCT/EP2018/064524, dated Sep. 3, 2018.

Nakashima, E., et al., A candidate for cancer gene therapy: MIP-1 alpha gene transfer to an adenocarcinoma cell line reduced tumorigenicity and induced protective immunity in immunocompetent mice, Pharm Res. Dec. 1996;13(12):1896-901.

Kaufman, H. L., et al., Oncolytic viruses: a new class of immunotherapy drugs, Nat Rev Drug Discov. Sep. 2015;14(9):642-62.

Ferrantini, M., et al., Interferon-alpha and cancer: mechanisms of action and new perspectives of clinical use, Biochimie. Jun.-Jul. 2007;89(6-7):884-93.

Plasmids 101: Multicistronic Vectors. Jan. 29, 2015, https://web.archive.org/web/20150129022727/https://blog.addgene.org/plasmids-101-multicistronic-vectors.

Gene Therapy Vaccinia Virus Vectors Explained. Feb. 1, 2015, https://web.archive.org/web/20150201083914/www.genetherapynet.com/viral-vector/vaccinia-viruses.html.

\* cited by examiner

Figure 1
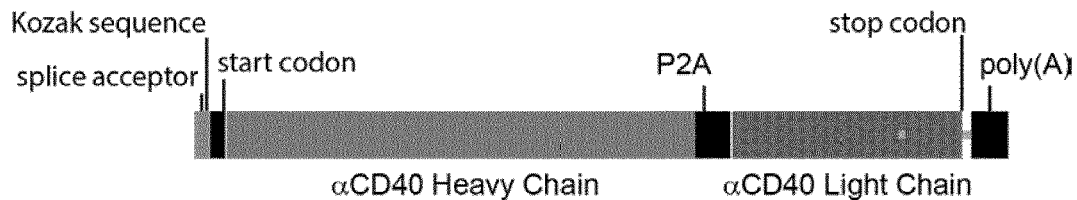
Figure 2 Total Virus Production (A) & Virus in the Supernatant (B)
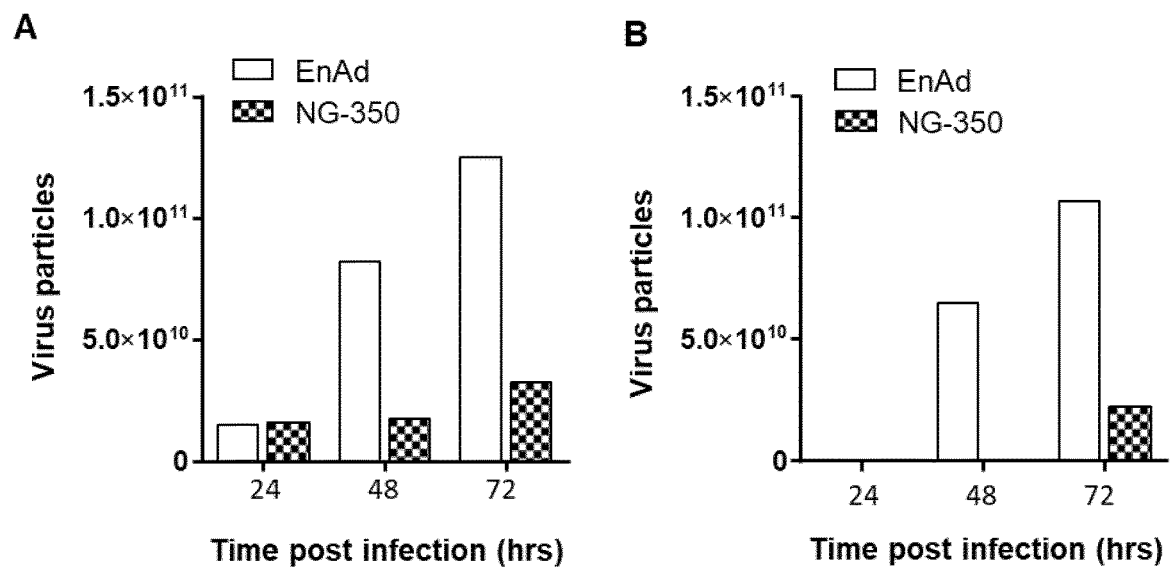
Concentration of Secreted Antibody
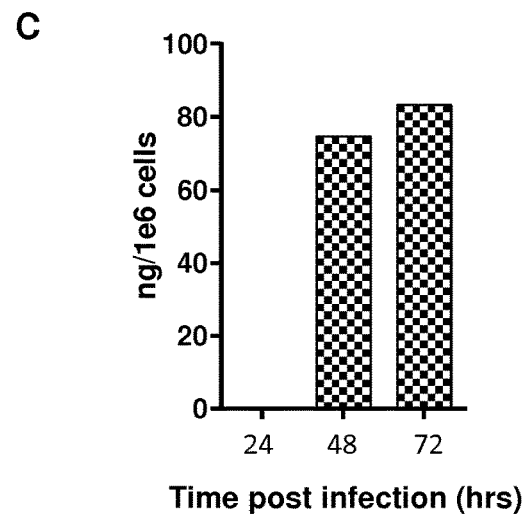

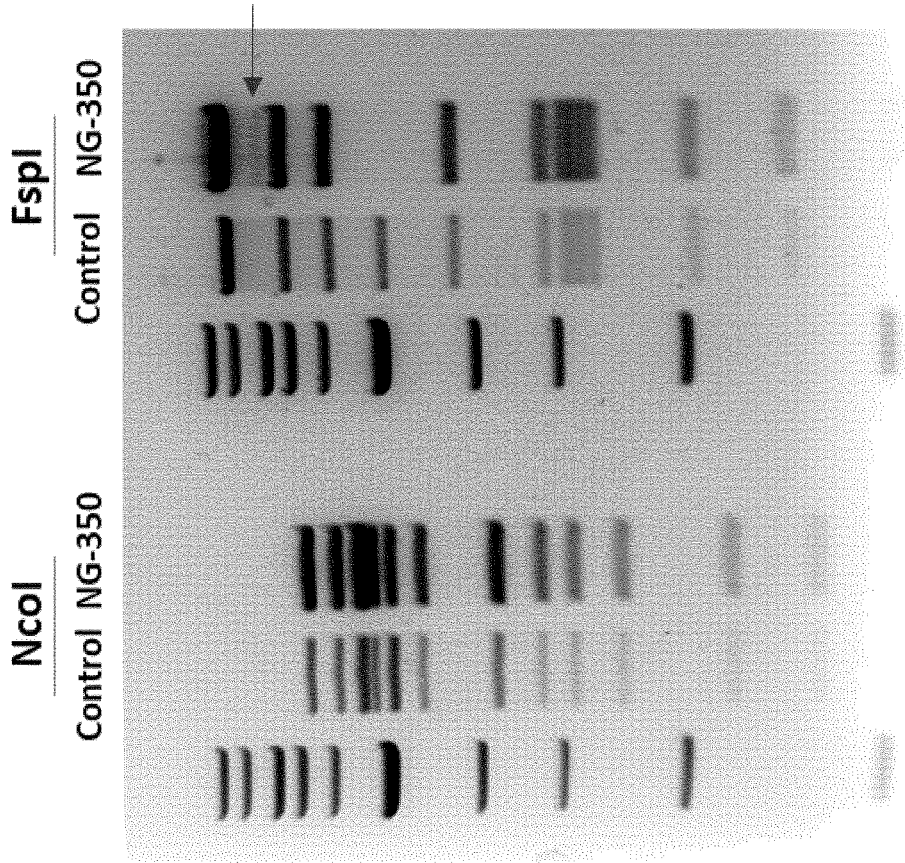
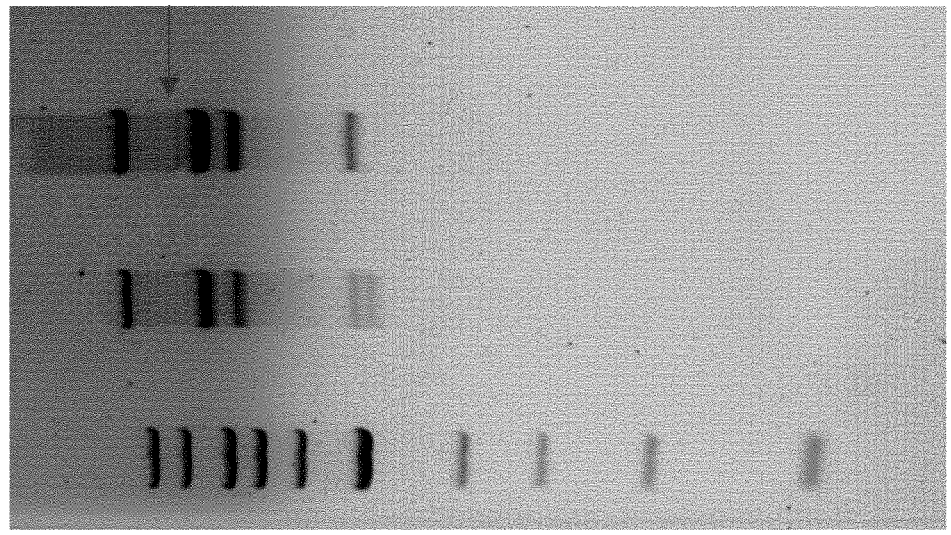
Figure 3

Figure 4  Primer Details are Shown in Table 1 in the specification
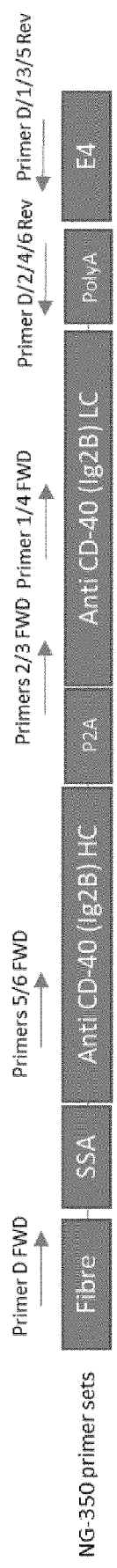
Figure 5  PCR products by Gel Electrophoresis
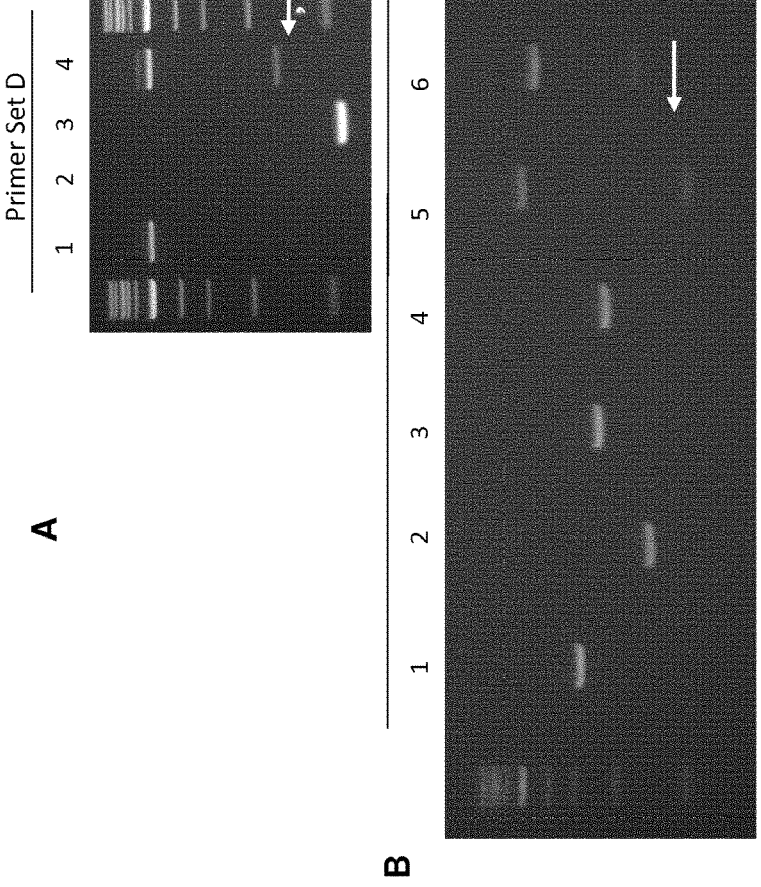

Figure 6 PCR Products
A
Primer Set D
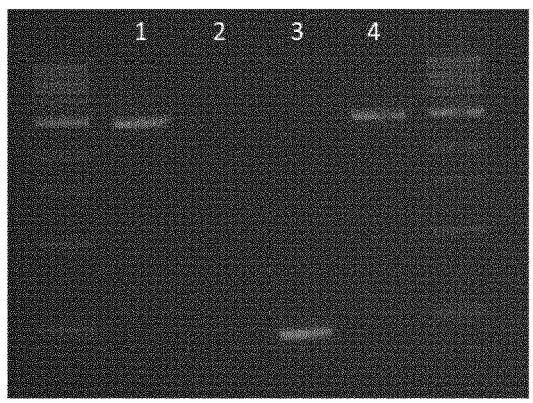
| Sample # | Sample ID |
|---|---|
| 1 | pNG-350A-PSI-01 (Plasmid DNA) |
| 2 | Negative control (Water) |
| 3 | enadenotucirev |
| 4 | NG-350A |
B
Primer Set K
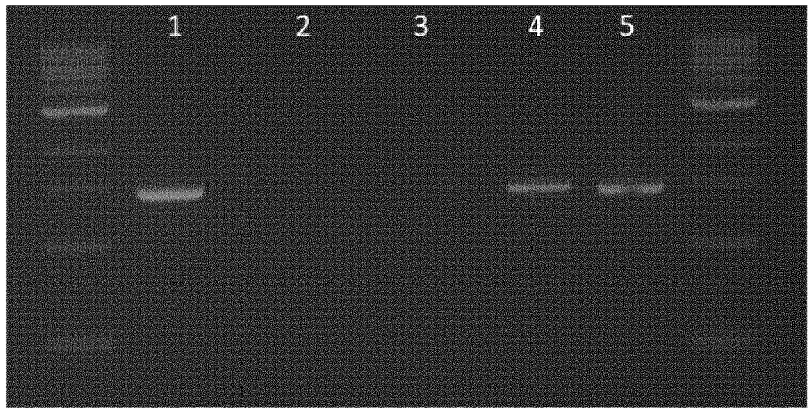
| Sample # | Sample ID |
|---|---|
| 1 | pNG-350A-PSI-01 (Plasmid DNA) |
| 2 | Negative control (Nuclease free water) |
| 3 | EnAd (Ark Trial run 1) |
| 4 | NG-350A |
| 5 | NG-350A |

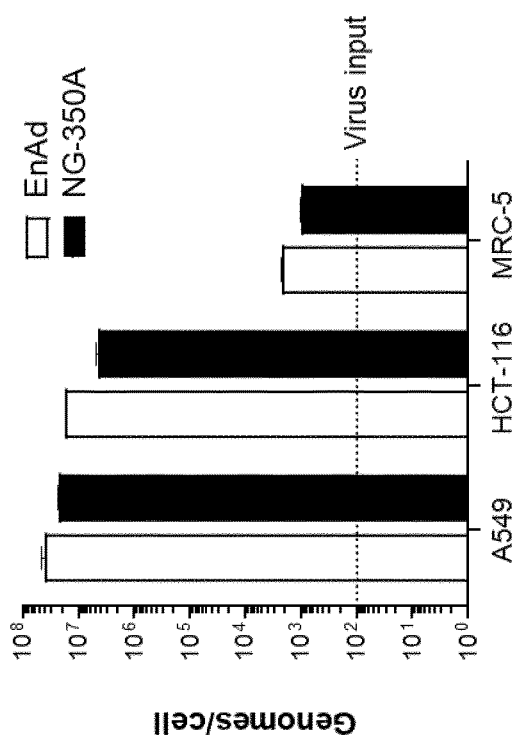
Figure 11A
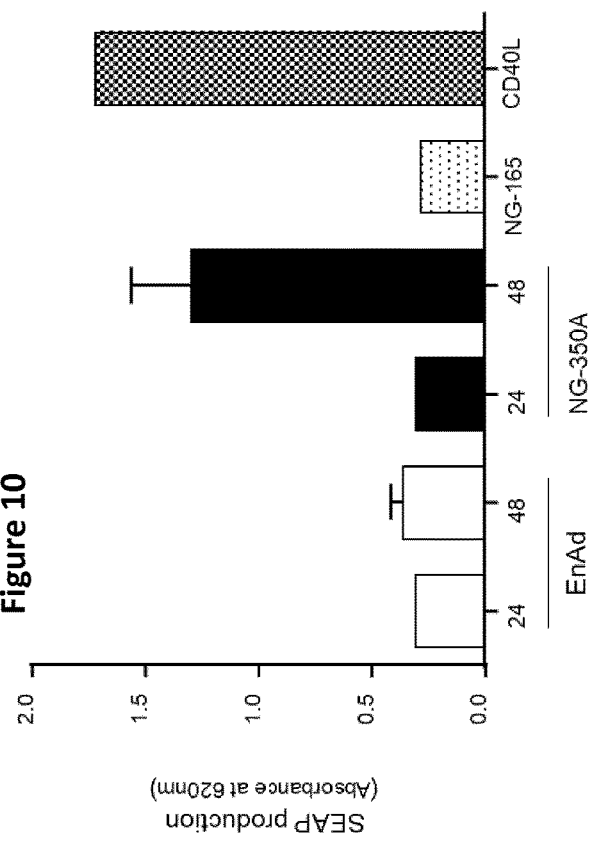
Figure 10
Figure 11B
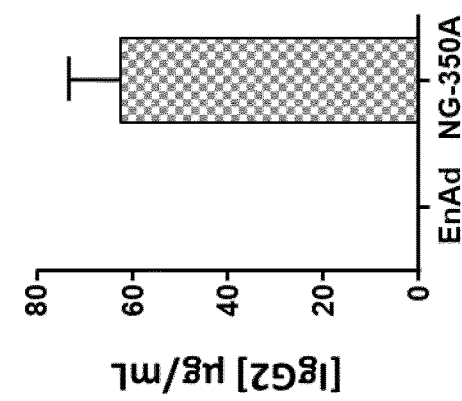
Figure 12
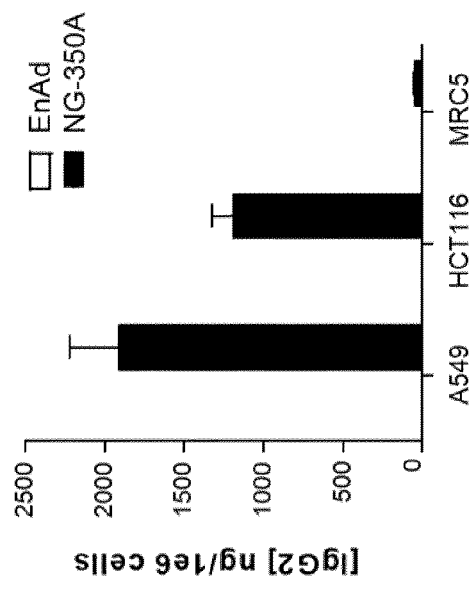

Figure 13
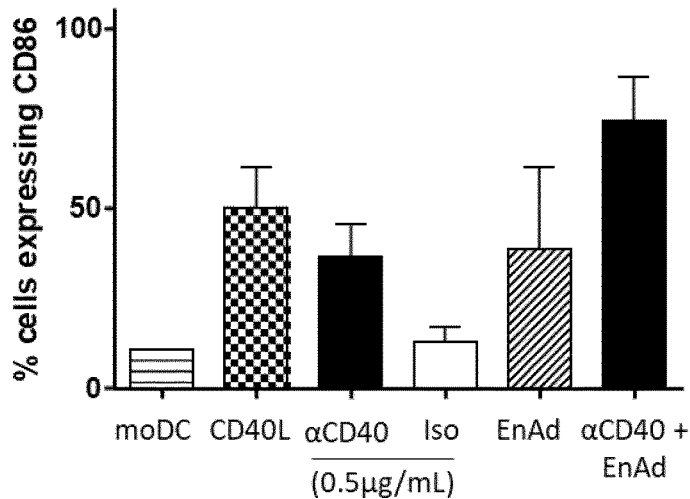
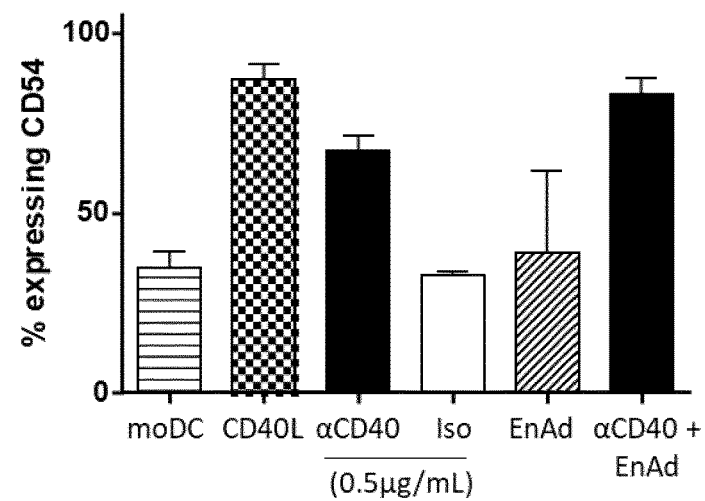
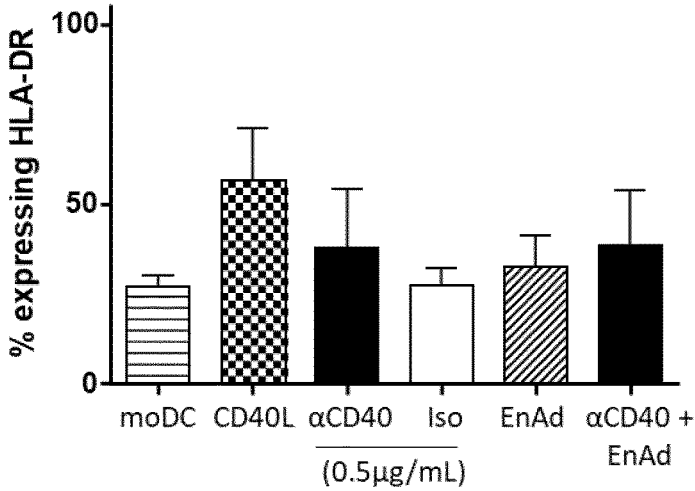

Figure 14
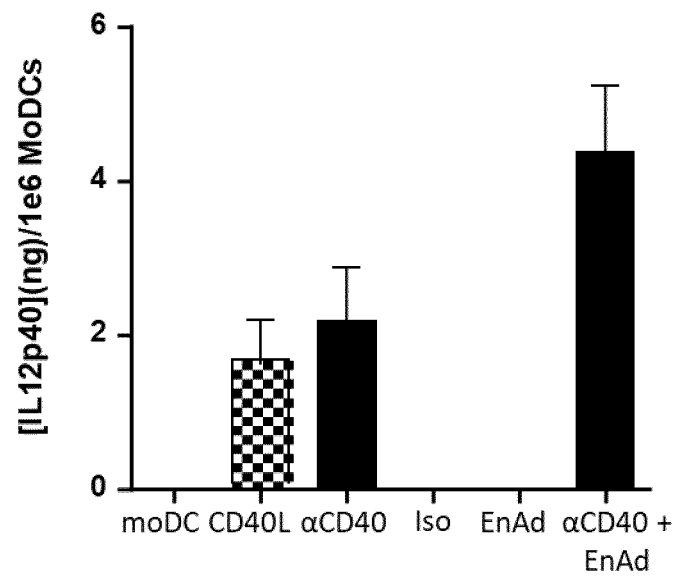
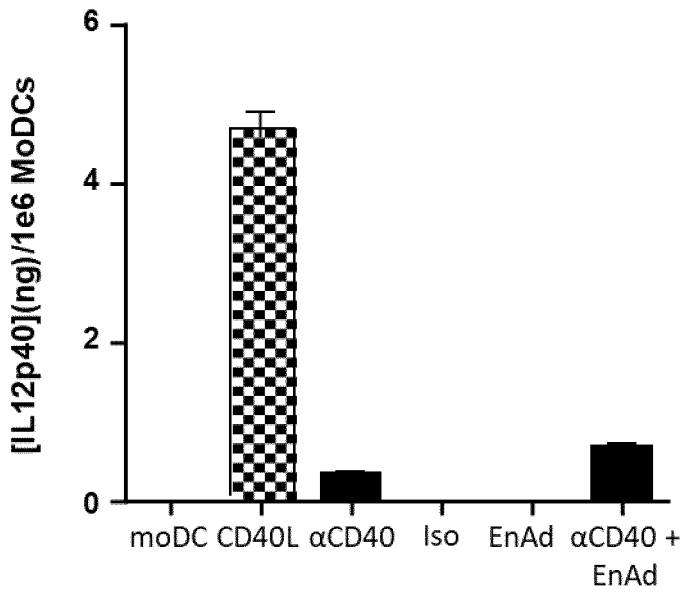

Figure 15
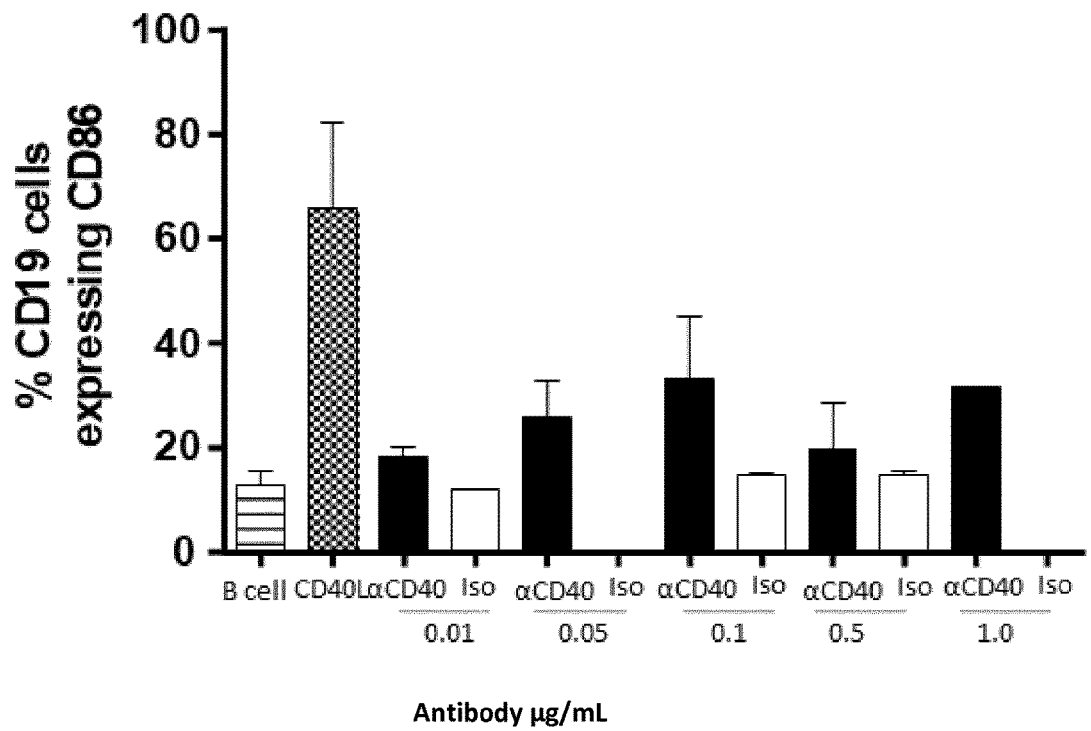
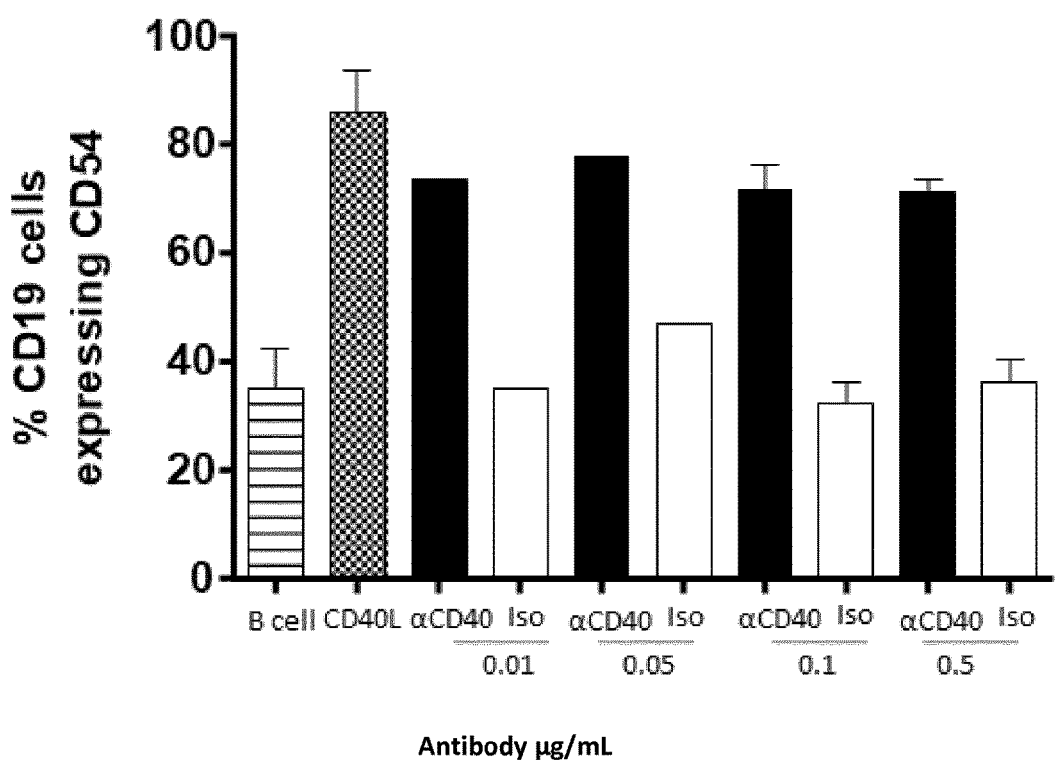

Figure 15
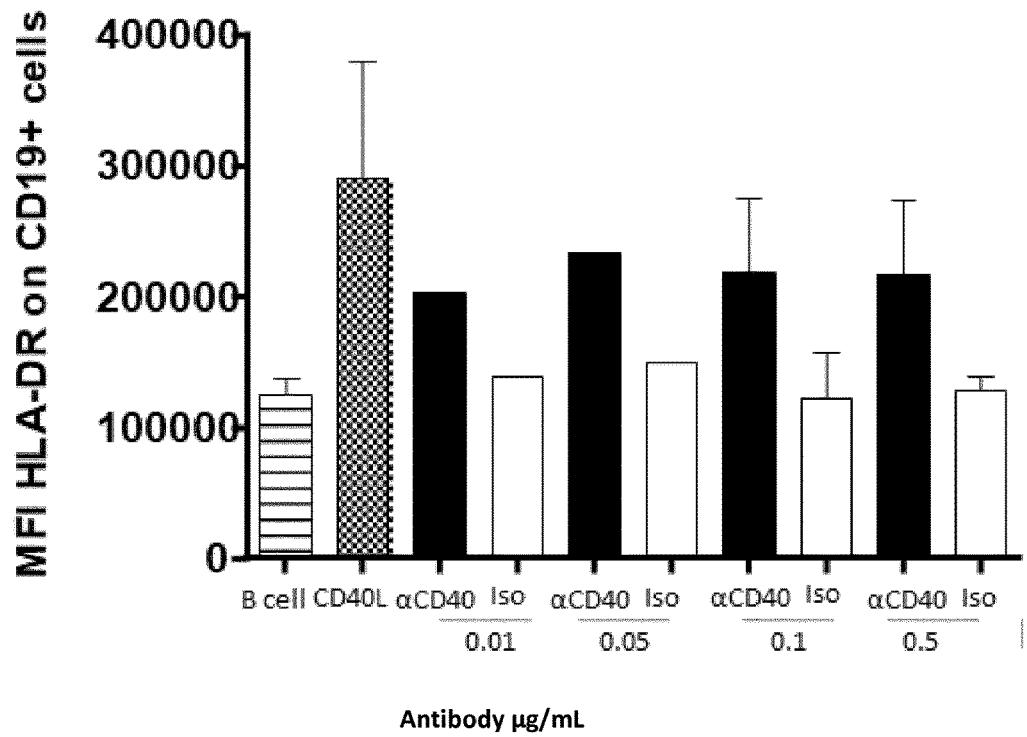
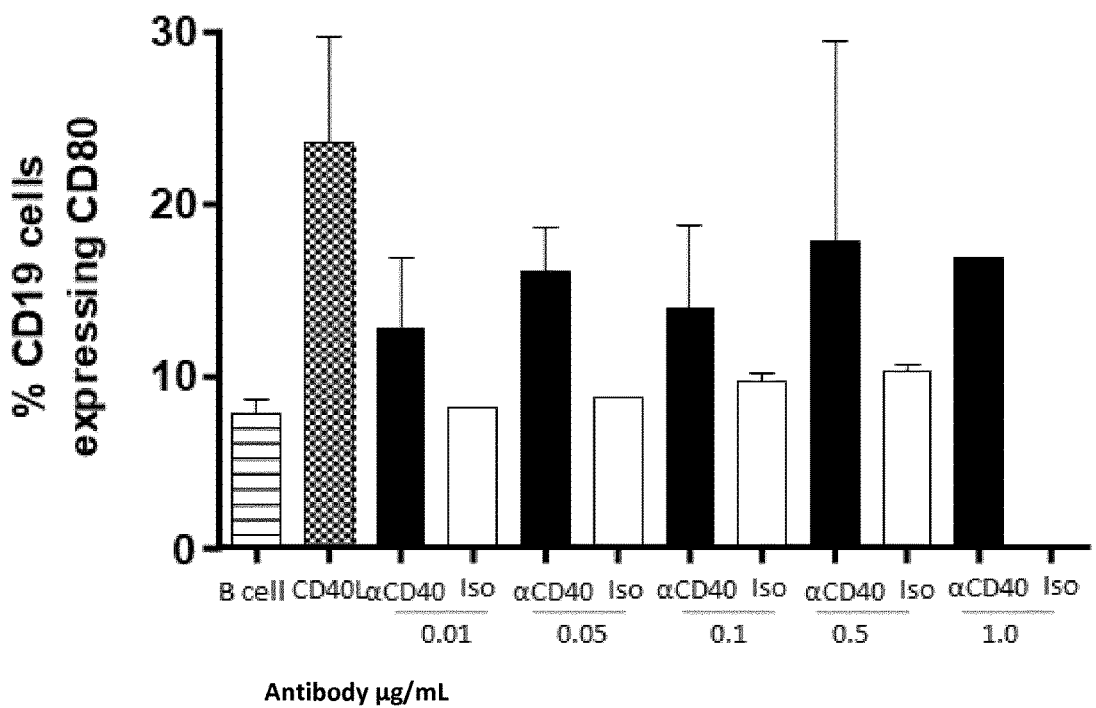

Figure 25A
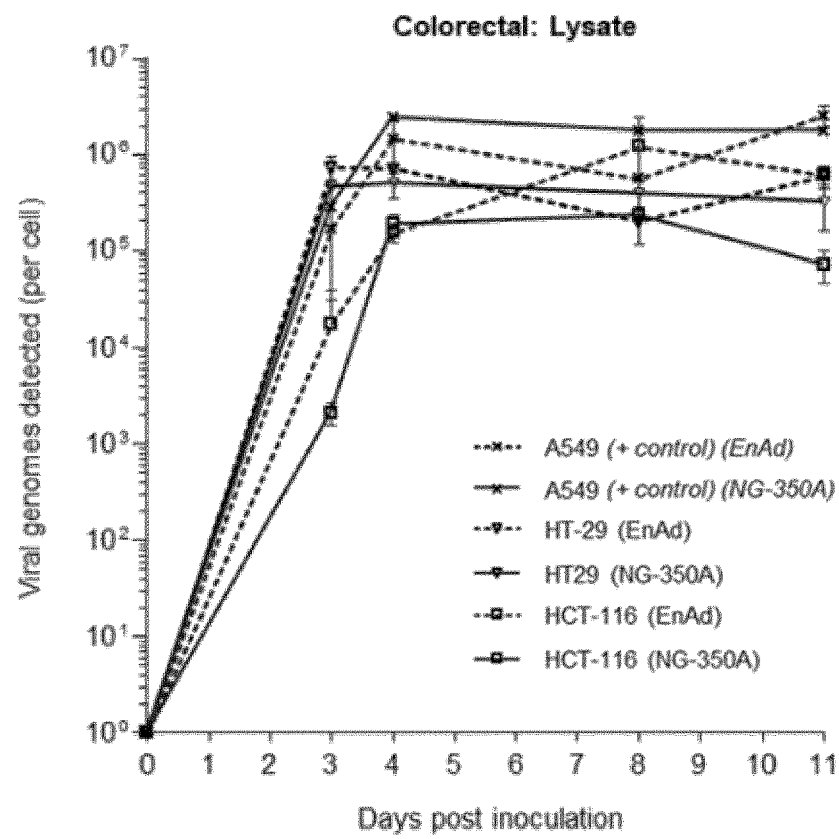
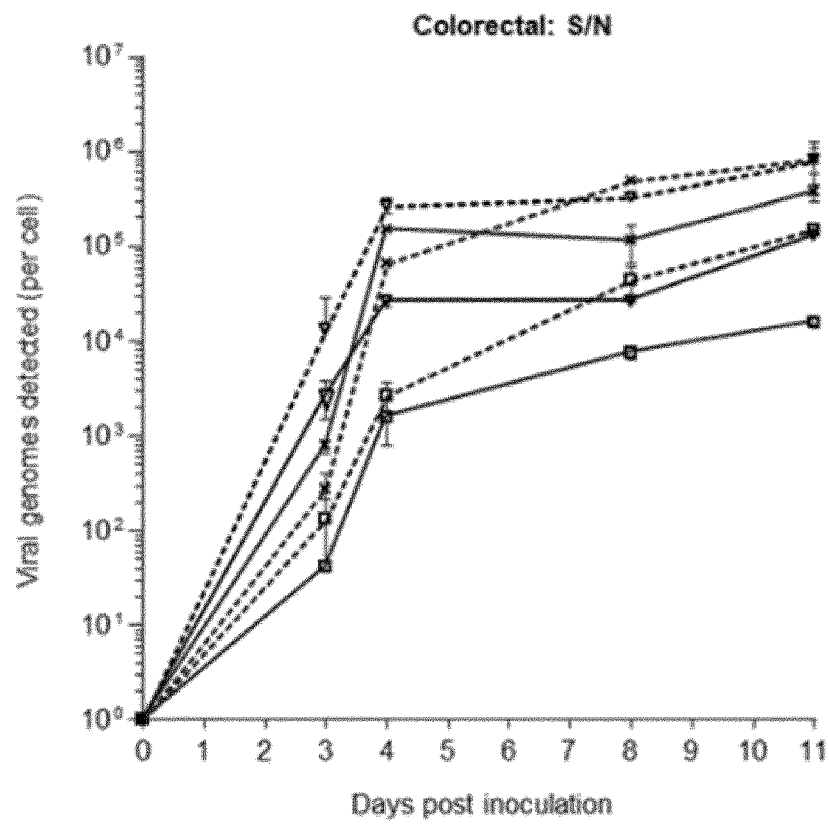

Figure 25C
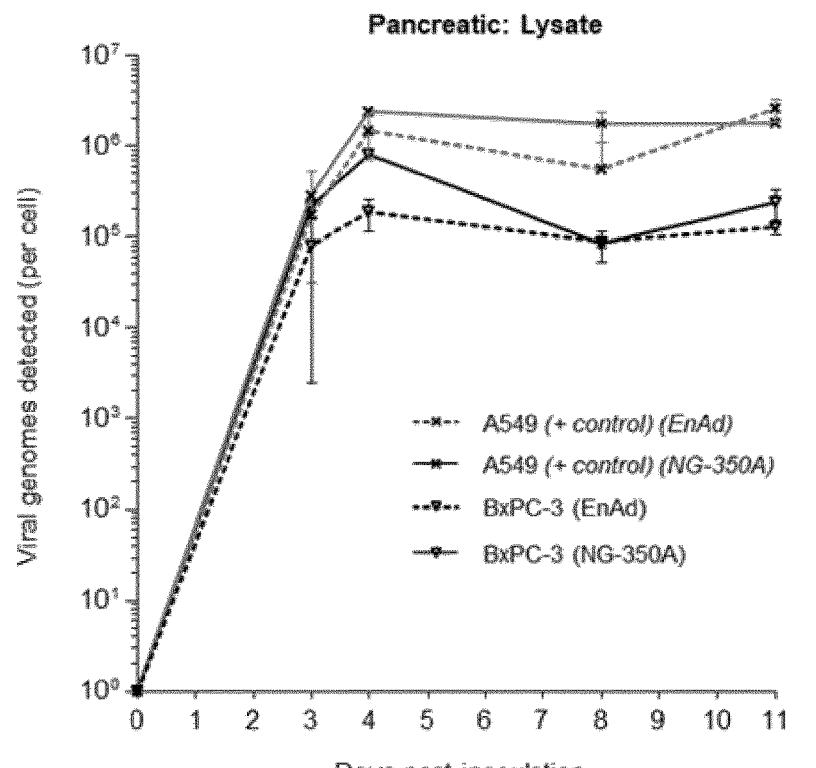
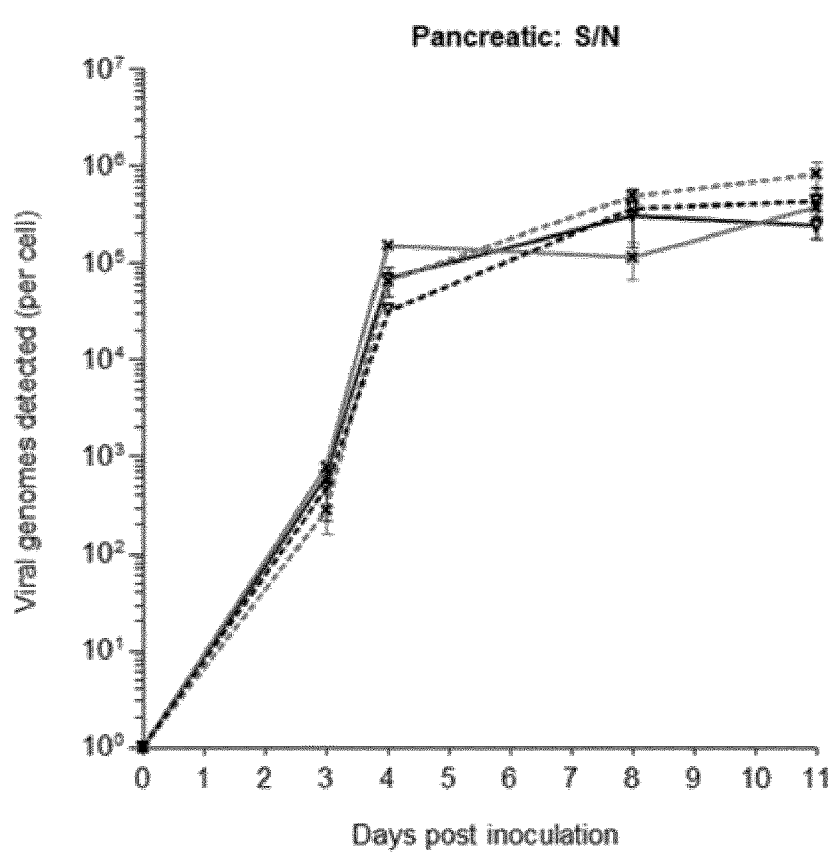

Figure 25D
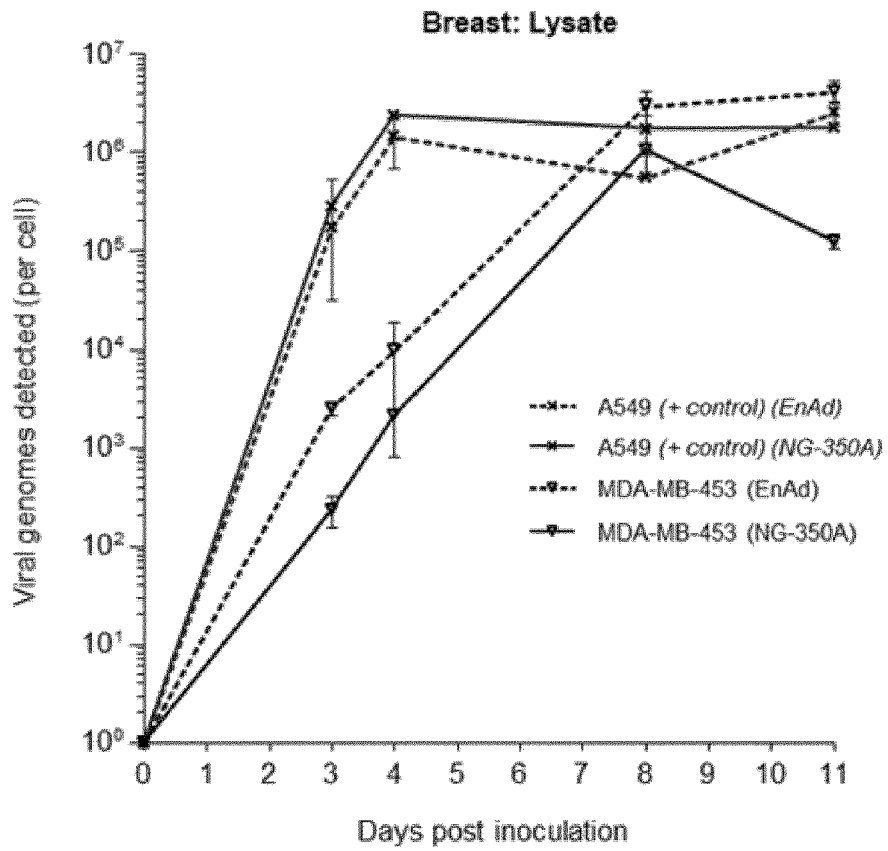
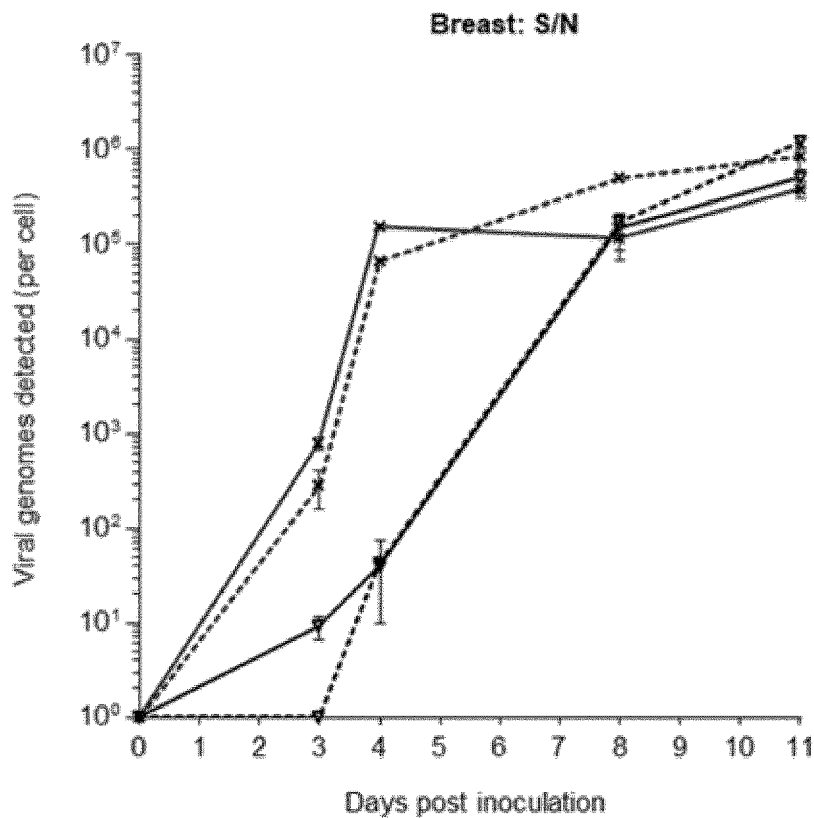

Figure 27
A
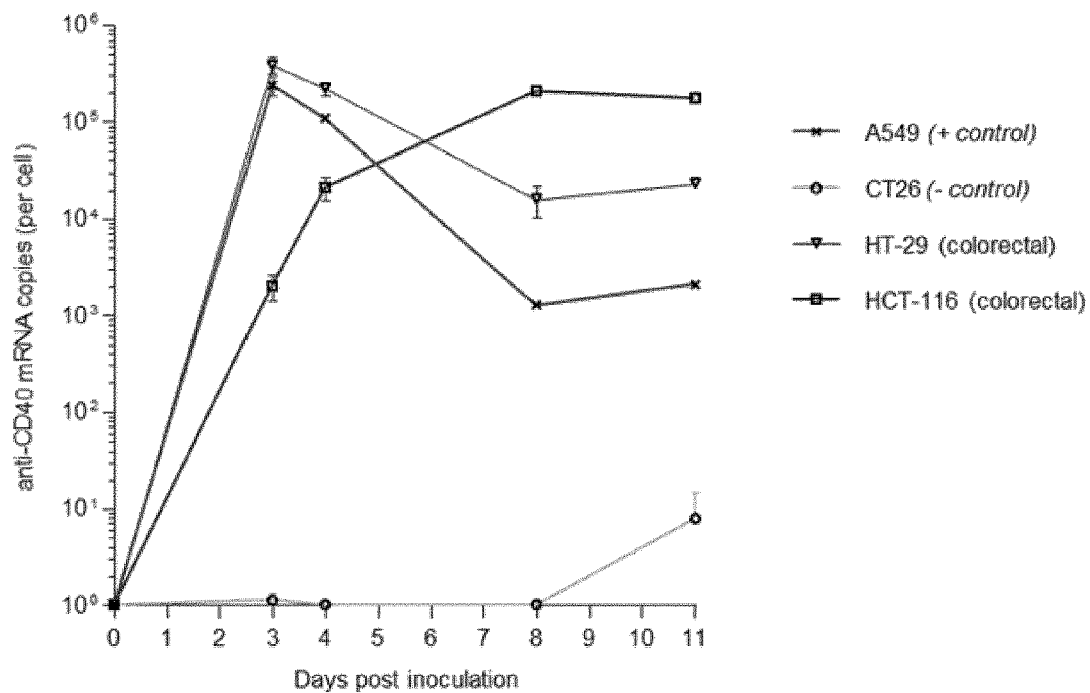
B
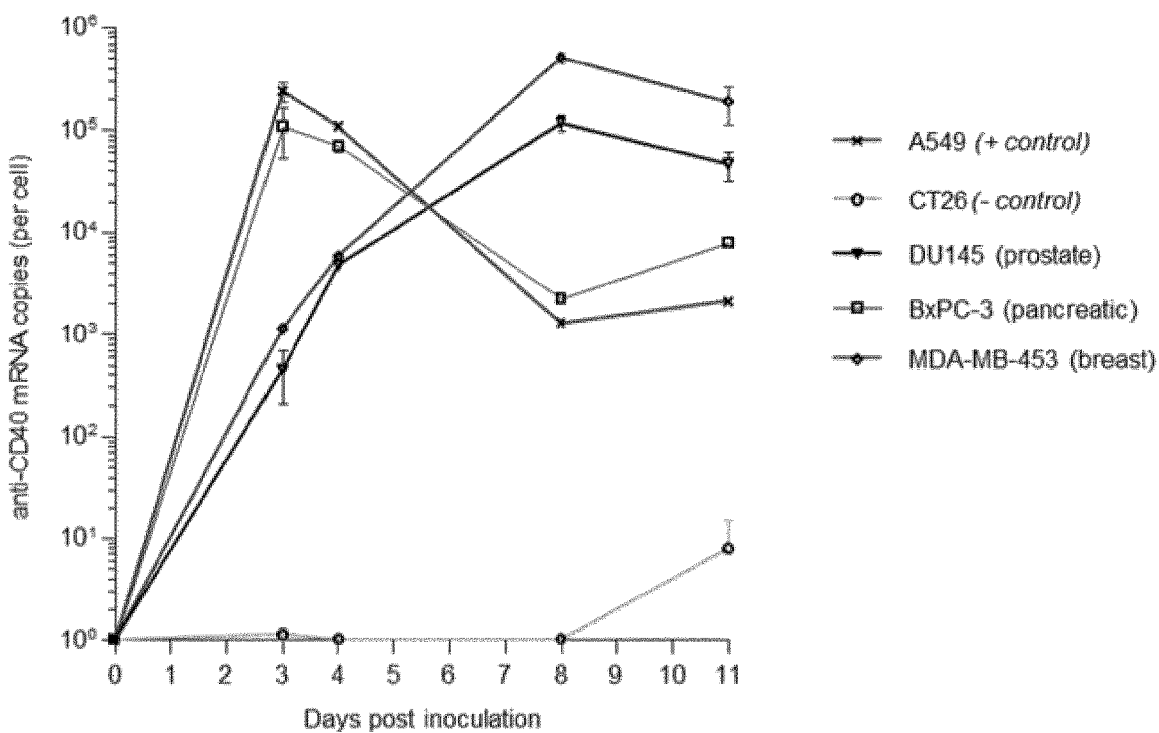

Figure 27 cont.
C
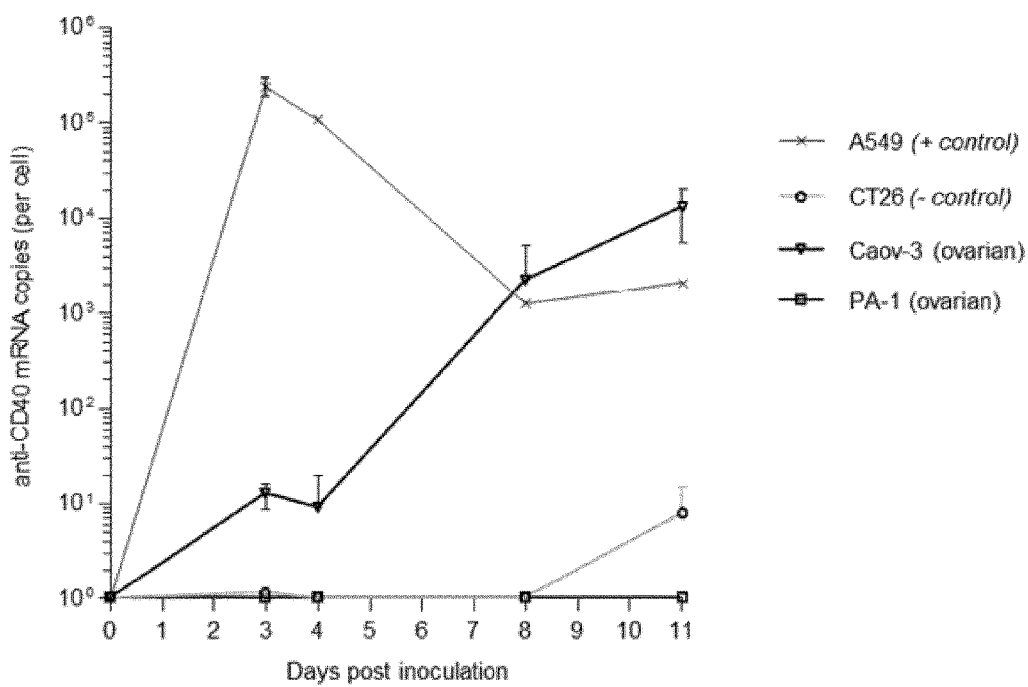
D
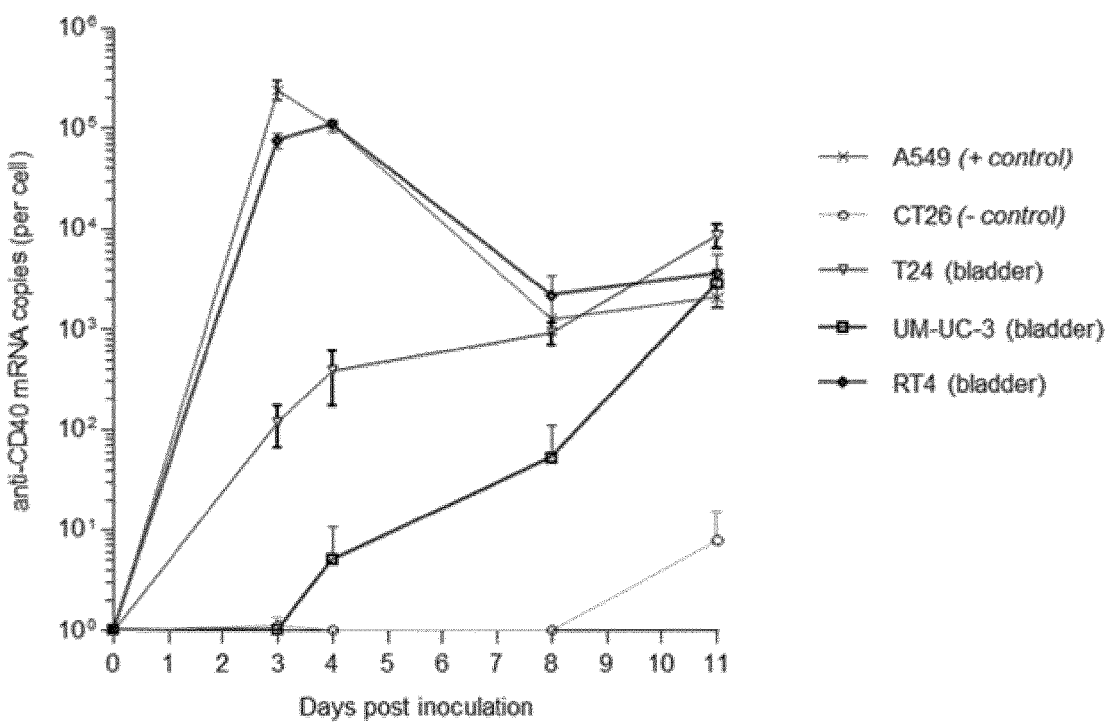

Figure 31A
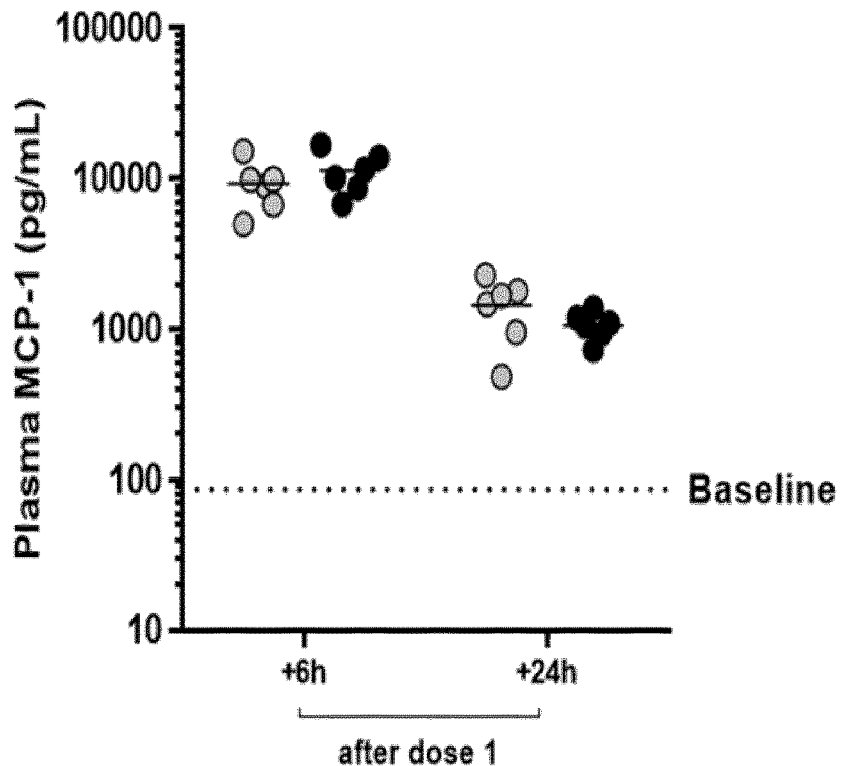
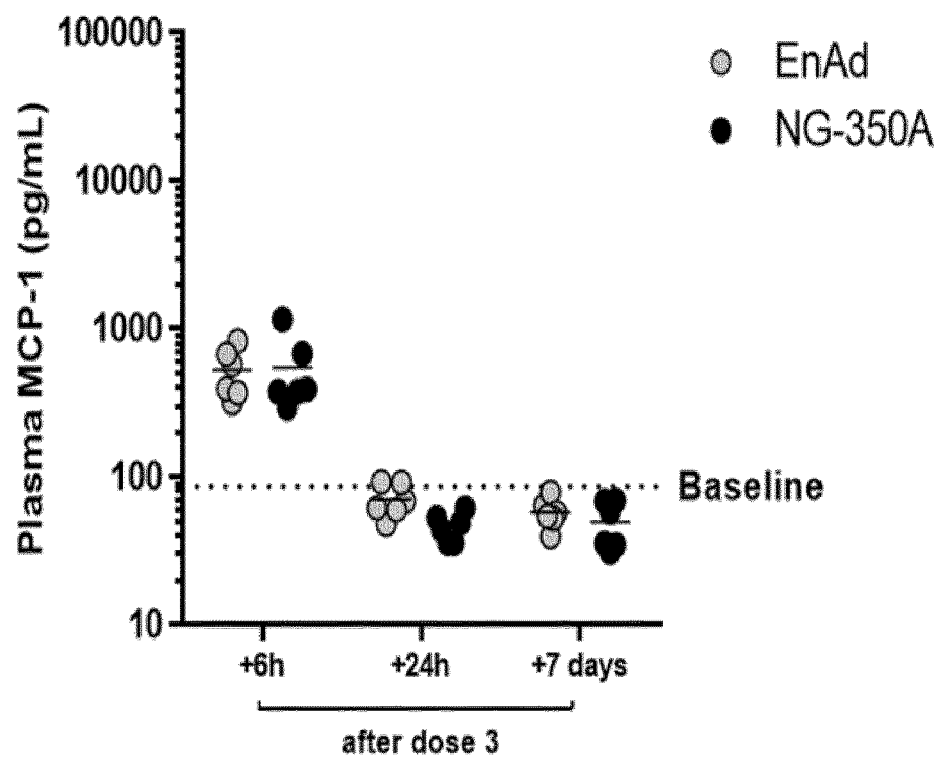

Figure 31B
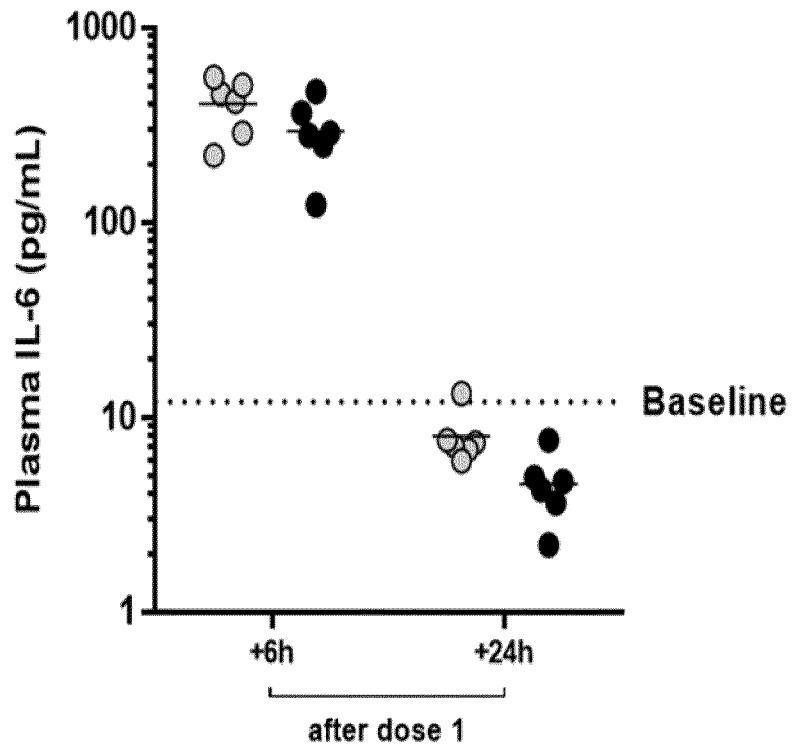
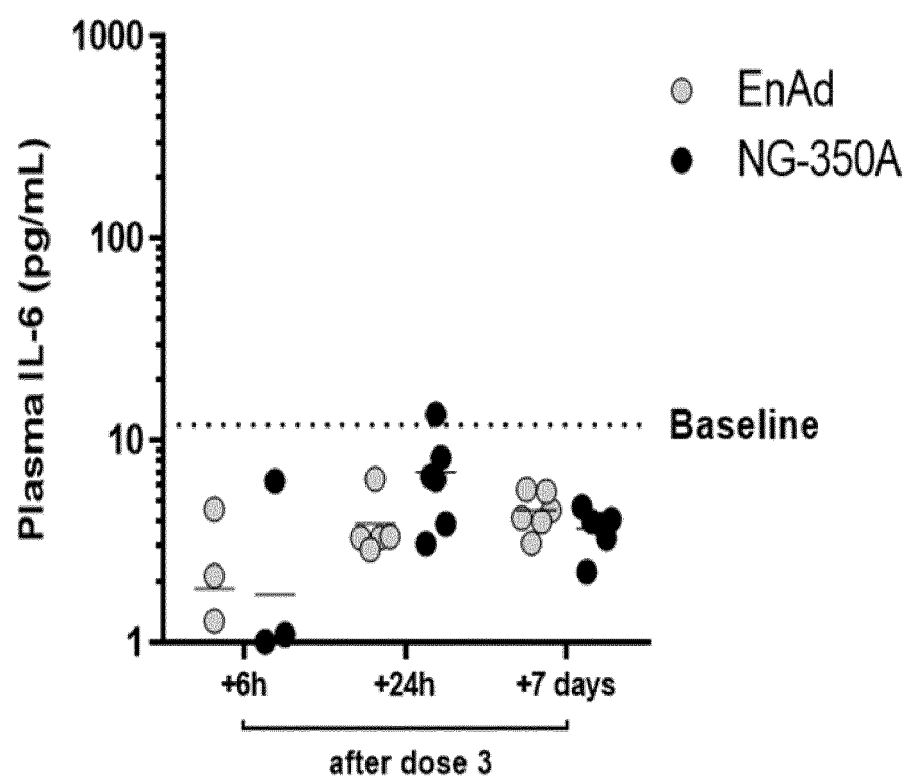

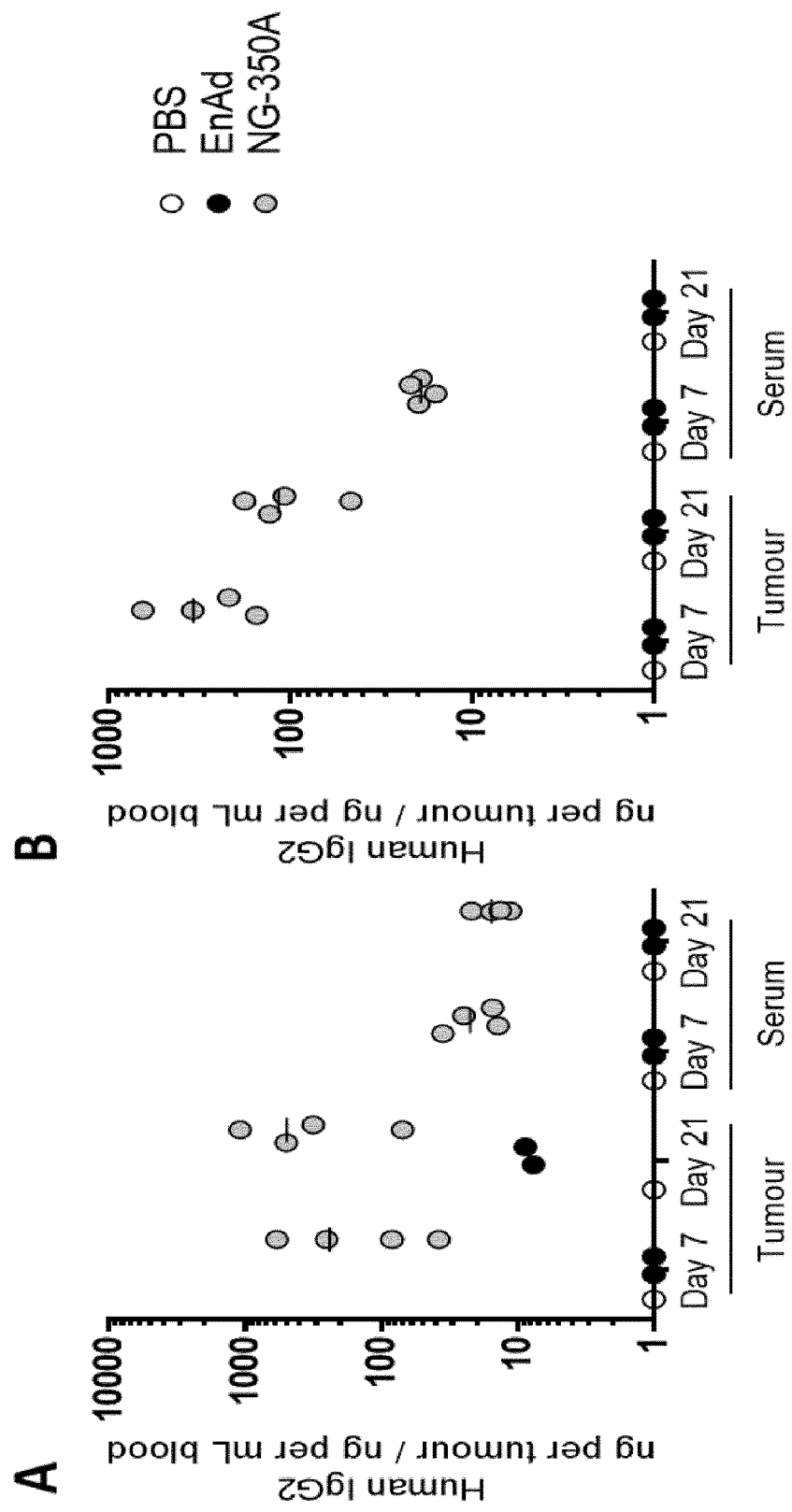
Figure 37  αCD40 agonist antibody protein detection in subcutaneous A549 tumours after three IV injections or a single fractionated IT dose

ONCOLYTIC VIRUS AND METHOD

CROSS-REFERENCE TO RELATED APPLICATIONS

The present application is a 35 U.S.C. § 371 national phase application from, and claims priority to, International Application No. PCT/EP2018/064524, filed Jun. 1, 2018, and published under PCT Article 21(2) in English, which designated the U.S., and claims the benefit of priority from United Kingdom Patent Application Nos. GB1708779.2 and GB1708778.4, both filed on Jun. 1, 2017, each of which are incorporated by reference herein into this application in their entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Nov. 26, 2019, is named 314641-00040_Sequence_Listing.txt and is 106 kilobytes in size.

The present disclosure relates to an oncolytic virus, such as an adenovirus, compositions comprising the oncolytic virus of the present disclosure, methods of preparing said oncolytic virus and compositions and use of the oncolytic virus or composition in treatment, in particular in the treatment of cancer. Also provided is the treatment of a patient population characterised as having a cancer expressing CD40, in particular a cancer over expressing CD40, with a therapy according to the present disclosure.

BACKGROUND

CD40 is an activator for B and T cells, for example CD40 on antigen presenting cells binds CD40L (also known as CD154) on T cells to activate the same. CD40 is also present on a number of tumour cells, which use the CD40 to obtain cytokines and growth factors from the surrounding cells to support the growth and expansion of the cancer.

Agonistic anti-CD40 antibodies in vivo may be able to stimulate anti-tumor immune responses due to action on immune cells. This may be because the CD40 has the ability to, for example activate macrophages and to "precondition" dendritic cells, allowing them to prime effective cytotoxic T-cell responses.

At the present time there is a significant interest in immune oncology therapies and/or therapies directed to tumor associated macrophages (TAMs). These tumor-associated-macrophages surround the tumor and contribute to creating a microenvironment, which is permissive to tumor growth and development. This microenvironment is often hypoxic and can neutralize immune cells sent to attach and eliminate the tumor. Thus, the microenvironment physically protects the tumor. Furthermore, it supplies energy and nutrients to support tumor growth.

However, to be effective the therapies need to be really targeted to this environment to re-invigorate, liberate, recruit and re-activate immune cells, for example already trapped in the microenvironment. This targeting of the microenvironment is not easy to do because sometimes the tumor has development mechanisms for protection, such as active transport mechanisms which move therapeutics out of the tumor environment. This is, for example one of the mechanisms involved in resistance.

Oncolytic viruses, such as group B oncolytic adenoviruses, which home to the tumor cells and selectively infect the cancer cells may be harnessed to deliver the anti-CD40 antibody to the microenvironment of the tumor. The oncolytic virus has anti-cancer properties, which result in the death of the cancer cell and release of the content of said cell. The contents of the cell include the anti-CD40 antibody made by the oncolytic virus. Thus death of the cancer cell releases the antibody into the microenvironment of the tumor.

Surprisingly, the present inventors have found that anti-CD40 antibodies can be efficiently delivered by a variety of different oncolytic viruses by incorporating transgenes encoding anti-CD40 antibodies into such viruses, for example by transducing the viruses with a transgene cassette of the present disclosure.

In addition, because tumors have developed multiple mechanisms for protection, it is thought going forward that the most effective cancer therapies in the future will need to attack the cancer via two or more biological mechanisms.

Employing agonistic anti-CD40 antibodies may be have the additional benefit that once the antibody is in the tumor microenvironment at suitable concentrations it can compete with CD40-expressing cancer cells to bind to CD40L. This means ultimately that there will be less opportunity for the cancer cells to bind CD40L on T cell. In turn this may mean that the amount to energy and nutrients available to the tumor may be reduced.

The present inventors have designed a transgene cassette encoding an anti-CD40 antibody or binding fragment thereof that can be used to make stable viruses.

PARAGRAPHS SUMMARISING THE DISCLOSURE

The present disclosure provides:
1. An oncolytic virus (for example a replication competent virus) comprising a transgene cassette encoding an anti-CD40 antibody or binding fragment thereof, wherein the transgene cassette comprises an amino acid sequence given in SEQ ID NO: 12 or a sequence at least 95% identical thereto (such as 96, 97, 98 or 99% identical thereto, especially over the fully the length of the sequence), in particular a cassette of SEQ ID NO:12.
(Alternative) paragraph 1: An oncolytic adenovirus (for example a replication competent oncolytic adenovirus) encoding an anti-CD40 antibody or binding fragment thereof, wherein the adenovirus comprises SEQ ID NO: 1 or a sequence at least 95% identical thereto (such as a 96, 97, 98 or 99% identical thereto).
2. An oncolytic virus according to paragraph 1, wherein the virus is selected from an adenovirus, herpes simplex virus, reovirus, measles virus, Newcastle disease virus, Seneca Valley virus, Vesicular stomatitis virus, polio virus, ECHO enterovirus, Coxsackie virus, and vaccinia virus, in particular an adenovirus.
3. An oncolytic virus according to paragraphs 1 or 2, wherein the virus is selected from the group consisting of Enadenotucirev, talimogene laherparepvec, RIGVIR, Ad5-yCD/mutTKSR39rep-hIL12, Cavatak™, CG0070, DNX-2401, G207, HF10, Imlygic®, JX-594, MG1-MA3, MV-NIS, OBP-301, Reolysin, Toca 511, in particular Enadenotucirev.
4. An oncolytic virus according to any one of paragraphs 1 to 3, wherein the virus comprises SEQ ID NO: 1.
5. An oncolytic virus according to paragraph 4, consists of SEQ ID NO: 1.

6. A pharmaceutical composition comprising a virus according to any one of paragraphs 1 to 5, and a pharmaceutically acceptable excipient, diluent or carrier.
7. An oncolytic virus according to any one of paragraphs 1 to 5 or a pharmaceutical composition according to paragraph 6, for use in treatment.
8. An oncolytic virus according to any one of paragraphs 1 to 5 or a pharmaceutical composition according to paragraph 6, for use in the treatment of cancer, insulin resistance, obesity and/or immune deficiency.
9. A use according to paragraph 6, wherein the virus or composition is for use in the treatment of cancer, for example for the treatment of cancer expressing CD40 (such as cancer with upregulated expression of CD40).
10. A combination therapy (for example for use in the treatment of cancer) comprising a virus according to any one of paragraphs 1 to 5 or a composition according to paragraph 6 and a further anti-cancer therapy.
11. A combination therapy according to paragraph 10, wherein the further anti-cancer therapy is chemotherapy.
12. A combination therapy according to paragraph 10 or 11, wherein the further anti-cancer therapy is a check point inhibitor.
13. A combination therapy according to paragraph 12, wherein the anti-cancer therapy is selected from the group comprising a PD-1 inhibitor, a PD-L1 inhibitor, a CTLA-4 inhibitor, a TIM-3 inhibitor, a LAG-3 inhibitor, a TIGIT inhibitor, a B7-H3 (CD276) inhibitor, a B7-H4 (B7S1) inhibitor, a B7H7 (HHLA2) inhibitor, a CD96 inhibitor, a VISTA inhibitor and a combination of two or more of the same.
14. A combination therapy according to paragraph 13, wherein the inhibitor is an antibody or binding fragment thereof.
15. A combination therapy according to any one of paragraphs 10 to 14, wherein the further anti-cancer therapy is a costimulatory pathway agonist.
16. A combination therapy according to paragraph 15, wherein the further anti-cancer therapy is selected from the group comprising a CD27 agonist, a CD28 agonist, an ICOS agonist, a TMIGD2 (IGPR-1/CD28H) agonist, a CD226 agonist, an OX40 agonist, a 4-113B agonist, and a combination of two or more of the same.
17. A combination therapy according to paragraph 16, wherein the therapy is an antibody or binding fragment thereof.
18. A combination therapy according to any one of paragraphs 10 to 17, wherein the further anti-cancer therapy activates immune responses or reverse suppression of immune responses, for example selected from IL-10, TGFβ, IDO inhibitors, and a combination of two or more of the same.
19. A combination therapy according to any one of paragraphs 10 to 18, wherein the further cancer therapy is an oncolytic virus (further oncolytic virus), for example a replication competent oncolytic virus, such as an adenovirus, in particular a group B adenovirus.
20. A combination therapy according to paragraph 19, wherein the oncolytic virus (further oncolytic virus) encodes therapeutic gene encoding material selected from the group consisting of an RNAi sequence, an antibody or binding fragment thereof, chemokines, cytokines, immunomodulator and enzymes.
21. A combination therapy according to paragraph 20, wherein the antibody or binding fragment thereof is specific to OX40, OX40 ligand, CD27, CD28, CD30, CD40, CD40 ligand, CD70, CD137, GITR, 4-1BB, ICOS, ICOS ligand, CTLA-4, PD-1, PD-L1, PD-L2, VISTA, B7-H3, B7-H4, HVEM, ILT-2, ILT-3, ILT-4, TIM-3, LAG-3, BTLA, LIGHT, CD160, CTLA-4, PD-1, PD-L1, PD-L2, CD40, CD40 ligand and combinations of two or more of the same.
22. A combination therapy according to paragraph 20 or 21, wherein the cytokine is independently selected from the group comprising IL-1α, IL-1θ, IL-6, IL-9, IL-12, IL-13, IL-17, IL-18, IL-22, IL-23, IL-24, IL-25, IL-26, IL-27, IL-33, IL-35, IL-2, IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF, for example IL-12, IL-18, IL-22, IL-7, IL-15, IL-21, IFNγ, TNFα, TGFβ and lymphotoxin α (LTA) and combinations of two or more of the same.
23. A combination therapy according to any one of paragraphs 20 to 22, wherein the chemokine independently selected from the group comprising IL-8, CCL3, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and CRTH2, for example CCL5, CXCL9, CXCL12, CCL2, CCL19, CCL21, CXCR2, CCR2, CCR4 and CXCR4, a receptor of any one of the same, and combinations of two or more of the same.
24. A combination therapy according to any one of paragraphs 19 to 23, wherein the oncolytic virus (further oncolytic virus) encodes a transmembrane anchored form of a B7 protein, for example B7-1 or B7-2.
25. A combination therapy according to any one of paragraphs 19 to 24, wherein the oncolytic virus (further oncolytic virus) encodes a checkpoint inhibitor selected from the group comprising a PD-1 inhibitor, a PD-L1 inhibitor, a CTLA-4 inhibitor, a TIM-3 inhibitor, a LAG-3 inhibitor, a TIGIT inhibitor, a B7-H3 (CD276) inhibitor, a B7-H4 (B7S1) inhibitor, a B7H7 (HHLA2) inhibitor, a CD96 inhibitor, a VISTA inhibitor and combinations of two or more of the same.
26. A combination therapy according to paragraph 25, wherein the inhibitor is an antibody or binding fragment thereof.
27. A combination therapy according to any one of paragraphs 19 to 26, wherein the oncolytic virus (further oncolytic virus) encodes a costimulatory pathway agonist.
28. A combination therapy according to paragraph 27, wherein the oncolytic virus (further oncolytic virus) encodes a costimulatory pathway agonist selected from the group comprising a CD27 agonist, a CD28 agonist, an ICOS agonist, a TMIGD2 (IGPR-1/CD28H) agonist, a CD226 agonist, an OX40 agonist, a 4-1BB agonist and a combination of two or more of the same.
29. A combination therapy according to any one of paragraphs 19 to 28, wherein the oncolytic virus (further oncolytic virus) encodes a molecule which activates immune responses or reverse suppression of immune responses, for example selected from IL-10, TGFβ, IDO inhibitors and a combination of two or more of the same.
30. A pharmaceutical formulation comprising an oncolytic adenovirus as defined in any one of paragraphs 1 to 5 and comprising a further oncolytic virus as defined in any one of paragraphs 19 to 29.
31. A combination therapy as defined in any one of paragraphs 19 to 29 or a pharmaceutical composition as defined in paragraph 30, for use in treatment.
32. An oncolytic virus according to any one of paragraphs 1 to 5 or a pharmaceutical composition according to paragraph 6 or 30, for use in the manufacture of a medicament for the treatment of cancer, insulin resistance, obesity, and/or immune deficiency.

33. A use according to paragraph 32, wherein the adenovirus or composition is for use in the manufacture of a medicament for the treatment of cancer.

34. A use according to paragraph 33, wherein the target patient population for treatment have cancer which expresses CD40, such as a population where CD40 is upregulated in the cancer.

35. A combination therapy for use in the manufacture of a medicament for the treatment of cancer comprising a virus according to any one of paragraphs 1 to 5 or a composition according to paragraph 6 or 30 and a further anti-cancer therapy, for example where the target patient population for treatment have cancer which expresses CD40, such as a population where CD40 is upregulated in the cancer.

36. A combination therapy according to paragraph 35, wherein the further anti-cancer therapy is chemotherapy.

37. A combination therapy according to paragraph 35 or 36, wherein the further anti-cancer therapy is a check point inhibitor.

38. A combination therapy according to paragraph 37, wherein the anti-cancer therapy is selected from the group comprising a PD-1 inhibitor, a PD-L1 inhibitor, a CTLA-4 inhibitor, a TIM-3 inhibitor, a LAG-3 inhibitor, a TIGIT inhibitor, a B7-H3 (CD276) inhibitor, a B7-H4 (B7S1) inhibitor, a B7H7 (HHLA2) inhibitor, a CD96 inhibitor, a VISTA inhibitor and combinations of two or more of the same.

39. A combination therapy according to any one of paragraphs 35 to 38, wherein the further cancer therapy is an oncolytic virus, for example a replication competent oncolytic virus, such ds defined in any one of paragraphs 19 to 29.

40. A method of treatment comprising administering a therapeutically effective amount of an oncolytic adenovirus according to any one of paragraphs 1 to 5 or a pharmaceutical composition according to paragraph 6 or 30 to a patient in need thereof.

41. A method according to paragraph 40, for the treatment of cancer, insulin resistance, obesity, and/or immune deficiency.

42. A method according to paragraph 41, for the treatment of cancer, for example a cancer expressing CD40 (such as a cancer with upregulated CD40 expression).

43. A method according to any one of paragraphs 37 to 42, wherein treatment further comprises an additional anti-cancer therapy.

44. A combination therapy according to paragraph 43, wherein the further anti-cancer therapy is chemotherapy.

45. A combination therapy according to paragraph 42 or 44, wherein the further anti-cancer therapy is a check point inhibitor.

46. A combination therapy according to paragraph 45, wherein the anti-cancer therapy is selected from the group comprising a PD-1 inhibitor, a PD-L1 inhibitor, a CTLA-4 inhibitor, a TIM-3 inhibitor, a LAG-3 inhibitor, a TIGIT inhibitor, a B7-H3 (CD276) inhibitor, a B7-H4 (B7S1) inhibitor, a B7H7 (HHLA2) inhibitor, a CD96 inhibitor, a VISTA inhibitor and combinations of two or more of the same.

47. A combination therapy according to any one of paragraphs 42 to 46, wherein the further cancer therapy is an oncolytic virus, for example a replication competent oncolytic virus, for example a virus defined in any one of pargraphs 19 to 29.

BRIEF DESCRIPTION OF FIGURES

FIG. 1 shows a schematic of the anti-CD40 transgene cassette.

FIGS. 2A &B shows NG-350 virus activity in terms of total particle production (A) and virus particle production in the cell supernatant (B).

FIG. 2C shows concentration of secreted IgG2 anti-CD40 antibody measured using ELISA.

FIG. 3 shows results of restriction digestion of control vs NG-350 DNA using the combination EcoRv/NheI (A) or individual enzymes NcoI or FspI (B).

FIG. 4 shows location in NG-350 transgene cassette where primers bind.

FIG. 5 shows separation of PCR products using gel electrophoresis.

FIG. 6 shows separation of PCR products using Primer set D (A) and Primer set K (B).

FIG. 7A shows quantification of the % cell survival at various infection density for EnAd and NG-350A (virus of SEQ ID NO: 1).

FIG. 10 shows absorbance at 620 nm measured for each sample using a plate reader for NG-350A, EnAd or NG-165 infected cells.

FIGS. 11A & B shows absorbance at 450 nm in each well of the plate was measured using a plate reader (BioTek) and the concentrations of secreted IgG2 anti-CD40 antibody.

FIG. 12 shows concentration of secreted IgG2 anti-CD40 antibody measured using ELISA.

FIG. 13 shows percentage of moDCs expressing CD86 (A), CD54 (B) and HLA-DR (C) activation markers.

FIG. 14 shows secretion of IL12p40 by moDCs cultured with purified anti-CD40 antibody produced by NG-350A infected tumour cells in the presence or absence of EnAd virus, or EnAd virus only.

FIG. 15 shows percentage of CD19+ cells expressing CD86 (A), CD54 (B), MFI HLA-DR (C) and CD80 (D).

FIG. 27 shows time courses of anti-CD40 antibody mRNA expression by 10 different tumour cell lines infected with NG-350A.

FIG. 31 shows acute plasma cytokine responses following first and third dose of a repeat IV dosing regimen with NG-350A particles compared to those for EnAd; MCP-1 (A), IL-6 (B).

FIG. 37 shows anti-CD40 antibody protein in subcutaneous A549 tumours after three IV injections or a single fractionated IT dose or NG-350A or EnAd.

DETAILED DISCLOSURE

Figure 7:
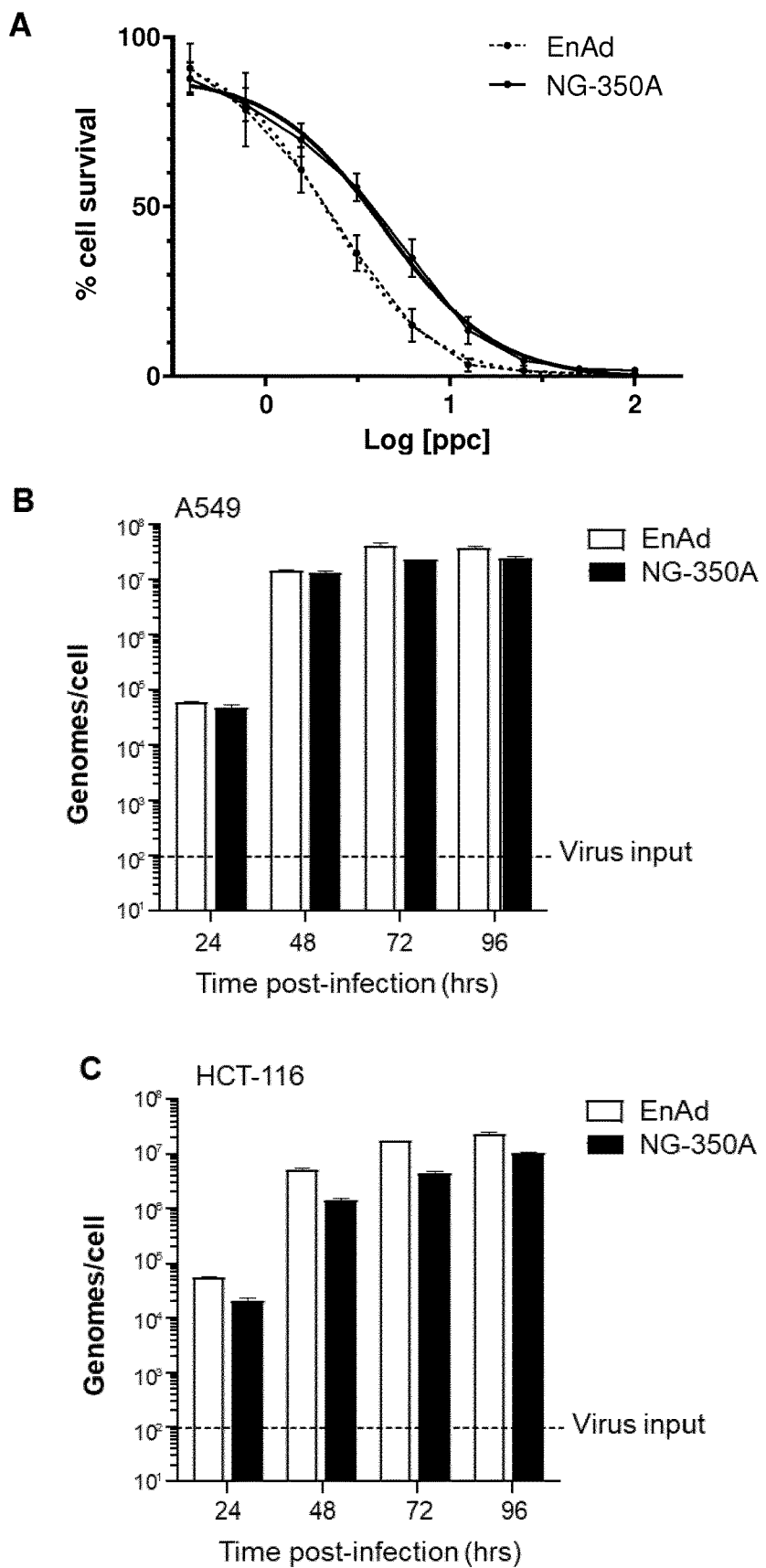
FIGS. 7 & 8 shows quantification of the number of detected virus genomes per cell for NG-350A and EnAd.

CD40 is a co-stimulatory protein found, for example on antigen presenting cells. CD40 is also known as Bp50, CDW40, TNFRSF5, p50, CD40 protein, CD40 molecule. The human protein has the UniProt number P25942. The murine protein has the UniProt number P27512.

Oncolytic virus with selectivity for cancer cells as employed herein refers to a virus that preferentially kills cancer cells, for example because it preferentially infects cancer cells and/or the virus life cycle is dependent on a gene, such as p53 that is disregulated, for example overexpressed in cancer cells. In one embodiment the oncolytic virus preferentially infects cancer cells and goes on to replicate its genome and produce capsid proteins to generate new virus particles, for example as per EnAd.

The selectivity for cancer cells (therapeutic index) can be tested as described in WO2005/118825 incorporated herein by reference.

In one embodiment, the oncolytic virus is a virus selected from an adenovirus, herpes simplex virus, reovirus, measles virus, Newcastle disease virus, Seneca Valley virus, Vesicular stomatitis virus, polio virus, ECHO enterovirus, Coxsackie virus, and vaccinia virus, in particular an adenovirus.

In one embodiment, the adenovirus is selected from the group consisting of Enadenotucirev, talimogene laherparepvec, RIGVIR, Ad5-yCD/mutTKSR39rep-hIL12, Cavatak™, CG0070, DNX-2401, G207, HF10, Imlygic®, JX-594, MG1-MA3, MV-NIS, OBP-301, Reolysin®, Toca 511, in particular Enadenotucirev.

In one embodiment the oncolytic adenovirus employed in the combination therapy of the present disclosure is replication competent.

In one embodiment the oncolytic adenovirus employed in the combination of the present disclosure is replication deficient.

In one embodiment the virus of the present disclosure is employed in a combination therapy.

In one embodiment an oncolytic adenovirus employed in the present disclosure or as a second component in combination therapy of the present disclosure, for example has a formula (I):

$$5'ITR-B_1-B_A-B_2-B_X-B_B-B_Y-B_3-3'ITR \quad (I)$$

wherein:
$B_1$ is a bond or comprises: E1A, E1B or E1A-E1B (in particular E1A, E1B or E1A-E1B);
$B_A$ is E2B-L1-L2-L3-E2A-L4;
$B_2$ is a bond or comprises E3 or a transgene, for example under an endogenous or exogenous promoter;
$B_X$ is a bond or a DNA sequence comprising: a restriction site, one or more transgenes or both;
$B_B$ comprises L5;
$B_Y$ comprises the transgene cassette which encodes a therapeutic protein or an active fragment thereof (in particular, comprises SEQ ID NO: 12); and
$B_3$ is a bond or comprises E4.

In one embodiment the oncolytic adenovirus has a formula (Ia):

$$5'ITR-B_1-B_A-B_2-B_B-B_Y-B_3-3'ITR \quad (Ia)$$

wherein:
$B_1$ is a bond or comprises: E1A, E1B or E1A-E1B (in particular E1A, E1B or E1A-E1B);
$B_A$ is E2B-L1-L2-L3-E2A-L4;
$B_2$ is a bond or comprises E3;
$B_B$ comprises L5;
$B_Y$ comprises the transgene cassette which encodes a therapeutic protein or an active fragment thereof (in particular, comprises SEQ ID NO: 12); and
$B_3$ is a bond or comprises E4.

In one embodiment the virus genome in constructs of formula (I) and/or (Ia) is from Ad11 or EnAd, in particular EnAd.

In one embodiment the transgene cassette is under the control of an endogenous promoter, for example the major late promoter.

Therapeutic proteins include an antibody or binding fragment (for example selected from the group comprising antibodies or fragments specific to CTLA-4, PD-1, PD-L1, PD-L2, VISTA, $B_7$-H3, $B_7$-H4, HVEM, ILT-2, ILT-3, ILT-4, TIM-3, LAG-3, BTLA, LIGHT or CD160 for example CTLA-4, PD-1, PD-L1 and/or PD-L2), a B-7 protein (such as $B_7$-1 and/or $B_7$-2), a cytokine (for example selected from IL-1α, IL-1β, IL-6, IL-9, IL-12, IL-13, IL-17, IL-18, IL-22, IL-23, IL-24, IL-25, IL-26, IL-27, IL-33, IL-35. Interleukin-2 (IL-2), IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF), and a chemokine (for example IL-8, CCL3, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and/or CRTH2), and combinations of two or more of the same.

The therapy of the present disclosure may comprise two or more oncolytic viruses.

Regulatory Elements

In one embodiment $B_Y$ comprises a transgene cassette according to the present disclosure, said cassette further comprises a transgene encoding a checkpoint inhibitor, for example an anti-CTLA-4 antibody, an anti-PD-1, and anti-PD-L1 antibody or a binding fragment of any one of the same and a regulatory element, such as combination of regulatory elements.

In one embodiment the regulatory element is splice acceptor sequence.

In one embodiment the regulatory element is a Kozak sequence.

In one embodiment, for example where the transgene encodes a polycistronic RNA molecule, the regulatory element is an IRES sequence.

In one embodiment the regulatory sequence is a high efficiency self-cleavable peptide sequence such as P2A, T2A, F2A, E2A.

In one embodiment the regulatory sequence is a polyA tail.

In one embodiment there are at least two regulatory sequences, for example a splice acceptor and a Kozak sequence or a splice acceptor and a polyA tail, or a splice acceptor and an IRES sequence, or a splice acceptor and a P2A sequence.

In one embodiment there are at least three regulator sequences, for example a splice acceptor sequence, a Kozak sequence and polyA tail, or a splice acceptor sequence an IRES or 2A sequence and a polyA tail; or a splice acceptor sequence, Kozak sequence and an IRES or 2A sequence.

In one embodiment there are at least four regulatory sequences, for example a splice acceptor sequence, a Kozak sequence, an IRES or 2A sequence and a polyA tail, in particular located between L5 and E4 in the order splice acceptor sequence, Kozak sequence, IRES or 2A sequence and a polyA tail.

In one embodiment the transgene encodes a polycistronic RNA molecule comprising both an IRES and a 2A regulatory sequence.

In one embodiment the protein or proteins encoded in the transgene cassette for cell membrane expression may also comprise a peptide linker or spacer between the transmembrane domain or GPI anchor and the extracellular ligand binding domain. Such linkers or spacers may add flexibility to the cell surface expressed protein that enhances the ability of the protein to interact with its target molecule, for example on an adjacent cell. Such linkers or spacers may also be designed or selected to promote dimerisation or trimerisation of the proteins at the cell surface, via disulphide bond formation or protein-protein interactions. For example, the hinge regions of immunoglobulin molecules or CD8 may be employed to enhance both flexibility and dimerisation.

In one embodiment the protein or proteins encoded in the transgene cassette may also comprise a peptide tag.

The peptide tag may include c-myc, poly-histidine, V5 or FLAG tags and can be located on the N-terminus or C-terminus of the polypeptide, for example intracellularly or extracellularly, or may be encoded within the protein for example in an extracellular loop or between the transmembrane domain and the extracellular domain. Peptide tags can be used as spacers or linkers between different protein domains, for example the transmembrane and the extracellular domain, and can be used for detection or purification or detection of the protein, or cells expressing the protein.

In one embodiment the one or more additional transgenes, for example in the virus of formula (I) or (Ia) is under the control of an exogenous or endogenous promoter, for example an endogenous promoter. In one embodiment a transgene in the E3 region ($B_2$) is under control of an exogenous promoter.

In one embodiment the one or more additional transgenes genes are between the E3 region and the fibre L5 in the adenovirus genome, for example at a position $B_X$ in the construct of formula (I), in particular under the control of an exogenous promoter. Thus, in one embodiment a transgene in $B_X$ is under the control of an exogenous promoter.

In one embodiment the one or more additional transgenes genes are between the E4 region and the fibre L5 in the adenovirus genome, for example at a position $B_Y$ in the construct of formula (I) or (Ia), in particular under the control of an endogenous promoter, such as the major late promoter. This may be in addition to the therapeutic protein or active fragment thereof encoded in the region $B_Y$.

Transgene as employed herein refers to a gene that has been inserted into the genome sequence of the adenovirus, wherein the gene is unnatural to the virus (exogenous) or not normally found in that particular location in the virus. Examples of transgenes are given herein. Transgene as employed herein also includes a functional fragment of the gene that is a portion of the gene which when inserted is suitable to perform the function or most of the function of the full-length gene, for example 50% of the function or more.

Transgene and coding sequence are used interchangeably herein in the context of inserts into the viral genome, unless the context indicates otherwise. Coding sequence as employed herein means, for example a DNA sequence encoding a functional RNA, peptide, polypeptide or protein. Typically, the coding sequence is cDNA for the transgene that encodes the functional RNA, peptide, polypeptide or protein of interest. Functional RNA, peptides, polypeptide and proteins of interest are described below.

In one embodiment transgene as employed herein refers to a segment of DNA containing a gene or cDNA sequence that has been isolated from one organism is introduced into a different organism i.e. the virus of the present disclosure. In one embodiment this non-native segment of DNA will generally retain the ability to produce functional RNA, peptide, polypeptide or protein. Transgenes employed may for example encode a single protein or active fragment thereof, chimeric protein or a fusion protein.

Clearly the virus genome contains coding sequences of DNA. Endogenous (naturally occurring genes) in the genomic sequence of the virus are not considered a transgene, within the context of the present specification unless then have been modified by recombinant techniques, such as that they are in a non-natural location or in a non-natural environment.

Thus, in one embodiment the transgene(s) inserted encode(s) a human or humanised protein, polypeptide or peptide. The transgene(s) may be located within a transgene cassette for example.

GPI anchor as employed herein refers to is a glycolipid that can be attached to the C-terminus of a protein during posttranslational modification. It is composed of a phosphatidylinositol group linked through a carbohydrate-containing linker (glucosamine and mannose glycosidically bound to the inositol residue) and via an ethanolamine phosphate (EtNP) bridge to the C-terminal amino acid of a mature protein. The two fatty acids within the hydrophobic phosphatidyl-inositol group anchor the protein to the cell membrane.

Glypiated (GPI-linked) proteins generally contain a signal peptide, thus directing them into the endoplasmic reticulum (ER). The C-terminus is composed of hydrophobic amino acids that stay inserted in the ER membrane. The hydrophobic end is then cleaved and replaced by the GPI-anchor. As the protein progresses through the secretory pathway, it is transferred via vesicles to the Golgi apparatus and finally to the extracellular space where it remains attached to the exterior leaflet of the cell membrane. Since the glypiation is the sole means of attachment of such proteins to the membrane, cleavage of the group by phospholipases will result in controlled release of the protein from the membrane. The latter mechanism is used in vitro; i.e., the membrane proteins released from the membranes in the enzymatic assay are glypiated protein.

Phospholipase C (PLC) is an enzyme that is known to cleave the phospho-glycerol bond found in GPI-anchored proteins. Treatment with PLC will cause release of GPI-linked proteins from the outer cell membrane. The T-cell marker Thy-1 and acetylcholinesterase, as well as both intestinal and placental alkaline phosphatases, are known to be GPI-linked and are released by treatment with PLC. GPI-linked proteins are thought to be preferentially located in lipid rafts, suggesting a high level of organization within plasma membrane microdomains.

A review of GPI anchors written by Ferguson, Kinoshita and Hart is available in Chapter 11 of Essentials of Glycobiology $2^{nd}$ Edition.

Viruses

Replication competent in the context of the present specification refers to a virus that possesses all the necessary machinery to replicate in cells in vitro and in vivo, i.e. without the assistance of a packaging cell line. A viral vector, for example deleted in at least the E1A region, which is capable of replicating in a complementary packaging cell line is not a replication competent virus in the present context.

A viral vector is a replication deficient virus, which requires a packaging cell line (comprising a complementary transgene) to replicate.

A replication capable virus as employed herein refers to a replication competent virus or a virus whose replication is dependent on a factor in the cancer cells, for example an upregulated factor, such as p53 or similar:

In one embodiment the adenovirus is a human adenovirus. "Adenovirus", "serotype" or adenoviral serotype" as employed herein refers to any adenovirus that can be assigned to any of the over 50 currently known adenoviral serotypes, which are classified into subgroups A-F, and further extends to any, as yet, unidentified or unclassified adenoviral serotypes. See, for example, Strauss, "Adenovirus infections in humans," in The Adenoviruses, Ginsberg, ea., Plenum Press, New York, N.Y., pp. 451-596 (1984) and Shenk, "Adenoviridae: The Viruses and Their Replication," in Fields Virology, Vol. 2, Fourth Edition, Knipe, 35ea., Lippincott Williams & Wilkins, pp. 2265-2267 (2001), as shown in below:

| SubGroup | Adenoviral Serotype |
| --- | --- |
| A | 12, 18, 31 |
| B | 3, 7, 11, 14, 16, 21, 34, 35, 51 |
| C | 1, 2, 5, 6 |
| D | 8-10, 13, 15, 17, 19, 20, 22-30, 32, 33, 36-39, 42- |
| E | 4 |
| F | 40, 41 |

Adenoviruses are grouped based on their capsid.

In one embodiment the adenovirus is a subgroup B, for example independently selected from the group comprising or consisting of: Ad3, Ad7, Ad11, Ad14, Ad16, Ad21, Ad34 and Ad51, such as Ad11, in particular Ad11p (the Slobitski strain). In one embodiment the adenovirus of the invention has the capsid, such as the hexon and/or fibre of a subgroup B adenovirus, such as Ad11, in particular Ad11p. In one embodiment the adenovirus is Ad or has the fibre and/or hexon and/or penton of Ad, such as Ad11p.

In one embodiment the virus of the present disclosure is not a group A virus.

In one embodiment the virus of the present disclosure does not comprise an adeno death protein (ADP).

In one embodiment the virus of the present disclosure is not a group C virus.

In one embodiment the virus of the present disclosure does not comprise one more fragments of an Ad5 virus.

In one embodiment the virus of the present disclosure is not Ad5.

Enadenotucirev (EnAd) is a chimeric oncolytic adenovirus, formerly known as ColoAd1 (WO2005/118825), with fibre, penton and hexon from Ad11p, hence it is a subgroup B virus. It has a chimeric E2B region, which comprises DNA from Ad11p and Ad3. Almost all of the E3 region and part of the E4 region is deleted in EnAd. Therefore, it has significant space in the genome to accommodate additional genetic material whilst remaining viable. Furthermore, because EnAd is a subgroup B adenovirus, pre-existing immunity in humans is less common than, for example, Ad5. Other examples of chimeric oncolytic viruses with Ad1 fibre, penton and hexon include OvAd1 and OvAd2 (see WO2006/060314).

EnAd seems to preferentially infect tumour cells, replicates rapidly in these cells and causes cell lysis. This, in turn, can generate inflammatory immune responses thereby stimulating the body to also fight the cancer. Part of the success of EnAd is hypothesised to be related to the fast replication of the virus in vivo.

Importantly, it has been demonstrated clinically that EnAd can be administered systemically (e.g. by intravenous or intraperitoneal injection or infusion) and then subsequently selectively infect and express proteins within tumour cells. This property of EnAd, which may be shared by Ad11p and other group B adenoviruses in particular those expressing the capsid proteins of Ad11p (such as those described herein), makes it possible to express the encoded proteins in the tumor and/or tumor microenvironment.

Whilst EnAd selectively lyses tumour cells, it may be possible to introduce further beneficial properties, for example increasing the therapeutic activity of the virus or reducing side-effects of the virus by arming it with transgenes, such as a transgene which encodes a cell signalling protein or an antibody, or a transgene which encodes an entity which stimulates a cell signalling protein(s).

Advantageously arming a virus, with DNA encoding certain proteins that can be expressed inside the cancer cell, may enable the body's own defences to be employed to combat tumour cells more effectively, for example by making the cells more visible to the immune system or by delivering a therapeutic gene/protein preferentially to target tumour cells.

In one embodiment the oncolytic adenovirus of the present disclosure stimulates the patient's immune system to fight the tumor, for example by reducing the cancers ability to suppress immune responses.

In one embodiment the anti-CD40 antibody or binding fragment encoded by the virus of the present disclosure has the ability to activate immune cells, for example T cells, in the tumor microenvironment and/or in the vicinity of the tumor.

In one embodiment the oncolytic virus has a fibre, hexon and penton proteins from the same serotype, for example Ad, in particular Ad11p, for example found at positions 30812-31789, 18254-21100 and 13682-15367 of the genomic sequence of the latter wherein the nucleotide positions are relative to Genbank ID 217307399 (accession number: GC689208).

In one embodiment the adenovirus is enadenotucirev (also known as EnAd and formerly as ColoAd1). Enadenotucirev as employed herein refers the chimeric adenovirus of SEQ ID NO: 21 disclosed in WO2016/174200 and incorporated by reference. It is a replication competent oncolytic chimeric adenovirus which has enhanced therapeutic properties compared to wild type adenoviruses (see WO2005/118554). EnAd has a chimeric E2B region, which features DNA from Ad11p and Ad3, and deletions in E3/E4. The structural changes in enadenotucirev result in a genome that is approximately 3.5 kb smaller than Ad11p thereby providing additional "space" for the insertion of transgenes.

In one embodiment the cassette according to the present disclosure is located between L5 and the E4 region in an adenovirus such as a group B adenovirus, in particular under the control of the major late promoter.

In one embodiment the virus employed in not EnAd.

Other viruses that may be employed in the present invention include herpes simplex virus, reovirus, measles virus, Newcastle disease virus, Seneca Valley virus, Vesicular stomatitis virus, polio virus, ECHO enterovirus, Coxsackie virus, and vaccinia virus, in particular an adenovirus, for example selected from the group consisting of talimogene laherparepvec, RIGVIR, Ad5-yCD/mutTKSR39rep-hIL12, Cavatak™, CG0070, DNX-2401, G207, HF10, Imlygic®, JX-594, MG1-MA3, MV-NIS, OBP-301, Reolysin®, Toca 511.

Antibody or Antibody Fragment

In one embodiment the virus of the present disclosure encodes a full-length anti-CD40 antibody.

The term antibody as used herein refers to an immunoglobulin molecule capable of specific binding to a target antigen, such as a carbohydrate, polynucleotide, lipid, polypeptide, peptide etc., via at least one antigen recognition site (also referred to as a binding site herein), located in the variable region of the immunoglobulin molecule.

As used herein antibody molecule includes antibodies and binding fragments thereof and molecules comprising one or more of the same.

Antigen binding site as employed herein refers to a portion of the molecule, which comprises a pair of variable regions, in particular a cognate pair that interact specifically with the target antigen.

Antibody binding fragment as employed herein refers to less than the whole antibody, which is still capable of specifically binding to a target antigen.

Specifically, as employed herein, is intended to refer to a binding site that only recognises the antigen to which it is specific or a binding site that has significantly higher binding affinity to the antigen to which is specific compared to affinity to antigens to which it is non-specific, for example 5, 6, 7, 8, 9, 10 times higher binding affinity.

Antibody molecules as employed may comprise a complete antibody molecule having full length heavy and light chains, bispecific antibody format comprising full length antibodies or a fragment of any one of the same including, but are not limited to Fab, modified Fab, Fab', modified Fab', F(ab')2, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one embodiment an antibody molecule employed in the virus of the present disclosure is humanised, chimeric or non-human.

Humanised (which include CDR-grafted antibodies) as employed herein refers to molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present disclosure has a variable domain comprising human acceptor framework regions as well as one or more of the CDRs provided herein.

Examples of human frameworks which can be used in the present disclosure are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: vbase.mrc-cpe.cam.ac.uk.

In a humanised antibody of the present disclosure, the acceptor heavy and light chains do not necessarily need to be derived from the same antibody and may, if desired, comprise composite chains having framework regions derived from different chains.

The framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

Chimeric antibodies generally contain non-human variable regions and human constant regions.

In one embodiment the antibody molecules of the present disclosure are fully human, in particular one or more of the variable domains are fully human.

Fully human molecules are those in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts eg. as described in general terms in EP0546073, U.S. Pat. Nos. 5,545,806, 5,569,825, 5,625,126, 5,633,425, 5,661,016, 5,770,429, EP0438474 and EP0463151.

Definitions Relevant to Formula (I) and (Ia)

A bond refers to a covalent bond connecting one DNA sequence to another DNA sequence, for example connecting one section of the virus genome to another. Thus when a variable in formula (I) and (Ia) herein represents a bond the feature or element represented by the bond is absent i.e. deleted.

As the structure of adenoviruses is, in general, similar the elements below are discussed in terms of the structural elements and the commonly used nomenclature referring thereto, which are known to the skilled person. When an element is referred to herein then we refer to the DNA sequence encoding the element or a DNA sequence encoding the same structural protein of the element in an adenovirus. The latter is relevant because of the redundancy of the DNA code. The viruses' preference for codon usage may need to be considered for optimised results.

Any structural element from an adenovirus employed in the viruses of the present disclosure may comprise or consist of the natural sequence or may have similarity over the given length of at least 96%, such as 96%, 97%, 98%, 99% or 100%. The original sequence may be changed or modified to omit 10%, 9%, 8%, 7%, 6%, 5%, 4%, 3%, 2% or 1% of the genetic material. However, in one embodiment the DNA sequence which is at least 95% similar or identical encodes the same gene product i.e. RNA and/or protein. The skilled person is aware that when making changes the reading frames of the virus must be not disrupted such that the expression of structural proteins is disrupted. The present disclosure also extents to a polynucleotide sequence that hybridises to a sequence disclosed herein under stringent conditions.

In one embodiment the given element is a full-length sequence i.e. the full-length gene. Full-length gene as employed herein refers to at least the entirety of the coding sequence of a gene, but may include any associated non-coding regions, especially if they are relevant to the function of the gene.

In one embodiment the given element is less than a full-length sequence and retains the same or corresponding function as the full-length sequence.

In one embodiment for a given element which is optional in the constructs of the present disclosure, the DNA sequence may be less than a full-length and have no functionality, for example the E3 region may be totally or partly deleted. However, it may be useful to delete essentially all the E3 region as this optimises the space available for inserting transgenes.

The structural genes encoding structural or functional proteins of the adenovirus are generally linked by non-coding regions of DNA. Thus, there is some flexibility about where to "cut" the genomic sequence of the structural element of interest (especially in non-coding regions thereof) for the purpose of inserting a transgene into the viruses of the present disclosure. Thus, for the purposes of the present specification, the element will be considered a structural element of reference to the extent that it is fit for purpose and does not encode extraneous material. Thus, if appropriate the gene will be associated with suitable non-coding regions, for example as found in the natural structure of the virus.

Thus, in one embodiment an insert, such as DNA encoding a transgene, is inserted into a non-coding region of genomic virus DNA, such as an intron or intergenic sequence. Having said this some non-coding regions of adenovirus may have a function, for example in alternative splicing, transcription regulation or translation regulation, and this may need to be taken into consideration.

The sites identified herein, that are associated with the L5 region, are suitable for accommodating a variety of DNA sequences encoding complex entities such as RNAi, cytokines, single chain or multimeric proteins, such as antibodies, in particular SEQ ID NO:12.

Gene as employed herein refers to coding and any non-coding sequences associated therewith, for example introns and associated exons. In one embodiment a gene comprises or consists of only essential structural components, for example coding region.

Below follows a discussion relating to specific structural elements of adenoviruses.

The Inverted Terminal Repeat (ITR) sequences are common to all known adenoviruses (so named because of their symmetry) and are the viral chromosome origins of replication. Another property of these sequences is their ability to form a hairpin.

The 5'ITR as employed herein refers to part or all of an ITR from the 5' end of an adenovirus, which retains the function of the ITR when incorporated into an adenovirus in an appropriate location. In one embodiment the 5'ITR comprises or consists of the sequence from about 1 bp to 138 bp of SEQ ID NO: 21 of WO2016/174200 (said sequence is incorporated herein by reference) or a sequence 90, 95, 96, 97, 98 or 99% identical thereto along the whole length, in particular the sequence consisting of from about 1 bp to 138 bp of SEQ ID NO: 17 disclosed in WO2016/174200 (said sequence is incorporated herein by reference).

The 3'ITR as employed herein refers to part or all of an ITR from 3' end of an adenovirus which retains the function of the ITR when incorporated into an adenovirus in an appropriate location. In one embodiment the 3'ITR comprises or consists of the sequence from about 32189 bp to 32326 bp of SEQ ID NO: 17 disclosed in WO2016/174200 or a sequence 90, 95, 96, 97, 98 or 99% identical thereto along the whole length, in particular the sequence consisting of from about 32189 bp to 32326 bp of SEQ ID NO: 17 disclosed in WO2016/174200.

B1 as employed herein refers to the DNA sequence encoding: part or all of an E1A from an adenovirus, part or all of the E1B region of an adenovirus, and independently part or all of E1A and E1B region of an adenovirus.

When B1 is a bond then E1A and E1B sequences will be omitted from the virus. In one embodiment B1 is a bond and thus the virus is a vector.

In one embodiment B1 further comprises a transgene. It is known in the art that the E1 region can accommodate a transgene which may be inserted in a disruptive way into the E1 region (i.e. in the "middle" of the sequence) or part or all of the E1 region may be deleted to provide more room to accommodate genetic material.

E1A as employed herein refers to the DNA sequence encoding part or all of an adenovirus E1A region. The latter here is referring to the polypeptide/protein E1A. It may be mutated such that the protein encoded by the E1A gene has conservative or non-conservative amino acid changes (e.g. 1, 2, 3, 4 or 5 amino acid changes, additions and/or deletions over the whole length) such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same as appropriate.

E1B as employed herein refers to the DNA sequence encoding part or all of an adenovirus E1B region (i.e. polypeptide or protein), it may be mutated such that the protein encoded by the E1B gene/region has conservative or non-conservative amino acid changes (e.g. 1, 2, 3, 4 or 5 amino acid changes, additions and/or deletions over the whole length) such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same, as appropriate.

Thus, B1 can be modified or unmodified relative to a wild-type E1 region, such as a wild-type E1A and/or E1B. The skilled person can easily identify whether E1A and/or E1B are present or (part) deleted or mutated.

Wild-type as employed herein refers to a known adenovirus or a sequence from a known adenovirus. A known adenovirus is one that has been identified and named, regardless of whether the sequence information is available.

In one embodiment B1 has the sequence from 139 bp to 3932 bp of SEQ ID NO: 17 disclosed in WO2016/174200.

$B_A$ as employed herein refers to the DNA sequence encoding the E2B-L1-L2-L3-E2A-L4 regions including any non-coding sequences, as appropriate (in particular corresponding to the natural sequence from an adenovirus). Generally, this sequence will not comprise a transgene. In one embodiment the sequence is substantially similar or identical to a contiguous sequence from a known adenovirus, for example a serotype shown in Table 1, in particular a group B virus, for example Ad3, Ad7, Ad11, Ad14, Ad16, Ad21, Ad34, Ad35, Ad51 or a combination thereof, such as Ad3, Ad11 or a combination thereof. In one embodiment is E2B-L1-L2-L3-E2A-L4 refers to comprising these elements and other structural elements associated with the region, for example BA will generally include the sequence encoding the protein IV2a, for example as follows: IV2A IV2a-E2B-L1-L2-L3-E2A-L4.

In one embodiment the E2B region is chimeric. That is, comprises DNA sequences from two or more different adenoviral serotypes, for example from Ad3 and Ad11, such as Ad11p. In one embodiment the E2B region has the sequence from 5068 bp to 10355 bp of SEQ ID NO: 17 disclosed in WO2016/174200 or a sequence 95%, 96%, 97%, 98% or 99% identical thereto over the whole length.

In one embodiment the E2B in component $B_A$ comprises the sequences shown in SEQ ID NO: 18 disclosed in WO2016/174200 (said sequence is incorporated herein by reference).

In one embodiment $B_A$ has the sequence from 3933 bp to 27184 bp of SEQ ID NO: 18 disclosed in WO2016/174200.

E3 as employed herein refers to the DNA sequence encoding part or all of an adenovirus E3 region (i.e. protein/polypeptide), it may be mutated such that the protein encoded by the E3 gene has conservative or non-conservative amino acid changes (e.g. 1, 2, 3, 4 or 5 amino acid changes, additions and/or deletions over the whole length), such that it has the same function as wild-type (the corresponding unmutated protein); increased function in comparison to wild-type protein; decreased function, such as no function in comparison to wild-type protein or has a new function in comparison to wild-type protein or a combination of the same, as appropriate.

In one embodiment the E3 region is form an adenovirus serotype given in Table 1 or a combination thereof, in particular a group B serotype, for example Ad3, Ad7, Ad11 (in particular Ad11p), Ad14, Ad16, Ad21, Ad34, Ad35, Ad51 or a combination thereof, such as Ad3, Ad11 (in particular Ad11p) or a combination thereof.

In one embodiment the E3 region has a sequence shown in SEQ ID NO: 19 disclosed in WO2016/174200.

In one embodiment the E3 region is partially deleted, for example is 95%, 90%, 85%, 80%, 75%, 70%, 65%, 60%, 55%, 50%, 45%, 40%, 35%, 30%, 25%, 20%, 15%, 10%, 5% deleted.

In one embodiment $B_2$ is a bond, wherein the DNA encoding the E3 region is absent.

In one embodiment the DNA encoding the E3 region can be replaced or interrupted by a transgene. As employed herein "E3 region replaced by a transgene as employed herein includes part or all of the E3 region is replaced with a transgene.

In one embodiment the $B_2$ region comprises the sequence from 27185 bp to 28165 bp of SEQ ID NO: 98 disclosed in WO2016/174200 (said sequence is incorporated herein by reference).

In one embodiment $B_2$ consists of the sequence from 27185 bp to 28165 bp of SEQ ID NO: 98 disclosed in WO2016/174200.

$B_X$ as employed herein refers to the DNA sequence in the vicinity of the 5' end of the L5 gene in BB. In the vicinity of or proximal to the 5' end of the L5 gene as employed herein refers to: adjacent (contiguous) to the 5' end of the L5 gene or a non-coding region inherently associated herewith i.e. abutting or contiguous to the 5' prime end of the L5 gene or a non-coding region inherently associated therewith. Alternatively, in the vicinity of or proximal to may refer to being close the L5 gene, such that there are no coding sequences between the BX region and the 5' end of L5 gene.

Thus, in one embodiment $B_X$ is joined directly to a base of L5 which represents, for example the start of a coding sequence of the L5 gene.

Thus, in one embodiment $B_X$ is joined directly to a base of L5 which represents, for example the start of a non-coding sequence, or joined directly to a non-coding region naturally associated with L5. A non-coding region naturally associated L5 as employed herein refers to part of all of a non-coding regions which is part of the L5 gene or contiguous therewith but not part of another gene.

In one embodiment $B_X$ comprises the sequence of SEQ ID NO: 98 disclosed in WO2016/174200. This sequence is an artificial non-coding sequence wherein a DNA sequence, for example comprising a transgene (or transgene cassette), a restriction site or a combination thereof may be inserted therein. This sequence is advantageous because it acts as a buffer in that allows some flexibility on the exact location of the transgene whilst minimising the disruptive effects on virus stability and viability.

The insert(s) can occur anywhere within SEQ ID NO: 98 disclosed in WO2016/174200 from the 5' end, the 3' end or at any point between bp 1 to 201, for example between base pairs 1/2, 2/3, 3/4, 4/5, 5/6, 6/7, 7/8, 8/9, 9/10, 10/11, 11/12, 12/13, 13/14, 14/15, 15/16; 16/17, 17/18, 18/19, 19/20, 20/21, 21/22, 22/23, 23/24, 24/25, 25/26, 26/27, 27/28, 28/29, 29/30, 30/31, 31/32, 32/33, 33/34, 34/35, 35/36, 36/37, 37/38, 38/39, 39/40, 40/41, 41/42, 42/43, 43/44, 44/45, 45/46, 46/47, 47/48, 48/49, 49/50, 50/51, 51/52, 52/53, 53/54, 54/55, 55/56, 56/57, 57/58, 58/59, 59/60, 60/61, 61/62, 62/63, 63/64, 64/65, 65/66, 66/67, 67/68, 68/69, 69/70, 70/71, 71/72, 72/73, 73/74, 74/75, 75/76, 76/77, 77/78, 78/79, 79/80, 80/81, 81/82, 82/83, 83/84, 84/85, 85/86, 86/87, 87/88, 88/89, 89/90, 90/91, 91/92, 92/93, 93/94, 94/95, 95/96, 96/97, 97/98, 98/99, 99/100, 100/101, 101/102, 102/103, 103/104, 104/105, 105/106, 106/107, 107/108, 108/109, 109/110, 110/111, 111/112, 112/113, 113/114, 114/115, 115/116, 116/117, 117/118, 118/119, 119/120, 120/121, 121/122, 122/123, 123/124, 124/125, 125/126, 126/127, 127/128, 128/129, 129/130, 130/131, 131/132, 132/133, 133/134, 134/135, 135/136, 136/137, 137/138, 138/139, 139/140, 140/141, 141/142, 142/143, 143/144, 144/145, 145/146, 146/147, 147/148, 148/149, 150/151, 151/152, 152/153, 153/154, 154/155, 155/156, 156/157, 157/158, 158/159, 159/160, 160/161, 161/162, 162/163, 163/164, 164/165, 165/166, 166/167, 167/168, 168/169, 169/170, 170/171, 171/172, 172/173, 173/174, 174/175, 175/176, 176/177, 177/178, 178/179, 179/180, 180/181, 181/182, 182/183, 183/184, 184/185, 185/186, 186/187, 187/188, 189/190, 190/191, 191/192, 192/193, 193/194, 194/195, 195/196, 196/197, 197/198, 198/199, 199/200 or 200/201.

In one embodiment $B_X$ comprises SEQ ID NO: 98 disclosed in WO2016/174200 with a DNA sequence inserted between bp 27 and bp 28 or a place corresponding to between positions 28192 bp and 28193 bp of SEQ ID NO: 98 disclosed in WO2016/174200.

In one embodiment $B_X$ has the sequence from 28166 bp to 28366 bp of SEQ ID NO: 21 disclosed in WO2016/174200 (said sequence is incorporated herein by reference). In one embodiment $B_X$ is a bond.

$B_B$ as employed herein refers to the DNA sequence encoding the L5 region. As employed herein the L5 region refers to the DNA sequence containing the gene encoding the fibre polypeptide/protein, as appropriate in the context. The fibre gene/region encodes the fibre protein which is a major capsid component of adenoviruses. The fibre functions in receptor recognition and contributes to the adenovirus' ability to selectively bind and infect cells.

In viruses of the present disclosure the fibre can be from any adenovirus serotype and adenoviruses which are chimeric as result of changing the fibre for one of a different serotype are also envisaged with the present disclosure. In one embodiment the fibre is from a group B virus, in particular Ad11, such as Ad11p.

In one embodiment $B_B$ has the sequence from 28367 bp to 29344 bp of SEQ ID NO: 17 disclosed in WO2016/174200 (said sequence is incorporated herein by reference).

DNA sequence in relation to $B_Y$ as employed herein refers to the DNA sequence in the vicinity of the 3' end of the L5 gene of $B_B$. In the vicinity of or proximal to the 3' end of the L5 gene as employed herein refers to: adjacent (contiguous) to the 3' end of the L5 gene or a non-coding region inherently associated therewith i.e. abutting or contiguous to the 3' prime end of the L5 gene or a non-coding region inherently associated therewith (i.e. all or part of an non-coding sequence endogenous to L5). Alternatively, in the vicinity of or proximal to may refer to being close the L5 gene, such that there are no coding sequences between the $B_Y$ region and the 3' end of the L5 gene.

Thus, in one embodiment $B_Y$ is joined directly to a base of L5 which represents the "end" of a coding sequence.

Thus, in one embodiment $B_Y$ is joined directly to a base of L5 which represents the "end" of a non-coding sequence, or joined directly to a non-coding region naturally associated with L5.

Inherently and naturally are used interchangeably herein. In one embodiment $B_Y$ comprises the sequence of SEQ ID NO: 99 disclosed in WO2016/174200 (said sequence is incorporated herein by reference). This sequence is a non-coding sequence wherein a DNA sequence, for example comprising a transgene (or transgene cassette), a restriction site or a combination thereof may be inserted. This sequence is advantageous because it acts a buffer in that allows some flexibility on the exact location of the transgene whilst minimising the disruptive effects on virus stability and viability.

The insert(s) can occur anywhere within SEQ ID NO: 18 disclosed in WO2016/174200 (said sequence is incorporated herein by reference) from the 5' end, the 3' end or at any point between bp 1 to 35, for example between base pairs 1/2, 2/3, 3/4, 4/5, 5/6, 6/7, 7/8, 8/9, 9/10, 10/11, 11/12, 12/13, 13/14, 14/15, 15/16, 16/17, 17/18, 18/19, 19/20, 20/21, 21/22, 22/23, 23/24, 24/25, 25/26, 26/27, 27/28, 28/29, 29/30, 30/31, 31/32, 32/33, 33/34, or 34/35.

In one embodiment $B_Y$ comprises SEQ ID NO: 99 disclosed in WO2016/174200 (said sequence is incorporated herein by reference) with a DNA sequence inserted between positions bp 12 and 13 or a place corresponding to 29356 bp and 29357 bp in SEQ ID NO: 17 disclosed in WO2016/174200 (said sequence is incorporated herein by reference). In one embodiment the insert is a restriction site insert. In one embodiment the restriction site insert comprises one or two restriction sites. In one embodiment the restriction site is a 19 bp restriction site insert comprising 2 restriction sites. In one embodiment the restriction site insert is a 9 bp restriction site insert comprising 1 restriction site. In one embodiment the restriction site insert comprises one or two restriction sites and at least one transgene, for example one or two or three transgenes, such as one or two transgenes. In one embodiment the restriction site is a 19 bp restriction site insert comprising 2 restriction sites and at least one transgene, for example one or two transgenes. In one embodiment the restriction site insert is a 9 bp restriction site insert comprising 1 restriction site and at least one transgene, for example one or two transgenes. In one embodiment two restriction sites sandwich one or more, such as two transgenes (for example in a transgene cassette). In one embodiment when $B_Y$ comprises two restrictions sites the said restriction sites are different from each other. In one embodiment said one or more restrictions sites in $B_Y$ are non-naturally occurring (such as unique) in the particular adenovirus genome into which they have been inserted. In one embodiment said one or more restrictions sites in $B_Y$ are different to other restrictions sites located elsewhere in the adenovirus genome, for example different to naturally occurring restrictions sites or restriction sites introduced into other parts of the genome, such as $B_X$. Thus in one embodiment the restriction site or sites allow the DNA in the section to be cut specifically.

In one embodiment $B_Y$ has the sequence from 29345 bp to 29379 bp of SEQ ID NO: 17 disclosed in WO2016/174200. In one embodiment $B_Y$ is a bond.

In one embodiment the insert is after bp 12 in SEQ ID NO: 99 disclosed in WO2016/174200.

In one embodiment the insert is at about position 29356 bp of SEQ ID NO: 17 disclosed in WO2016/174200.

In one embodiment the insert is a transgene cassette comprising one or more transgenes, for example 1, 2 or 3, such as 1 or 2.

E4 as employed herein refers to the DNA sequence encoding part or all of an adenovirus E4 region (i.e. polypeptide/protein region), which may be mutated such that the protein encoded by the E4 gene has conservative or non-conservative amino acid changes (e.g. 1, 2, 3, 4 or 5 amino acid changes, additions and/or deletions), and has the same function as wild-type (the corresponding non-mutated protein); increased function in comparison to wild-type protein; decreased function, such as no function in comparison to wild-type protein or has a new function in comparison to wild-type protein or a combination of the same as appropriate.

In one embodiment the E4 region is partially deleted, for example is 95%, 90%, 85%, 80%, 75%, 70%, 65%, 60%, 55%, 50%, 45%, 40%, 35%, 30%, 25%, 20%, 15%, 10% or 5% deleted. In one embodiment the E4 region has the sequence from 32188 bp to 29380 bp of SEQ ID NO: 17 disclosed in WO2016/174200.

In one embodiment E4 is present except for the E4orf4 region which is deleted.

In one embodiment $B_3$ is a bond, i.e. wherein E4 is absent.

In one embodiment $B_3$ has the sequence consisting of from 32188 bp to 29380 bp of SEQ ID NO: 17 disclosed in WO2016/174200.

As employed herein number ranges are inclusive of the end points.

The skilled person will appreciate that the elements in the formulas herein, such as formula (I), (Ia) are contiguous and may embody non-coding DNA sequences as well as the genes and coding DNA sequences (structural features) mentioned herein. In one or more embodiments the formulas of the present disclosure are attempting to describe a naturally occurring sequence in the adenovirus genome. In this context it will be clear to the skilled person that the formula is referring to the major elements characterising the relevant section of genome and is not intended to be an exhaustive description of the genomic stretch of DNA.

E1A, E1B, E3 and E4 as employed herein each independently refer to the wild-type and equivalents thereof, mutated or partially deleted forms of each region as described herein, in particular a wild-type sequence from a known adenovirus.

"Insert" as employed herein refers to a DNA sequence that is incorporated either at the 5' end, the 3' end or within a given DNA sequence reference segment such that it interrupts the reference sequence. A reference sequence employed as a reference point relative to which the insert is located. In the context of the present disclosure inserts generally occur within either SEQ ID NO: 98 or SEQ ID NO: 99 both disclosed in WO2016/174200. An insert will general contain a transgene cassette. When the sequence is interrupted the virus will still comprise the original sequence, but generally it will be as two fragments sandwiching the insert.

In one embodiment the transgene or transgene cassette does not comprise a non-biased inserting transposon, such as a TN7 transposon or part thereof. Tn7 transposon as employed herein refers to a non-biased insertion transposon as described in WO2008/080003.

In one embodiment the transgene or transgene cassette further comprises a regulatory element or sequence.

Promoters

Promoter as employed herein means a region of DNA that initiates transcription of a particular gene or genes. Promoters are generally located proximal to the genes they transcribe, on the same strand and upstream (i.e. 5') on the DNA. Proximal as employed in this context means sufficiently close to function as a promoter. In one embodiment the promoter is within 100 bp of the transcription start site. Thus endogenous promoter as employed herein refers to a promoter that naturally occurs in (i.e. is native to) the adenovirus (or construct) into which the transgene, is being inserted. In one or more embodiments the endogenous promoter employed is the naturally occurring promoter in the virus in its original location in the virus genome, in particular this is the primary or only promoter employed in the expression of the transgene or transgenes. In one embodiment the endogenous promoter used to promote the translation and optionally the transcription of the transgene is one resident, i.e. is one integrated in the genome of the adenovirus and not previously introduced by recombinant techniques.

Under the control of an endogenous promoter as employed herein refers to where the transgene/transgene cassette is inserted in the appropriate orientation to be under the control of said endogenous promoter. That is, where the promoter is generally on the antisense strand, the cassette is inserted, for example in the antisense orientation.

Having said this, genes can be expressed in one of two orientations. However, generally one orientation provides increased levels of expression over the other orientation, for a given (particular) transgene.

In one embodiment the cassette is in the sense orientation. That is transcribed in a 5' to 3' direction: In one embodiment the cassette is in the antisense orientation. That is, transcribed in the 3' to 5' orientation.

The endogenous promoters in the virus can, for example, be utilised by employing a gene encoding a transgene and a splice acceptor sequence. Thus in one embodiment the cassette will comprise a splice acceptor sequence which facilitates the transgene utilising an endogenous promoter. Thus in one embodiment the coding sequence, for example the sequence encoding the antibody or antibody binding fragment further comprises a splice acceptor sequence.

In one embodiment the transgene, transgenes, or transgene cassette are under the control of an E4 promoter or a major late promoter, such as the major late promoter (ML promoter).

Under the control of as employed herein means that the transgene is activated, i.e. transcribed, when a particular promoter dictates.

The Major Late Promoter (ML promoter or MLP) as employed herein refers to the adenovirus promoter that controls expression of the "late expressed" genes, such as the L5 gene. The MLP is a "sense strand" promoter. That is, the promoter influences genes that are downstream of the promoter in the 5'-3' direction. The major late promoter as employed herein refers the original major late promoter located in the virus genome.

E4 promoter as employed herein refers to the adenovirus promoter of the E4 region. The E4 region is an antisense region; therefore the promoter is an antisense promoter. That is, the promoter is upstream of the E4 region in the 3'-5' direction. Therefore any transgene cassette under control of the E4 promoter may need to be oriented appropriately. In one embodiment the cassette under the control of the E4 promoter is in the antisense orientation. In one embodiment the cassette is under the control of the E4 promoter in the sense orientation. The E4 promoter as employed herein refers to the original E4 promoter located in the virus genome.

Thus in one embodiment there is provided a replication competent oncolytic adenovirus serotype 11 (such as Ad11p) or virus-derivative thereof wherein the fibre, hexon and capsid are serotype 11 (such as Ad11p), wherein the virus genome comprises a DNA sequence encoding a therapeutic antibody or antibody-binding fragment, wherein said DNA sequence under the control of a promoter endogenous to the adenovirus selected from consisting of E4 and the major late promoter (i.e. the E4 promoter or the major late promoter), such that the transgene does not interfere with virus replication, for example is associated with the L5 region (i.e. before or after said region), such as located after L5 in the virus genome.

In one embodiment an endogenous promoter is introduced into the viral genome at a desired location by recombinant techniques, for example is introduced in the transgene cassette. However, in the context of the present specification this arrangement will generally be referred to as an exogenous promoter.

In one embodiment the transgene cassette comprises an exogenous promoter. Exogenous promoter as employed herein refers to a promoter that is not naturally occurring in the adenovirus into which the transgene is being inserted. Typically exogenous promoters are from other viruses or are mammalian promoters. Exogenous promoter as employed herein means a DNA element, usually located upstream of the gene of interest, that regulates the transcription of the gene.

In one embodiment the regulator of gene expression is an exogenous promoter, for example CMV (cytomegalovirus promoter), CBA (chicken beta actin promoter) or PGK (phosphoglycerate kinase 1 promoter), such as CMV promoter.

In one embodiment the exogenous promoter is inducible.

In one embodiment there is provided a replication competent oncolytic adenovirus serotype 11 (such as Ad11p) or virus-derivative thereof wherein the fibre, hexon and capsid are serotype 11 (such as Ad11p), wherein the virus genome comprises a DNA sequence encoding a therapeutic antibody or antibody-binding fragment located in a part of the virus genome which is expressed late in the virus replication cycle and such that the transgene does not interfere with virus replication, wherein said DNA sequence under the control of a promoter exogenous to the adenovirus (for example the CMV promoter). In one embodiment the DNA sequence encoding an antibody or fragment is associated with the L5 region as described elsewhere herein.

Other Regulatory Sequences

"Regulator of gene expression" (or regulator/regulatory element) as employed herein refers to a genetic element, such as a promoter, enhancer or a splice acceptor sequence that plays a role in gene expression, typically by initiating or enhancing transcription or translation.

"Splice acceptor sequence", "splice acceptor" or "splice site" as employed herein refers to a regulatory sequence determining when an mRNA molecule will be recognised by small nuclear ribonucleoproteins of the spliceosome complex. Once assembled the spliceosome catalyses splicing between the splice acceptor site of the mRNA molecule to an upstream splice donor site producing a mature mRNA molecule that can be translated to produce a single polypeptide or protein.

Different sized splice acceptor sequences may be employed in the present invention and these can be described as short splice acceptor (small), splice acceptor (medium) and branched splice acceptor (large).

SSA as employed herein refers to a short splice acceptor, typically comprising just the splice site, for example 4 bp. SA as employed herein refers to a splice acceptor, typically comprising the short splice acceptor and the polypyrimidine tract, for example 16 bp. bSA as employed herein refers to a branched splice acceptor, typically comprising the short splice acceptor, polypyrimidine tract and the branch point, for example 26 bp.

In one embodiment the splice acceptor employed in the constructs of the disclosure are CAGG or SEQ ID NO: 15 or 16 (both disclosed in WO2016/174200 as SEQ ID NO: 10 AND 11 therein said sequences incorporated herein by reference). In one embodiment the SSA has the nucleotide sequence of CAGG. In one embodiment the SA has the nucleotide sequence of SEQ ID NO: 15. In one embodiment the bSA has the nucleotide sequence of cagg. In one embodiment the splice acceptor sequence is independently selected from the group comprising: tgctaatctt cctttctctc ttcagg (SEQ ID NO: 15), tttctctctt cagg (SEQ ID NO: 16), and cagg.

In one embodiment the splice site is immediately proceeded (i.e. followed in a 5' to 3' direction) by a consensus Kozak sequence comprising CCACC. In one embodiment the splice site and the Kozak sequence are interspersed (separated) by up to 100 or less bp. In one embodiment the Kozak sequence has the nucleotide sequence of CCACC.

Typically, when under the control of an endogenous or exogenous promoter (such as an endogenous promoter), the coding sequence will be immediately preceded by a Kozak sequence. The start of the coding region is indicated by the initiation codon (AUG), for example is in the context of the sequence (gcc)gccRccAUGg (SEQ ID NO: 8) the start of the start of the coding sequences is indicated by the bases in bold. A lowercase letter denotes common bases at this position (which can nevertheless vary) and uppercase letters indicate highly-conserved bases; i.e. the 'AUGG' sequence is constant or rarely, if ever, changes; 'R' indicates that a purine (adenine or guanine) is usually observed at this position and the sequence in brackets (gcc) is of uncertain significance. Thus, in one embodiment the initiation codon AUG is incorporated into a Kozak sequence.

Internal Ribosome Entry DNA Sequence as employed herein refers to a DNA sequence encoding an Internal Ribosome Entry Sequence (IRES). IRES as employed herein means a nucleotide sequence that allows for initiation of translation a messenger RNA (mRNA) sequence, including initiation starting within an mRNA sequence. This is particularly useful when the cassette encodes polycistronic mRNA. Using an IRES results in a polycistronic mRNA that is translated into multiple individual proteins or peptides. In one embodiment the Internal Ribosome Entry DNA sequence has the nucleotide sequence disclosed in WO2016/174200 as SEQ ID NO: 6 therein (said sequence is incorporated herein by reference). In one embodiment a particular IRES is only used once in the genome. This may have benefits with respect to stability of the genome.

"High self-cleavage efficiency 2A peptide" or "2A peptide" as employed herein refers to a peptide which is efficiently cleaved following translation. Suitable 2A peptides include P2A, F2A, E2A and T2A. The present inventors have noted that once a specific DNA sequence encoding a given 2A peptide is used once, the same specific DNA sequence may not be used a second time. However, redundancy in the DNA code may be utilised to generate a DNA sequence that is translated into the same 2A peptide. Using 2A peptides is particularly useful when the cassette encodes polycistronic mRNA. Using 2A peptides results in a single polypeptide chain being translated which is modified post-translation to generate multiple individual proteins or peptides.

In one embodiment the encoded P2A peptide employed has the amino acid sequence of SEQ ID NO: 24. In one embodiment the encoded F2A peptide employed has the amino acid sequence of SEQ ID NO: 25. In one embodiment the encoded E2A peptide employed has the amino acid sequence of SEQ ID NO: 26. In one embodiment the encoded T2A peptide employed has the amino acid sequence of SEQ ID NO: 27.

In one embodiment an mRNA or each mRNA encoded by transgene is/are comprise a polyadenylation signal sequence, such as typically at the end of an mRNA sequence, for example a as shown in SEQ ID NO: 10 is employed. Thus, in one embodiment the transgene or the transgene cassette comprises at least one sequence encoding a polyadenylation signal sequence.

"PolyA", "Polyadenylation signal" or "polyadenylation sequence" as employed herein means a DNA sequence, usually containing an AATAAA site, that once transcribed can be recognised by a multiprotein complex that cleaves and polyadenylates the nascent mRNA molecule.

In one embodiment the polyadenylation sequence has the nucleotide sequence of SEQ ID NO: 6. disclosed in WO2016/174200 (said sequence is incorporated herein by reference).

In one embodiment the construct does not include a polyadenylation sequence. In one embodiment the regulator of gene expression is a splice acceptor sequence.

In one embodiment the sequence encoding a protein/polypeptide/peptide, such as an antibody or antibody binding fragment further comprises a polyadenylation signal.

Formulations

The present disclosure relates also extends to a pharmaceutical formulation of a virus as described herein.

In one embodiment there is provided a liquid parenteral formulation, for example for infusion or injection, of a replication capable oncolytic according to the present disclosure wherein the formulation provides a dose in the range of $1\times10^{10}$ to $1\times10^{14}$ viral particles per volume of dose.

Parenteral formulation means a formulation designed not to be delivered through the GI tract. Typical parenteral delivery routes include injection, implantation or infusion. In one embodiment the formulation is provided in a form for bolus delivery.

In one embodiment the parenteral formulation is in the form of an injection. Injection includes intravenous, subcutaneous, intra-tumoral or intramuscular injection. Injection as employed herein means the insertion of liquid into the body via a syringe. In one embodiment the method of the present disclosure does not involve intra-tumoral injection.

In one embodiment the parenteral formulation is in the form of an infusion.

Infusion as employed herein means the administration of fluids at a slower rate by drip, infusion pump, syringe driver or equivalent device. In one embodiment the infusion is administered over a period in the range of 1.5 minutes to 120 minutes, such as about 3, 4, 5, 6, 7, 8, 9, 10, 11, 12, 13, 14, 15, 16, 17, 18, 19 20, 25, 30, 35, 40, 45, 50, 55, 60, 65, 70, 65, 80, 85, 90, 95, 100, 105, 110 or 115 minutes.

In one embodiment one dose of the formulation less than 100 ms, for example 30 mls, such as administered by a syringe driver.

In one embodiment the injection is administered as a slow injection, for example over a period of 1.5 to 30 minutes.

In one embodiment the formulation is for intravenous (i.v.) administration. This route is particularly effective for delivery of oncolytic virus because it allows rapid access to the majority of the organs and tissue and is particular useful for the treatment of metastases, for example established metastases especially those located in highly vascularised regions such as the liver and lungs.

Therapeutic formulations typically will be sterile and stable under the conditions of manufacture and storage. The composition can be formulated as a solution, microemulsion, liposome, or other parenteral formulation suitable for administration to a human and may be formulated as a pre-filled device such as a syringe or vial, particular as a single dose.

The formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40. In dispersions the maintenance of the required particle size may be assisted by the presence of a surfactant. Examples of isotonic agents include sugars, polyalcohols such as mannitol, sorbitol, or sodium chloride in the composition.

In one embodiment parenteral formulations employed may comprise one or more of the following a buffer, for example 4-(2-hydroxyethyl)-1-piperazineethanesulfonic acid, a phosphate buffer and/or a Tris buffer, a sugar for example dextrose, mannose, sucrose or similar, a salt such as sodium chloride, magnesium chloride or potassium chloride, a detergent such as a non-ionic surfactant such as brij, PS-80, PS-40 or similar. The formulation may also comprise a preservative such as EDTA or ethanol or a combination of EDTA and ethanol, which are thought to prevent one or more pathways of possible degradation.

In one embodiment the formulation will comprise purified oncolytic virus according to the present disclosure, for example $1 \times 10^{10}$ to $1 \times 10^{14}$ viral particles per dose, such as $1 \times 10^{10}$ to $1 \times 10^{12}$ viral particles per dose. In one embodiment the concentration of virus in the formulation is in the range $2 \times 10^8$ to $2 \times 10^{14}$ vp/ml, such as $2 \times 10^{12}$ vp/ml.

In one embodiment the parenteral formulation comprises glycerol.

In one embodiment the formulation comprises oncolytic adenovirus as described herein, HEPES (N-2-hydroxyethylpiperazine-N'-2-ethanesulfonic acid), glycerol and buffer.

In one embodiment the parenteral formulation consists of virus of the disclosure, HEPES for example 5 mM, glycerol for example 5-20% (v/v), hydrochloric acid, for example to adjust the pH into the range 7-8 and water for injection.

In one embodiment 0.7 mL of virus of the disclosure at a concentration of $2 \times 10^{12}$ vp/mL is formulated in 5 mM HEPES, 20% glycerol with a final pH of 7.8.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure will generally contain a virus as described herein with a physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, such as lactose or glucose, particularly but not exclusively in the form of their hydrates.

Particles for deposition in the lung require a particle size less than 10 microns, such as 1-9 microns for example from 0.1 to 5 m, in particular from 1 to 5 m. The size of the particle carrying the virus is of primary importance and thus in one embodiment the virus according to the present disclosure may be adsorbed or absorbed onto a particle, such as a lactose particle of the given size.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant gas-containing inhalable aerosols may also contain other ingredients, such as co-solvents, stabilisers, surface-active agents (surfactants), antioxidants, lubricants and means for adjusting the pH. All these ingredients are known in the art.

The propellant gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively, topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The virus of the invention can be delivered dispersed in a solvent, e.g. in the form of a solution or a suspension, for example as already described above for parenteral formulations. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The present disclosure also extends to liquid solutions or suspensions delivered intra-nasally, for example employing a device as disclosed in WO2009/068877 and US2004/0153033 both incorporated herein by reference.

Treatment

In a further aspect the present disclosure extends to a virus or a formulation thereof as described herein for use in treatment, in particular for the treatment of cancer.

In one embodiment the method of treatment is for use in the treatment of a tumour.

Tumour as employed herein is intended to refer to an abnormal mass of tissue that results from excessive cell division that is uncontrolled and progressive, also called a neoplasm. Tumours may be either benign (not cancerous) or malignant. Tumour encompasses all forms of cancer and metastases. In one embodiment the tumour is cancerous.

In one embodiment the tumour is a solid tumour. The solid tumour may be localised or metastasised.

In one embodiment the tumour is of epithelial origin.

In one embodiment the tumour is a malignancy, such as colorectal cancer, hepatoma, prostate cancer, pancreatic cancer, breast cancer, ovarian cancer, thyroid cancer, renal cancer, bladder cancer, head and neck cancer or lung cancer.

In one embodiment the tumour is a colorectal malignancy.

Malignancy as employed herein refers to cancerous cells.

In one embodiment the oncolytic adenovirus is employed in the treatment or prevention of metastasis.

In one embodiment the method or formulation herein is employed in the treatment of drug resistant cancers.

In one embodiment the virus is administered in combination with the administration of a further cancer treatment or therapy.

In one embodiment there is provided a virus or formulation according to the present disclosure for use in the manufacture of a medicament for the treatment of cancer, for example a cancer described above.

In a further aspect there is provide a method of treating cancer comprising administering a therapeutically effective amount of a virus or formulation according to the present disclosure to a patient in need thereof, for example a human patient.

In one embodiment the oncolytic virus or formulation herein is administered in combination with another therapy.

"In combination" as employed herein is intended to encompass where the oncolytic virus is administered before, concurrently and/or post cancer treatment or therapy. However, generally the treatment regimens for the combination therapy will generally overlap.

A "combination therapy" as employed herein refers to the two drug products together, for example as a kit, or co-formulated, in particular for use in the treatment of cancer.

Cancer therapy includes surgery, radiation therapy, targeted therapy and/or chemotherapy.

Cancer treatment as employed herein refers to treatment with a therapeutic compound or biological agent, for example an antibody intended to treat the cancer and/or maintenance therapy thereof.

In one embodiment the cancer treatment is selected from any other anti-cancer therapy including a chemotherapeutic agent; a targeted anticancer agent, such as an antibody drug conjugate; radiotherapy, radio-isotope therapy or any combination thereof.

In one embodiment the virus of the present disclosure such as an oncolytic adenovirus may be used as a pre-treatment to a therapy, such as a surgery (neoadjuvant therapy), for example to shrink the tumour, for example to treat metastasis and/or prevent metastasis or further metastasis. The oncolytic adenovirus may be used after the therapy, such as a surgery (adjuvant therapy), for example to keep cancer in remission, to treat metastasis and/or prevent metastasis or further metastasis.

In one embodiment a virus or formulation of the present disclosure is employed in maintenance therapy.

Concurrently as employed herein is the administration of the additional cancer treatment at the same time or approximately the same time as the oncolytic adenovirus formulation. The treatment may be contained within the same formulation or administered as a separate formulation.

In one embodiment the virus is administered in combination with the administration of a chemotherapeutic agent.

Chemotherapeutic agent as employed herein is intended to refer to specific antineoplastic chemical agents or drugs that are selectively destructive to malignant cells and tissues. For example, alkylating agents, antimetabolites, anthracyclines, plant alkaloids, topoisomerase inhibitors, and other antitumour agents. Examples of specific chemotherapeutic agents include doxorubicin, 5-fluorouracil (5-FU), paclitaxel, capecitabine, irinotecan, and platins such as cisplatin and oxaliplatin. The dose may be chosen by the practitioner based on the nature of the cancer being treated.

In one embodiment the therapeutic agent is ganciclovir, which may assist in controlling immune responses and/or tumour vascularisation.

In one embodiment one or more therapies employed in the method herein are metronomic, that is a continuous or frequent treatment with low doses of anticancer drugs, often given concomitant with other methods of therapy.

Subgroup B oncolytic adenoviruses, in particular Ad11 and those derived therefrom such as EnAd may be particularly synergistic with chemotherapeutics because they seem to have a mechanism of action that is largely independent of apoptosis, killing cancer cells by a predominantly necrolytic mechanism. Moreover, the immunosuppression that occurs during chemotherapy may allow the oncolytic virus to function with greater efficiency.

Therapeutic dose as employed herein refers to the amount of virus, such as oncolytic adenovirus that is suitable for achieving the intended therapeutic effect when employed in a suitable treatment regimen, for example ameliorates symptoms or conditions of a disease, in particular without eliciting dose limiting side effects. A dose may be considered a therapeutic dose in the treatment of cancer or metastases when the number of viral particles may be sufficient to result in the following: tumour or metastatic growth is slowed or stopped, or the tumour or metastasis is found to shrink in size, and/or the life span of the patient is extended. Suitable therapeutic doses are generally a balance between therapeutic effect and tolerable toxicity, for example where the side-effect and toxicity are tolerable given the benefit achieved by the therapy.

In one embodiment there is provided systemically administering multiple doses of a parenteral formulation of an oncolytic adenovirus according to the present disclosure in a single treatment cycle, for example wherein the total dose given in each administration is in the range of $1\times10^{10}$ to $1\times10^{14}$ viral particles per dose.

In one embodiment one or more doses (for example each dose) of virus or composition comprising the same is administered such that the rate of viral particle delivery is in the range of $2\times10^{10}$ particles per minute to $2\times10^{12}$ particles per minute.

In one embodiment a virus or therapeutic construct according to the present disclosure (including a formulation comprising same) is administered weekly, for example one week 1 the dose is administered on day 1, 3, 5, followed by one dose each subsequent week.

In one embodiment a virus or therapeutic construct according to the present disclosure (including a formulation comprising same) is administered bi-weekly or tri-weekly, for example is administered in week 1 one on days 1, 3 and 5, and on week 2 or 3 is also administered on days 1, 3 and 5 thereof. This dosing regimen may be repeated as many times as appropriate.

In one embodiment a virus or therapeutic construct according to the present disclosure (including a formulation comprising same) is administered monthly, for example in a treatment cycle or as maintenance therapy.

In one embodiment the viruses and constructs of the present disclosure are prepared by recombinant techniques. The skilled person will appreciate that the armed adenovirus genome can be manufactured by other technical means, including entirely synthesising the genome or a plasmid comprising part of all of the genome. The skilled person will appreciate that in the event of synthesising the genome the region of insertion may not comprise the restriction site nucleotides as the latter are artefacts following insertion of genes using cloning methods.

In one embodiment the armed adenovirus genome is entirely synthetically manufactured.

The disclosure herein further extends to an adenovirus of formula (I) or a sub-formula thereof, obtained or obtainable from inserting a transgene or transgene cassette.

"Is" as employed herein means comprising.

In the context of this specification "comprising" is to be interpreted as "including".

Embodiments of the invention comprising certain features/elements are also intended to extend to alternative embodiments "consisting" or "consisting essentially" of the relevant elements/features.

Where technically appropriate, embodiments of the invention may be combined. Technical references such as patents and applications are incorporated herein by reference.

Any embodiments specifically and explicitly recited herein may form the basis of a disclaimer either alone or in combination with one or more further embodiments.

Headings herein are employed to divide the document into sections and are not intended to be used to construe the meaning of the disclosure provided herein.

The present disclosure also extents to any virus sequence or cassette sequence specifically disclosure herein, compositions comprising said viruses, use of the said cassettes to generate viruses, and use of viruses according to the disclosure in therapy, in particular cancer therapy.

The present application claims priority for GB1708779.2 and GB1708778.4 both filed 1 Jun. 2017. The disclosure of each is incorporated herein by reference, in particular incorporated are the amino acid and polynucleotide sequences disclosed therein. The priority documents may be employed as basis for a correction to the present specification.

The present invention is further described by way of illustration only in the following examples.

EXAMPLES

Example 1: Production of EnAd Viruses Expressing Anti-CD40 Monoclonal Antibodies (NG-350)

The first enadenotucirev virus genome generated encoding an anti-CD40 monoclonal antibody was designated NG-350 (SEQ ID NO. 13).

To produce the NG-350 genome a plasmid, pNG-350, was generated by direct insertion of a cassette encoding; a 5' short splice acceptor sequence (CAGG, SEQ ID NO.2); a heavy chain leader sequence (SEQ ID NO. 3), the anti-CD40 VH chain (SEQ ID NO. 4), antibody heavy chain constant region (SEQ ID NO. 5), a P2A high efficiency self-cleavable peptide (SEQ ID NO. 6), a light chain leader sequence (SEQ ID NO. 7), the anti-CD40 VL chain (SEQ ID NO. 8), an antibody light chain constant region (SEQ ID NO. 9) and a SV40 poly(A) tail (SEQ ID NO.10), into the plasmid pEnAd2.4. A schematic of the transgene cassette (SEQ ID NO. 11) is shown in FIG. 1.

Virus Production and Characterisation

The plasmid pNG-350 was linearised by restriction digest with the enzyme AscI to produce the virus genome NG-350 (SEQ ID NO. 13). The virus NG-350 was amplified and purified according to methods given below.

Digested DNA was purified by phenol/chloroform extraction and precipitated for 16 hrs, −20° C. in 300 μl>95% molecular biology grade ethanol and 10 μl 3M Sodium Acetate. The precipitated DNA was pelleted by centrifuging at 14000 rpm, 5 mins and was washed in 500 μl 70% ethanol, before centrifuging again, 14000 rpm, 5 mins. The clean DNA pellet was air dried, resuspended in 500 μl OptiMEM containing 150 pllipofectamine transfection reagent and incubated for 30 mins, RT. The transfection mixture was then added drop wise to a T-25 flask containing 293 cells grown to 70% confluency. After incubation of the cells with the transfection mix for 2 hrs at 37° C., 5% $CO_2$ 4 mls of cell media (DMEM high glucose with glutamine supplemented with 2% FBS) was added to the cells and the flasks was incubated 37° C., 5% $CO_2$.

The transfected 293 cells were monitored every 24 hrs and were supplemented with additional media every 48-72 hrs. The production of virus was monitored by observation of a significant cytopathic effect (CPE) in the cell monolayer. Once extensive CPE was observed the virus was harvested from 293 cells by three freeze-thaw cycles. The harvested viruses were used to re-infect 293 cells in order to amplify the virus stocks. Viable virus production during amplification was confirmed by observation of significant CPE in the cell monolayer. Once CPE was observed the virus was harvested from 293 cells by three freeze-thaw cycles. The amplified stock was used for further amplification before the virus was purified by double caesium chloride banding to produce a NG-350 virus stock.

Example 2: NG-350 Virus Activity and Anti-CD40 Antibody Production

NG-350 virus activity in terms of particle yield and secreted anti-CD40 antibody production was assessed in a HEK293 suspension culture cell line. HEK293 cells were seeded in shake flasks at a density of $1 \times 10^6$ vp/mL and infected with 50 NG-350 virus particles per cell. (ppc). HEK293 cells were also infected with the NG-350 parental virus, enadenotucirev (EnAd) as a control (50 ppc). At 48 and 72 hrs post-infection cellular supernatants were collected by centrifuging for 5 mins, 1200 rpm. Samples of the clarified supernatant were used for assessing virus particle concentration by HPLC or anti-CD40 antibody concentration by human IgG2 ELISA.

HPLC Analysis

Virus particle concentration in the supernatants was quantified by High Performance Liquid Chromatography (HPLC) using a Resource Q (anion exchange) column. Virus elution was detected at 260 nm and virus concentration was determined by integrating the 260 nm signal peak and calculating the concentration from an enadenotucirev standard curve. Comparison of virus production from NG-350 and enadenotucirev cells showed that NG-350 virus activity in terms of total particle production and virus particle production in the cell supernatant was significantly lower than enadenotucirev (FIGS. 2A and 2B).

IgG2 ELISA

The clarified supernatants were diluted 1 in 2 into PBS 10% BSA. A standard curve and negative control samples were prepared according to the manufacturer's protocol (IgG2 Human SimpleStep ELISA kit, ab202402, Abcam). Samples and standards were added to the ELISA plates and the assay performed according to the manufacturer's protocol. The absorbance at 450 nm in each well of the plate was measured using a plate reader (BioTek) and the concentrations of secreted IgG2 anti-CD40 antibody were determined by interpolating from the standard curve (FIG. 2C). Anti-CD40 was produced and secreted from NG-350 but not enadenotucirev infected cells.

Taken together these data indicated that although NG-350 was able to produce anti-CD40 antibody the virus activity of this modified virus was significantly compromised. Further characterisation of the NG-350 virus particle was therefore carried out (Example 3).

Example 3: NG-350 Virus Identity Testing and Genome Analysis Restriction Enzyme Analysis The identity of the NG-350 virus stock material was initially investigated by analysing genome identity via restriction enzyme analysis. NG-350 or enadenotucirev virus particles ($3.5 \times 10^{11}$ vp) were diluted in PBS to a final volume of 200 µL. DNA was extracted from the virus using the QIAgen Minelute virus spin kit according to the manufacturer's protocol. Control DNA was prepared for the assay by linearizing the pNG-350 plasmid with the enzyme AscI for 2 hrs, 37° C. and then purifying the DNA by agarose gel electrophoresis and gel extraction with a QiaQuick Gel extraction Kit (Qiagen). Purified control or NG-350 DNA were restriction digested using a combination of restriction enzymes, EcoRv/NheI (FIG. 3A) or individual restriction enzymes, NcoI or FspI (FIG. 3B). Digested DNA was separated by agarose gel electrophoresis and visualised using a UV transilluminator. Digestion with FspI or EcoRV/NheI showed an additional band in the NG-350 virus genome material, that was not predicted (FIG. 3, red arrows).

PCR Analysis

The genome identity was further assessed by PCR analysis of the virus genome using 8 different primer probe sets, shown in Table 1:

sets 5 and 6 were used. These data indicated that two virus species were present in the NG-350 virus stock, one containing the full length anti-CD40 transgene cassette and one containing a truncated version of the cassette. This truncation was confirmed by sequencing of the contaminant PCR product.

Transgene Cassette Optimisation

An explanation for the truncation occurring during virus amplification was an unexpected instability in the transgene cassette resulting in recombination between the VH region and the SV40 polyA and therefore loss of most of the antibody coding region. The transgene cassette DNA sequence therefore needed to be modified to overcome this issue. Therefore, the DNA sequence was changed to reduce homology with other cassette and virus sequences and to remove minor direct and inverted repeats (carried out by Oxford Genetics, UK). The optimised cassette sequence was used to generate a new plasmid pNG-350A according to Example 4.

Example 4: Production of EnAd Viruses Expressing an Anti-CD40 Monoclonal Antibody (NG-350A)

To produce the NG-350A genome a plasmid, pNG-350A, was generated by direct insertion of a cassette encoding; a 5' short splice acceptor sequence (CAGG, SEQ ID NO.2); a heavy chain leader sequence (SEQ ID NO. 3), the anti-CD40 VH chain (SEQ ID NO. 4), antibody constant heavy chain (SEQ ID NO. 5), a P2A high efficiency self-cleavable peptide (SEQ ID NO. 6), a light chain leader sequence (SEQ

| Primer Set | Forward Primer | Reverse Primer |
|---|---|---|
| D | ACGGAACTTGTTACTACACAGC | CTTTCACAGTCCAACTGCTGC |
| 1 | AGCCGGAGAACAACTACAAGAC | CTTTCACAGTCCAACTGCTGC |
| 2 | CATCCAGATGACCCAGTCTCC | GGACAAACCACAACTAGAATGCAG |
| 3 | CATCCAGATGACCCAGTCTCC | CTTTCACAGTCCAACTGCTGC |
| 4 | AGCCGGAGAACAACTACAAGAC | GGACAAACCACAACTAGAATGCAG |
| 5 | CCTCAGTGAAGGTCTCCTGC | CTTTCACAGTCCAACTGCTGC |
| 6 | CCTCAGTGAAGGTCTCCTGC | GGACAAACCACAACTAGAATGCAG |

These PCRs were designed to determine whether more than one genome species was present in the NG-350 viral stock and if this species contained the anti-CD40 antibody transgene cassette. NG-350 or enadenotucirev virus particles ($2 \times 10^{10}$ vp) were diluted in PBS to a final volume of 200 µL. DNA was extracted from the virus using the QIAgen Minelute virus spin kit according to the manufacturer's protocol. Control DNA was prepared as for the restriction enzyme analysis. PCR reactions were set up using 1 µL DNA (100 ng/µL) in a 50 µL reaction volume containing forward and reverse primer (2 µM) and Phusion high fidelity master mix (NEB). PCR products were separated by agarose gel electrophoresis and visualised using a UV transilluminator (FIGS. 5A and 5B). Analysis with Primer set D revealed the expected band size of 2920 bp in the positive control DNA and NG-350 test sample. However, the NG-350 test sample additionally contained a second PCR product of ~800 bp, which was not seen with the pNG-350-PSI-01 plasmid DNA used to generate the NG-350 virus. Analysis with Primer sets 1-6 also showed additional contaminant bands when primer ID NO. 7), the anti-CD40 VL chain (SEQ ID NO. 8), an antibody constant light chain (SEQ ID NO. 9) and a SV40 poly(A) tail (SEQ ID NO.10), into the plasmid pEnAd2.4. The amino acid sequence of the NG-350A encoded anti-CD40 antibody were identical to those encoded in the NG-350 virus and the cassette structure was the same (FIG. 1). However, the nucleic acid sequence of the transgene cassette was modified and significantly different to that of NG-350 (SEQ ID NO.11).

Virus Production and Characterisation

The plasmid pNG-350A was linearised by restriction digest with the enzyme AscI to produce the virus genome NG-350A (SEQ ID NO. 1). The virus NG-350A was amplified and purified according to methods described in Example 1.

Example 5: NG-350A Virus Identity Testing by PCR

NG-350A genome identity was confirmed by PCR analysis using 2 primer probe sets (Table 2; D and K), which generate products spanning the transgene cassette. NG-350A DNA and control DNA was prepared according to the methods detailed in Example 3. PCR analysis was carried out using Primer Sets D and K according to the methods detailed in Example 3. Visualisation of the PCR products showed single products of the predicted size (FIG. 6). No contaminating products were detected with either primer set.

TABLE 2

Identity PCR Primer Sets

| Primer Set | Fwd Primer | Rev Primer |
|---|---|---|
| D | ACGGAACTTGTTACTACACAGC | CTTTCACAGTCCAACTGCTGC |
| K | AGCCGGAGAACAACTACAAGAC | CTTTCACAGTCCAACTGCTGC |

Example 6: Replication and Oncolytic Activity of the NG-350A Virus in Colon Carcinoma Cells Virus Oncolytic Potency HT-29 colon carcinoma cells were seeded in 96 well plates at a cell density of 2.5e4 cells/well. Plates were incubated for 4 hrs, 37° C., 5% $CO_2$, before cells were either infected with EnAd or NG-350A virus particles at an infection density range of 100-0.39 particles per cell (ppc). HT-29 cell viability was assessed using Cell Titre 96 MTS Reagent (Promega: G3581) 72 hrs post infection. Quantification of the % cell survival at each infection density demonstrated that similar to EnAd, NG-350A shows strong oncolytic activity against HT-29 cells (FIG. 7A).

Virus Replication

Lung carcinoma cells (A549) or colon carcinoma cells (HCT-116) were infected for 24, 48, 72 or 96 hrs with 100 ppc NG-350A or the NG-350A parental virus, enadenotucirev, or were left uninfected. Colon carcinoma cells (HT-29) or bladder carcinoma cells (HTB-5, HT-1197 and HT-1376) were infected for 24, 48, 72, 144 and 168 hrs with 100 ppc NG-350A or enadenotucirev or were left uninfected. At each time point, cell supernatants were collected and clarified by centrifuging for 5 mins, 1200 rpm. DNA was extracted from 10 μL (HT-29, A549 or HCT-116) or 50 μL (HTB-5, HT-1197 and HT-1376) of supernatant using the DNeasy Blood and Tissue Kit (Qiagen) according to the manufacturer's protocol. A standard curve using EnAd virus particles (2.5e10-2.5e5vp) was also prepared and extracted using the DNeasy Blood and Tissue Kit (Qiagen). Each extracted sample or standard was analysed by qPCR using an enadenotucirev E3 gene specific primer-probe set.

Figure 8:
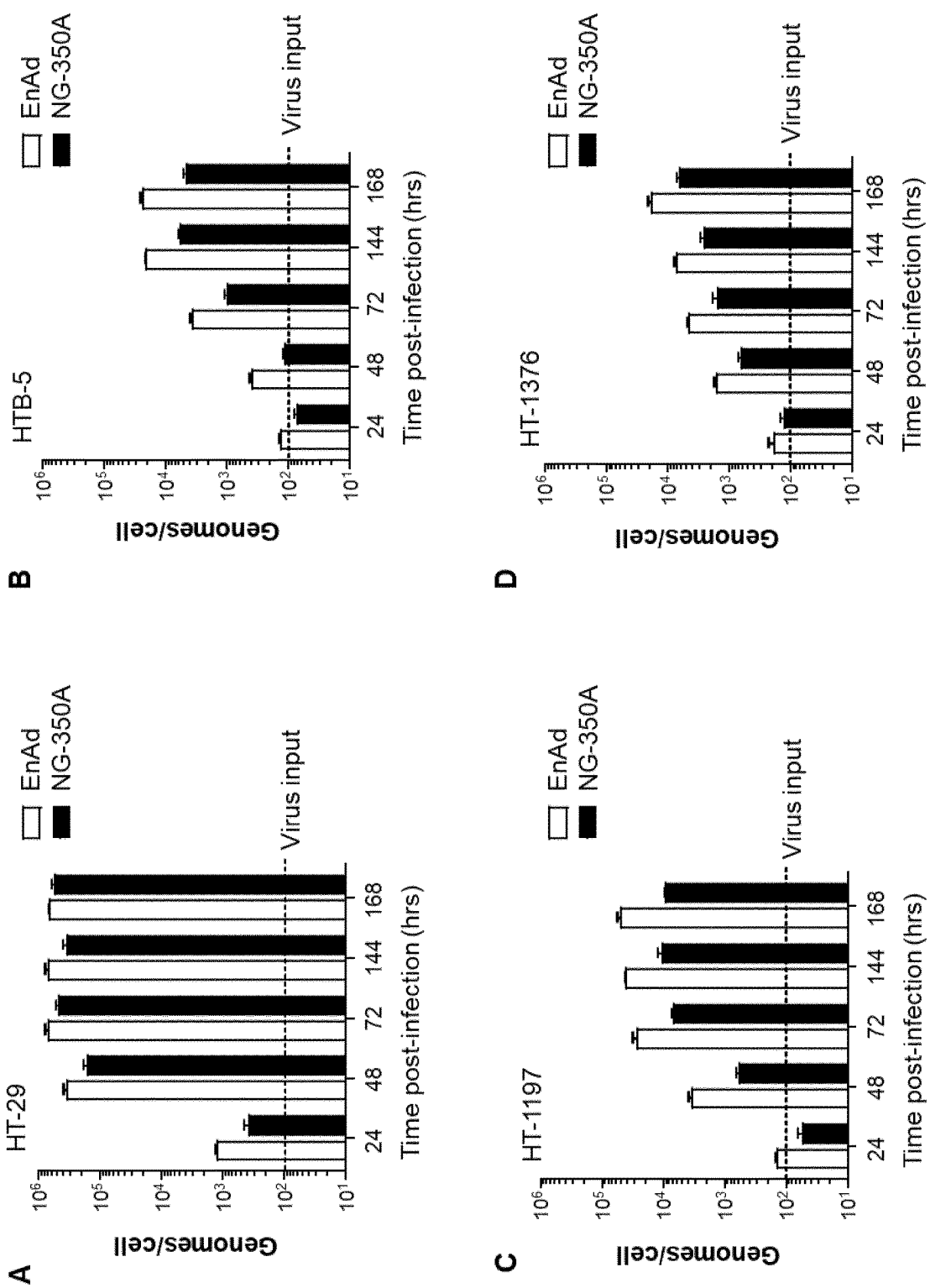

Quantification of the number of detected virus genomes per cell demonstrated that NG-350A and enadenotucirev kinetics of virus replication was comparable in all cell lines tested and at all time points analysed (FIG. 7 and FIG. 8). No virus genomes could be detected in uninfected cells (data not shown).

Figure 9:
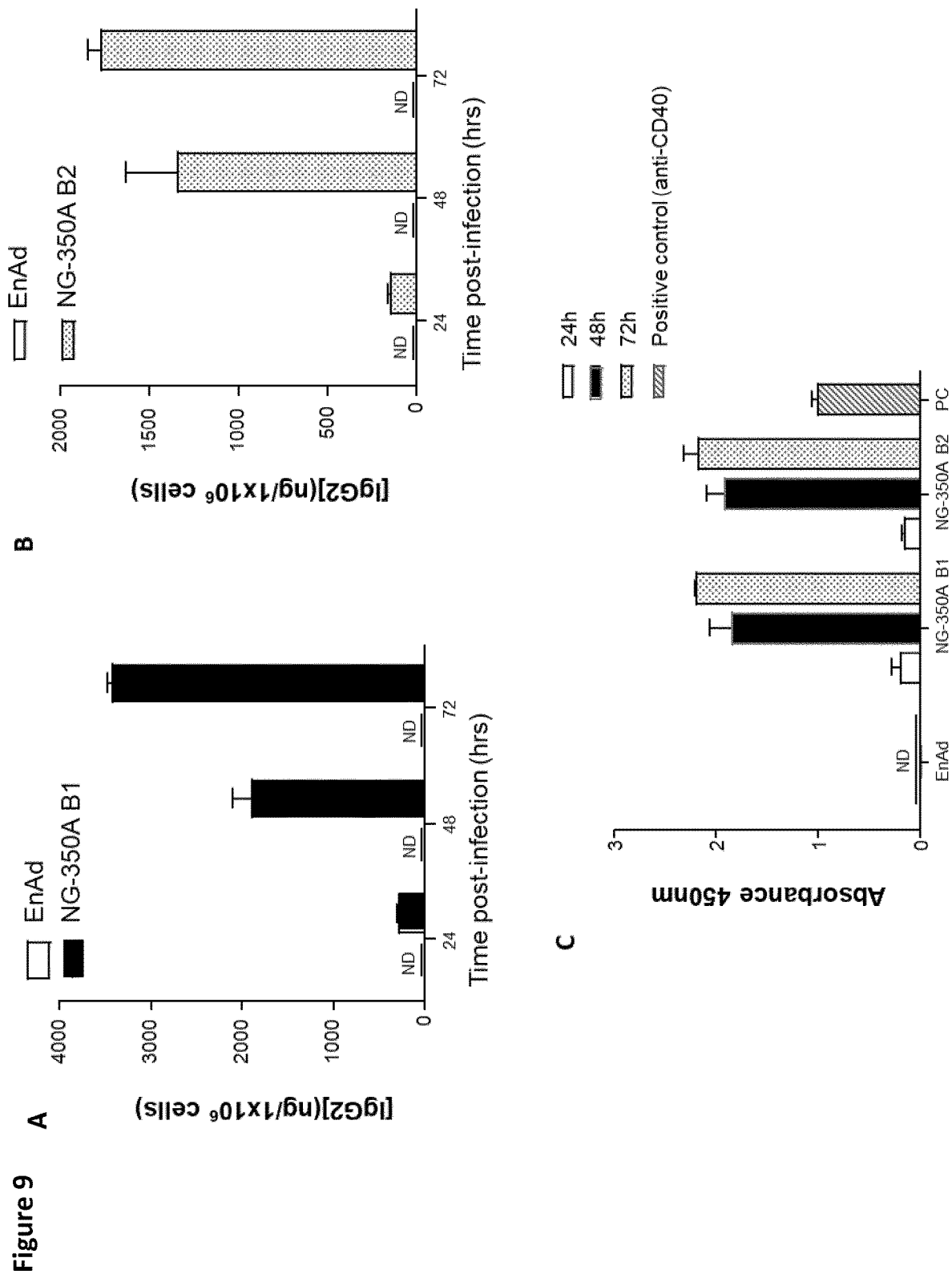
FIGS. 9A & B show absorbance at 450 nm in each well of the plate measured using a plate reader (BioTek) and the concentrations of secreted IgG2 anti-CD40 antibody.
FIG. 9C shows absorbance at 450 nm for EnAd, NG-350A and positive controls (FIG. 4C) and specific binding to CD40 by the secreted anti-CD40 antibody present in the supernatant of NG-350A infected cells.

Example 7: Anti-CD40 Antibody Expression in NG-350A Infected Colon Carcinoma Cell Lines IgG2 ELISA A549 cells either infected for 24, 48 or 72 hrs with 100 ppc EnAd, two different batches of NG-350A (NG-350A B1 or NG-350A B2) or left uninfected were used for analysis of anti-CD40 antibody expression by IgG2 ELISA (IgG2 Human SimpleStep ELISA kit, ab202402, Abcam). Culture supernatants were removed from each well and centrifuged for 5 mins, 1200 rpm to remove cell debris. The clarified supernatants were diluted 1 in 2 into PBS 10% BSA. A standard curve and negative control samples were prepared according to the manufacturer's protocol. Samples and standards were added to the ELISA plates and the assay performed according to the manufacturer's protocol. The absorbance at 450 nm in each well of the plate was measured using a plate reader (BioTek) and the concentrations of secreted IgG2 anti-CD40 antibody were determined by interpolating form the standard curve (FIGS. 9A & 9B).

CD40 Binding ELISA

A549 cells either infected for 24, 48 or 72 hrs with 100 ppc EnAd, two different batches of NG-350A (NG-350A B1 or NG-350A B2) or left uninfected were used for analysis of anti-CD40 antibody expression by CD40 binding ELISA.

Culture supernatants were removed from each well and centrifuged for 5 mins, 1200 rpm to remove cell debris. ELISA plates (A Nunc Immuno MaxiSorp 96 well microplate) were prepared by coating overnight at 4° C. with human CD40 (100 g/mL, R and D Systems, 1493-CD) in carbonate/bicarbonate buffer. Plates were washed between all subsequent binding steps with PBS 0.05% Tween 20. The plates were blocked for 1 hour at room temperature with PBS 5% BSA.

Clarified infection supernatants were diluted into PBS 5% BSA (1 in 2, 1 in 10 and 1 in 100). In this assay, anti-CD40 antibody (BioLegend, 334308) was used as a positive control for human CD40 binding to the ELISA plate. It was prepared in PBS 5% BSA at a concentration of 30 ng/mL. All samples were added to the CD40 coated plates and incubated for 1 hr at room temperature. The detection antibodies, HRP conjugated anti-human IgG2-Fc (Abcam, ab97225) for virus supernatants or anti-mouse IgG Abs (HRP) (Abcam, ab6728), for the positive control antibody were then applied for 1 hr at room temperature to all wells. HRP detection was performed with HRP substrate solution 3.3.5.5'-teramethylethylenediamine (TMB, Thermo-Fisher). 1M HCl was used for stopping the reaction and the developed colour was measured at 450 nm on a plate reader. Absorbance at 450 nm was plotted for the EnAd, NG-350A and positive controls (FIG. 9C) and demonstrated specific binding to CD40 by the secreted anti-CD40 antibody present in the supernatant of NG-350A infected cells.

Example 8: CD40 Functional Signalling Reporter Assay

A549 cells either infected for 24 or 48 hrs with 10 ppc EnAd, NG-350A or for 48 hrs with NG-165 (a virus expressing a control antibody [anti-VEGF]) or left uninfected were used for analysis of anti-CD40 antibody functional activity using CD40+ HEK-Blue reporter cells that secrete alkaline phosphatase (Invivogen) in response to activation via their membrane expressed CD40 molecules. Post infection, culture supernatants from A549 cells were removed from each well and centrifuged for 5 mins, 1500 rpm to remove cell debris.

20 μL of culture supernatants were diluted in 180 μL of culture media and applied to Hek-Blue CD40 cells for 20 hrs. CD40 μL at a concentration of 10 ng/mL was prepared in culture media as a positive control. The supernatants were then collected from the HEK-Blue CD40 cells and clarified by centrifuging. 40 μL of the clarified supernatant was assayed for alkaline phosphatase activity by incubating for 1 hr at 37 degrees with 160 μL Quanti-Blue reagent.

Absorbance at 620 nm was measured for each sample using a plate reader and demonstrated that supernatants from NG-350A but not EnAd or NG-165 infected cells triggered SEAP production from the CD40 expressing HEK-Blue reporter cells (FIG. 10).

Example 9: Selective Activity of the NG-350A Virus in Carcinoma Cell Lines

Lung carcinoma cells (A549), colon carcinoma cells (HCT-116) or lung fibroblast cells (MRC-5), which are semi-permissive to EnAd virus activity, were used to demonstrate the selectivity of NG-350A virus for cancer cells. The cell lines were infected for 72 hrs with 100 ppc NG-350A or the NG-350A parental virus, enadenotucirev or were left uninfected. At each time point culture supernatant was removed from each well and used for analysis of virus genome replication by qPCR or anti-CD40 antibody expression by ELISA. The cells remaining in the well were analysed for expression of the viral gene E3 and transgene by RT-qPCR.

Virus Replication

Cell supernatants were collected and clarified by centrifuging for 5 mins, 1200 rpm. DNA was extracted from 10 μL (A549, HCT-116) or 100 μL (MRC-5) of supernatant using the Sigma Genelute DNA extraction Kit, according to the manufacturer's protocol. A standard curve using EnAd virus particles (2.5e10-2.5e5vp) was also prepared and extracted using the Sigma Genelute Kit. Each extracted sample or standard was analysed by qPCR using an enadenotucirev E3 gene specific primer-probe set.

Quantification of the number of detected virus genomes per cell demonstrated that NG-350A and enadenotucirev virus replication was detectable at comparable levels in A549 and HCT-116 cells but expression in MRC-5 was significantly lower than in the carcinoma cell lines (FIG. 11A). No virus genomes could be detected in uninfected cells (data not shown).

IgG2 Antibody Expression

Antibody expression was in cell supernatants was assessed by IgG2 ELISA (IgG2 Human SimpleStep ELISA kit, ab202402, Abcam). Culture supernatants were removed from each well and centrifuged for 5 mins, 1200 rpm to remove cell debris. The clarified supernatants were diluted 1 in 2 into PBS 10% BSA. A-standard curve and negative control samples were prepared according to the manufacturer's protocol. Samples and standards were added to the ELISA plates and the assay performed according to the manufacturer's protocol. The absorbance at 450 nm in each well of the plate was measured using a plate reader (BioTek) and the concentrations of secreted IgG2 anti-CD40 antibody were determined by interpolating form the standard curve (FIG. 11B).

Example 10: Purification of Anti-CD40 Antibody from NG-350A Infected Cells

Suspension HEK293 cells were seeded at $1 \times 10^6$ cells/mL in Erlenmeyer flasks and infected with 100 ppc NG-350A. After 72 hrs, 5% FBS and protease inhibitor cocktail (1:2000) were added to the cells and the suspension was centrifuged for 15 minutes, 4600 rpm. The supernatant was carefully removed and filtered through a 500 kDa molecular weight cut off hollow fibre membrane to separate the NG-350A virus particles from the anti-CD40 antibody. The flow through from the filtration step, which contained the anti-CD40 antibody was passed through a second hollow fibre membrane with a 30 kDa molecular weight cutoff. The anti-CD40 antibody was purified from the retentate from the second filtration step on a protein A column using an AKTA. The purified antibody was filter sterilised and stored at −80° C. The concentration of purified antibody was determined by IgG2 ELISA using the IgG2 Human SimpleStep ELISA kit, ab202402, Abcam according to the manufacturer's protocol (FIG. 12).

Example 11: NG-350A Derived Anti-CD40 Antibody Activity and Synergy with Virus Activity in Primary Human Monocyte Derived DCs PBMCs were isolated by Ficoll-Paque gradient centrifugation from a NC24 leucocyte cone sourced from NHS Blood and Transplant unit in Oxford, UK. CD14+ monocytes were isolated using the CD14 MicroBeads kit (MiltenyiBiotec). Monocytes were then counted, centrifuged (300×g) and resuspended at $5 \times 10^5$ cells/mL in 10% RPMI culture media supplemented with GM-CSF (800 U/mL) and IL-4 (500 U/mL). 40 mL of monocyte suspension were transferred into one T175 flask.

After 72 hrs culture, monocyte derived DCs (moDCs) were seeded at a density of $1 \times 10^6$ cells per well in 24 well plates in 10% RPMI culture media. They were treated with 0.5 μg/mL of anti-CD40 antibody (purified from virus infected cells according to Example 10), EnAd (100 ppc), human CD40L or were left untreated. In parallel, moDCs were treated with both the purified anti-CD40 antibody (0.5 g/mL) and EnAd (100 ppc). The plates were then incubated for 48 hrs before supernatants and cells were harvested.

Supernatants and cells were removed from culture wells and centrifuged (300×g). The supernatant was diluted 1 in 2 with PBS 5% BSA and stored for ELISA analysis. Cell pellets were washed in 200 μL of PBS, centrifuged, then resuspended in 50 μL of PBS containing LIVE/DEAD® Fixable Near-IR (Life tech) for 15 minutes at RT. The cells were washed once in FACs buffer (1% FBS/PBS) before staining with panels of directly conjugated antibodies: anti-CD86 conjugated to BV421; anti-CD54 conjugated to AF647 and anti-HLA-DR conjugated to PeCy5. A sample of cells from each co-culture condition was also stained with relevant isotype control antibodies. All staining was carried out in FACs buffer in a total volume of 50 μL/well for 15 minutes, 4° C. Cells were then washed twice with FACs buffer (200 μL) before resuspension in 200 μL of FACs buffer and analysis by Flow cytometry (Attune).

Supernatant samples were thawed and analysed by ELISA (IL-12 Quantikine ELISA, DP400, R&D systems) by diluting in and carrying out the assay according to the manufacturer's protocol.

Treatment with anti-CD40 antibody purified from virus infected cells led to an increase in the percentage of moDCs expressing CD86, CD54 and HLA-DR activation markers and to the secretion of IL12p40 (FIG. 13 and FIG. 14). Significantly, combination treatment of moDCs with both the anti-CD40 antibody and EnAd virus resulted in a stronger moDC activation compared to treatment with anti-CD40 Ab or EnAd virus alone.

Example 12: NG-350A Derived Anti-CD40 Antibody Activity and Synergy with Virus Activity in Primary Human B Cells PBMCs were isolated by Ficoll-Paque gradient centrifugation from a NC24 leucocyte cone sourced from NHS Blood and Transplant unit in Oxford, UK. CD19+ B cells were isolated using the Pan B Cell Isolation Kit (MiltenyiBiotec). B cells were then seeded at a density of $1 \times 10^6$ cells per well in 24 well plates in 10% RPMI culture media. They were treated with increasing concentration of purified anti-CD40 Transgene Abs, human CD40L or were left untreated. The plates were then incubated for 48 hrs before supernatants and cells were harvested.

Supernatants and cells were removed from culture wells and centrifuged (300×g). The supernatant was carefully removed, diluted 1 in 2 with PBS 5% BSA and stored for ELISA analysis. Cell pellets were washed in 200 μL of PBS, centrifuged then resuspended in 50 μL of PBS containing LIVE/DEAD® Fixable Near-IR (Life tech) for 15 minutes at RT. The cells were washed once in FACs buffer before staining with panels of directly conjugated antibodies: anti-CD86 conjugated to BV421; anti-CD54 conjugated to AF647; anti-HLA-DR conjugated to PeCy5 and anti-CD80 conjugated to BV605. A sample of cells from each co-culture condition was also stained with relevant isotype control antibodies. All staining was carried out in FACs buffer in a total volume of 50 μL/well for 15 minutes, 4° C. Cells were then washed twice with FACs buffer (200 μL) before resuspension in 200 μL of FACs buffer and analysis by Flow cytometry (Attune).

Figure 16:
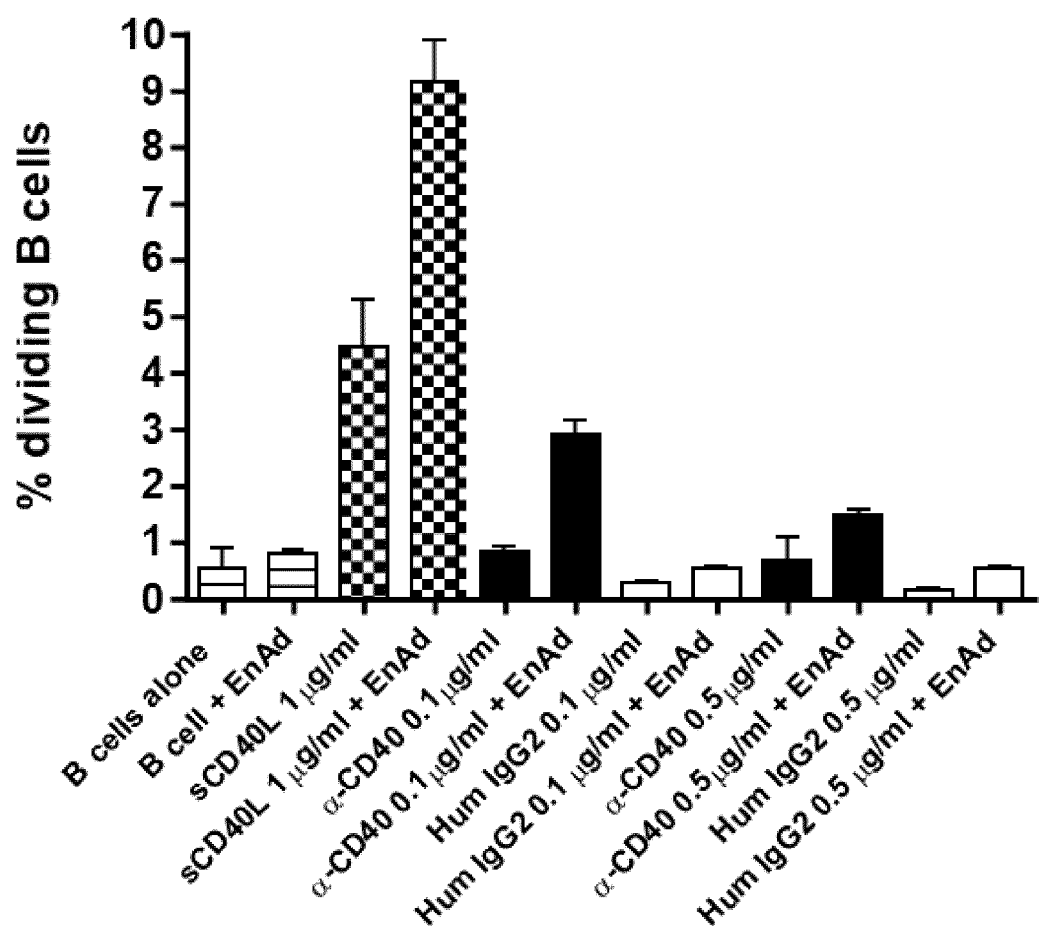
FIG. 16 shows percentage of dividing B cells after treatment with purified anti-CD40 antibody produced by NG-350A infected tumour cells and EnAd virus together compared with antibody or virus treatment alone.

Treatment of B cells with anti-CD40 antibody at all concentrations tested resulted in B cell activation in terms of an increase in the percentage of B cells expressing CD86, CD19 and CD80 and an increase in the HLA-DR MFI on CD19+ cells, compared to untreated or isotype control treated B cells (FIG. 15). Treatment with anti-CD40 antibody also resulted in B cell activation in terms of increasing the percentage of proliferating cells (FIG. 16). Significantly, combination treatment of B cells with anti-CD40 antibody and EnAd virus resulted in an enhancement in the % of proliferating B cells compared to antibody or virus treatment alone (FIG. 16).

Example 13: NG-350A Derived Anti-CD40 Antibody Activity on Primary Human Monocyte Derived DCs A549 tumor cells were seeded in T175 flasks or Hyperflasks at a density of, respectively, $10 \times 10^6$ or $50 \times 10^6$ cells per flask. After 4 hrs, cells were infected with 10 EnAd or NG-350A virus particles per cell. After 72 hrs, supernatants were harvested and virus depleted using 300 kDa cut-off size exclusion columns. Virus-depleted supernatants were subsequently enriched for antibodies using 50 kDa cut-off size exclusion columns. These virus-depleted Ab-enriched fractions were stored at −80° C. Anti-CD40 Ab titer was determined using IgG2 ELISA and functionality confirmed using the HEK Blue reporter cell assay described in Example 8.

Monocyte-derived dendritic cells (MoDCs) were prepared essentially as outlined in Example 11 for a further set of studies. PBMCs (donor 177) were isolated by Ficoll-Paque gradient centrifugation from a NC24 leucocyte cone sourced from NHS Blood and Transplant unit in Oxford, UK. CD14+ monocytes were isolated using the CD14 MicroBeads kit (MiltenyiBiotec). After 72 hrs culture with GM-CSF and IL-4, MoDCs were seeded at a density of $1.25 \times 10^5$ cells per well in 48 well plates or $2.5 \times 10^5$ cells per well in 24 well plates in 10% RPMI culture media and incubated with the virus-depleted NG-350A or EnAd culture supernatants described in paragraph above. The cells were stained for flow cytometry analysis. Supernatants were used for cytokine analysis by cytokine bead arrays (Legendplex, BioLegend).

Figure 17:
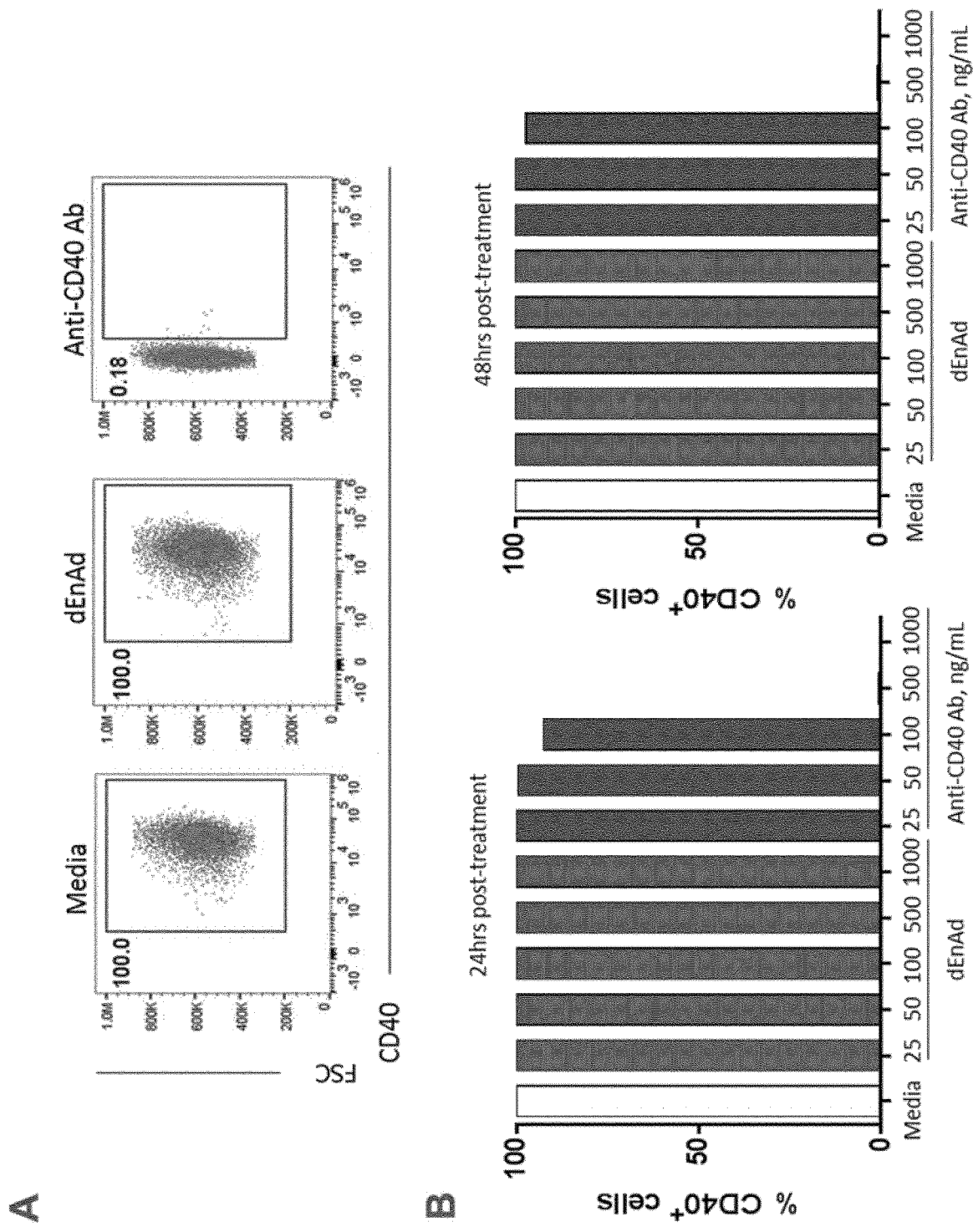
FIG. 17 shows that a virus-depleted antibody preparation produced by NG-350A infected tumor cells binds to CD40 on the surface of human MoDC's.

To demonstrate anti-CD40 Ab binding to CD40 on the surface of MoDCs, cells were treated with increasing concentrations of the virus-depleted, anti-CD40 Ab enriched supernatant from NG-350A infected cells (different dilutions used to provide different amounts of antibody) or were left untreated (media). As a control, they were also treated with virus-depleted EnAd supernatant (dEnAd), with volumes matching those of the NG-350A anti-CD40 Ab containing samples. After 24 hrs and 48 hrs, cells were harvested and stained with fluorescent labelled antibodies to CD40 before flow cytometry analysis was carried out. Cells were gated on single (FSC-H versus FSC-A) live cells (LIVE/DEAD® Fixable Aqua negative). FIG. 17A shows a representative flow cytometric result obtained 24 hrs post-treatment with 1000 ng/mL Ab, with FIG. 17B showing CD40 expression on MoDCs 24 hrs and 48 hrs post-treatment with different concentrations of virus-depleted supernatants. At the higher antibody concentrations, CD40 FACS staining is reduced or absent, reflecting blockade by binding of the anti-CD40 antibody in the NG-350A virus-depleted culture supernatants.

Figure 18:
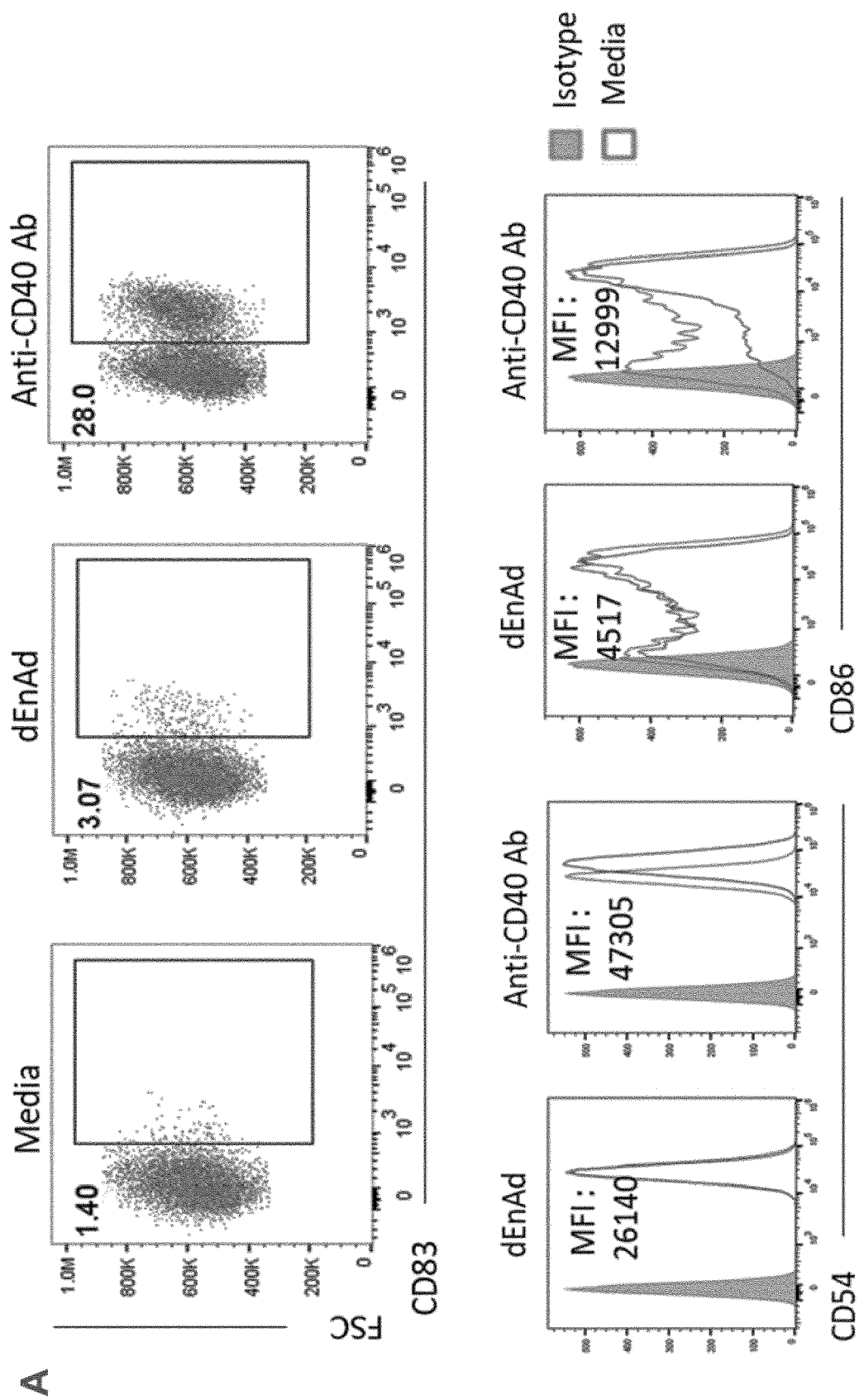
FIG. 18 shows effects of virus-depleted anti-CD40 Ab produced by NG-350A infected tumour cells on cell surface marker upregulation on human MoDCs as an example (A) and dose responses at 24 and 48 hours for 4 different MoDC donors (B-E).
Figure 18B:
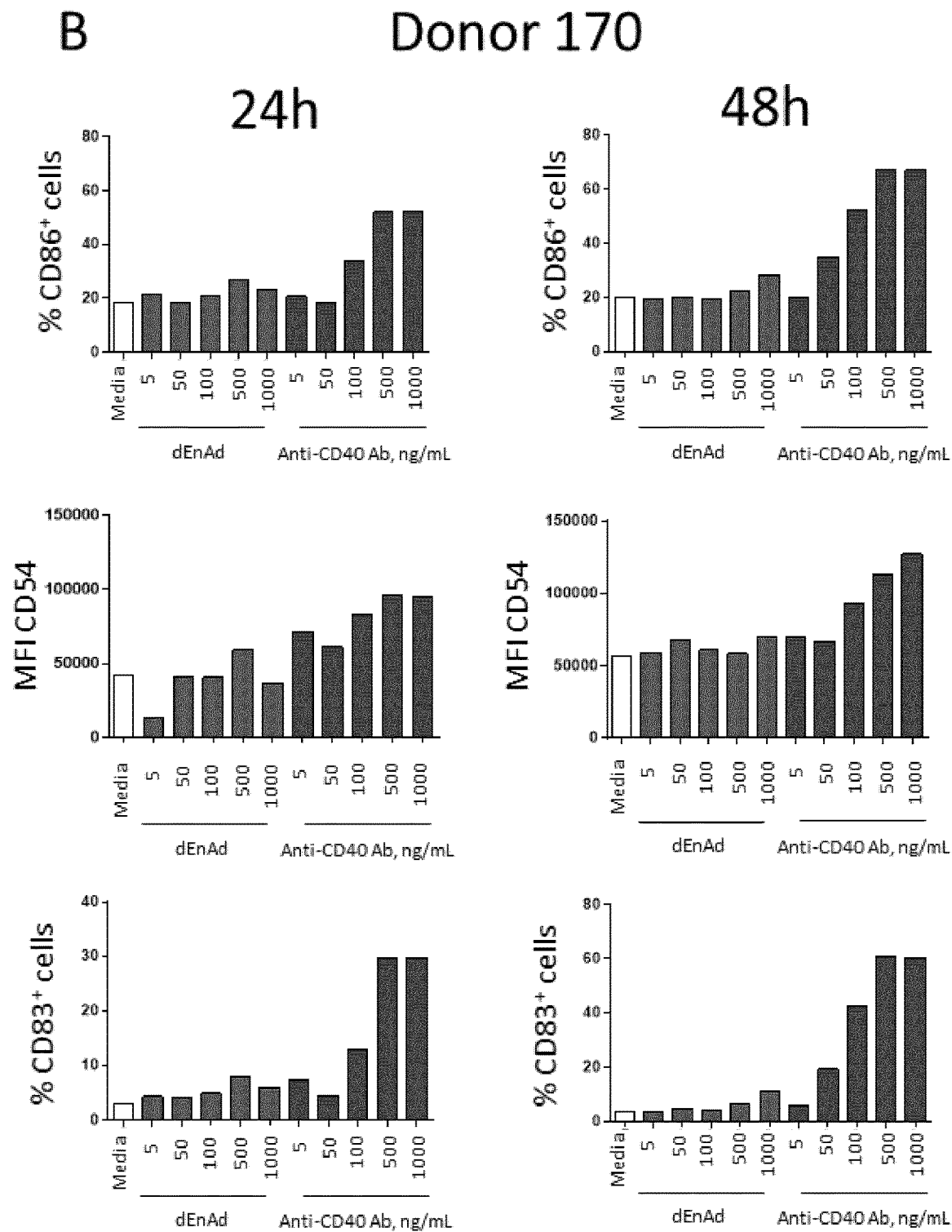
Figure 18C:
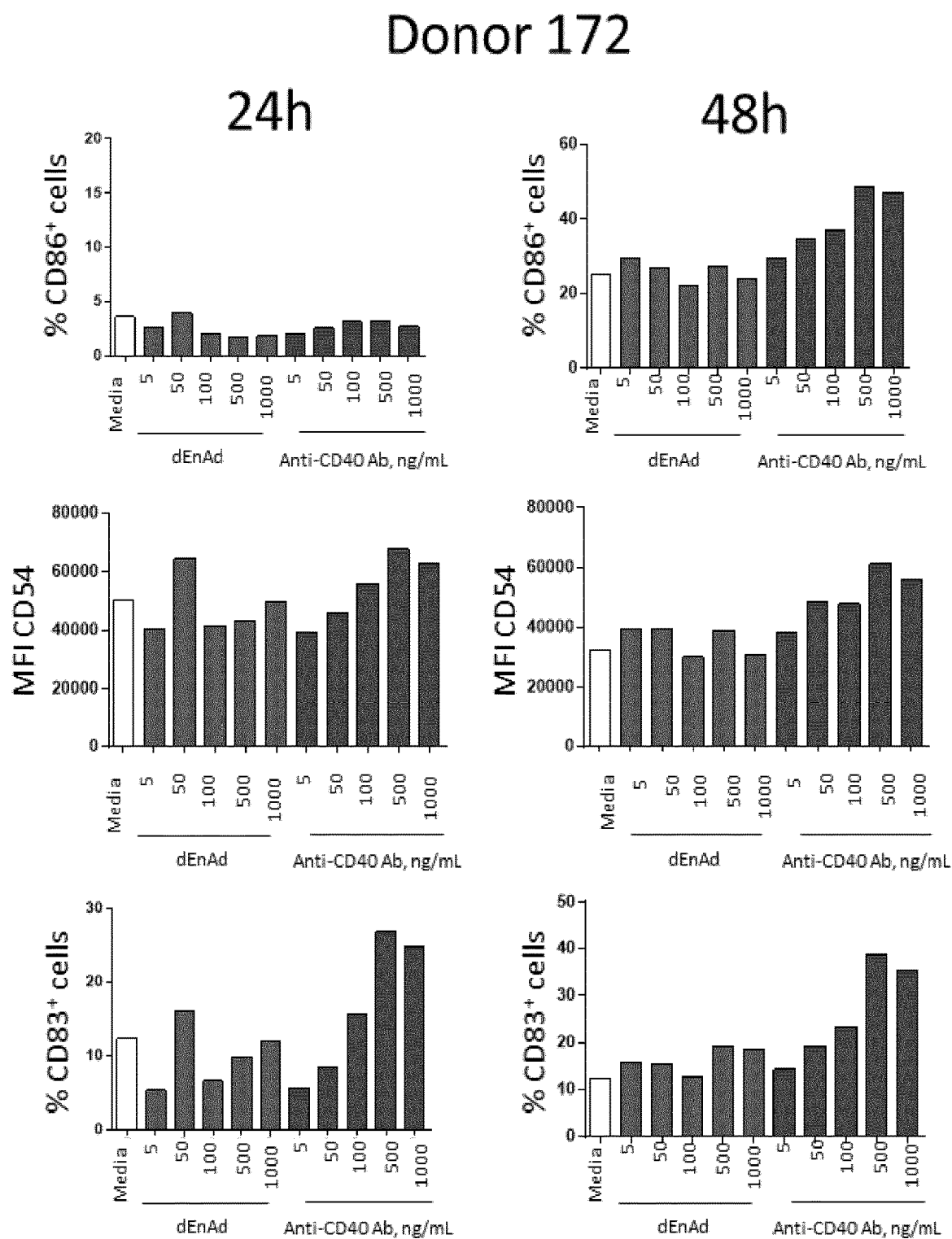
Figure 18D:
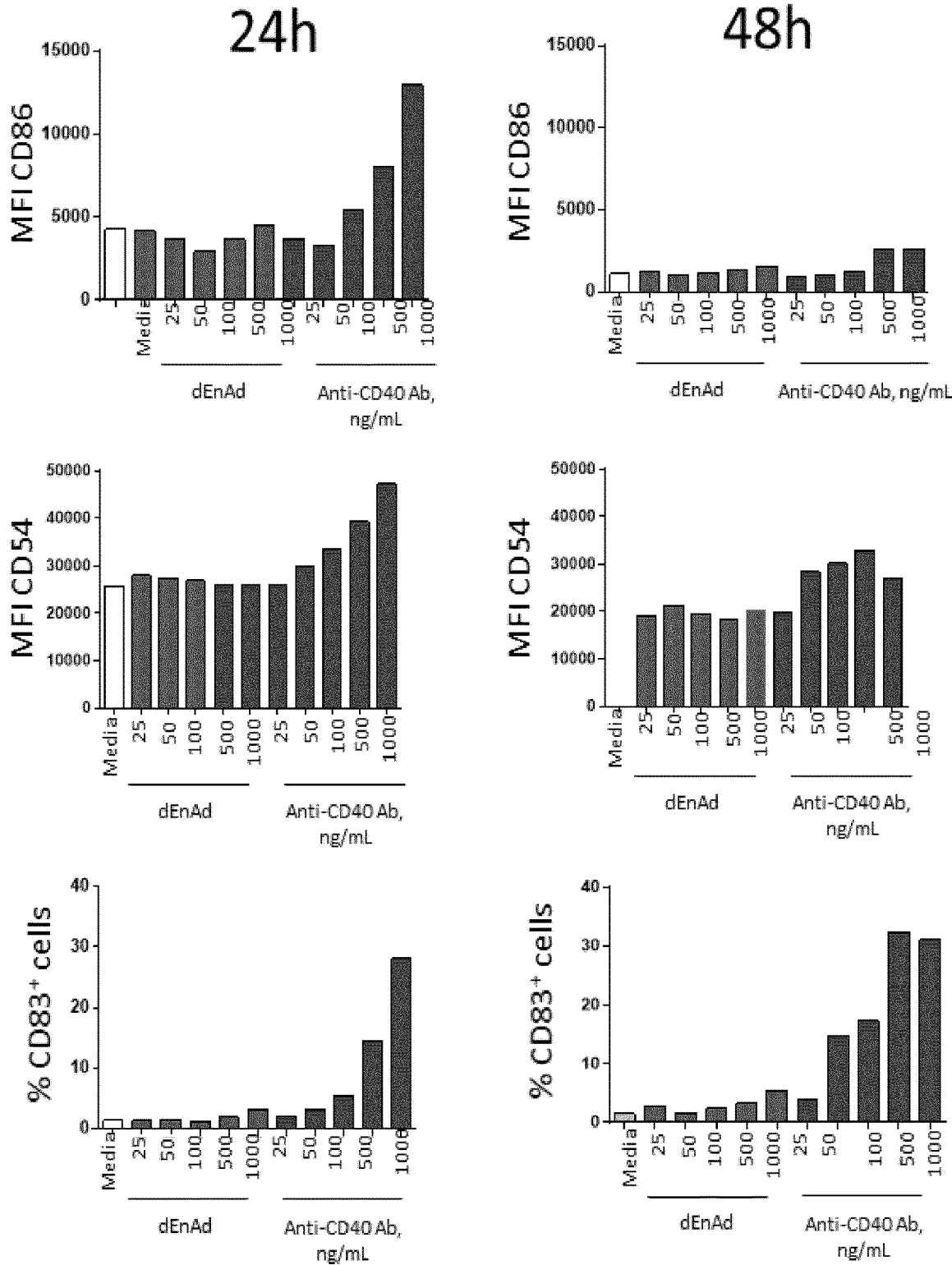
Figure 18E:
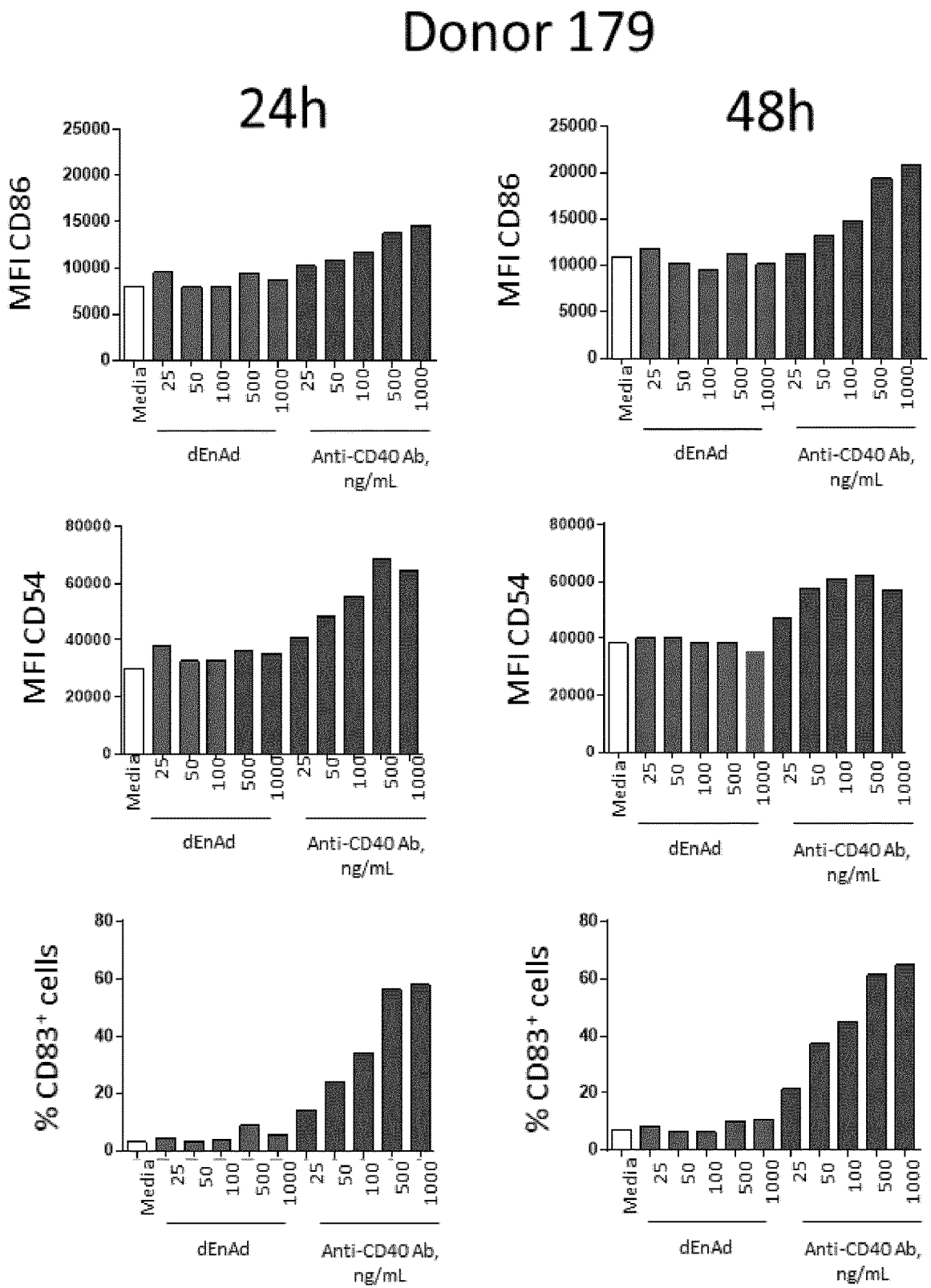
Figure 19A:
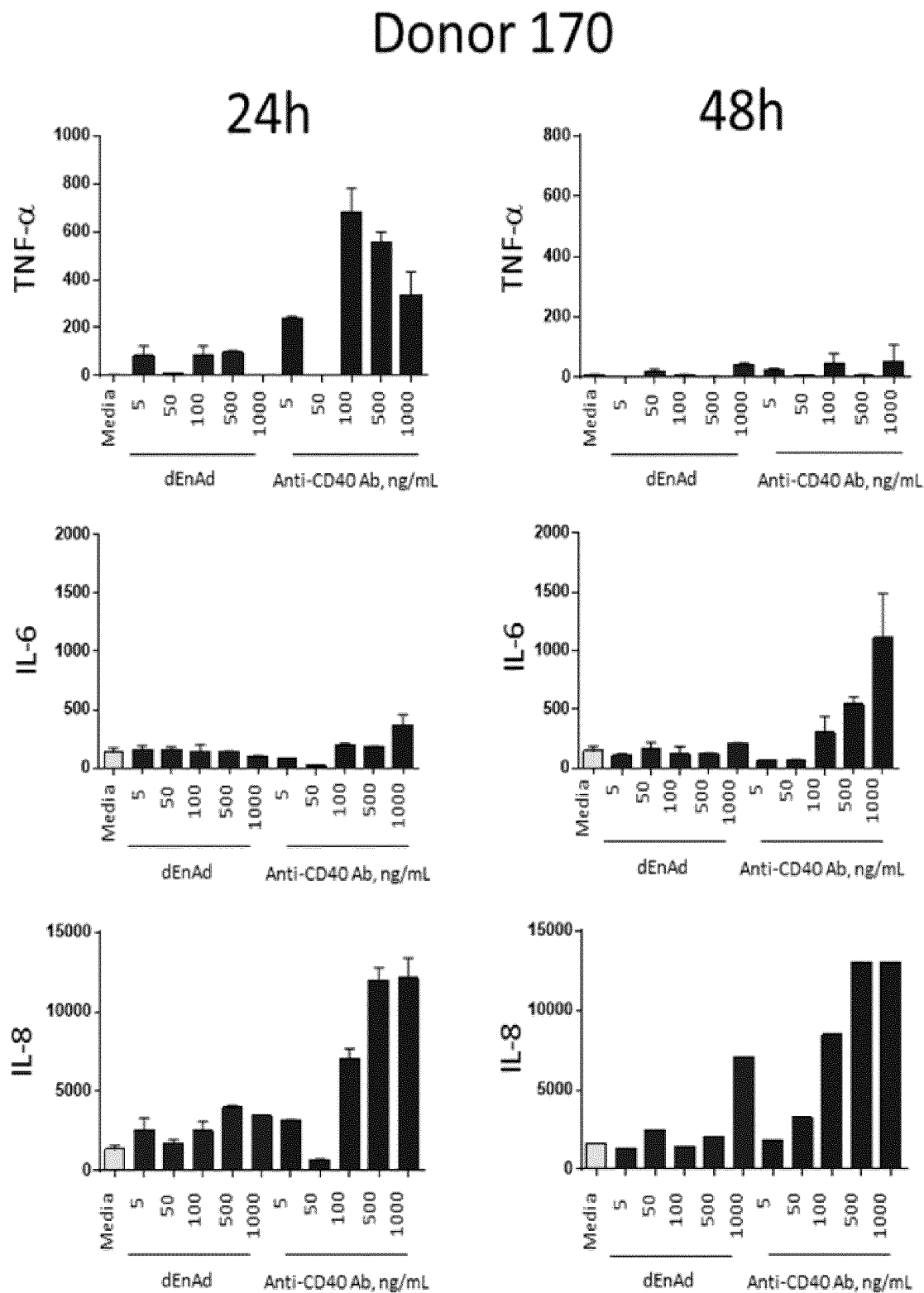
FIG. 19 shows effects of virus-depleted anti-CD40 Ab produced by NG-350A infected tumour cells on cytokine secretions by human MoDCs as dose responses at 24 and 48 hours for 4 different MoDC donors (B-D).
Figure 19B:
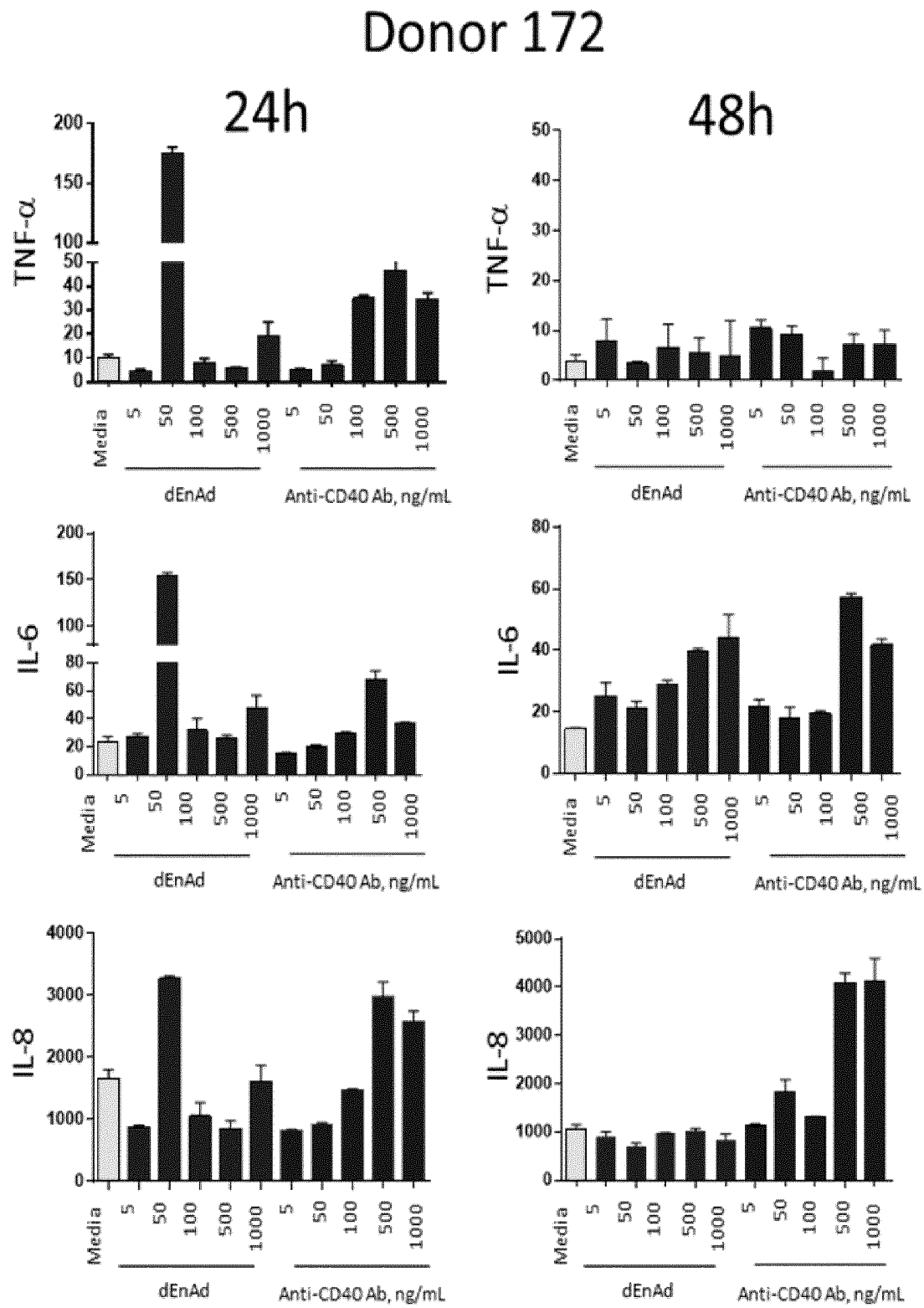
Figure 19C:
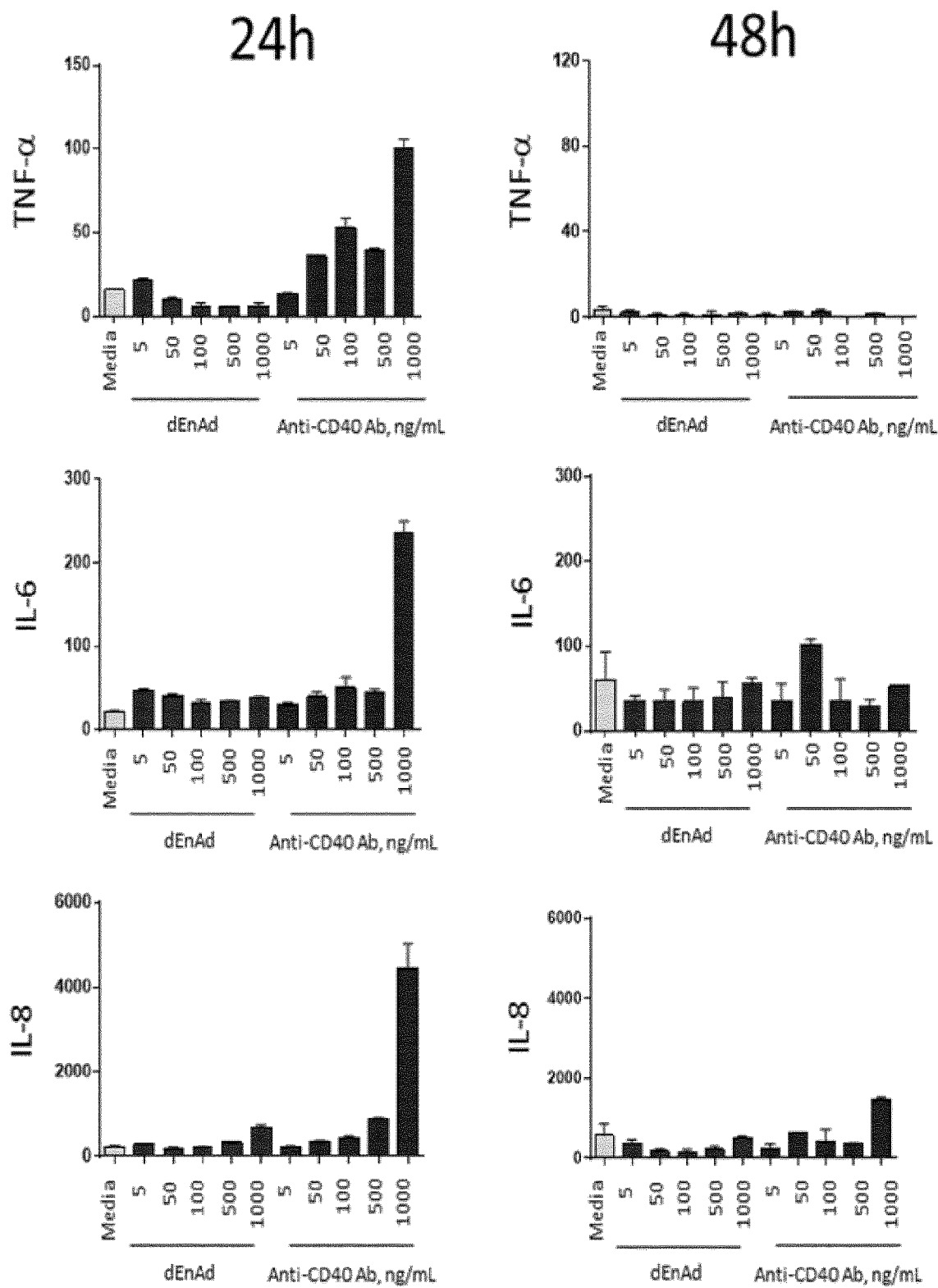
Figure 19D:
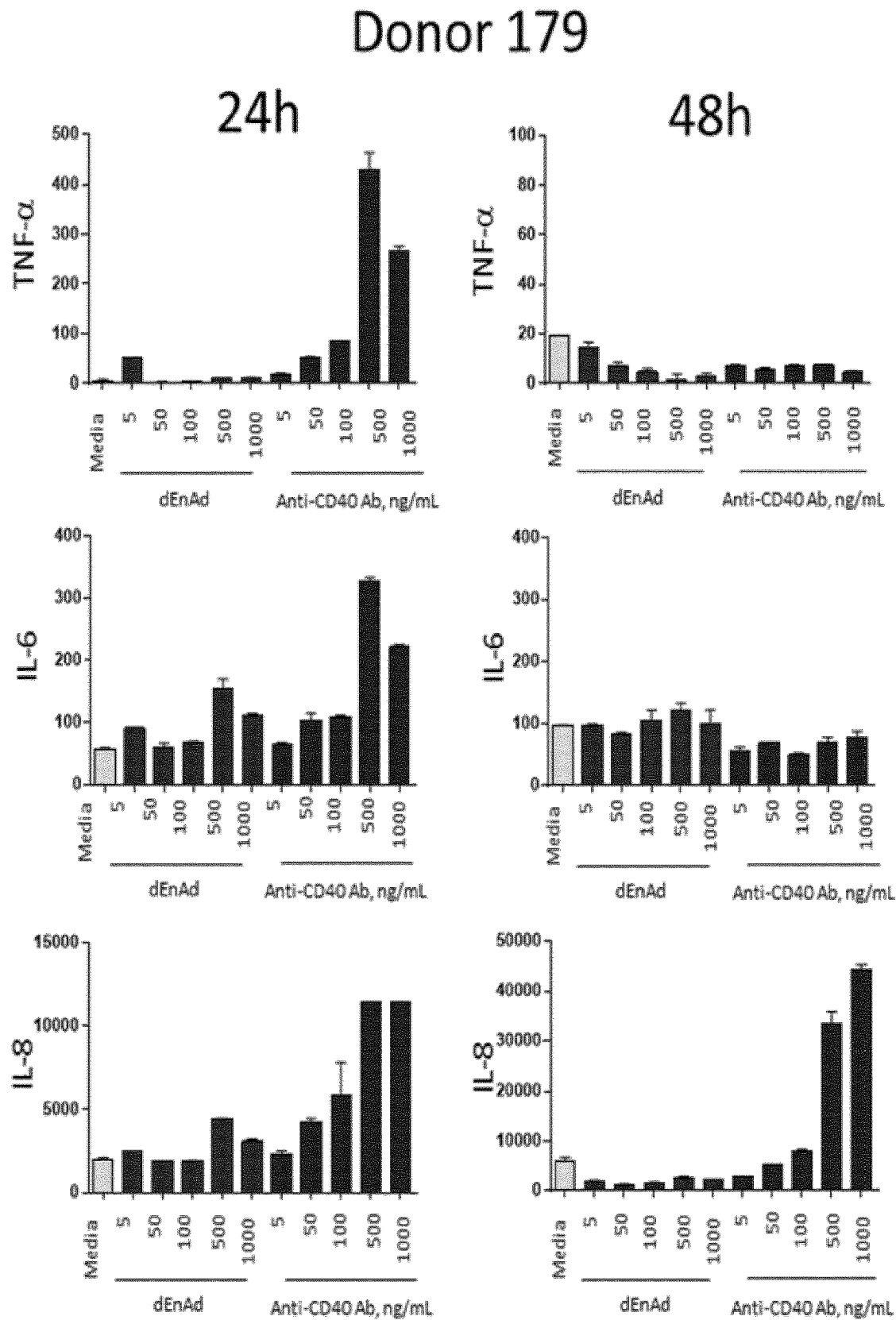

The effects of anti-CD40 Tg Ab treatment (using the virus-depleted supernatants) on cell surface marker upregulation on MoDCs was then evaluated. MoDCs were treated with increasing concentrations of purified anti-CD40 Tg Ab or were left untreated (media). They were also treated with virus-depleted EnAd supernatant (dEnAd), with volumes matching those of anti-CD40 Ab. After 24 hrs and 48 hrs, cells were harvested and stained with antibodies to CD54, CD83 and CD86 surface markers before flow cytometry analysis was carried out. Cells were gated on single (FSC-H versus FSC-A) live cells (LIVE/DEAD® Fixable Aqua negative). A representative flow cytometric result obtained 24 hrs post-treatment with 1000 ng/mL Ab is shown in FIG. 18A for MoDCs prepared with PBMCs from donor 177. FIG. 18B shows activation marker expression on MoDCs from 4 different donors 24 hrs and 48 hrs post-treatment.

Effects of anti-CD40 Tg Ab on MoDC cytokine production were then evaluated. MoDCs from four different donors were treated with increasing concentrations of anti-CD40 Ab containing virus-depleted supernatant or were left untreated (media). They were also treated with virus-depleted EnAd supernatant (dEnAd), with volumes matching those of anti-CD40 Ab. After 24 hrs and 48 hrs, supernatants were collected and analysed for inflammatory cytokine secretion using a LEGENDplex™ bead-based immunoassays (BioLegend). FIG. 19 shows selective induction of TNFα, IL-6 and IL-8.

Example 14: Activity of NG-350A Virus and Derived Anti-CD40 Antibody Containing Virus Infected Tumour Cell Supernatants on Activity of Primary Human Monocyte Derived DCs In a similar study to that described in Example 13, A549 cells were seeded in T25 flasks at a density of $4 \times 10^6$ cells. After 4 hrs, cells were infected with 10 EnAd or NG-350A virus particles per cell. After 72 hrs, supernatants were harvested and centrifuged at 1600 rpm for 5 minutes. In this study, these clarified supernatants were kept at 37° C. until use (within 1h) rather than removing the virus. Thus, supernatants contain the products of NG-350A (or EnAd control) infected tumor cells, including both virus and anti-CD40 antibody transgene product.

PBMCs were isolated by Ficoll-Paque gradient centrifugation from a NC24 leucocyte cone sourced from NHS Blood and Transplant unit in Oxford, UK. CD14$^+$ monocytes were isolated using the CD14 MicroBeads kit (MiltenyiBiotec). After 72 hrs culture with GM-CSF and IL-4, MoDCs were seeded at a density of $1.25 \times 10^5$ cells per well in 48 well plates and treated with EnAd and NG-350A virus supernatants at different dilutions. The plates were then incubated for 24 hrs and 48 hrs before supernatants and cells were harvested. Supernatants were centrifuged and removed from cell pellets and stored at −80° C. The cells were stained for flow cytometry analysis. Supernatants were used for cytokine analysis by CBA.

Figure 20:
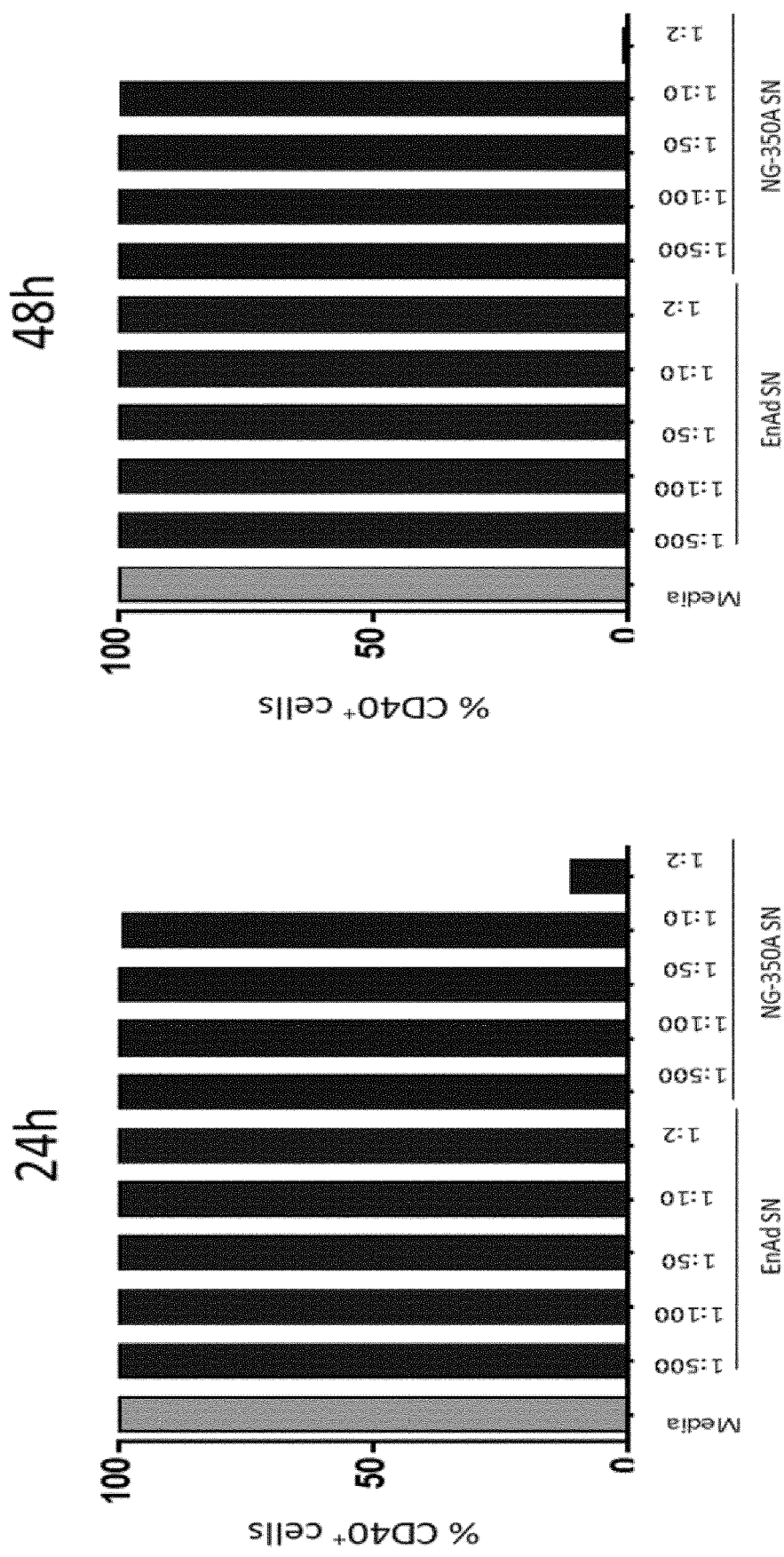
FIG. 20 shows that an antibody preparation produced by NG-350A infected tumor cells, not depleted of virus, binds to CD40 on the surface of human MoDC's.

To demonstrate anti-CD40 Ab binding to CD40 on the surface of MoDCs, cells were treated with increasing concentrations of the supernatants from NG-350A or EnAd infected cells (different dilutions used to provide different amounts of antibody) or were left untreated (media). After 24 hrs and 48 hrs, cells were harvested and stained with fluorescent labelled antibodies to CD40 before flow cytometry analysis was carried out. Cells were gated on single (FSC-H versus FSC-A) live cells (LIVE/DEAD® Fixable Aqua negative). FIG. 20 shows CD40 expression on MoDCs 24 hrs and 48 hrs post-treatment with different concentrations of supernatants. At the 1:2 supernatant dilution from NG-350A (but not EnAd) infected tumour cells, CD40 FACS staining is reduced or absent, reflecting blockade by binding of the anti-CD40 antibody in the NG-350A virus-treated culture supernatants.

Figure 21A:
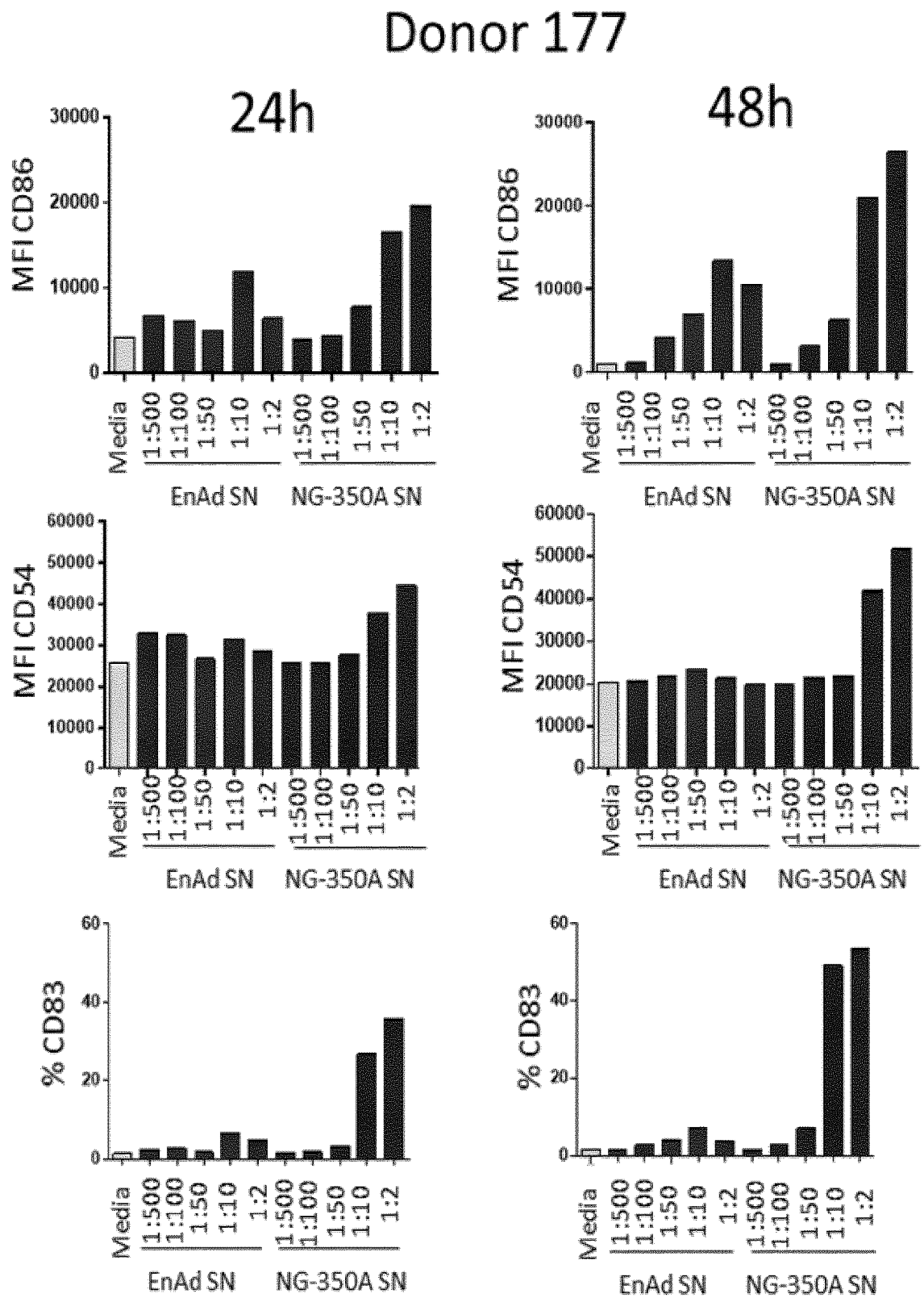
FIG. 21 shows effects of anti-CD40 Ab produced by NG-350A infected tumour cells, not depleted of virus, on cell surface marker upregulation at 24 and 48 hours on human MoDC's from 2 different donors.
Figure 21B:
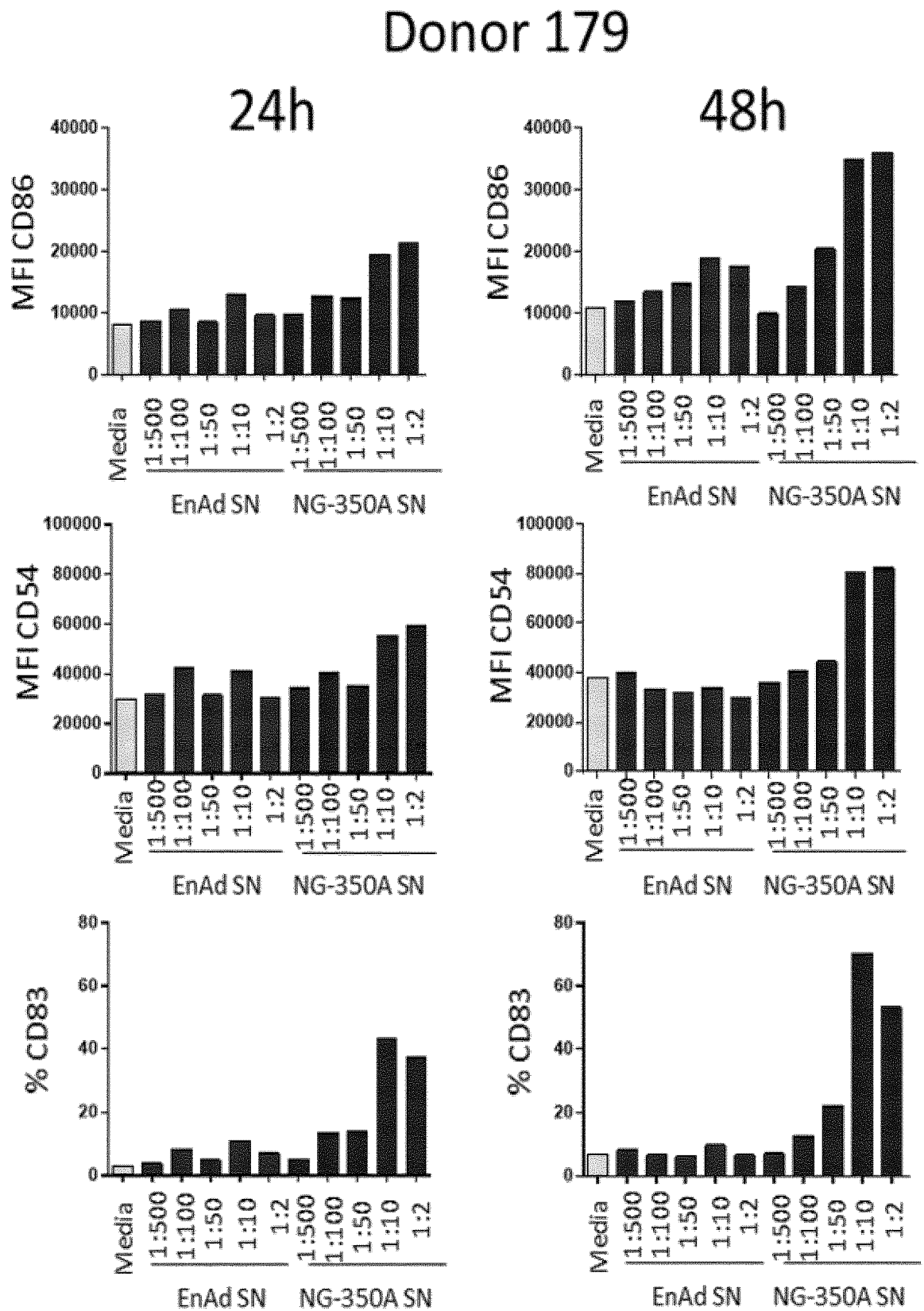

The effects of NG-350A virus treated tumour cell supernatant on cell surface marker upregulation on MoDCs from two donors (177 & 179) was then evaluated. MoDCs were treated with diluted EnAd or NG-350A virus supernatants or were left untreated (media). After 24 hrs and 48 hrs, cells were harvested and stained with antibodies to CD86, CD54 and CD83 before flow cytometry analysis was carried out. Cells were gated on single (FSC-H versus FSC-A) live cells (LIVE/DEAD® Fixable Aqua negative). Results in FIG. 21 show NG-350A selectively upregulated all three MoDC activation markers.

Figure 22A:
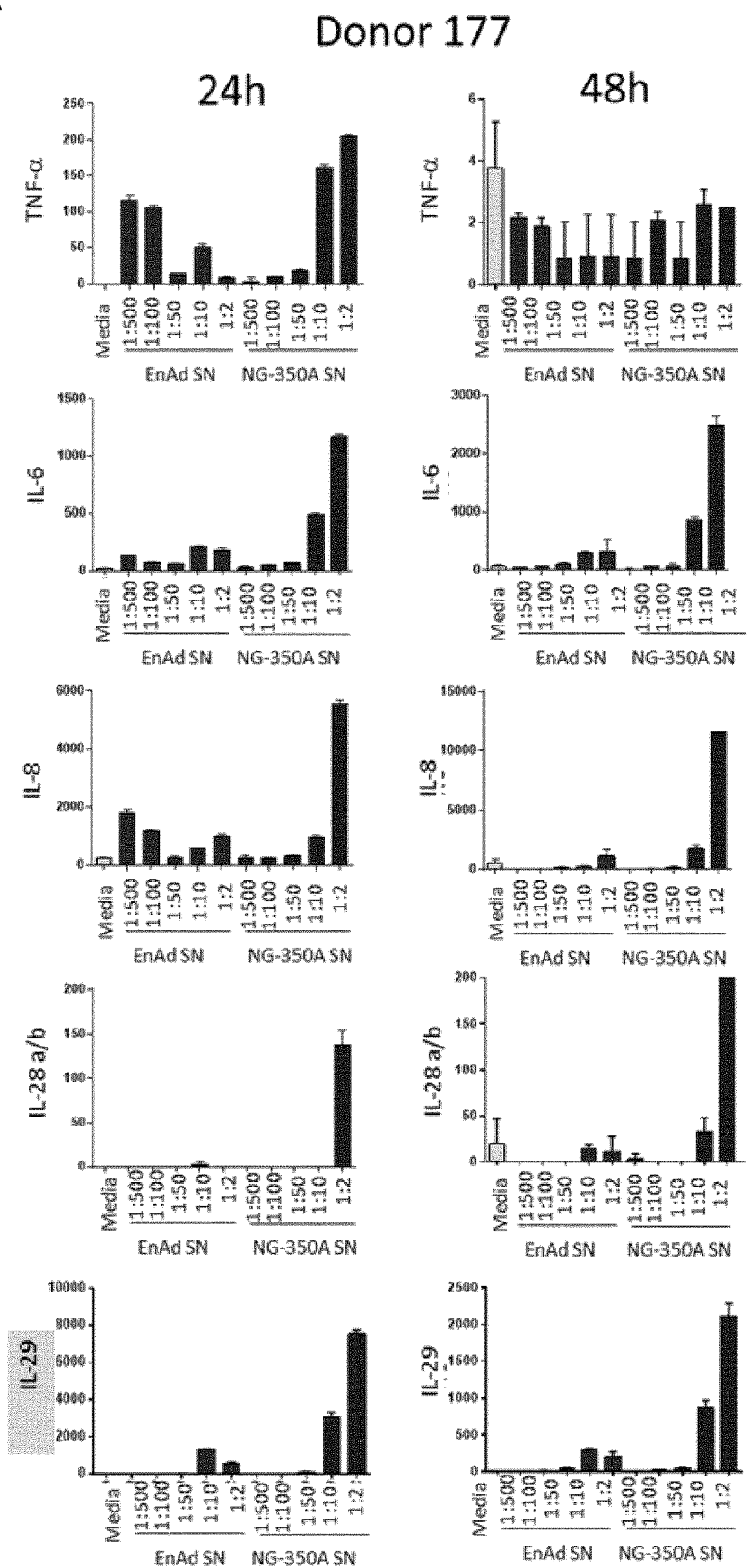
FIG. 22 shows effects of anti-CD40 Ab produced by NG-350A infected tumour cells, not depleted of virus, on cytokine secretions by human MoDCs as dose responses at 24 and 48 hours for 2 different donors.
Figure 22B:
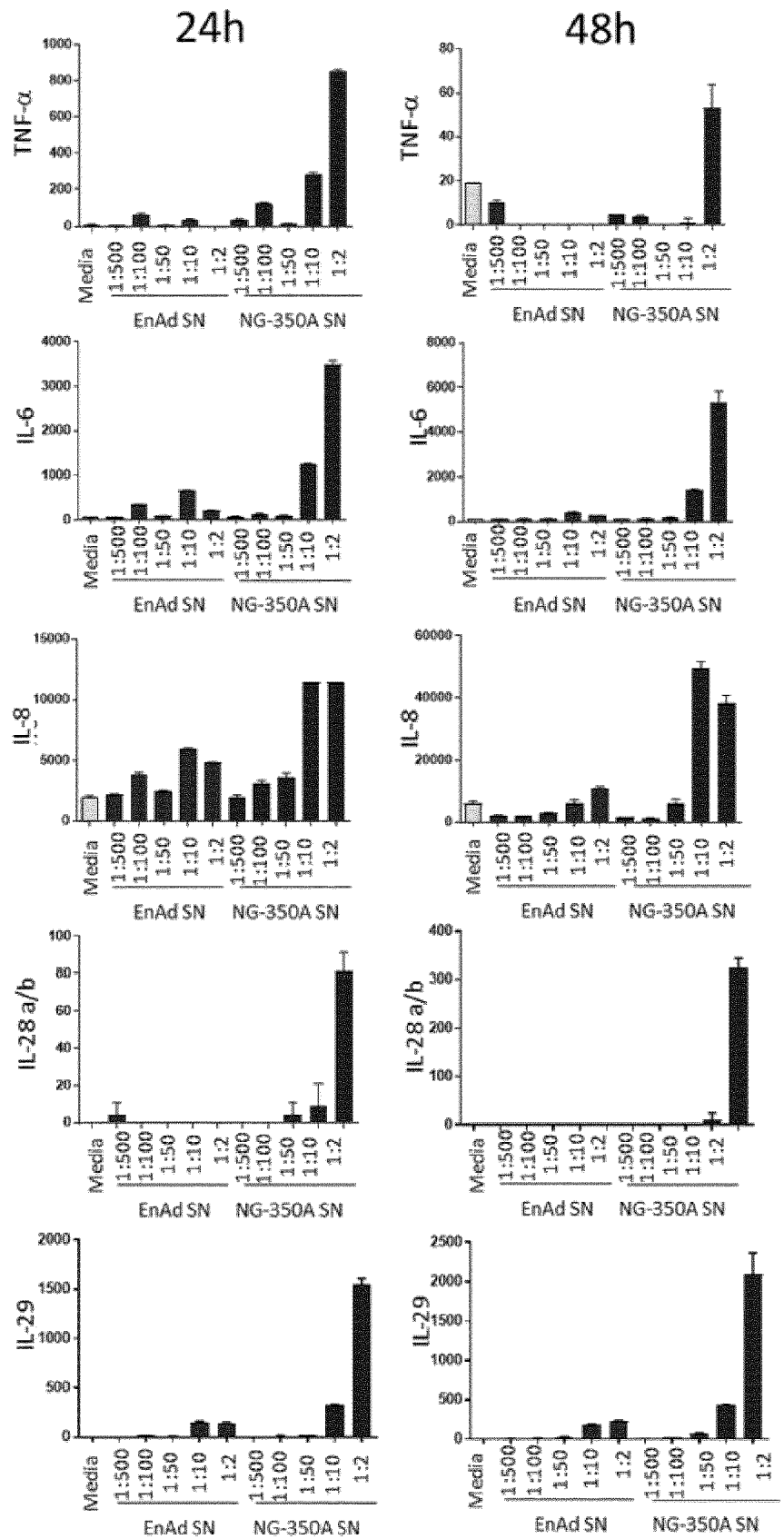

Effects of NG-350A virus supernatant on MoDC cytokine production was then evaluated. MoDCs from two donors (177 & 179) were treated with diluted EnAd or NG-350A virus-treated tumour cell supernatants or were left untreated (media). After 24 hrs and 48 hrs, supernatants were collected and analysed for inflammatory cytokine secretion using a LEGENDplex™ bead-based immunoassays (BioLegend). The results in FIG. 22 show selective upregulation of TNFα, IL-6, IL-8, IL-28 and IL-29 by NG-350A treated cell supernatants.

Figure 23A:
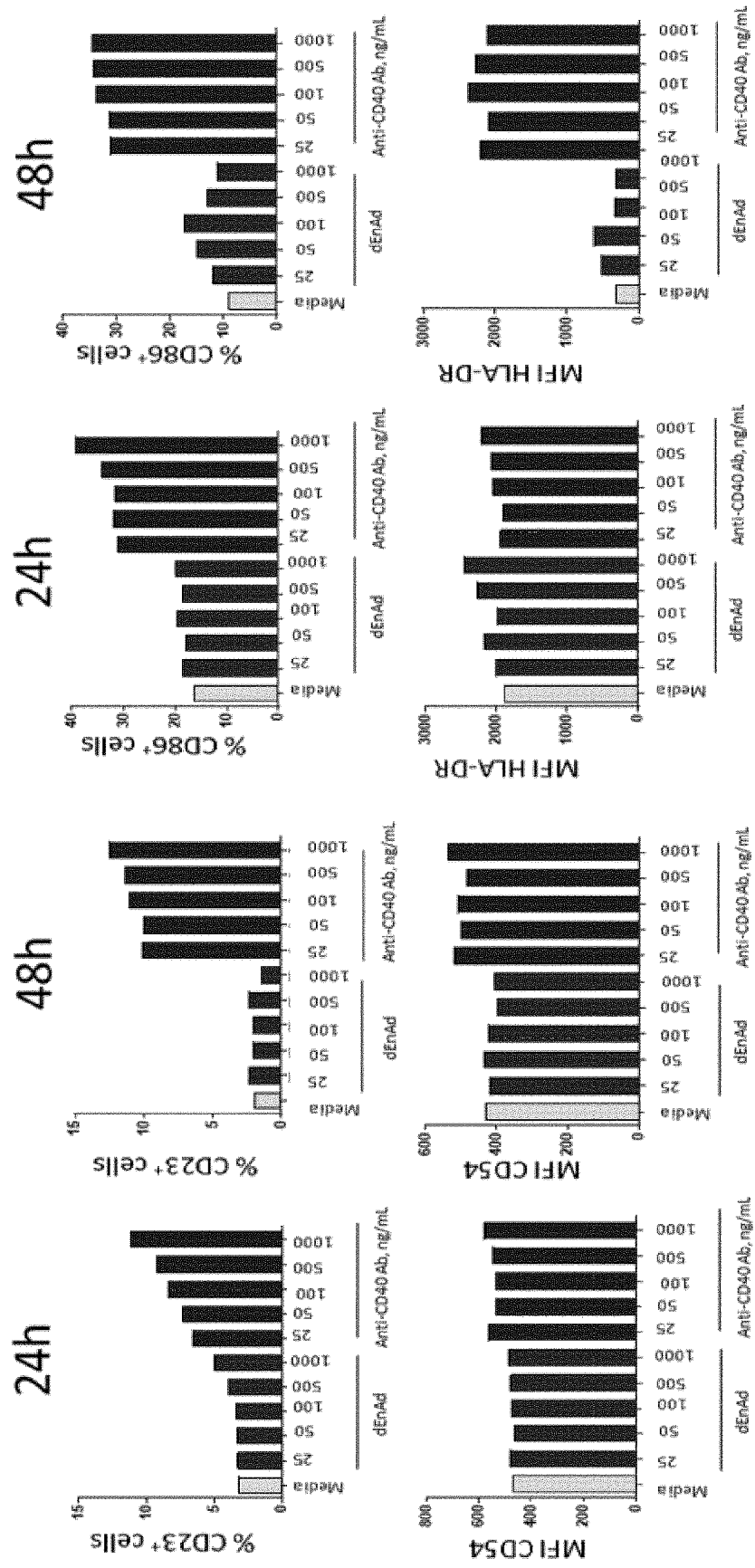
FIG. 23 shows effects of virus-depleted anti-CD40 Ab produced by NG-350A infected tumour cells on cell surface marker upregulation on human B-cells as dose responses at 24 and 48 hours for 3 different B-cell donors.
Figure 23B:
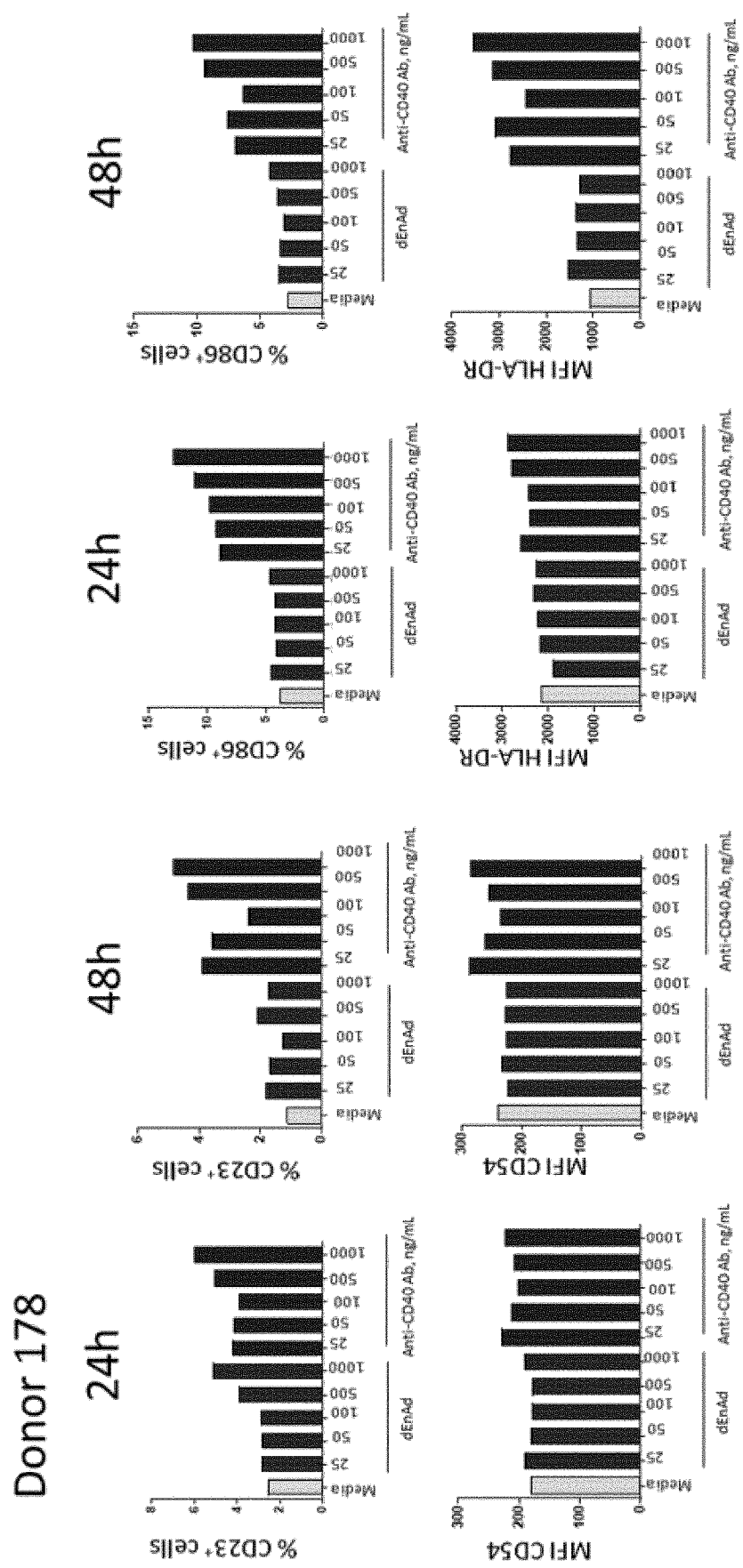
Figure 23C:
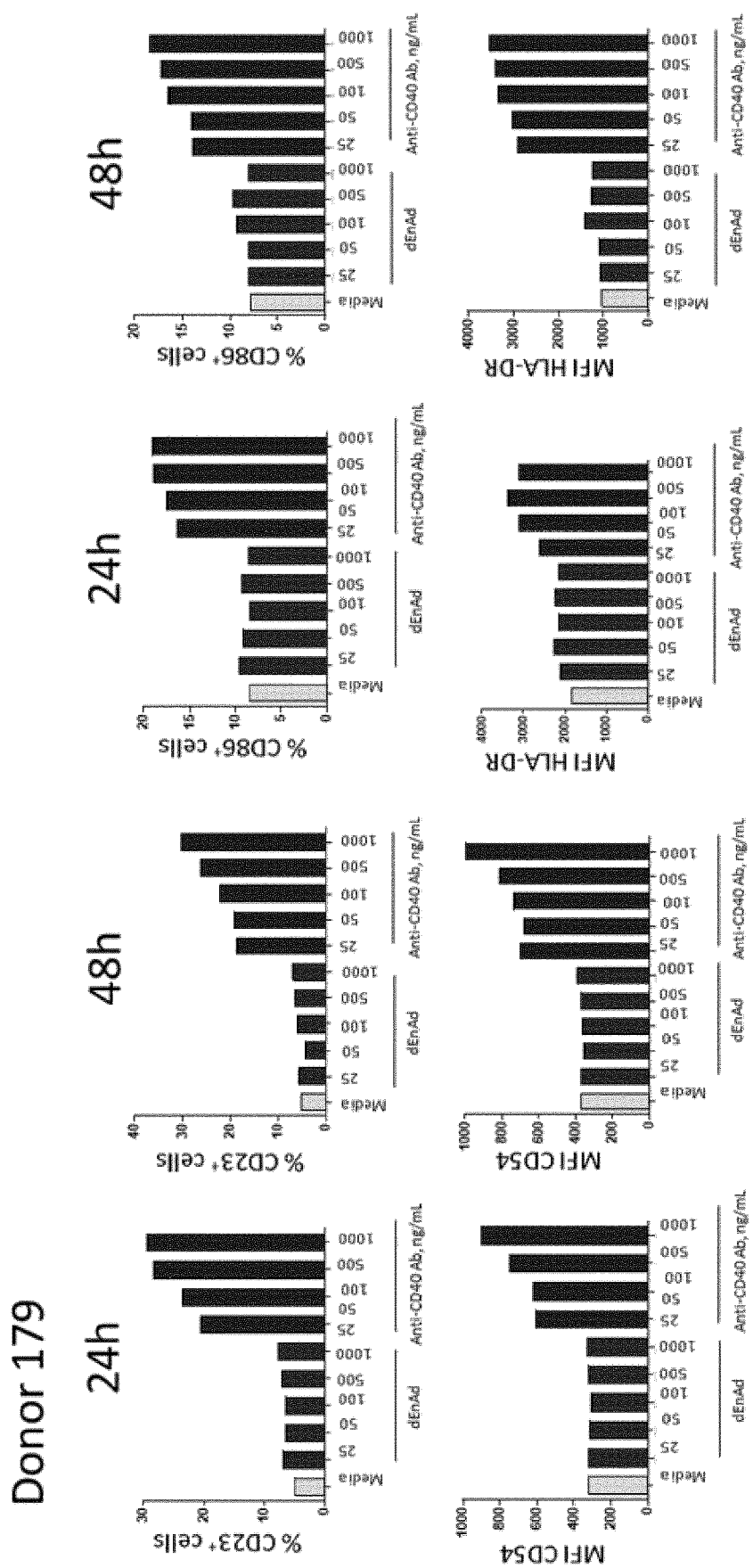

Example 15: NG-350A Derived Anti-CD40 Antibody Activity on Primary Human B-Cells PBMCs were isolated by Ficoll-Paque gradient centrifugation from NC24 leucocyte cones sourced from NHS Blood and Transplant unit in Oxford, UK. B cells were isolated using the Pan B Cell Isolation Kit (MiltenyiBiotec). Cells were seeded at a density of $1.25 \times 10^5$ cells per well in 48 well plates in 10% RPMI culture media. They were treated with the different concentrations of the virus-depleted, anti-CD40 Ab enriched supernatant from NG-350A infected cells described in Example 13 or were left untreated. B cells were also treated with the virus-depleted EnAd virus supernatant as a control. The plates were then incubated for 24 hrs and 48 hrs before cells were harvested. The cells were stained with antibodies to CD23, CD54, CD86 and HLA-DR before flow cytometry analysis was carried out. Cells were gated on single (FSC-H versus FSC-A) live cells (LIVE/DEAD® Fixable Aqua negative). FIG. 23 shows selective upregulation of all four surface markers (CD23, CD54, CD86 & HLA-DR) on B-cells from 3 different donors (177, 178, 179) by the virus-depleted NG-350A anti-CD40 antibody containing supernatants.

Figure 24A:
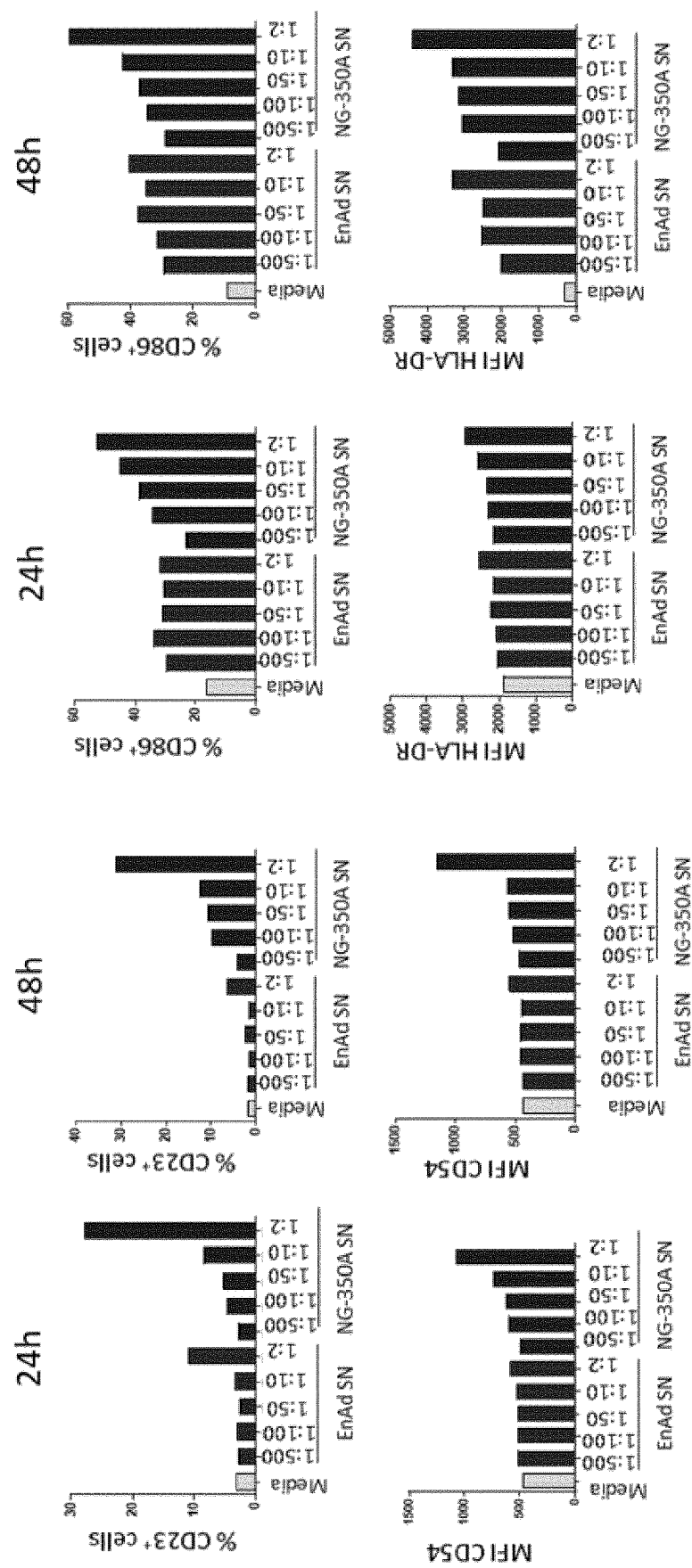
FIG. 24 shows effects of anti-CD40 Ab produced by NG-350A infected tumour cells, not depleted of virus, on cell surface marker upregulation at 24 and 48 hours on human B-cells from 3 different donors.
Figure 24B:
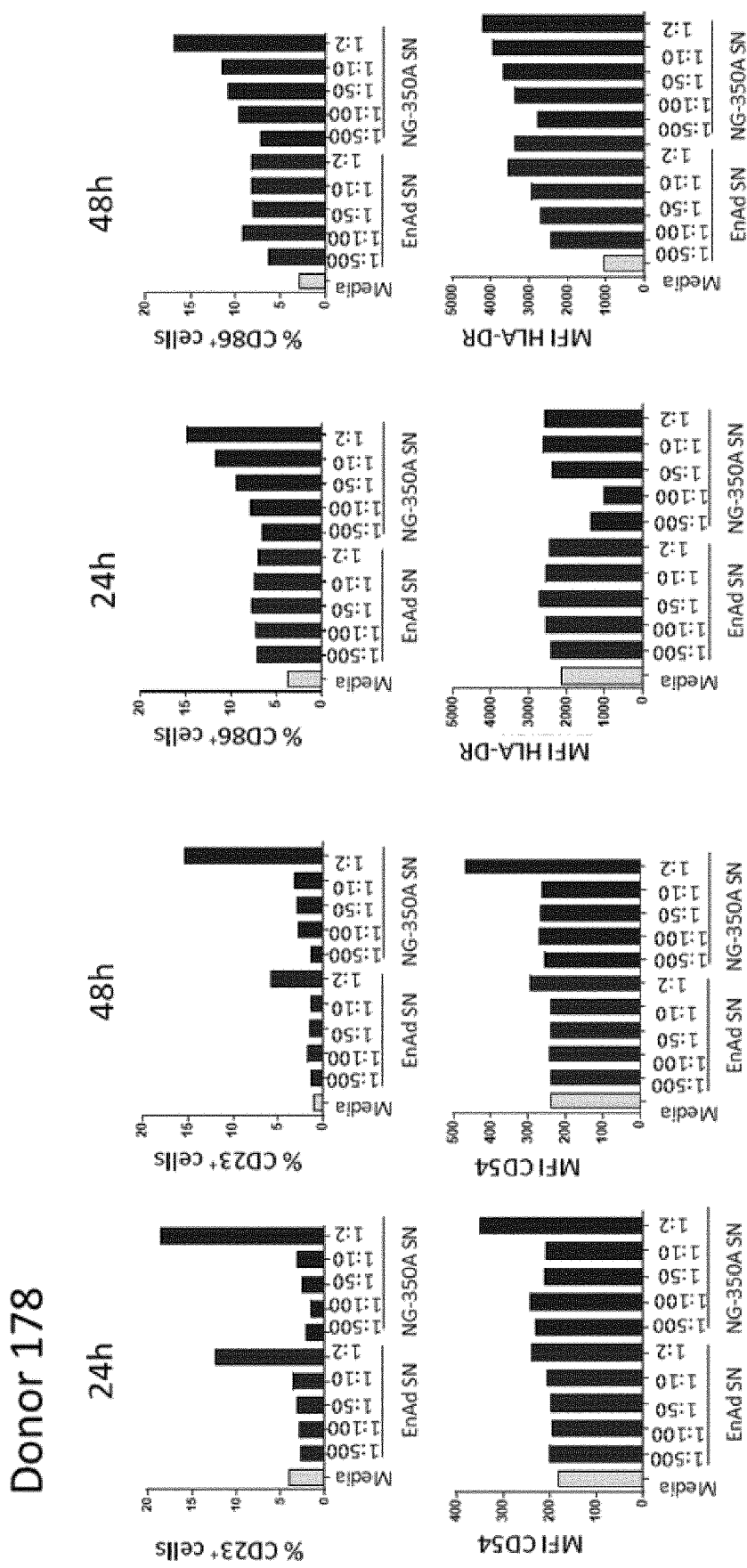
Figure 24C:
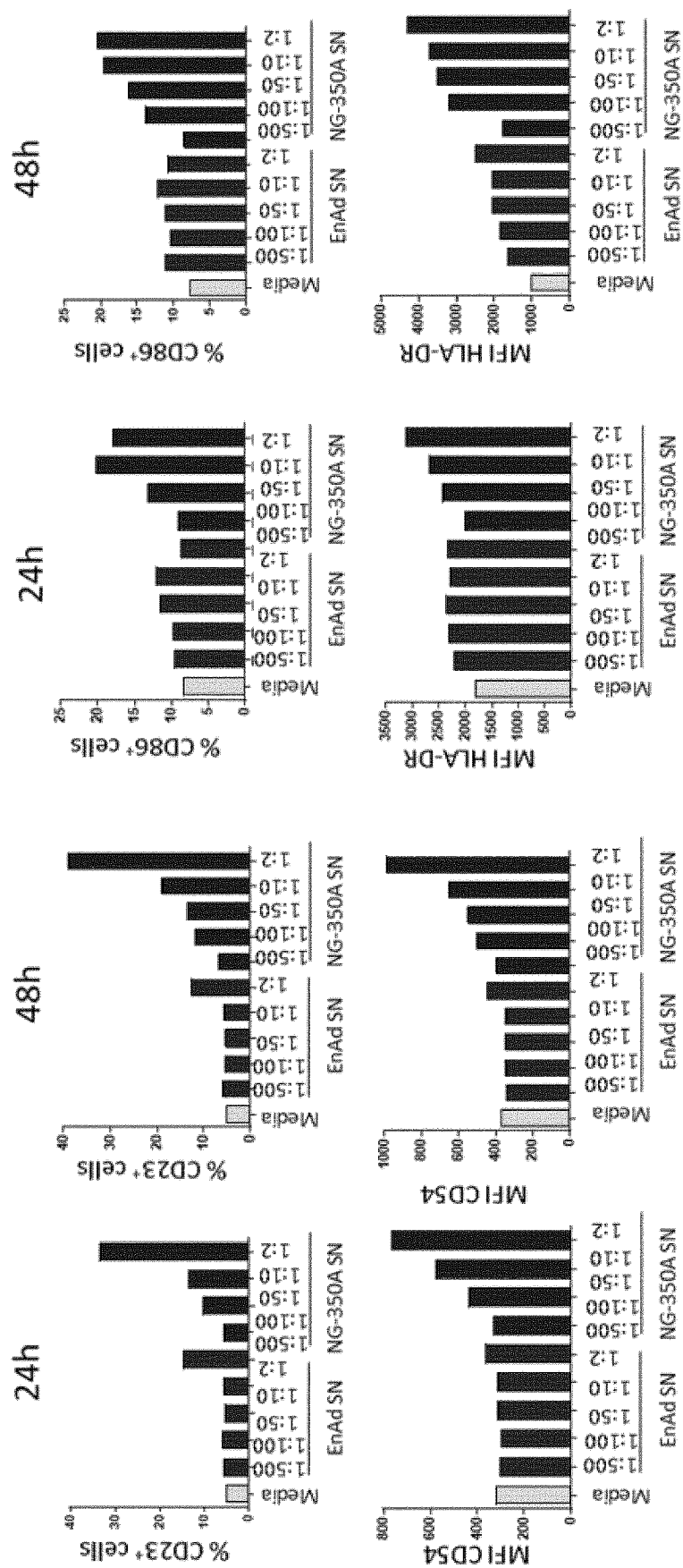

Example 16: Activity of NG-350A Virus and Derived Anti-CD40 Antibody Containing Virus Infected Tumour Cell Supernatants on Activity of Primary Human B-Cells PBMCs were isolated by Ficoll-Paque gradient centrifugation from NC24 leucocyte cones sourced from NHS Blood and Transplant unit in Oxford, UK. B cells were isolated using the Pan B Cell Isolation Kit (MiltenyiBiotec). Cells were seeded at a density of $1.25 \times 10^5$ cells per well in 48 well plates and treated with different dilutions of samples of the same EnAd and NG-350A virus supernatants described in Example 14. The plates were then incubated for 24 hrs and 48 hrs before cells were harvested and stained with antibodies to CD23, CD54, CD86 and HLA-DR before flow cytometry analysis was carried out. Cells were gated on single (FSC-H versus FSC-A) live cells (LIVE/DEAD® Fixable Aqua negative). FIG. 24 shows selective upregulation of all four markers (CD23, CD54, CD86 & HLA-DR) on B-cells from 3 different donors (177, 178, 179) by the virus and anti-CD40 antibody containing supernatants from NG-350A infected tumour cells.

Example 17

In another study, the activity of NG-350A was evaluated against a range of different tumour cell lines across six cancer indications (colorectal, prostate, pancreatic, breast, ovarian and bladder). Cells were infected with 1 or 100 particles per cell (ppc) of enadenotucirev (EnAd) or NG-350A and cultured for 3-11 days, evaluating viral genome replication, virus mediated oncolysis, viral transgene expression (at the mRNA and protein level) and functional viral transgene expression in NG-350A-infected tumour cells. In all experiments, the activity of NG-350A was compared to that of EnAd. A549 (non-small cell lung carcinoma) cells were used as a positive control, and CT26 (mouse colon tumour) cells as a negative control.

Virus Genome Replication

Tumour cell lines were cultured in 175 cm$^2$ flasks in high glucose DMEM supplemented with L-glutamine, non-essential amino acids, sodium pyruvate and 10% foetal bovine serum (FBS) (growth media). Before use, cells were inspected using a microscope to ensure 60-80% confluency. The cells were then washed with PBS and 0.25% Trypsin-EDTA added to detach the cells from the bottom of the flask. The cells were incubated for 2-10 minutes at 37° C., 5% $CO_2$ until the cells detached, after which the trypsin was deactivated using growth media. The cell suspension was mixed and spun at 300 g for 5 minutes. The supernatant was discarded, and the cell pellet resuspended in 10 mL of assay media; DMEM media as described above, supplemented with 2% (instead of 10%) FBS. Cells were counted, and the cell suspension diluted using assay media to achieve a concentration of $5 \times 10^5$ cells/mL, 100 µL of which was seeded into flat bottom 96 well plates (each cell line was seeded into two wells per virus and 2 wells per uninfected control (UIC) per plate—with one plate per timepoint). Samples for EnAd and UIC were seeded (and infected) on one set of plates, and samples for NG-350A and UIC were seeded (and infected) on another set of plates. The plates were incubated at 37° C., 5% $CO_2$ before inoculation 4-6 hours post-cell seeding.

Following this time, EnAd and NG-350A viruses were diluted in assay media to achieve a concentration of $5 \times 10^5$ virus particles/mL, 100 μL of which was added to each relevant well of cells (each virus was added to each cell line in duplicate on each plate). This resulted in an inoculation of 1 ppc of EnAd or 1 ppc of NG-350A. Instead of the addition of virus, 100 μL of assay media was also added to duplicate wells of each cell line (UIC) on each plate.

20 hours post-inoculation, media was removed from the cells and replaced with 200 μL of fresh assay media. The plates were then incubated at 37° C., 5% $CO_2$ for 3, 4, 8 or 11 days post inoculation. If the cells were to be incubated for 8 or more days, they were fed with 50 μL of assay media 4 days post-inoculation.

DNA Harvest: Post incubation, media was removed from the cells and centrifuged in 96 well V-bottom plates. The supernatant was then transferred to fresh 96 well flat bottom plates and stored at −80° C. 200 μL of 1×Reporter Lysis Buffer (RLB) was then added to the original plates of cells, and stored at −80° C.

Standard curve preparation: Stock EnAd was diluted to between $1.25 \times 10^{11}$ and $1.25 \times 10^6$ virus particles/ml before DNA extraction with the Qiagen DNeasy 96 kit according to the manufacturer's protocol (200 μL of each standard curve sample was extracted, and the purified DNA eluted in a volume of 200 μL). The purified DNA was then aliquoted and stored at −20° C. before use on each qPCR plate. 2 μL of these standard curve samples were used in each qPCR reaction which equates to $2.5 \times 10^3$-$2.5 \times 10^8$ genomes per qPCR well.

DNA extraction: Supernatant and lysate test samples were thawed before DNA extraction with the Qiagen DNeasy 96 kit according to the manufacturer's protocol (50 μL of the test samples was extracted and the purified DNA eluted in a volume of 200 L). An extraction control of 1×RLB was extracted on each plate.

Figure 25B:
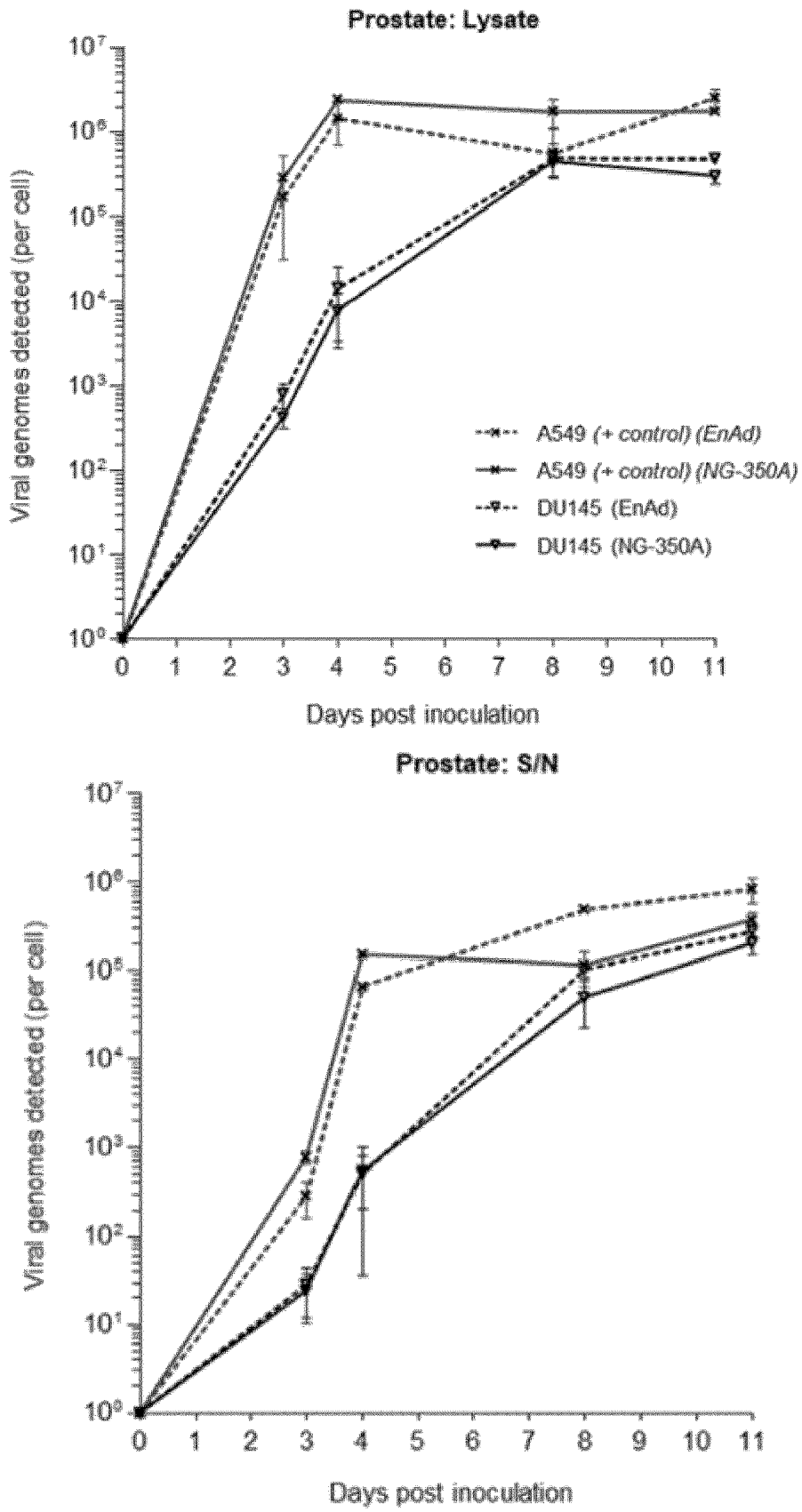
FIG. 25 shows time courses of viral genome replication (qPCR) by 10 different tumour cell lines infected with NG-350A, compared to those for EnAd.
Figure 25E:
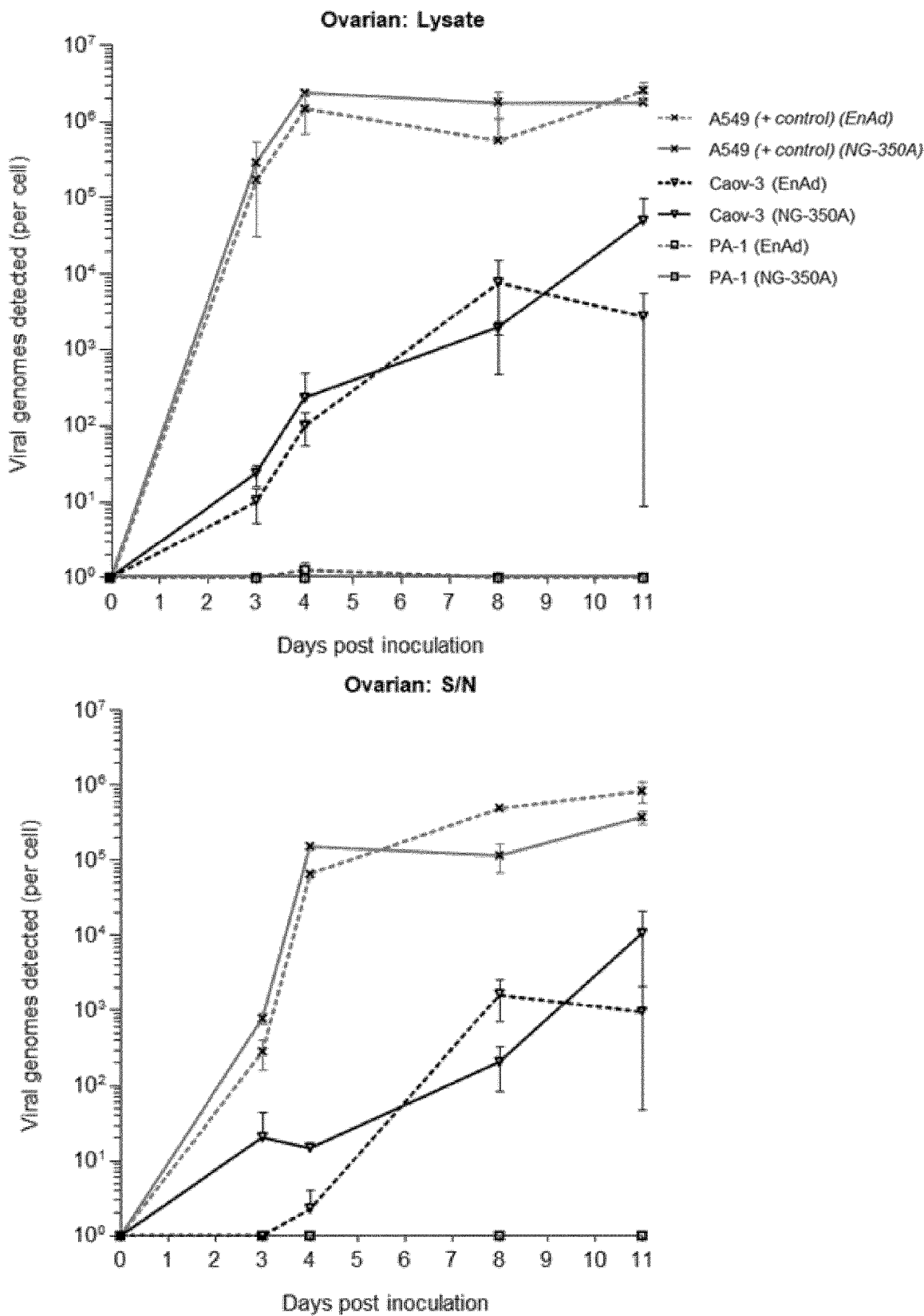
Figure 25F:
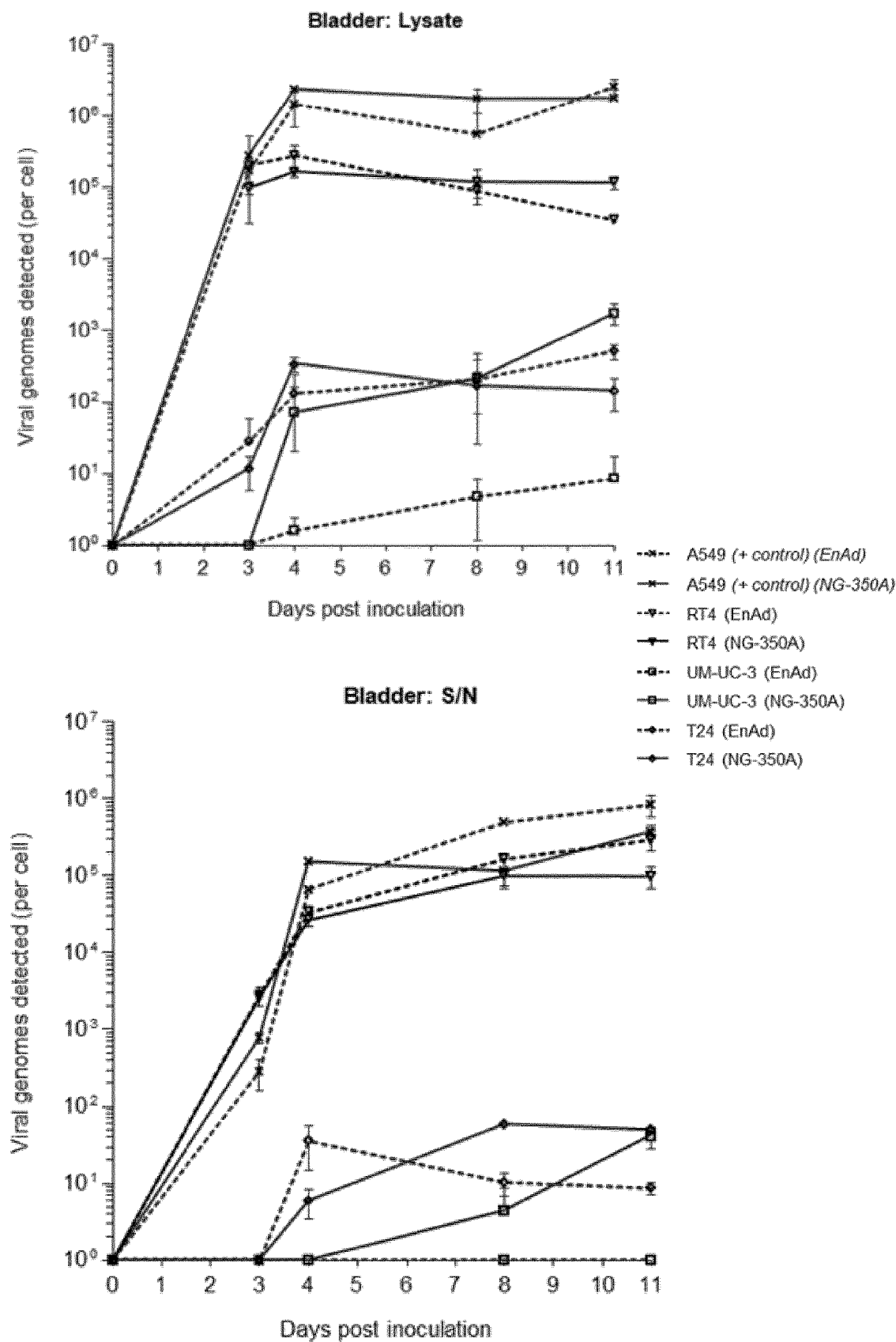

Virus genome replication was assessed by qPCR of cell lysates and supernatants (S/N) using an E3 primer-probe set as outlined in Example 6. Time courses for both cell lysate and supernatant samples from 10 test tumour cell lines, plus positive (A549) cells are plotted according to tumour type (Colorectal, HT-29 & HCT-116; Prostate DU145; Pancreatic BxPC-3; Breast MBA-MB-453; Ovarian PA-1 & Caov-3; Bladder RT24, T24 & UM-UC-3) in FIG. 25 A-F. Negative control cells (mouse CT26) were negative and not plotted. Viral genomes detected in EnAd infected cells are shown with dotted lines and viral genomes detected in NG-350A infected cells are shown with solid lines. The data shows that NG-350A replicates its genomic DNA comparably to the EnAd parental virus across a range of different carcinoma cell types.

Figure 26A:
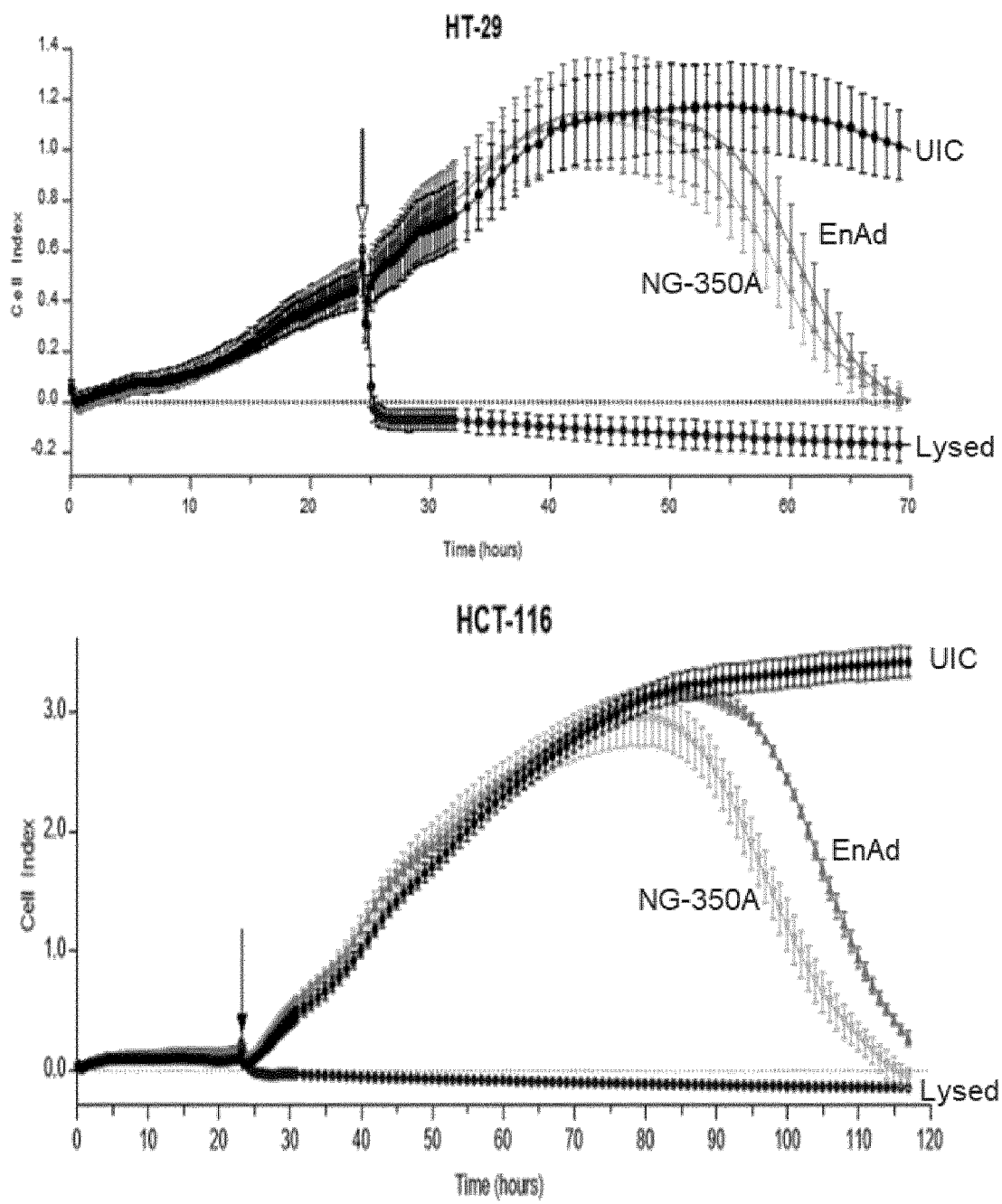
FIG. 26 shows time courses of virus-induced oncolysis (xCELLigence assay) in four example tumour cells lines infected with NG-350A, compared to those for EnAd.
Figure 26B:
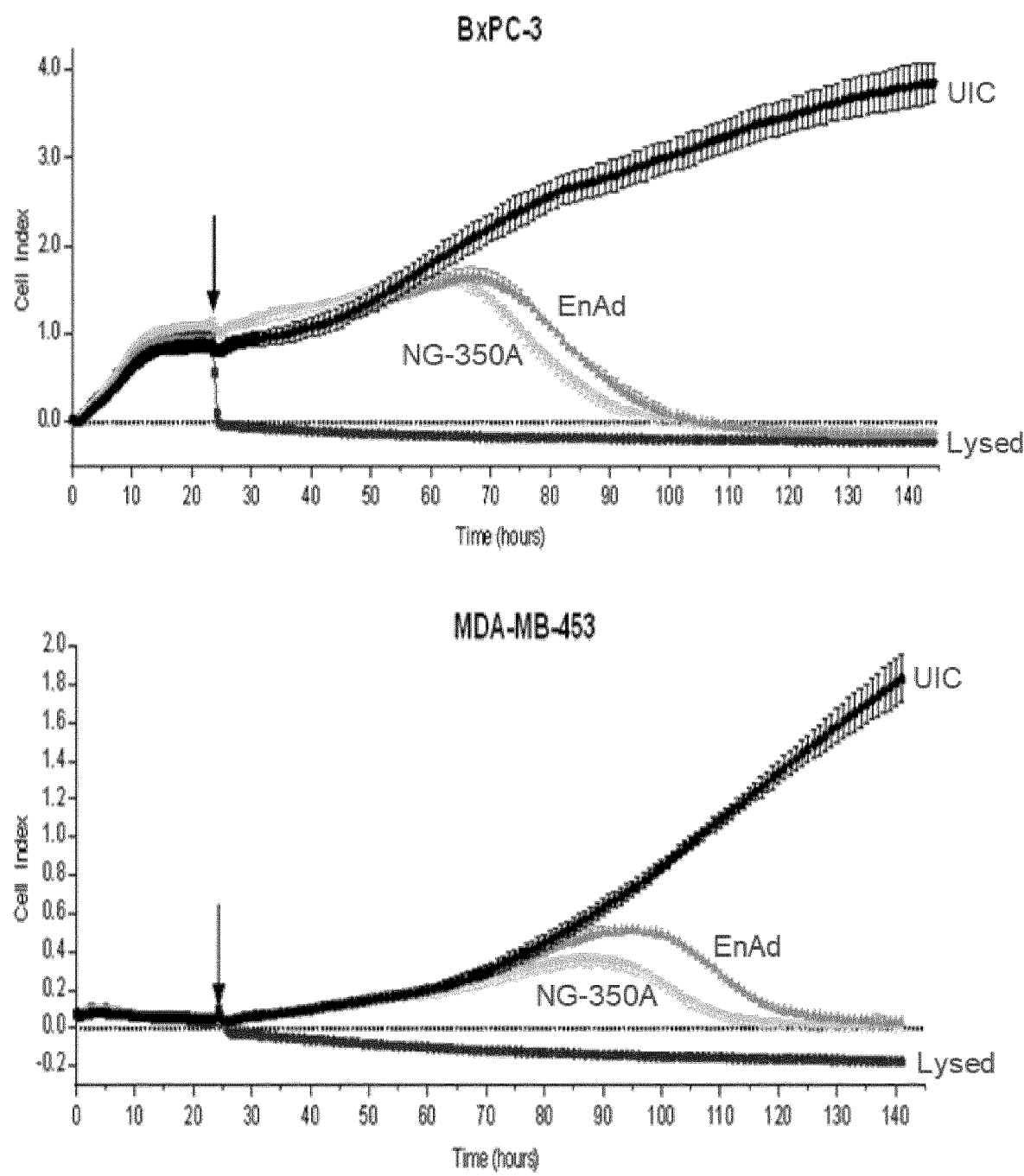

To evaluate the oncolytic effects of NG-350A, four tumour cell lines were inoculated with 100 ppc of EnAd, 100 ppc of NG-350A, assay media alone (uninfected control) or 4% tween (lysed). The growth and viability of the cells were monitored by the xCELLigence Real Time Cell Analzyer (RTCA) until over 50% lysis of cells inoculated with virus had occurred. The Cell Index (CI) across all timepoints was calculated by the xIMT software, and mean and SD of the uninfected, EnAd, NG-350A and lysed triplicates was determined; the mean was plotted in the graphs, and the SD represented by error bars. xCELLigence traces for uninfected controls, EnAd and NG-350A inoculated cells, and lysed cells are shown in FIG. 26. Cells were seeded at 0 hours, and infected 24 hours post seeding (at the timepoint indicated by the arrow on each graph). Tumour cell lines are shown as one cell line per graph: colorectal (HT-29 & HCT-116), prostate (BxPC-3) and breast (MDA-MB-453). NG-350A showed comparable oncolytic activity to the EnAd parental virus.

Anti-CD40 transgene mRNA expression was also evaluated in lysates taken at different times from tumour cell lines infected with NG-350A. The same 10 test tumour cell lines as used for the genome replication part of this study, plus positive (A549) and negative (CT26) control cell lines, were inoculated with 1 ppc of EnAd, 1 ppc of NG-350A or assay media alone (uninfected control). At different times (3, 4, 8 and 11 days) post-inoculation, cell lysates were harvested before RNA extraction and DNase clean-up was carried out. One-Step RT-qPCR was then run using an anti-CD40 specific primer/probe set. A synthetic RNA oligonucleotide corresponding to the sense strand of anti-CD40 was used to create a standard curve from which RNA quantity of the test samples was calculated. Mean RNA quantity for each uninfected control triplicate was background subtracted from the corresponding individual EnAd and NG-350A values. Anti-CD40 mRNA copies per cell was then calculated and the mean of the two EnAd and the two NG-350A RT-qPCR triplicates determined. The mean and SD of these duplicate values was then calculated for each cell line, at each time point (n=2 except for BxPC-3 day 8 sample where n=1). The mean was plotted and the graphs presented in FIG. 27, with the SD represented by error bars. EnAd inoculated cells gave negligible response whereby the mean genomes per cell calculated from biological duplicates ranged from $0 \times 10^0$ to $6.26 \times 10^0$ across all timepoints and cell lines. As such, EnAd data was not plotted. For the uninfected control samples, mean anti-CD40 copies per cell calculated from biological duplicates ranged from $0.00 \times 10^0$ to $9.09 \times 10^0$. The graphs depict anti-CD40 transgene expression in colorectal (A), prostate, pancreatic and breast (B), ovarian (C) and bladder (D) tumour cell lines. NG-350A infection led to anti-CD40 transgene mRNA expression in all human tumour cell lines, with differences in kinetics observed for different cells.

Figure 28:
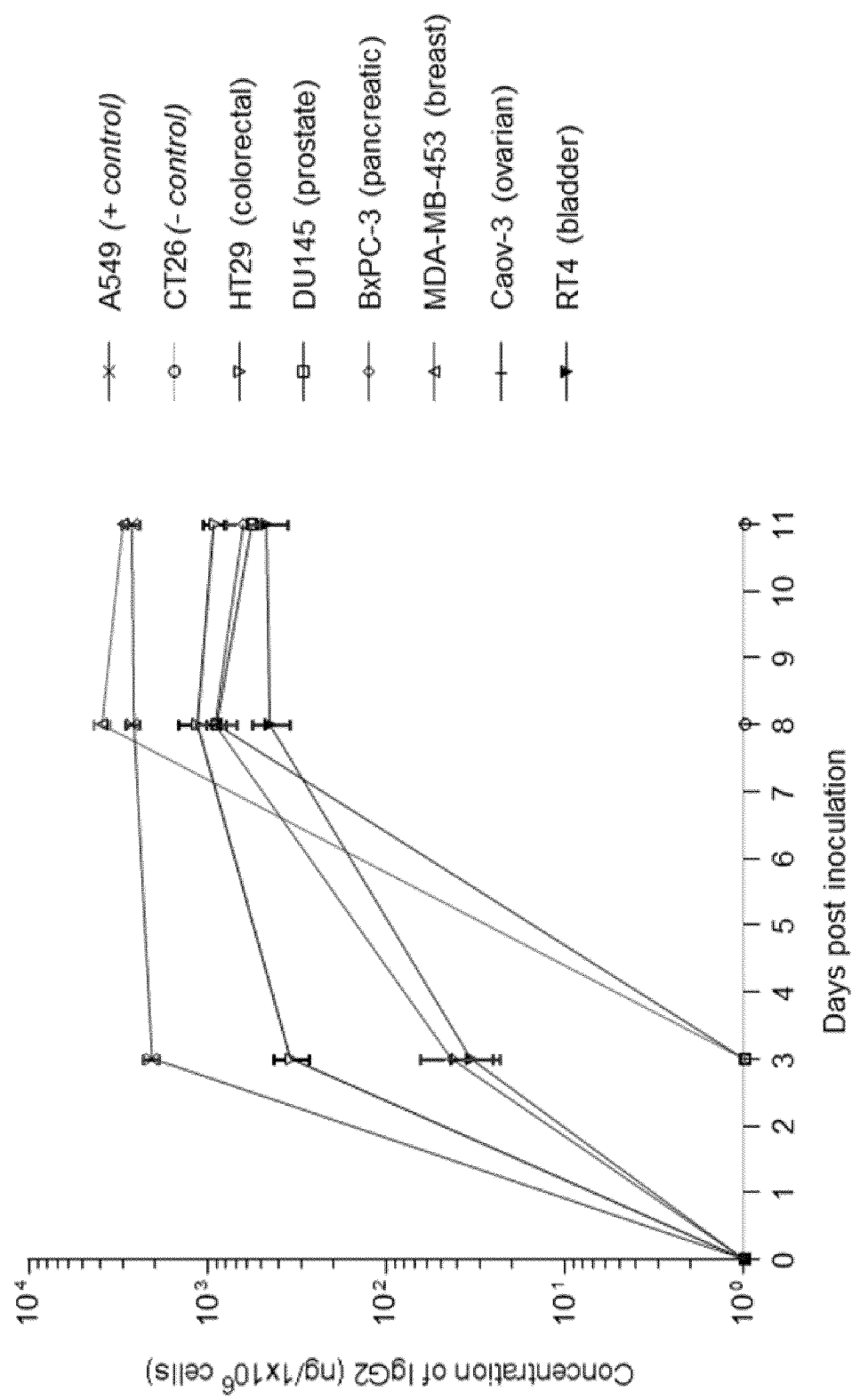
FIG. 28 shows detection of anti-CD40 transgene protein expression by IgG2 ELISA by different tumour cells lines.

To evaluate transgene protein IgG2 expression, production of human IgG2 (the isotype of the anti-CD40 antibody heavy chain encoded by NG-350A) by different tumour cell lines infected with NG-350A was measured. Six test tumour cell lines, plus positive (A549) and negative (CT26) control cell lines, were inoculated with 1 ppc of NG-350A, 1 ppc of EnAd or assay media alone (uninfected control). At different times (3, 4, 8 and 11 days) post-inoculation, supernatant was harvested and stored at −80° C. before use. Supernatant from NG-350A-inoculated test cell lines and A549 cells was diluted 1:2, 1:5, 1:10, 1:20, 1:40 and 1:80. Supernatant from all uninfected control samples, EnAd infected cells, and NG-350A infected CT26 cells was diluted 1:2 only. The human IgG2 in vitro SimpleStep ELISA (Abcam) was then carried out according to the manufacture's protocol. Human IgG2 purified protein (supplied with the ELISA kit) was used to create a standard curve from which the concentration of IgG2 protein in the samples was determined (ng/mL). The quantity of IgG2 protein per $1 \times 10^6$ cells (ng/$1 \times 10^6$ cells) was then calculated. Mean and SD was determined from the means of the ELISA duplicates that sat within the standard curve. The mean was plotted and the graphs presented in FIG. 28, with the SD represented by error bars. Background subtraction using uninfected control samples was not carried out as for each cell line and timepoint these samples gave no response ($0 \times 10^0$ ng/$1 \times 10^6$ cells). EnAd inoculated cells also gave no response therefore EnAd data was not plotted. IgG2 antibody production was detected with all cell lines infected with NG-350A. The HEK-Blue CD40 signaling reporter assay described in Example 8 was used to test the functionality of the antibody produced by different tumour cell lines infected with NG-350A. Six test tumour cell lines plus positive (A549) and negative (CT26) control cell lines were inoculated with 1 ppc of EnAd, 1 ppc of NG-348 or assay media alone (UIC). 8 or 11 days post-inoculation, supernatant was harvested. Supernatant was then incubated with HEK-Blue cells for 20-24 hours. Supernatant was then removed from the treated HEK-Blue cells, added to Quanti-Blue and incubated for 1 hour before reading the optical density (OD) on a SpectraMax i3x set to read an absorbance of 620 nm. Mean optical density for each UIC assay duplicate was subtracted from the corresponding individual EnAd and NG-350A values, giving an assessment of CD40 signaling activity of the antibodies in the supernatants of infected tumour cells. The mean of the UIC background-subtracted EnAd and NG-350A assay duplicates was then taken, giving 2 values for each cell line (per condition), corresponding to each seeding and inoculation replicate. Mean and standard deviation (SD) of these replicates was then determined, and shown in Table 3.

TABLE 3

Functional anti-CD40 antibody activity in supernatants from NG-350A infected tumour cells (HEk-Blue reporter assay) Summary of NG-350A transgene (anti-CD40 antibody) function, detected by the HEK-Blue assay

| Cancer | | SEAP activity (Optical Density at 620 nm) | | | |
|---|---|---|---|---|---|
| | | NG-350A | | EnAd | |
| Indication | Cell line | Mean | SD | Mean | SD |
| Positive control | A549 | 1.0600 | 0.0933 | 0.1488 | 0.0124 |
| Negative control | CT26 | 0.0000 | 0.0103 | 0.0017 | 0.0088 |
| Colorectal | HT-29 | 0.7175 | 0.0212 | 0.0650 | 0.0021 |
| Prostate | DU145 | 0.5555 | 0.0276 | 0.0910 | 0.0120 |
| Pancreatic | BxPC-3 | 0.7118 | 0.2054 | 0.0428 | 0.0088 |
| Breast | MDA-MB-453 | 0.8578 | 0.1439 | 0.1033 | 0.0011 |
| Ovarian | Caov-3 | 0.0273 | 0.0293 | 0.0198 | 0.0124 |
| Bladder | RT4 | 0.3653 | 0.0209 | 0.0470 | 0.0085 |

Example 18

Figure 29:
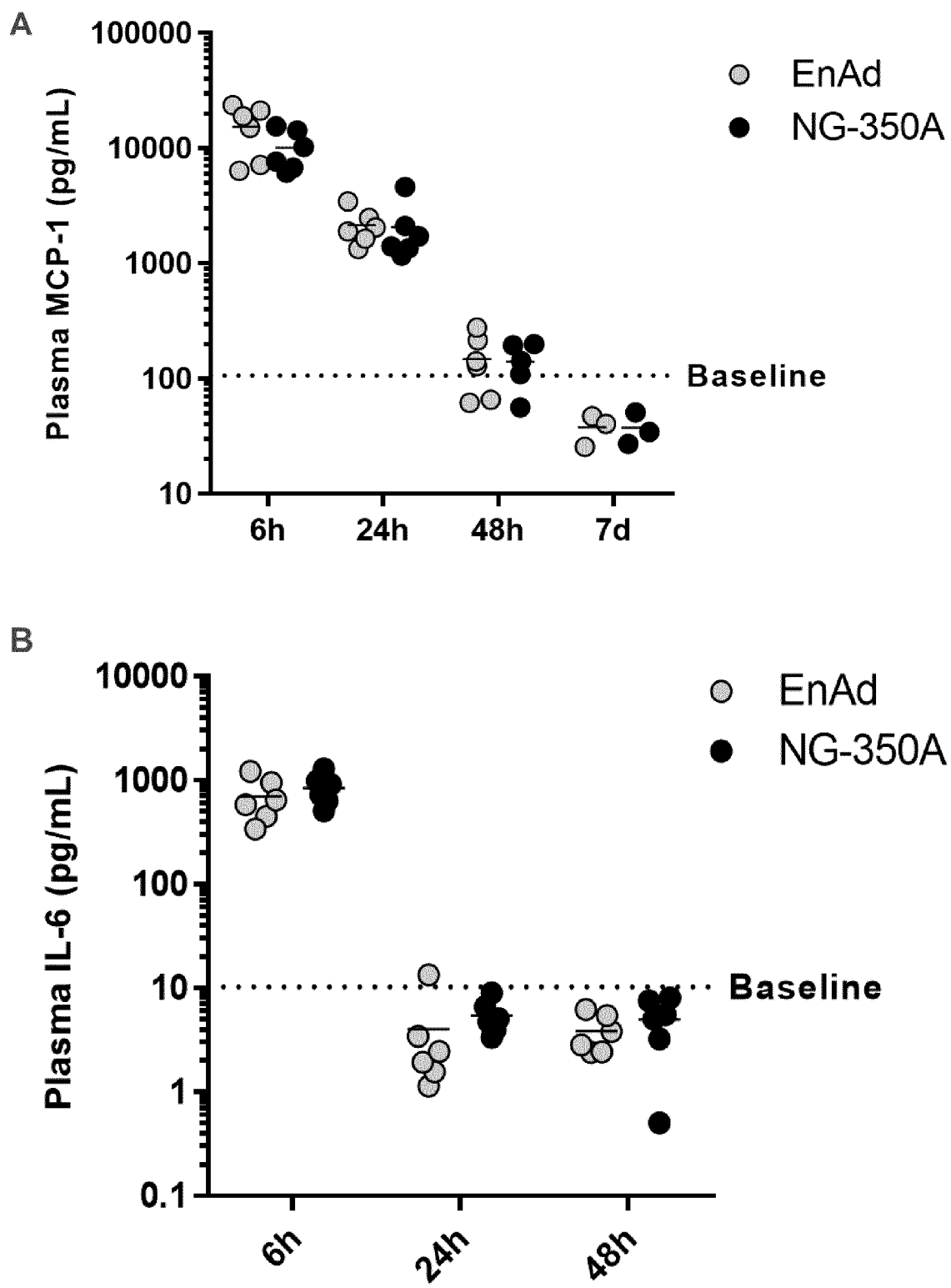
FIG. 29 shows a time course of acute plasma cytokine responses following IV dosing with NG-350A particles compared to those of EnAd; MCP-1 (A), IL-6 (B) and TNFα (C).
Figure 29:
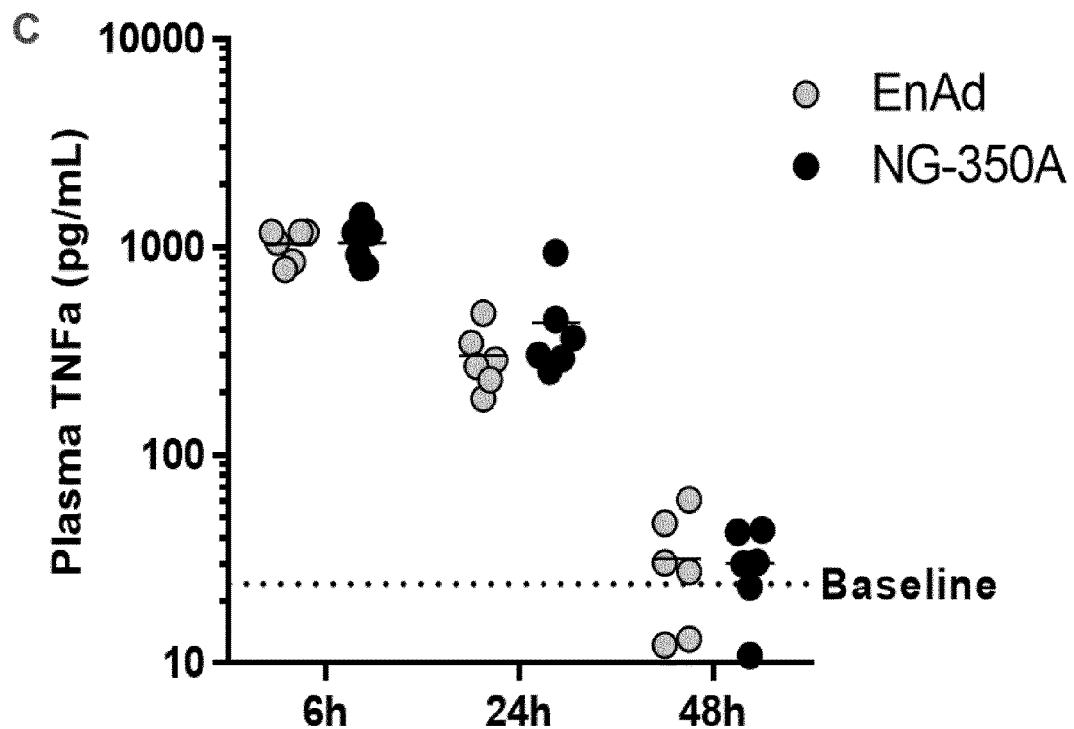

In a further series of experiments, the in vivo virus particle-mediated effects of NG-350A virus were monitored and compared to those of EnAd following single or multiple intravenous doses in mice. Female CD-1 mice were injected IV with vehicle control or $2.2 \times 10^{10}$ particles of either EnAd or NG-350A. Mice were cardiac bled 6 hours, 24 hours, 48 hours, or 7 days post injection and blood was collected into anticoagulant tubes and processed to recover plasma. Plasma samples were tested by ELISA assays to detect acute cytokine responses to the virus particles Data shown in FIG. 29 represents 3-6 mice per group. MCP-1 (FIG. 29A), IL-6 (FIG. 29B) and TNFα (FIG. 29C) levels stimulated by NG-350A dosing were similar to those for EnAd. Solid black lines represent the mean. Baseline represents the mean of vehicle control group+3×SD.

Figure 30:
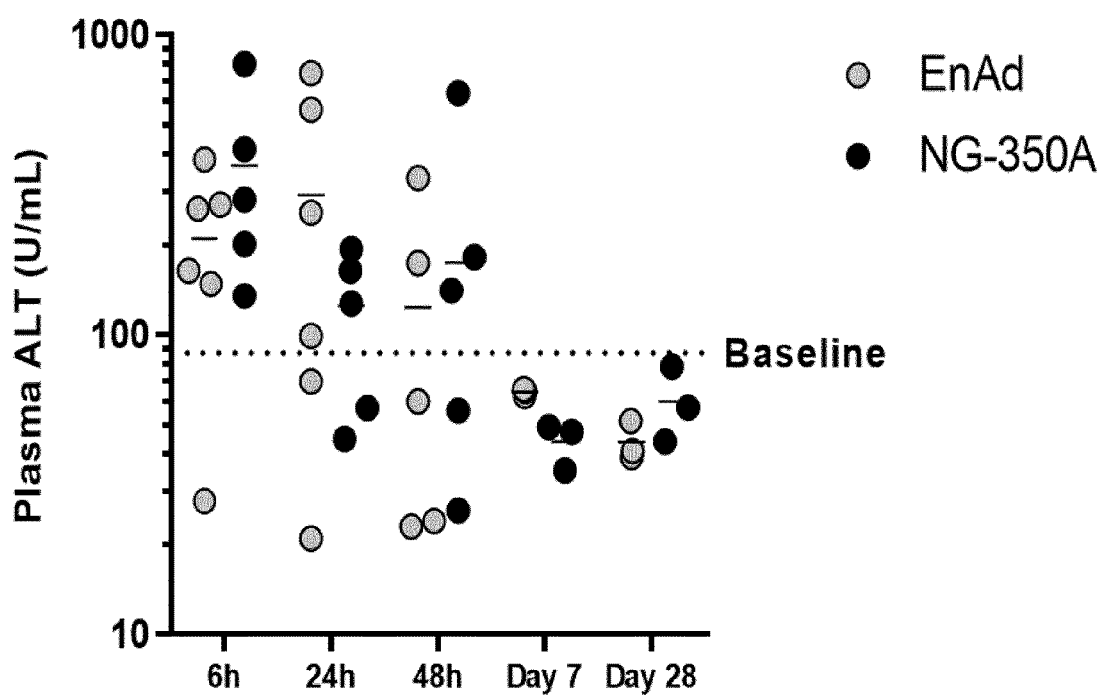
FIG. 30 shows a time course of alanine transaminase (ALT) concentrations in plasma after a single intravenous dose of EnAd or NG-350A.

Other aliquots of the plasma samples were tested for alanine amino transferase (ALT) levels as a measure of acute liver toxicity. Plasma samples were analysed using an ALT colorimetric endpoint enzymatic assay kit. Data shown in FIG. 30 represents 3-6 mice per group. Solid black lines represent the mean. Baseline represents the mean of vehicle control group+3×SD. ALT levels were variable between different mice but NG-350A and EnAd induced similar response profiles.

Further groups of female CD-1 mice were injected IV with PBS on day 1, or $2.2 \times 10^{10}$ viral particles of either EnAd or NG-350A on days 1, 3 and 5. PBS treated mice were cardiac bled 6 hours after dosing. Virus treated mice were bled via a lateral tail vein and cardiac puncture 6 hours and 24 hours (respectively) after the first dose, or via cardiac puncture 6 hours, 24 hours or 7 days after the third dose. Plasma samples were tested by ELISA assays to detect acute cytokine responses to the virus particles data shown in FIG. 31 represents 3-6 mice per group. MCP-1 (FIG. 31A) and IL-6 (FIG. 31B) levels stimulated by NG-350A dosing were similar to those for EnAd. Solid black lines represent the mean. Baseline represents the mean of vehicle control group+3×SD.

Example 19

Figure 32:
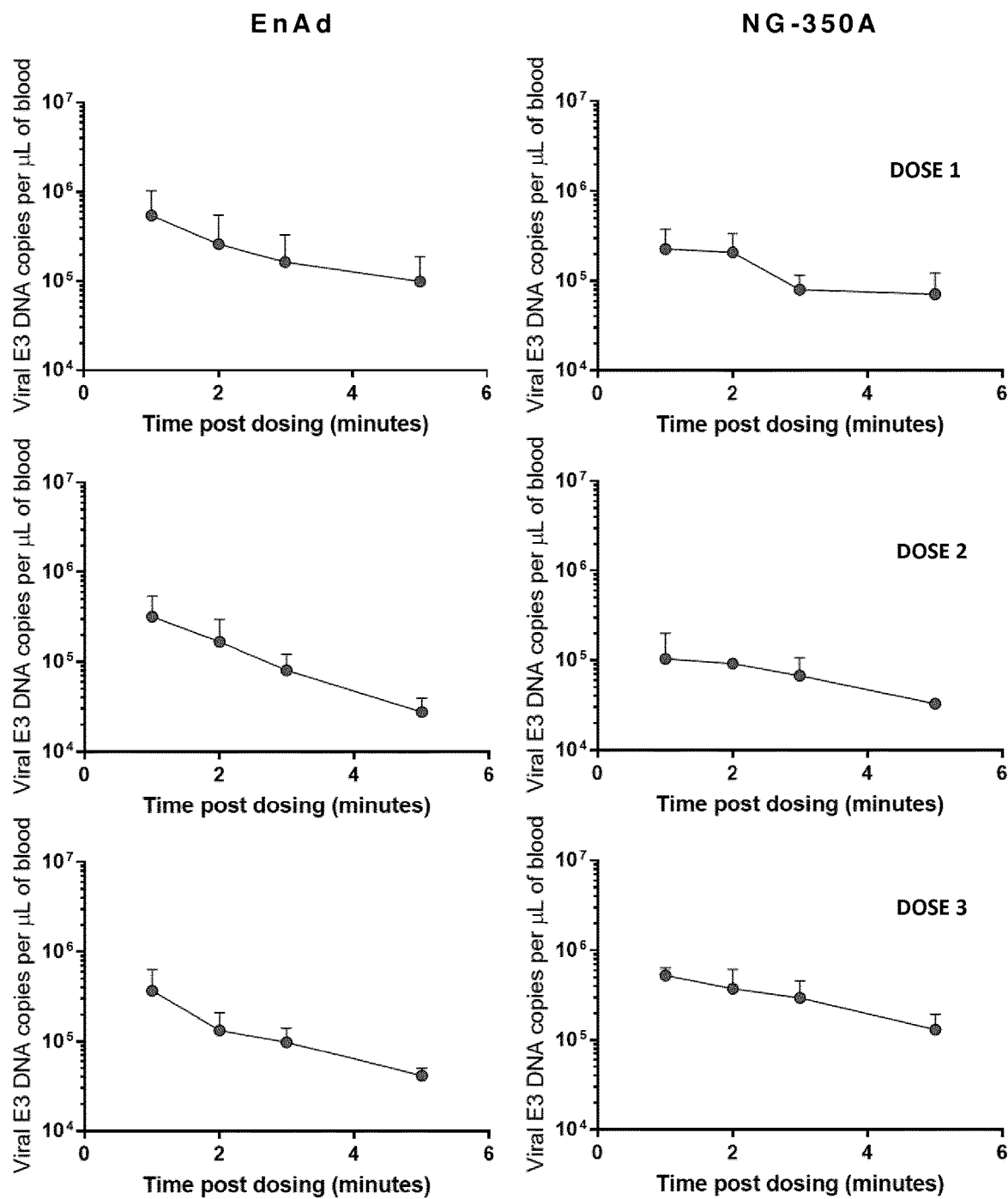
FIG. 32 shows virus pharmacokinetics in peripheral blood after each of three intravenous doses of EnAd or NG-350A.

Blood pharmacokinetics of NG-350A were compared to enadenotucirev (EnAd) after the administration of each of three intravenous (IV) doses of $2.2 \times 10^{10}$ viral particles on days 1, 3 and 5 in immunocompetent CD-1 mice. Female CD-1 mice were injected IV with $2.2 \times 10^{10}$ viral particles of either EnAd or NG-350A on days 1, 3 and 5. After each dose, a group of 4 mice treated with each virus were bled at 1, 2, 3, 5, 7, 10 and 60 minutes post-dosing. DNA was extracted and analysed by qPCR targeting the viral E3 gene common to both EnAd and NG-350A. Data shown in FIG. 32 represent 4 mice per group+SD. Where values fell below the limit of quantitation for the assay they were excluded. Data beyond 7 minutes was not plotted as they fell consistently below the limit of quantitation for the assay. NG-350A showed a comparable pharmacokinetic profile to that of EnAd.

Example 20

Figure 33:
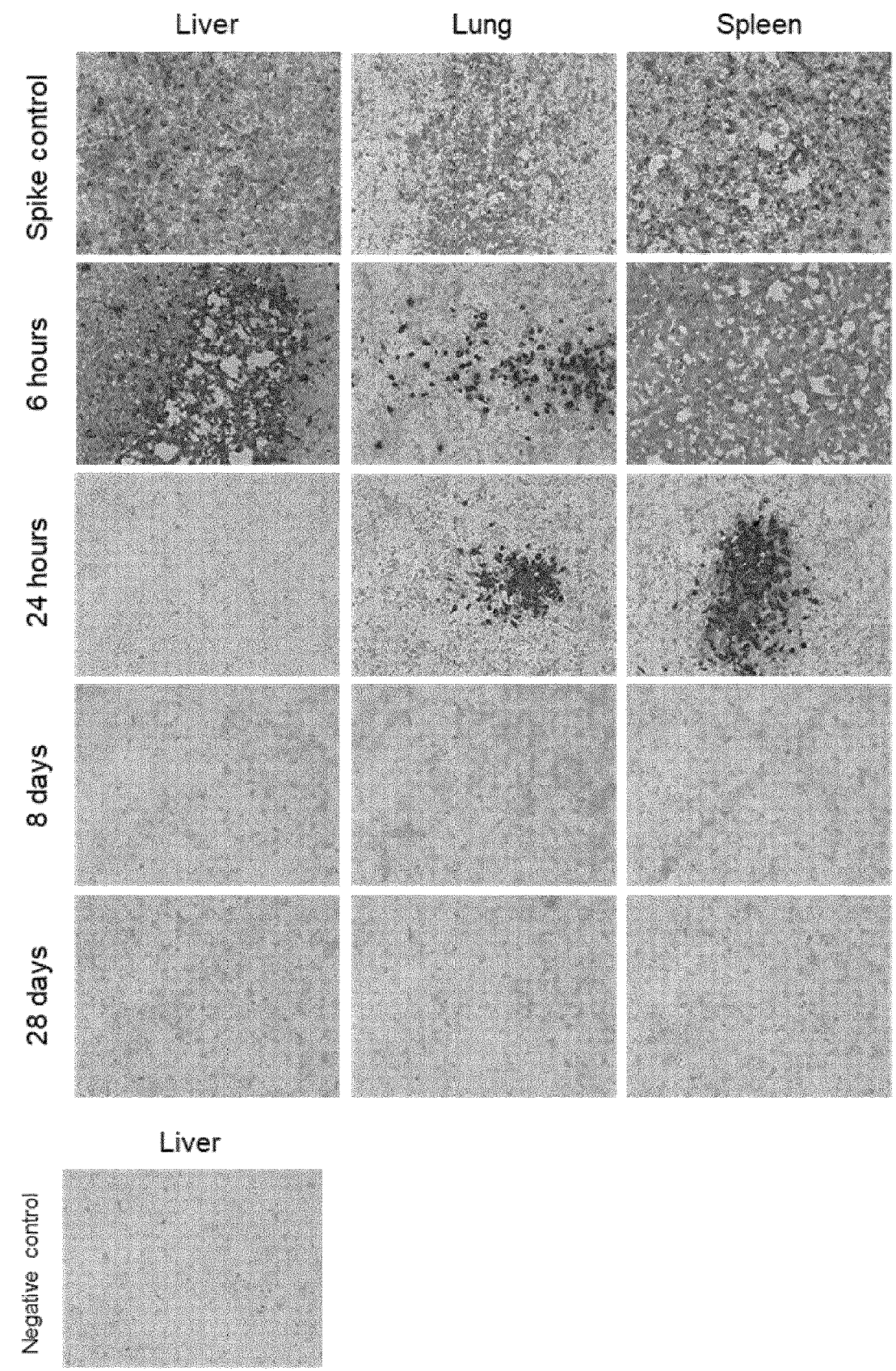
FIG. 33 shows recovery of live virus from murine tissues after a single intravenous dose of NG-350A virus particles.

Virus biodistribution was evaluated following dosing of mice with NG-350A by measuring the recovery of live virus from tissues after a single intravenous dose. Female CD-1 mice were injected IV with vehicle control or $2.2 \times 10^{10}$ particles of NG-350A. Groups of mice were euthanised at either 6 hours, 24 hours, 8 days or 28 days post dosing and their liver, lungs and spleens were resected and immediately frozen on dry ice. Samples were later thawed, homogenised in a protein-preserving lysis buffer and the lysate was diluted and added to confluent A549 monolayers, with NG-350A-spiked tissue homogenate for each organ as a positive control and negative controls. Monolayers were cultured for 96 hours before being fixed and subjected to an immunostaining assay utilising an anti-adenovirus hexon antibody. The data are represented by sample photos of each well in FIG. 33. Hexon positive cells stained brown (shown as dark grey in the figure). No live virus could be detected in liver, lung or spleen of mice (the primary sites of virus biodistribution in mice) later than 24 hours.

Example 21

In this series of studies, NG-350A virus activity was assessed in vivo in human tumor xenograft bearing immunodeficient mice.

Figure 34:
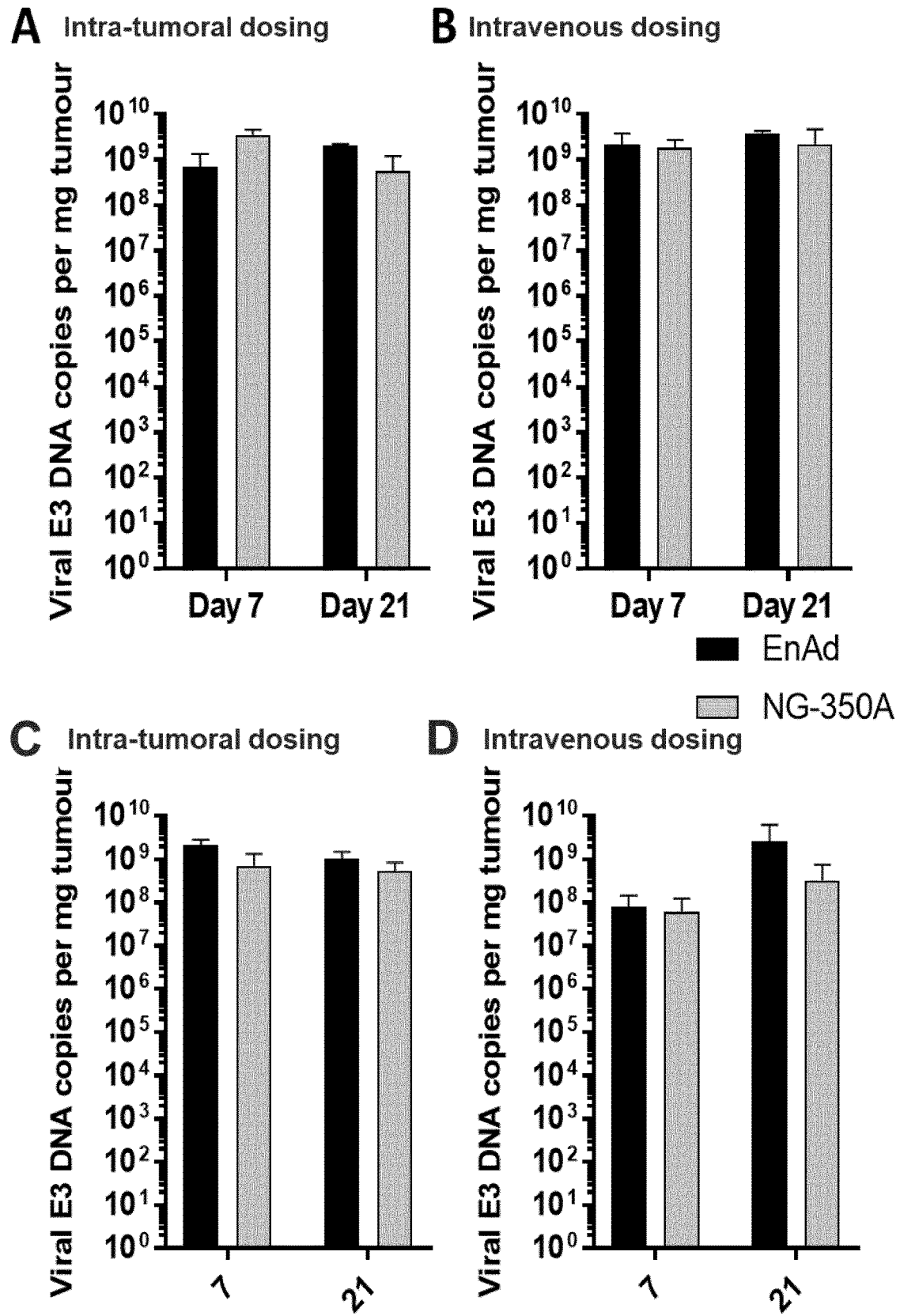
FIG. 34 shows virus genome replication in subcutaneous A549 (A&B) and HCT116 (C&D) tumours after three IV injections or a single fractionated IT dose of NG-350A or EnAd.

Virus replication was evaluated in subcutaneous A549 lung cell line tumours after three IV injections or a single fractionated intratumoral (IT) dose. Female SCID mice were implanted subcutaneously with A549 tumour cells on their flank and injected either IT or IV with virus or control once tumours reached at least 50 mm$^3$. IT dosed mice were injected with two 10 μL injections of PBS, or 2.2×10$^9$ viral particles of either EnAd or NG-350A into spatially separate regions of the tumour for a total dose of 20 μL/4.4×10$^9$ viral particles. IV dosed mice were injected with 100 μL of PBS, or 2.2×10$^9$ viral particles of either EnAd or NG-350A on days 1, 3 and 5 for a total dose of 300 μL/6.6×10$^9$ viral particles. Tumours were resected from mice after euthanasia, either 7 or 21 days post-dosing, and frozen. Tumours were later homogenised, DNA extracted and analysed by qPCR using primers and probe targeting the viral E3 region common to both EnAd and NG-350A. Data shown in FIGS. 34 A&B represent 2-4 mice per group+/−SD. NG-350A showed comparable genome replication in the A549 tumour xenografts to that of EnAd following either IT (FIG. 34A) or IV (FIG. 34B) dosing.

This experiment was also repeated using a second tumour xenograft model using the HCT-116 colorectal cancer cell line. Female SCID mice were implanted subcutaneously with HCT116 tumour cells on their flank and injected either IT or IV with virus or control once tumours reached at least 50 mm$^3$. IT dosed mice were injected with two 10 μL injections of PBS, or 2.2×10$^9$ viral particles of either EnAd or NG-350A into spatially separate regions of the tumour for a total dose of 20 μL/4.4×10$^9$ viral particles. IV dosed mice were injected with 100 μL of PBS, or 2.2×10$^9$ viral particles of either EnAd or NG-350A on days 1, 3 and 5 for a total dose of 300 μL/6.6×10$^9$ viral particles. Tumours were resected from mice after euthanasia, either 7 or 21 days post-dosing, and frozen. Tumours were later homogenised, DNA extracted and analysed by qPCR using primers and probe targeting the viral E3 region common to both EnAd and NG-350A. Data shown in FIGS. 34 C&D represent 2-4 mice per group+/−SD. NG-350A showed comparable genome replication in the HCT-116 tumour xenografts to that of EnAd following either IT (FIG. 34C) or IV (FIG. 34D) dosing.

Figure 35:
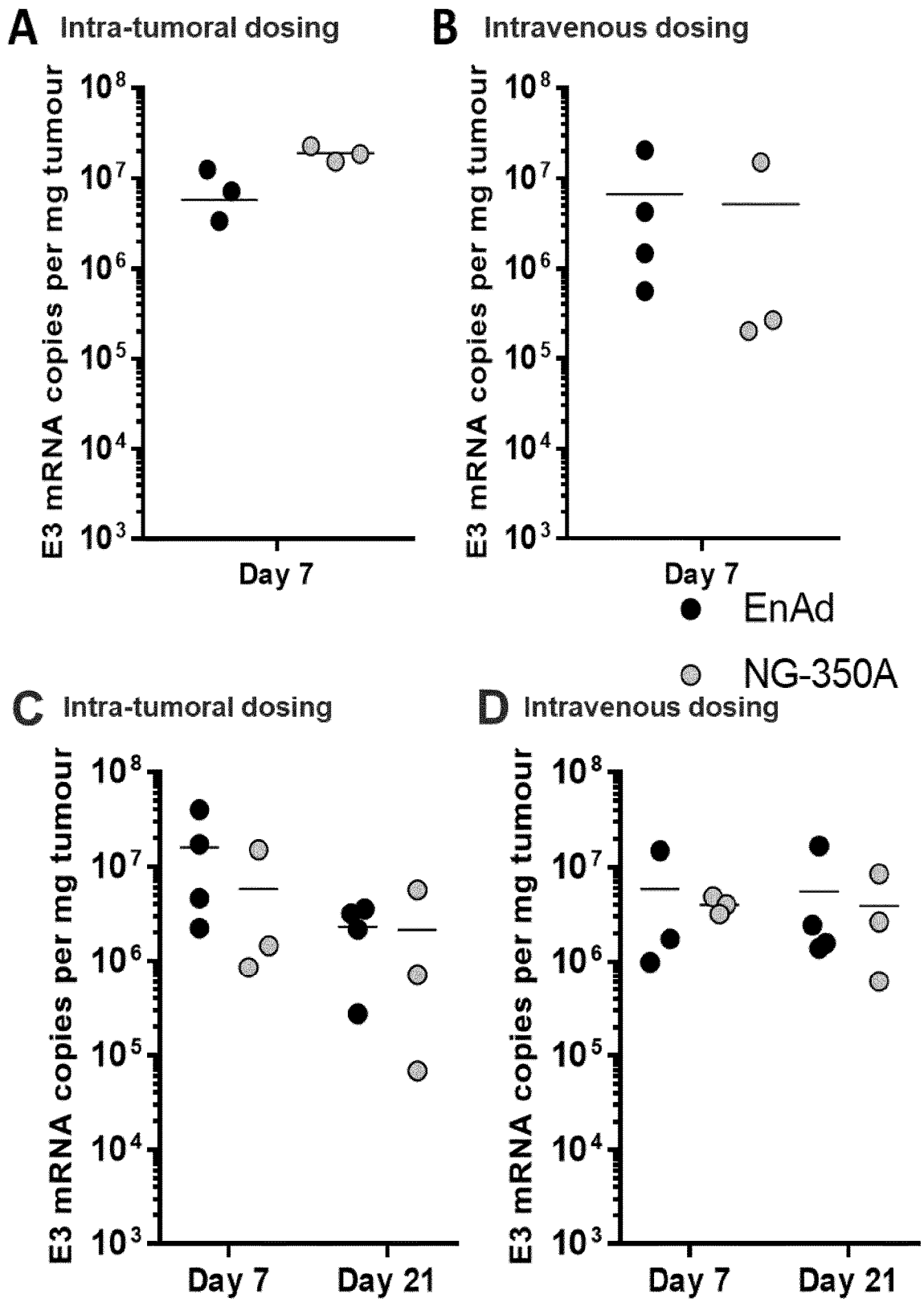
FIG. 35 shows virus E3 mRNA expression in subcutaneous A549 (A&B) or HCT-116 (C&D) tumours after three IV injections or a single fractionated IT dose of NG-350A or EnAd.

In similar experiments with both A549 and HCT-116 subcutaneous xenograft tumours in SCID mice, virus RNA expression was measured in the tumours. Female SCID mice were implanted subcutaneously with A549 or HCT-116 tumour cells on their flank and injected either IT or IV with virus or control once tumours reached at least 50 mm$^3$. IT dosed mice were injected with two 10 μL injections of PBS, or 2.2×10$^9$ viral particles of either EnAd or NG-350A into spatially separate regions of the tumour for a total dose of 20 μL/4.4×10$^9$ viral particles. IV dosed mice were injected with 100 μL of PBS, or 2.2×10$^9$ viral particles of either EnAd or NG-350A on days 1, 3 and 5 for a total dose of 300 μL/6.6×10$^9$ viral particles. Tumours were resected from mice after euthanasia, 7 days post-dosing, and frozen. Tumours were later homogenised, RNA extracted and analysed by RT-qPCR using primers and probe targeting viral E3 mRNA common to both EnAd and NG-350A. Data shown in FIG. 35 represent 3-4 mice per group. Black lines represent the mean. A549 IT (FIG. 35A), IV (FIG. 35B), HCT-116 IT (FIG. 35C) and HCT-116 IV (FIG. 35D) show comparable virus E3 mRNA expression following either NG-350A or EnAd dosing.

Figure 36:
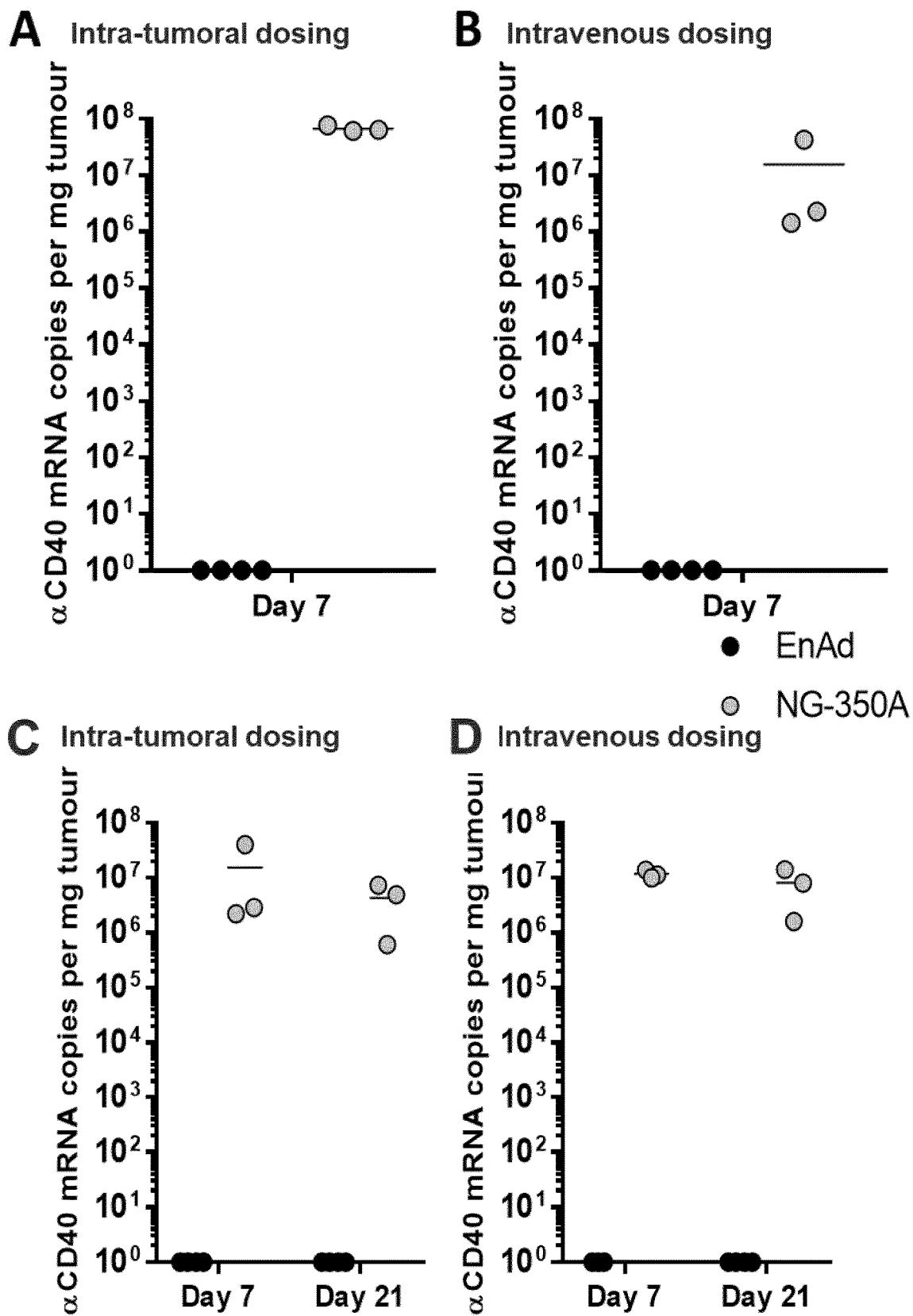
FIG. 36 shows anti-CD40 agonist antibody transgene mRNA expression in subcutaneous A549 (A&B) and HCT-116 (C&D) tumours after three IV injections or a single fractionated IT dose of NG-350A or EnAd.

Levels of anti-CD40 antibody transgene mRNA expression were also measured in the same subcutaneous A549 and HCT-116 xenograft tumour RNA samples. RNA was analysed by RT-qPCR using primers and probe targeting αCD40 antibody transgene mRNA. Data shown in FIG. 36 represent 3-4 mice per group. Black lines represent the mean. Anti-CD40 antibody transgene mRNA expression was readily detected only in NG-350A treated tumours. A549 IT (FIG. 36A), IV (FIG. 36B), HCT-116 IT (FIG. 36C) and HCT-116 IV (FIG. 36D).

Levels of anti-CD40 antibody protein were also measured in both tumour lysates and sera of mice bearing A549 tumours using an IgG2 ELISA. The data shown in FIG. 37 show selective detection of antibody following NG-350A administration, either IT (A) or IV (B), with higher levels in tumours than in the blood.

```
SEQUENCES
anti-CD40 VH chain amino acid sequence
                                                     SEQ ID NO. 4
QVQLVQSGAEVKKPGASVKVSCKASGYTFTGYYMHWVRQAPGQGLEWMGWINPDSGGTNYAQKFQGR

VTMTRDTSISTAYMELNRLRSDDTAVYYCARDQPLGYCTNGVCSYFDYWGQGTLVTVSS antibody constant heavy chain amino acid sequence
                                                     SEQ ID NO. 5
ASTKGPSVFPLAPCSRSTSESTAALGCLVKDYFPEPVTVSWNSGALTSGVHTFPAVLQSSGLYSLSS

VVTVPSSNFGTQTYTCNVDHKPSNTKVDKTVERKCCVECPPCPAPPVAGPSVFLFPPKPKDTLMISR

TPEVTCVVVDVSHEDPEVQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGFYPSDIAVEWESNGQPEN

NYKTTPPMLDSDGSFFLYSKLTVDKSRWQQGNVFSCSVMHEALHNHYTQKSLSLSPGK anti-CD40 VL chain amino acid sequence
                                                     SEQ ID NO. 8
DIQMTQSPSSVSASVGDRVTITCRASQGIYSWLAWYQQKPGKAPNLLIYTASTLQSGVPSRFSG

SGSGTDFTLTISSLQPEDFATYYCQQANIFPLTFGGGTKVEIK
``` constant light chain amino acid sequence

SEQ ID NO. 9

RTVAAPSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

NG-350A transgene cassette nucleic acid sequence

SEQ ID NO. 12

```
GCGATCGCCAGGCCCACCATGGACTGGACCTGGCGCATCCTGTTCTTGGTGGCAGCTGCTACGG

GAGCTCATTCCCAGGTGCAGCTGGTGCAATCCGGCGCTGAGGTGAAGAAACCCGGGGCTTCAGT

CAAAGTCAGCTGCAAGGCTAGCGGCTACACCTTTACTGGCTATTACATGCACTGGGTGAGGCAG

GCTCCGGGACAGGGTCTGGAATGGATGGGATGGATCAATCCGGACAGCGGCGGGACCAATTACG

CACAAAAGTTCCAAGGCCGCGTGACGATGACCCGGGACACTTCGATCTCAACCGCCTACATGGA

GCTGAACCGCCTGAGGTCGGATGACACCGCTGTGTACTACTGCGCTCGCGACCAACCCCTGGGG

TACTGCACCAACGGAGTGTGTTCATACTTCGACTACGGGGCCAAGGCACGCTGGTCACTGTGT

CATCGGCGTCCACTAAGGGCCCGTCGGTCTTCCCACTAGCTCCGTGCTCGCGGTCGACTTCGGA

ATCAACTGCGGCACTCGGATGCCTTGTCAAGGACTACTTCCCAGAACCCGTGACCGTCTCGTGG

AACTCAGGCGCCCTGACGAGCGGTGTCCACACTTTCCCGGCGGTGCTGCAGTCATCGGGCTAT

ACAGCCTGAGCAGCGTGGTTACTGTGCCGTCATCAAACTTCGGGACCCAGACTTACACTTGCAA

TGTGGACCACAAGCCGTCAAATACCAAAGTGGACAAGACTGTGGAACGCAAATGTTGCGTGGAA

TGCCCTCCGTGCCCGGCCCCCCCAGTCGCTGGCCCATCCGTGTTCCTCTTCCCTCCGAAGCCAA

AAGACACTCTGATGATTTCGAGAACTCCGGAGGTCACTTGCGTGGTGGTCGACGTGTCGCACGA

GGATCCAGAGGTGCAGTTCAACTGGTACGTGGATGGAGTGGAGGTGCACAATGCCAAGACCAAG

CCGCGCGAAGAACAATTCAACTCCACCTTTCGGGTCGTGTCCGTGCTGACCGTGGTACACCAAG

ACTGGCTGAACGGAAAGGAGTACAAATGCAAGGTGAGCAACAAGGGGCTGCCGGCTCCAATCGA

AAAGACCATCTCAAAGACTAAGGGGCAACCTCGCGAGCCACAGGTGTATACCCTGCCTCCAAGC

AGGGAGGAAATGACCAAAAACCAGGTGAGCCTGACCTGTCTGGTGAAGGGCTTTTACCCCAGCG

ACATCGCCGTCGAGTGGGAAAGCAACGGACAACCCGAGAACAACTACAAGACCACTCCGCCCAT

GCTGGACTCCGACGGGTCATTTTTCCTGTACTCAAAGCTGACTGTGGACAAGTCCCGGTGGCAG

CAAGGTAACGTGTTCTCCTGCTCGGTGATGCACGAAGCTTTGCACAACCACTACACTCAAAAGT

CACTTTCCTTGTCACCGGGCAAGGGGTCGGGCGCCACTAACTTTTCCTTGCTCAAGCAGGCGGG

CGATGTGGAGGAGAATCCGGGCCCGCGCCTCCCGGCGCAACTGCTGGGCCTCCTCCTCCTCTGG

TTTCCCGGCTCCCGCTGTGACATCCAGATGACTCAGTCGCCCAGCTCCGTGTCCGCATCGGTGG

GGGACAGAGTCACCATCACCTGCAGAGCTTCACAAGGGATCTATTCCTGGCTGGCGTGGTATCA

GCAGAAGCCTGGAAAGGCCCCCAACCTCCTGATTTACACCGCATCGACTCTCCAGTCAGGCGTG

CCATCCCGGTTCTCAGGGTCCGGCTCCGGAACCGACTTCACTCTGACTATCAGCTCCCTGCAAC

CAGAAGATTTCGCTACCTACTACTGCCAGCAGGCAAACATCTTTCCGCTAACTTTCGGCGGAGG

CACGAAGGTGGAGATCAAGAGAACCGTGGCGGCCCCTTCCGTCTTCATCTTCCCACCGTCAGAC

GAACAACTCAAATCCGGTACCGCCTCCGTCGTGTGCCTGCTCAATAACTTCTATCCACGCGAGG

CCAAGGTCCAGTGGAAAGTGGATAACGCCCTGCAGTCCGGAAACAGCCAGGAGTCAGTGACCGA

ACAGGATTCCAAGGACAGCACTTACTCGCTCTCAAGCACCCTCACCCTGTCGAAGGCGGATTAC

GAGAAGCACAAAGTCTACGCCTGCGAAGTGACTCATCAAGGACTCTCATCACCGGTAACTAAGA

GCTTCAATCGCGGAGAATGCTAGGCTAGCTTGACTGACTGAGATACAGCGTACCTTCAGCTCAC

AGACATGATAAGATACATTGATGAGTTTGGACAAACCACAACTAGAATGCAGTGAAAAAAATGC
```

-continued

TTTATTTGTGAAATTTGTGATGCTATTGCTTTATTTGTAACCATTATAAGCTGCAATAAACAAG

TTAACAACAACAATTGCATTCATTTTATGTTTCAGGTTCAGGGGGAGGTGTGGGAGGTTTTTTA

AAGCAAGTAAAACCTCTACAAATGTGGTCCTGCAGG

---

The invention claimed is:

1. An oncolytic virus comprising a transgene cassette encoding an anti-CD40 antibody or binding fragment thereof, wherein the transgene cassette comprises SEQ ID NO: 12.

2. An oncolytic virus according to claim 1, wherein the virus is selected from an adenovirus, herpes simplex virus, reovirus, measles virus, Newcastle disease virus, Seneca Valley virus, Vesicular stomatitis virus, polio virus, ECHO enterovirus, Coxsackie virus, and vaccinia virus.

3. An oncolytic virus according to claim 1, wherein the virus is selected from the group consisting of Enadenotucirev, talimogene laherparepvec, RIGVIR, Ad5-yCD/mutTKSR39rep-hIL12, CVA21, CG0070, DNX-2401, G207, HF10, JX-594, MG1-MA3, MV-NIS, OBP-301, Pelareorep, and Toca 511.

4. An oncolytic virus according to claim 1, wherein the virus comprises SEQ ID NO:1.

5. An oncolytic virus according to claim 4, which consists of SEQ ID NO: 1.

6. A pharmaceutical composition comprising a virus according to claim 1, and a pharmaceutically acceptable excipient, diluent or carrier.

7. A method of treating a disease comprising administering a therapeutically effective amount of an oncolytic virus according to claim 1 to a patient in need thereof.

8. The method according to claim 7, wherein the disease is cancer, insulin resistance, obesity and/or immune deficiency.

9. The method according to claim 7, wherein the disease is cancer.

10. A method of treating a disease comprising administering a therapeutically effective amount of a virus according to claim 1 and a further anti-cancer therapy to a patient in need thereof.

11. The method according to claim 10, wherein the further anti-cancer therapy is chemotherapy.

12. The method according to claim 10, wherein the further anti-cancer therapy is a check point inhibitor.

13. The method according to claim 12, wherein the anti-cancer therapy is selected from the group comprising a PD-1 inhibitor, a PD-L1 inhibitor, a CTLA-4 inhibitor, a TIM-3 inhibitor, a LAG-3 inhibitor, a TIGIT inhibitor, a B7-H3 (CD276) inhibitor, a B7-H4 (B7S1) inhibitor, a B7H7 (HHLA2) inhibitor, a CD96 inhibitor, a VISTA inhibitor and a combination of two or more of the same.

14. The method according to claim 13, wherein the inhibitor is an antibody or binding fragment thereof.

15. The method according to claim 10, wherein the further anti-cancer therapy is a costimulatory pathway agonist.

16. The method according to claim 15, wherein the further anti-cancer therapy is selected from the group comprising a CD27 agonist, a CD28 agonist, an ICOS agonist, a TMIGD2 (IGPR-1/CD28H) agonist, a CD226 agonist, an OX40 agonist, a 4-1BB agonist, and a combination of two or more of the same.

17. The method according to claim 16, wherein the therapy is an antibody or binding fragment thereof.

18. The method according to claim 10, wherein the further anti-cancer therapy activates immune responses or reverses suppression of immune responses.

* * * * *

SEQUENCE LISTING

<160> NUMBER OF SEQ ID NOS: 27

<210> SEQ ID NO 1
<211> LENGTH: 34794
<212> TYPE: DNA
<213> ORGANISM: Artificial Sequence
<220> FEATURE:
<223> OTHER INFORMATION: NG-350A genome sequence

<400> SEQUENCE: 1

```
tctatctata taatatacct tatagatgga atggtgccaa tatgtaaatg aggtgatttt      60
aaaaagtgtg gatcgtgtgg tgattggctg tggggttaac ggctaaaagg ggcggtgcga     120
ccgtgggaaa atgacgtttt gtgggggtgg agtttttttg caagttgtcg cgggaaatgt     180
gacgcataaa aaggcttttt tctcacggaa ctacttagtt ttcccacggt atttaacagg     240
aaatgaggta gttttgaccg gatgcaagtg aaaattgttg attttcgcgc gaaaactgaa     300
tgaggaagtg tttttctgaa taatgtgta tttatggcag ggtggagtat ttgttcaggg     360
ccaggtagac tttgacccat tacgtggagg tttcgattac cgtgtttttt acctgaattt     420
ccgcgtaccg tgtcaaagtc ttctgttttt acgtaggtgt cagctgatcg ctagggtatt     480
tatacctcag ggtttgtgtc aagaggccac tcttgagtgc cagcgagaag agttttctcc     540
tctgcgccgg cagtttaata ataaaaaaat gagagatttg cgatttctgc ctcaggaaat     600
aatctctgct gagactggaa atgaaatatt ggagcttgtg gtgcacgccc tgatgggaga     660
cgatccggag ccacctgtgc agcttttga gcctcctacg cttcaggaac tgtatgattt      720
agaggtagag ggatcggagg attctaatga ggaagctgta aatggctttt ttaccgattc     780
tatgctttta gctgctaatg aagggttaga attagatccg cctttggaca cttttgatac     840
tccaggggta attgtggaaa gcggtacagg tgtaagaaaa ttacctgatt tgagttccgt     900
ggactgtgat ttgcactgct atgaagacgg gtttcctccg agtgatgagg aggaccatga     960
aaaggagcag tccatgcaga ctgcagcggg tgagggagtg aaggctgcca atgttggttt    1020
tcagttggat tgcccggagc ttcctggaca tggctgtaag tcttgtgaat tcacaggaa     1080
aaatactgga gtaaaggaac tgttatgttc gctttgttat atgagaacgc actgccactt    1140
tatttacagt aagtgtgttt aagttaaaat ttaaaggaat atgctgtttt tcacatgtat    1200
attgagtgtg agttttgtgc ttcttattat aggtcctgtg tctgatgctg atgaatcacc    1260
atctcctgat tctactacct cacctcctga gattcaagca cctgttcctg tggacgtgcg    1320
caagcccatt cctgtgaagc ttaagcctgg gaaacgtcca gcagtggaaa aacttgagga    1380
cttgttacag ggtgggacg gacctttgga cttgagtaca cggaaacgtc caagacaata    1440
agtgttccat atccgtgttt acttaaggtg acgtcaatat ttgtgtgaca gtgcaatgta    1500
ataaaaatat gttaactgtt cactggtttt tattgctttt tgggcgggga ctcaggtata    1560
taagtagaag cagacctgtg tggttagctc ataggagctg gctttcatcc atggaggttt    1620
gggccatttt ggaagacctt aggaagacta ggcaactgtt agagaacgct tcggacggag    1680
tctccggttt ttggagattc tggttcgcta gtgaattagc tagggtagtt tttaggataa    1740
```

```
aacaggacta taaacaagaa tttgaaaagt tgttggtaga ttgcccagga cttttttgaag    1800 ctcttaattt gggccatcag gttcacttta aagaaaaagt tttatcagtt ttagactttt    1860 caacccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg aagggatga   2340 agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg ttgtagctt    2700 ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gttttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata acaagcttg ttgttgattt aaaatcaagt    3960
gtttttattt catttttcgc gcacggtatg ccctagacca ccgatctcta tcattgaaaa   4020
ctcggtggat ttttttccagg atcctataga ggtgggattg aatgtttaga tacatggca    4080 ttaggccgtc tttggggtgg agatagctcc attgaaggga ttcatgctcc ggggtagtgt   4140
```

```
tgtaaatcac ccagtcataa caaggtcgca gtgcatggtg ttgcacaata tcttttagaa    4200
gtaggctgat tgccacagat aagcccttgg tgtaggtgtt tacaaaccgg ttgagctggg    4260
atgggtgcat tcggggtgaa attatgtgca ttttggattg gattttttaag ttggcaatat   4320 tgccgccaag atcccgtctt gggttcatgt tatgaaggac caccaagacg gtgtatccgg    4380
tacatttagg aaatttatcg tgcagcttgg atggaaaagc gtggaaaaat tggagacac     4440 ccttgtgtcc tccaagattt tccatgcact catccatgat aatagcaatg gggccgtggg    4500
cagcggcgcg ggcaaacacg ttccgtgggt ctgacacatc atagttatgt tcctgagtta    4560
aatcatcata agccatttta atgaatttgg ggcggagagt accagattgg ggtatgaatg    4620
ttccttcggg ccccggagca tagttcccct cacagatttg catttcccaa gctttcagtt    4680
ccgagggtga atcatgtcc acctgggggg ctatgaaaaa caccgtttct ggggcggggg     4740
tgattaattg tgatgatagc aaatttctga gcaattgaga tttgccacat ccggtggggc    4800
cataaatgat tccgattacg ggttgcaggt ggtagtttag ggaacggcaa ctgccgtctt    4860
ctcgaagcaa gggggccacc tcgttcatca tttcccttac atgcatattt tcccgcacca    4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
gtctgttcca cagttcagtg atgtgttcta tggcatctcg atccagcaga cctcctcgtt    5100
tcgcgggttt ggacggctcc tggaataggg tatgagacga tgggcgtcca gcgctgccag    5160
ggttcggtcc ttccagggtc tcagtgttcg agtcagggtt gtttccgtca cagtgaaggg    5220
gtgtgcgcct gcttgggcgc ttgccagggt gcgcttcaga ctcatcctgc tggtcgaaaa    5280
cttctgtcgc ttggcgccct gtatgtcggc caagtagcag tttaccatga gttcgtagtt    5340
gagcgcctcg gctgcgtggc cttggcgcg gagcttacct ttggaagttt tcttgcatac    5400
cgggcagtat aggcatttca gcgcatacaa cttgggcgca aggaaaacgg attctgggga    5460
gtatgcatct gcgccgcagg aggcgcaaac agtttcacat tccaccagcc aggttaaatc    5520
cggttcattg gggtcaaaaa caagttttcc gccatatttt ttgatgcgtt tcttaccttt    5580
ggtctccatg agttcgtgtc ctcgttgagt gacaaacagg ctgtccgtgt ccccgtagac    5640
tgattttaca ggcctcttct ccagtggagt gcctcggtct tcttcgtaca ggaactctga    5700
ccactctgat acaaaggcgc gcgtccaggc cagcacaaag gaggctatgt gggaggggta    5760
gcgatcgttg tcaaccaggg ggtccacctt ttccaaagta tgcaaacaca tgtcaccctc    5820
ttcaacatcc aggaatgtga ttggcttgta ggtgtatttc acgtgacctg ggtccccgc    5880 tgggggggta taaaaggggg cggttctttg ctcttcctca ctgtcttccg gatcgctgtc    5940
caggaacgtc agctgttggg gtaggtattc cctctcgaag gcgggcatga cctctgcact    6000
caggttgtca gtttctaaga acgaggagga tttgatattg acagtgccgg ttgagatgcc    6060
tttcatgagg ttttcgtcca tctggtcaga aaacacaatt ttttttattgt caagtttggt    6120 ggcaaatgat ccatacaggg cgttggataa agtttggca atggatcgca tggtttggtt     6180
cttttccttg tccgcgcgct ctttggcggc gatgttgagt tggacatact cgcgtgccag    6240
gcacttccat tcggggaaga tagttgttaa ttcatctggc acgattctca cttgccaccc    6300
tcgattatgc aaggtaatta aatccacact ggtggccacc tcgcctcgaa ggggttcatt    6360
ggtccaacag agcctacctc ctttcctaga acagaaaggg ggaagtgggt ctagcataag    6420
ttcatcggga gggtctgcat ccatggtaaa gattcccgga agtaaatcct tatcaaaata    6480
```

```
gctgatggga gtggggtcat ctaaggccat ttgccattct cgagctgcca gtgcgcgctc    6540
atatgggtta aggggactgc cccatggcat gggatgggtg agtgcagagg catacatgcc    6600
acagatgtca tagacgtaga tgggatcctc aaagatgcct atgtaggttg gatagcatcg    6660 ccccctctg atacttgctc gcacatagtc atatagttca tgtgatggcg ctagcagccc    6720
cggacccaag ttggtgcgat tgggttttc tgttctgtag acgatctggc gaaagatggc    6780
gtgagaattg gaagagatgg tgggtctttg aaaaatgttg aaatgggcat gaggtagacc    6840
tacagagtct ctgacaaagt gggcataaga ttcttgaagc ttggttacca gttcggcggt    6900
gacaagtacg tctagggcgc agtagtcaag tgtttcttga atgatgtcat aacctggttg    6960
gttttctttt cccacagtt cgcggttgag aaggtattct tcgcgatcct tccagtactc    7020
ttctagcgga aacccgtctt tgtctgcacg gtaagatcct agcatgtaga actgattaac    7080
tgccttgtaa gggcagcagc ccttctctac gggtagagag tatgcttgag cagcttttcg    7140
tagcgaagcg tgagtaaggg caaaggtgtc tctgaccatg actttgagga attggtattt    7200
gaagtcgatg tcgtcacagg ctccctgttc ccagagttgg aagtctaccc gtttcttgta    7260
ggcggggttg ggcaaagcga aagtaacatc attgaagaga atcttgccgg ccctgggcat    7320
gaaattgcga gtgatgcgaa aaggctgtgg tacttccgct cggttattga taacctgggc    7380
agctaggacg atctcgtcga aaccgttgat gttgtgtcct acgatgtata attctatgaa    7440
acgcggcgtg cctctgacgt gaggtagctt actgagctca tcaaaggtta ggtctgtggg    7500
gtcagataag gcgtagtgtt cgagagccca ttcgtgcagg tgaggattcg ctttaaggaa    7560
ggaggaccag aggtccactg ccagtgctgt ttgtaactgg tcccggtact gacgaaaatg    7620
ccgtccgact gccattttt ctggggtgac gcaatagaag gtttgggggt cctgccgcca    7680
gcgatcccac ttgagttta tggcgaggtc ataggcgatg ttgacgagcc gctggtctcc    7740
agagagtttc atgaccagca tgaaggggat tagctgcttg ccaaaggacc ccatccaggt    7800
gtaggtttcc acatcgtagg tgagaaagag ccttttctgtg cgaggatgag agccaatcgg    7860
gaagaactgg atctcctgcc accagttgga ggaatggctg ttgatgtgat ggaagtagaa    7920
ctccctgcga cgcgccgagc attcatgctt gtgcttgtac agacggccgc agtagtcgca    7980
gcgttgcacg ggttgtatct cgtgaatgag ttgtacctgg cttcccttga cgagaaattt    8040
cagtgggaag ccgaggcctg gcgattgtat tcgtgctttt actatgttgt ctgcatcggc    8100
ctgttcatct tctgtctcga tggtggtcat gctgacgagc cctcgcggga ggcaagtcca    8160
gacctcggcg cggcagggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
cattttggac ggcggtggct ctgttgcttc ttgcatgttt agaagcggtg tcgagggcgc    8460
gcaccgggcg gcaggggcgg ctcgggaccc ggcggcatgg ctggcagtgg tacgtcggcg    8520
ccgcgcgcgg gtaggttctg gtactgcgcc ctgagaagac tcgcatgcgc gacgacgcgg    8580
cggttgacat cctggatctg acgcctctgg gtgaaagcta ccggcccgt gagcttgaac    8640 ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacggtgg ccgcgaggtc gttggagatg    8820
cgcccaatga gttgagagaa tgcattcatg cccgcctcgt tccagacgcg gctgtagacc    8880
```

```
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggaggggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540 aaccttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt cggcgaggaa tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt ttttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
```

```
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg gaaaatatt  acgctcgcaa aatctacaag   11460
actccatacg ttcccataga caaggaggtg aagatagatg ggttctacat gcgcatgacg   11520
ctcaaggtct tgaccctgag cgatgatctt ggggtgtatc gcaatgacag aatgcatcgc   11580
gcggttagcg ccagcaggag gcgcgagtta agcgacaggg aactgatgca cagtttgcaa   11640
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940 catgcgttg  acgactcgca accccgaagc ctttagacag caaccccagg ccaaccgtct   12000
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt tccagcgtga   12240
tgccaacctg ggttcgctgg tggcgttaaa tgctttcttg agtactcagc ctgctaatgt   12300
gccgcgtggt caacaggatt atactaactt tttaagtgct ttgagactga tggtatcaga   12360
agtacctcag agcgaagtgt atcagtccgg tcctgattac ttctttcaga ctagcagaca   12420
gggcttgcag acggtaaatc tgagccagc  ttttaaaaac cttaaaggtt tgtggggagt   12480
gcatgccccg gtaggagaaa gagcaaccgt gtctagcttg ttaactccga actccgcct   12540 attattactg ttggtagctc ctttcaccga cagcggtagc atcgaccgta attcctattt   12600
gggttaccta ctaaacctgt atcgcgaagc catagggcaa agtcaggtgg acgagcagac   12660
ctatcaagaa attccccaag tcagtcgcgc tttgggacag gaagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac ctttcattaa caaactgctg gactacttgc acagagctgc   12960
cgctatgaac tctgattatt tcaccaatgc catcttaaac ccgcactggc tgcccccacc   13020
tggtttctac acgggcgaat atgacatgcc cgaccctaat gacggatttc tgtgggacga   13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca gtcctttttc ctagtctacc cttttctcta cacagtgtac gtagcagcga   13260
agtgggtaga ataagtcgcc cgagtttaat gggcgaagag gagtatctaa acgattcctt   13320
gctcagaccg gcaagagaaa aaaatttccc aaacaatgga atagaaagtt tggtggataa   13380
aatgagtaga tggaagactt atgctcagga tcacagagac gagcctggga tcatgggat   13440 tacaagtaga gcgagccgta gacgccagcg ccatgacaga cagaggggtc ttgtgtggga   13500
cgatgaggat tcgccgatg  atagcagcgt gctggacttg ggtgggagag gaaggggcaa   13560
cccgtttgct catttgcgcc ctcgcttggg tggtatgttg taaaaaaaaa taaaaaaaaa   13620
```

```
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
cctttgtgcc tccgcgatac ctggcaccta cggaggcag aaacagcatt cgttattcgg    13860
aactggcacc tcagtacgat accaccaggt tgtatctggt ggacaacaag tcggcggaca   13920
ttgcttctct gaactatcag aatgaccaca gcaacttctt gaccacggtg gtgcaaaaca   13980
atgactttac ccctacggaa gccagcaccc agaccattaa ctttgatgaa cgatcgcggt   14040
ggggcggtca gctaaagacc atcatgcata ctaacatgcc aaacgtgaac gagtatatgt   14100
ttagtaacaa gttcaaagcg cgtgtgatgg tgtccagaaa acctcccgac ggtgctgcag   14160
ttggggatac ttatgatcac aagcaggata ttttgaaata tgagtggttc gagtttactt   14220
tgccagaagg caacttttca gttactatga ctattgattt tgatgaacaat gccatcatag   14280 ataattactt gaaagtgggt agacagaatg gagtgcttga agtgacatt ggtgttaagt     14340 tcgacaccag gaacttcaag ctgggatggg atcccgaaac caagttgatc atgcctggag   14400
tgtatacgta tgaagccttc catcctgaca ttgtcttact gcctggctgc ggagtggatt   14460
ttaccgagag tcgtttgagc aaccttcttg gtatcagaaa aaaacagcca tttcaagagg   14520
gttttaagat tttgtatgaa gatttagaag gtggtaatat tccggccctc ttggatgtag   14580
atgcctatga gaacagtaag aaagaacaaa agccaaaat agaagctgct acagctgctg    14640
cagaagctaa ggcaaacata gttgccagcg actctacaag ggttgctaac gctggagagg   14700
tcagaggaga caattttgcg ccaacacctg ttccgactgc agaatcatta ttggccgatg   14760
tgtctgaagg aacggacgtg aaactcacta ttcaacctgt agaaaaagat agtaagaata   14820
gaagctataa tgtgttggaa gacaaaatca acacagccta tcgcagttgg tatctttcgt   14880
acaattatgg cgatcccgaa aaaggagtgc gttcctggac attgctcacc acctcagatg   14940
tcacctgcgg agcagagcag gtctactggt cgcttccaga catgatgaag gatcctgtca   15000
ctttccgctc cactagacaa gtcagtaact accctgtggt gggtgcagag cttatgcccg   15060
tcttctcaaa gagcttctac aacgaacaag ctgtgtactc ccagcagctc cgccagtcca   15120
cctcgcttac gcacgtcttc aaccgctttc ctgagaacca gattttaatc cgtccgccgg   15180
cgcccaccat taccaccgtc agtgaaaacg ttcctgctct cacagatcac gggaccctgc   15240
cgttgcgcag cagtatccgg ggagtccaac gtgtgaccgt tactgacgcc agacgccgca   15300
cctgtcccta cgtgtacaag gcactgggca tagtcgcacc gcgcgtcctt tcaagccgca   15360
ctttctaaaa aaaaaaaaaa tgtccattct tatctcgccc agtaataaca ccggttgggg   15420
tctgcgcgct ccaagcaaga tgtacggagg cgcacgcaaa cgttctaccc aacatcctgt   15480
ccgtgttcgc ggacattttc gcgctccatg gggcgccctc aagggccgca ctcgcgttcg   15540
aaccaccgtc gatgatgtaa tcgatcaggt ggttgccgac gcccgtaatt atactcctac   15600
tgcgcctaca tctactgtgg atgcagttat tgacagtgta gtggctgacg ctcgcaacta   15660
tgctcgacgt aagagccggc gaaggcgcat tgccagacgc caccgagcta ccactgccat   15720
gcgagccgca agagctctgc tacgaagagc tagacgcgtg gggcgaagag ccatgcttag   15780
ggcggccaga cgtgcagctt cgggcgccag cgccggcagg tcccgcaggc aagcagccgc   15840
tgtcgcagcg gcgactattg ccgacatggc ccaatcgcga agaggcaatg tatactgggt   15900
gcgtgacgct gccaccggtc aacgtgtacc cgtgcgcacc cgtcccctc gcacttagaa     15960
```

```
gatactgagc agtctccgat gttgtgtccc agcggcgagg atgtccaagc gcaaatacaa   16020
ggaagaaatg ctgcaggtta tcgcacctga agtctacggc caaccgttga aggatgaaaa   16080 aaaacccgc  aaaatcaagc gggttaaaaa ggacaaaaaa gaagaggaag atggcgatga   16140
tgggctggcg gagtttgtgc gcgagtttgc cccacggcga cgcgtgcaat ggcgtgggcg   16200
caaagttcga catgtgttga gacctggaac ttcggtggtc tttacacccg gcgagcgttc   16260
aagcgctact tttaagcgtt cctatgatga ggtgtacggg gatgatgata ttcttgagca   16320
ggcggctgac cgattaggcg agtttgctta tggcaagcgt agtagaataa cttccaagga   16380
tgagacagtg tcgatacccct tggatcatgg aaatcccacc cctagtctta aaccggtcac   16440
tttgcagcaa gtgttacccg taactccgcg aacaggtgtt aaacgcgaag gtgaagattt   16500
gtatcccact atgcaactga tggtacccaa acgccagaag ttggaggacg ttttggagaa   16560
agtaaaagtg gatccagata ttcaacctga ggttaaagtg agacccatta agcaggtagc   16620
gcctggtctg ggggtacaaa ctgtagacat taagattccc actgaaagta tggaagtgca   16680
aactgaaccc gcaaagccta ctgccacctc cactgaagtg caaacggatc catggatgcc   16740
catgcctatt acaactgacg ccgccggtcc cactcgaaga tcccgacgaa agtacggtcc   16800
agcaagtctg ttgatgccca attatgttgt acacccatct attattccta ctcctggtta   16860
ccgaggcact cgctactatc gcagccgaaa cagtacctcc cgccgtcgcc gcaagacacc   16920
tgcaaatcgc agtcgtcgcc gtagacgcac aagcaaaccg actcccggcg ccctggtgcg   16980
gcaagtgtac cgcaatggta gtgcggaacc tttgacactg ccgcgtgcgc gttaccatcc   17040
gagtatcatc acttaatcaa tgttgccgct gcctccttgc agatatggcc ctcacttgtc   17100
gccttcgcgt tcccatcact ggttaccgag gaagaaactc gcgccgtaga agagggatgt   17160
tgggacgcgg aatgcgacgc tacaggcgac ggcgtgctat ccgcaagcaa ttgcggggtg   17220
gttttttacc agccttaatt ccaattatcg ctgctgcaat ggcgcgata  ccaggcatag   17280 cttccgtggc ggttcaggcc tcgcaacgac attgacattg aaaaaaacg tataaataaa   17340 aaaaaaaaa tacaatggac tctgacactc ctggtcctgt gactatgttt tcttagagat   17400
ggaagacatc aatttttcat ccttggctcc gcgacacggc acgaagccgt acatgggcac   17460
ctggagcgac atcggcacga gccaactgaa cgggggcgcc ttcaattgga gcagtatctg   17520
gagcgggctt aaaaattttg gctcaaccat aaaaacatac gggaacaaag cttgaaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaaccccca ggtgaaatgc aagtggagga   17760
agaaattcct ccgccagaaa aacgaggcga caagcgtccg cgtcccgatt tggaagagac   17820
gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttggatttgc cccctcccccc tgctgctact gctgtacccg cttctaagcc   18000
tgtcgctgcc ccgaaaccag tcgccgtagc caggtcacgt cccgggggcg ctcctcgtcc   18060
aaatgcgcac tggcaaaata ctctgaacag catcgtgggt ctaggcgtgc aaagtgtaaa   18120
acgccgtcgc tgcttttaat taaatatgga gtagcgctta acttgcctat ctgtgtatat   18180
gtgtcattac acgccgtcac agcagcagag gaaaaaagga agaggtcgtg cgtcgacgct   18240
gagttacttt caagatggcc accccatcga tgctgcccca atgggcatac atgcacatcg   18300
ccggacagga tgcttcggag tacctgagtc cgggtctggt gcagttcgcc cgcgccacag   18360
```

```
acacctactt caatctggga aataagttta gaaatcccac cgtagcgccg acccacgatg    18420
tgaccaccga ccgtagccag cggctcatgt tgcgcttcgt gcccgttgac cgggaggaca    18480
atacatactc ttacaaagtg cggtacaccc tggccgtggg cgacaacaga gtgctggata    18540
tggccagcac gttctttgac attaggggtg tgttggacag aggtcccagt ttcaaaccct    18600
attctggtac ggcttacaac tccctggctc ctaaaggcgc tccaaataca tctcagtgga    18660
ttgcagaagg tgtaaaaaat acaactggtg aggaacacgt aacagaagag gaaaccaata    18720
ctactactta cacttttggc aatgctcctg taaaagctga agctgaaatt acaaaagaag    18780
gactcccagt aggtttggaa gtttcagatg aagaaagtaa accgatttat gctgataaaa    18840
catatcagcc agaacctcag ctgggagatg aaacttggac tgaccttgat ggaaaaaccg    18900
aaaagtatgg aggcagggct ctcaaacccg atactaagat gaaaccatgc tacgggtcct    18960
tgccaaaacc tactaatgtg aaaggcggtc aggcaaaaca aaaaacaacg gagcagccaa    19020
atcagaaagt cgaatatgat atcgacatgg agttttttga tgcggcatcg cagaaaacaa    19080
acttaagtcc taaaattgtc atgtatgcag aaaatgtaaa tttggaaact ccagacactc    19140
atgtagtgta caaacctgga acagaagaca caagttccga agctaatttg ggacaacaat    19200
ctatgcccaa cagacccaac tacattggct tcagagataa ctttattgga cttatgtact    19260
ataacagtac tggtaacatg ggggtgctgg ctggtcaagc gtctcagtta aatgcagtgg    19320
ttgacttgca ggacagaaac acagaacttt cttaccaact cttgcttgac tctctgggcg    19380
acagaaccag atactttagc atgtggaatc aggctgtgga cagttatgat cctgatgtac    19440
gtgttattga aaatcatggt gtggaagatg aacttcccaa ctactgtttt ccactggacg    19500
gcataggtgt tccaacaacc agttacaaat caatagttcc aaatggagac aatgcgccta    19560
attggaagga acctgaagta aatggaacaa gtgagatcgg cagggtaat ttgtttgcca    19620 tggaaattaa ccttcaagcc aatctatggc gaagtttcct ttattccaat gtggctctat    19680
atctcccaga ctcgtacaaa tacaccccgt ccaatgtcac tcttccagaa aacaaaaaca    19740
cctacgacta catgaacggg cgggtggtgc cgccatctct agtagacacc tatgtgaaca    19800
ttggtgccag gtggtctctg gatgccatgg acaatgtcaa cccattcaac caccaccgta    19860
acgctggctt gcgttaccga tccatgcttc tgggtaacgg acgttatgtg cctttccaca    19920
tacaagtgcc tcaaaaattc ttcgctgtta aaaacctgct gcttctccca ggctcctaca    19980
cttatgagtg gaactttagg aaggatgtga acatggttct acagagttcc ctcggtaacg    20040
acctgcgggt agatggcgcc agcatcagtt tcacgagcat caacctctat gctacttttt    20100
tccccatggc tcacaacacc gcttccaccc ttgaagccat gctgcggaat gacaccaatg    20160
atcagtcatt caacgactac ctatctgcag ctaacatgct ctaccccatt cctgccaatg    20220
caaccaatat tcccatttcc attccttctc gcaactgggc ggctttcaga ggctggtcat    20280
ttaccagact gaaaaccaaa gaaactccct cttggggtc tggatttgac ccctactttg    20340
tctattctgg ttctattccc tacctggatg gtaccttcta cctgaaccac acttttaaga    20400
aggtttccat catgtttgac tcttcagtga gctggcctgg aaatgacagg ttactatctc    20460
ctaacgaatt tgaaataaag cgcactgtgg atggcgaagg ctacaacgta gcccaatgca    20520
acatgaccaa agactggttc ttggtacaga tgctcgccaa ctacaacatc ggctatcagg    20580
gcttctacat tccagaagga tacaaagatc gcatgtattc attttttcaga aacttccagc    20640 ccatgagcag gcaggtggtt gatgaggtca attacaaaga cttcaaggcc gtcgccatac    20700
```

```
cctaccaaca caacaactct ggctttgtgg gttacatggc tccgaccatg cgccaaggtc    20760
aaccctatcc cgctaactat ccctatccac tcattggaac aactgccgta aatagtgtta    20820
cgcagaaaaa gttcttgtgt gacagaacca tgtggcgcat accgttctcg agcaacttca    20880
tgtctatggg ggcccttaca gacttgggac agaatatgct ctatgccaac tcagctcatg    20940
ctctggacat gacctttgag gtggatccca tggatgagcc caccctgctt tatcttctct    21000
tcgaagtttt cgacgtggtc agagtgcatc agccacaccg cggcatcatc gaggcagtct    21060
acctgcgtac accgttctcg gccggtaacg ctaccacgta agaagcttct tgcttcttgc    21120
aaatagcagc tgcaaccatg gcctgcggat cccaaaacgg ctccagcgag caagagctca    21180
gagccattgt ccaagacctg ggttgcggac cctatttttt gggaacctac gataagcgct    21240
tcccgggggtt catggccccc gataagctcg cctgtgccat tgtaaatacg gccgacgtg    21300
agacgggggg agagcactgg ttggctttcg gttggaaccc acgttctaac acctgctacc    21360
tttttgatcc ttttggattc tcggatgatc gtctcaaaca gatttaccag tttgaatatg    21420
agggtctcct gcgccgcagc gctcttgcta ccaaggaccg ctgtattacg ctggaaaaat    21480
ctacccagac cgtgcagggt ccccgttctg ccgcctgcgg acttttctgc tgcatgttcc    21540
ttcacgcctt tgtgcactgg cctgaccgtc ccatggacgg aaaccccacc atgaaattgc    21600
taactggagt gccaaacaac atgcttcatt ctcctaaagt ccagcccacc ctgtgtgaca    21660
atcaaaaagc actctaccat tttcttaata cccattcgcc ttattttcgc tcccatcgta    21720
cacacatcga aagggccact gcgttcgacc gtatggatgt tcaataatga ctcatgtaaa    21780
caacgtgttc aataaacatc actttatttt tttacatgta tcaaggctct gcattactta    21840
tttatttaca agtcgaatgg gttctgacga gaatcagaat gacccgcagg cagtgatacg    21900
ttgcggaact gatacttggg ttgccacttg aattcgggaa tcaccaactt gggaaccggt    21960
atatcgggca ggatgtcact ccacagcttt ctggtcagct gcaaagctcc aagcaggtca    22020
ggagccgaaa tcttgaaatc acaattagga ccagtgcttt gagcgcgaga gttgcggtac    22080
accggattgc agcactgaaa caccatcagc gacggatgtc tcacgcttgc cagcacggtg    22140
ggatctgcaa tcatgcccac atccagatct tcagcattgg caatgctgaa cggggtcatc    22200
ttgcaggtct gcctacccat ggcgggcacc caattaggct tgtggttgca atcgcagtgc    22260
aggggggatca gtatcatctt ggcctgatcc tgtctgattc ctggatacac ggctctcatg    22320
aaagcatcat attgcttgaa agcctgctgg gctttactac cctcggtata aacatcccg    22380
caggacctgc tcgaaaactg gttagctgca cagccggcat cattcacaca gcagcgggcg    22440
tcattgttag ctatttgcac cacacttctg ccccagcggt tttgggtgat tttggttcgc    22500
tcggattctc cctttaaggc tcgttgtccg ttctcgctgg ccacatccat ctcgataatc    22560
tgctccttct gaatcataat attgccatgc aggcacttca gcttgccctc ataatcattg    22620
cagccatgag gccacaacgc acagcctgta cattcccaat tatggtgggc gatctgagaa    22680
aaagaatgta tcattccctg cagaaatctt cccatcatcg tgctcagtgt cttgtgacta    22740
gtgaaagtta actggatgcc tcggtgctcc tcgtttacgt actggtgaca gatgcgcttg    22800
tattgttcgt gttgctcagg cattagttta aaagaggttc taagttcgtt atccagcctg    22860
tacttctcca tcagcagaca catcacttcc atgcctttct cccaagcaga caccagggg    22920
aagctaatcg gattcttaac agtgcaggca gcagctcctt tagccagagg gtcatcttta    22980
gcgatcttct caatgcttct tttgccatcc ttctcaacga tgcgcacggg cgggtagctg    23040
aaacccactg ctacaagttg cgcctcttct ctttcttctt cgctgtcttg actgatgtct    23100
```

| | | | | | |
|---|---|---|---|---|---|
| tgcatggga | tatgtttggt | cttccttggc | ttcttttggg | ggggtatcgg | aggaggagga | 23160 |
| ctgtcgctcc | gttccggaga | cagggaggat | tgtgacgttt | cgctcaccat | taccaactga | 23220 |
| ctgtcggtag | aagaacctga | ccccacacgg | cgacaggtgt | ttctcttcgg | gggcagaggt | 23280 |
| ggaggcgatt | gcgaagggct | gcggtccgac | ctggaaggcg | gatgactggc | agaacccctt | 23340 |
| ccgcgttcgg | gggtgtgctc | cctgtggcgg | tcgcttaact | gatttccttc | gcggctggcc | 23400 |
| attgtgttct | cctaggcaga | gaaacaacag | acatggaaac | tcagccattg | ctgtcaacat | 23460 |
| cgccacgagt | gccatcacat | ctcgtcctca | gcgacgagga | aaaggagcag | agcttaagca | 23520 |
| ttccaccgcc | cagtcctgcc | accacctcta | ccctagaaga | taaggaggtc | gacgcatctc | 23580 |
| atgacatgca | gaataaaaaa | gcgaaagagt | ctgagacaga | catcgagcaa | gacccgggct | 23640 |
| atgtgacacc | ggtggaacac | gaggaagagt | tgaaacgctt | tctagagaga | gaggatgaaa | 23700 |
| actgcccaaa | acaacgagca | gataactatc | accaagatgc | tggaaatagg | gatcagaaca | 23760 |
| ccgactacct | catagggctt | gacggggaag | acgcgctcct | taaacatcta | gcaagacagt | 23820 |
| cgctcatagt | caaggatgca | ttattggaca | gaactgaagt | gcccatcagt | gtggaagagc | 23880 |
| tcagccgcgc | ctacgagctt | aacctctttt | cacctcgtac | tcccccaaa | cgtcagccaa | 23940 |
| acggcacctg | cgagccaaat | cctcgcttaa | acttttatcc | agcttttgct | gtgccagaag | 24000 |
| tactggctac | ctatcacatc | ttttttaaaa | atcaaaaaat | tccagtctcc | tgccgcgcta | 24060 |
| atcgcacccg | cgccgatgcc | ctactcaatc | tgggacctgg | ttcacgctta | cctgatatag | 24120 |
| cttccttgga | agaggttcca | aagatcttcg | agggtctggg | caataatgag | actcgggccg | 24180 |
| caaatgctct | gcaaaaggga | gaaaatggca | tggatgagca | tcacagcgtt | ctggtggaat | 24240 |
| tggaaggcga | taatgccaga | ctcgcagtac | tcaagcgaag | catcgaggtc | acacacttcg | 24300 |
| catatcccgc | tgtcaacctg | cccctaaag | tcatgacggc | ggtcatggac | cagttactca | 24360 |
| ttaagcgcgc | aagtcccctt | tcagaagaca | tgcatgaccc | agatgcctgt | gatgagggta | 24420 |
| aaccagtggt | cagtgatgag | cagctaaccc | gatggctggg | caccgactct | cccagggatt | 24480 |
| tggaagagcg | tcgcaagctt | atgatggccg | tggtgctggt | taccgtagaa | ctagagtgtc | 24540 |
| tccgacgttt | ctttaccgat | tcagaaacct | tgcgcaaact | cgaagagaat | ctgcactaca | 24600 |
| cttttagaca | cggctttgtg | cggcaggcat | gcaagatatc | taacgtggaa | ctcaccaacc | 24660 |
| tggtttccta | catgggtatt | ctgcatgaga | atcgcctagg | acaaagcgtg | ctgcacagca | 24720 |
| ccctgaaggg | ggaagcccgc | cgtgattaca | tccgcgattg | tgtctatctg | tacctgtgcc | 24780 |
| acacgtggca | aaccggcatg | ggtgtatggc | agcaatgttt | agaagaacag | aacttgaaag | 24840 |
| agcttgacaa | gctcttacag | aaatctctta | aggttctgtg | gacagggttc | gacgagcgca | 24900 |
| ccgtcgcttc | cgacctggca | gacctcatct | tcccagagcg | tctcagggtt | actttgcgaa | 24960 |
| acggattgcc | tgactttatg | agccagagca | tgcttaacaa | ttttcgctct | ttcatcctgg | 25020 |
| aacgctccgg | tatcctgccc | gccacctgct | gcgcactgcc | ctccgacttt | gtgcctctca | 25080 |
| cctaccgcga | gtgcccccg | ccgctatgga | gtcactgcta | cctgttccgt | ctggccaact | 25140 |
| atctctccta | ccactcggat | gtgatcgagg | atgtgagcgg | agacggcttg | ctggagtgtc | 25200 |
| actgccgctg | caatctgtgc | acgccccacc | ggtccctagc | ttgcaacccc | cagttgatga | 25260 |
| gcgaaaccca | gataataggc | accttgaat | tgcaaggccc | cagcagccaa | ggcgatgggt | 25320 |
| cttctcctgg | gcaaagttta | aaactgaccc | cgggactgtg | gacctccgcc | tacttgcgca | 25380 |
| agtttgctcc | ggaagattac | caccccctatg | aaatcaagtt | ctatgaggac | caatcacagc | 25440 |

```
ctccaaaggc cgaactttcg gcctgcgtca tcacccaggg ggcaattctg gcccaattgc    25500
aagccatcca aaaatcccgc caagaatttc tactgaaaaa gggtaagggg gtctaccttg    25560 accccccagac cggcgaggaa ctcaacacaa ggttccctca ggatgtccca acgacgagaa   25620
aacaagaagt tgaaggtgca gccgccgccc ccagaagata tggaggaaga ttgggacagt    25680
caggcagagg aggcggagga ggacagtctg gaggacagtc tggaggaaga cagtttggag    25740
gaggaaaacg aggaggcaga ggaggtggaa gaagtaaccg ccgacaaaca gttatcctcg    25800
gctgcggaga caagcaacag cgctaccatc tccgctccga gtcgaggaac ccggcggcgt    25860
cccagcagta gatgggacga gaccggacgc ttcccgaacc caaccagcgc ttccaagacc    25920
ggtaagaagg atcggcaggg atacaagtcc tggcggggc ataagaatgc catcatctcc     25980
tgcttgcatg agtgcggggg caacatatcc ttcacgcggc gctacttgct attccaccat    26040
ggggtgaact ttccgcgcaa tgttttgcat tactaccgtc acctccacag cccctactat    26100
agccagcaaa tcccggcagt ctcgacagat aaagacagcg gcggcgacct ccaacagaaa    26160
accagcagcg gcagttagaa aatacacaac aagtgcagca acaggaggat taaagattac    26220
agccaacgag ccagcgcaaa cccgagagtt aagaaatcgg atctttccaa ccctgtatgc    26280
catcttccag cagagtcggg gtcaagagca ggaactgaaa ataaaaaacc gatctctgcg    26340
ttcgctcacc agaagttgtt tgtatcacaa gagcgaagat caacttcagc gcactctcga    26400
ggacgccgag gctctcttca acaagtactg cgcgctgact cttaaagagt aggcagcgac    26460
cgcgcttatt caaaaaggc gggaattaca tcatcctcga catgagtaaa gaaattccca    26520
cgccttacat gtggagttat caaccccaaa tgggattggc ggcaggcgcc tcccaggact    26580
actccacccg catgaattgg ctcagcgccg ggccttctat gatttctcga gttaatgata    26640
tacgcgccta ccgaaaccaa atactttgg aacagtcagc tcttaccacc acgccccgcc    26700
aacaccttaa tcccagaaat tggcccgccg ccctagtgta ccaggaaagt cccgctccca    26760
ccactgtatt acttcctcga gacgcccagg ccgaagtcca aatgactaat gcaggtgcgc    26820
agttagctgg cggctccacc ctatgtcgtc acaggcctcg gcataatata aaacgcctga    26880
tgatcagagg ccgaggtatc cagctcaacg acgagtcggt gagctctccg cttggtctac    26940
gaccagacgg aatctttcag attgccggct gcgggagatc ttccttcacc cctcgtcagg    27000
ctgttctgac tttggaaagt tcgtcttcgc aaccccgctc gggcggaatc gggaccgttc    27060
aatttgtgga ggagtttact ccctctgtct acttcaaccc cttctccgga tctcctgggc    27120
attacccgga cgagttcata ccgaacttcg acgcgattag cgagtcagtg gacggctacg    27180
attgatgtct ggtgacgcgg ctgagctatc tcggctgcga catctagacc actgccgccg    27240 cttttcgctgc tttgcccggg aactcattga gttcatctac ttcgaactcc ccaaggatca    27300
ccctcaaggt ccggcccacg gagtgcggat ttctatcgaa ggcaaaatag actctcgcct    27360
gcaacgaatt ttctcccagc ggcccgtgct gatcgagcga gaccaggaa acaccacggt     27420 ttccatctac tgcatttgta atcaccccgg attgcatgaa agcctttgct gtcttatgtg    27480
tactgagttt aataaaaact gaattaagac tctcctacgg actgccgctt cttcaacccg    27540
gattttacaa ccagaagaac gaaacttttc ctgtcgtcca ggactctgtt aacttcacct    27600
ttcctactca caaactagaa gctcaacgac tacaccgctt ttccagaagc atttccccta   27660
ctaatactac tttcaaaacc ggaggtgagc tccaaggtct tcctcagaa aacccttggg    27720 tggaagcggg ccttgtagtg ctaggaattc ttgcgggtgg gcttgtgatt attctttgct   27780
acctatacac accttgcttc actttcttag tggtgttgtg gtattggttt aaaaaatggg   27840
```

```
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata cttaaagggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
cccctttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggttttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat tgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atccttttcaa  29100 tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttacctttt tactacatca gagaagacga  29340
ctgacaaata aagtttgcga tcgccaggcc caccatggac tggacctggc gcatcctgtt  29400
cttggtggca gctgctacgg gagctcattc ccaggtgcag ctggtgcaat ccggcgctga  29460
ggtgaagaaa cccggggctt cagtcaaagt cagctgcaag gctagcggct acacctttac  29520
tggctattac atgcactggg tgaggcaggc tccgggacag gtctggaat ggatgggatg  29580 gatcaatccg gacagcggcg ggaccaatta cgcacaaaag ttccaaggcc gcgtgacgat  29640
gacccgggac acttcgatct caaccgccta catggagctg aaccgcctga ggtcggatga  29700
caccgctgtg tactactgcg ctcgcgacca accctgggg tactgcacca acggagtgtg  29760
ttcatacttc gactactggg gccaaggcac gctggtcact gtgtcatcgg cgtccactaa  29820
gggcccgtcg gtcttcccac tagctccgtg ctcgcggtcg acttcggaat caactgcggc  29880
actcggatgc cttgtcaagg actacttccc agaacccgtg accgtctcgt ggaactcagg  29940
cgccctgacg agcggtgtcc acactttccc ggcggtgctg cagtcatcgg ggctatacag  30000
cctgagcagc gtggttactg tgccgtcatc aaacttcggg acccagactt acacttgcaa  30060 tgtgaccac aagccgtcaa ataccaaagt ggacaagact gtggaacgca atgttgcgt  30120 ggaatgccct ccgtgccgg ccccccagt cgctggccca tccgtgttcc tcttccctcc  30180
```

```
gaagccaaaa gacactctga tgatttcgag aactccggag gtcacttgcg tggtggtcga   30240
cgtgtcgcac gaggatccag aggtgcagtt caactggtac gtggatggag tggaggtgca   30300
caatgccaag accaagccgc gcgaagaaca attcaactcc acctttcggg tcgtgtccgt   30360
gctgaccgtg gtacaccaag actggctgaa cggaaaggag tacaaatgca aggtgagcaa   30420
caaggggctg ccggctccaa tcgaaaagac catctcaaag actaagggc aacctcgcga    30480 gccacaggtg tataccctgc ctccaagcag ggaggaaatg accaaaaacc aggtgagcct   30540
gacctgtctg gtgaagggct tttacccag cgacatcgcc gtcgagtggg aaagcaacgg    30600
acaacccgag aacaactaca agaccactcc gcccatgctg gactccgacg gtcattttt    30660 cctgtactca aagctgactg tggacaagtc ccggtggcag caaggtaacg tgttctcctg   30720
ctcggtgatg cacgaagctt tgcacaacca ctacactcaa aagtcacttt ccttgtcacc   30780
gggcaagggg tcgggcgcca ctaacttttc cttgctcaag caggcgggcg atgtggagga   30840
gaatccgggc ccgcgcctcc cggcgcaact gctgggcctc ctcctcctct ggtttccgg    30900 ctcccgctgt gacatccaga tgactcagtc gcccagctcc gtgccgcat cggtggggga    30960 cagagtcacc atcacctgca gagcttcaca agggatctat tcctggctgg cgtggtatca   31020
gcagaagcct ggaaaggccc ccaacctcct gatttacacc gcatcgactc tccagtcagg   31080
cgtgccatcc cggttctcag gtccggctc cggaaccgac ttcactctga ctatcagctc    31140
cctgcaacca gaagatttcg ctacctacta ctgccagcag gcaaacatct ttccgctaac   31200
tttcggcgga ggcacgaagg tggagatcaa gagaaccgtg gcggccccctt ccgtcttcat   31260 cttcccaccg tcagcgaac aactcaaatc cggtaccgcc tccgtcgtgt gcctgctcaa    31320
taacttctat ccacgcgagg ccaaggtcca gtggaaagtg gataacgccc tgcagtccgg   31380
aaacagccag gagtcagtga ccgaacagga ttccaaggac agcacttact cgctctcaag   31440 cacccctcacc ctgtcgaagg cggattacga gaagcacaaa gtctacgcct gcgaagtgac   31500
tcatcaagga ctctcatcac cggtaactaa gagcttcaat cgcggagaat gctaggctag   31560
cttgactgac tgagatacag cgtaccttca gctcacagac atgataagat acattgatga   31620
gtttggacaa accacaacta gaatgcagtg aaaaaaatgc tttatttgtg aaatttgtga   31680
tgctattgct ttatttgtaa ccattataag ctgcaataaa caagttaaca acaacaattg   31740
cattcatttt atgtttcagg ttcaggggga ggtgtgggag gttttttaaa gcaagtaaaa   31800
cctctacaaa tgtggtcctg caggaacttg tttatttgaa aatcaattca caaaatccga   31860
gtagttattt tgcctccccc ttcccatta acagaataca ccaatctctc cccacgcaca    31920
gctttaaaca tttggatacc attagatata gacatggttt tagattccac attccaaaca   31980
gtttcagagc gagccaatct ggggtcagtg atagataaaa atccatcggg atagtctttt   32040
aaagcgcttt cacagtccaa ctgctgcgga tgcgactccg gagtctggat cacggtcatc   32100
tggaagaaga acgatgggaa tcataatccg aaaacggtat cggacgattg tgtctcatca   32160
aacccacaag cagccgctgt ctgcgtcgct ccgtgcgact gctgtttatg ggatcagggt   32220
ccacagtgtc ctgaagcatg attttaatag cccttaacat caactttctg gtgcgatgcg   32280
cgcagcaacg cattctgatt tcactcaaat ctttgcagta ggtacaacac attattacaa   32340
tattgtttaa taaccataa ttaaaagcgc tccagccaaa actcatatct gatataatcg     32400
cccctgcatg accatcatac caaagtttaa tataaattaa atgacgttcc ctcaaaaaca   32460
cactacccac atacatgatc tcttttggca tgtgcatatt aacaatctgt ctgtaccatg   32520
gacaacgttg gttaatcatg caacccaata taaccttccg gaaccacact gccaacaccg   32580
```

-continued

```
ctcccccagc catgcattga agtgaaccct gctgattaca atgacaatga agaacccaat  32640
tctctcgacc gtgaatcact tgagaatgaa aaatatctat agtggcacaa catagacata  32700
aatgcatgca tcttctcata atttttaact cctcaggatt tagaaacata tcccagggaa  32760
taggaagctc ttgcagaaca gtaaagctgg cagaacaagg aagaccacga acacaactta  32820
cactatgcat agtcatagta tcacaatctg gcaacagcgg gtggtcttca gtcatagaag  32880
ctcgggtttc attttcctca caacgtggta actgggctct ggtgtaaggg tgatgtctgg  32940
cgcatgatgt cgagcgtgcg cgcaaccttg tcataatgga gttgcttcct gacattctcg  33000
tattttgtat agcaaaacgc ggccctggca gaacacactc ttcttcgcct tctatcctgc  33060
cgcttagcgt gttccgtgtg atagttcaag tacaaccaca ctcttaagtt ggtcaaaaga  33120
atgctggctt cagttgtaat caaaactcca tcgcatctaa tcgttctgag gaaatcatcc  33180
aagcaatgca actggattgt gtttcaagca ggagaggaga gggaagagac ggaagaacca  33240
tgttaatttt tattccaaac gatctcgcag tacttcaaat tgtagatcgc gcagatggca  33300
tctctcgccc ccactgtgtt ggtgaaaaag cacagctaga tcaaaagaaa tgcgattttc  33360
aaggtgctca acggtggctt ccagcaaagc ctccacgcgc acatccaaga acaaaagaat  33420
accaaaagaa ggagcatttt ctaactcctc aatcatcata ttacattcct gcaccattcc  33480
cagataattt tcagctttcc agccttgaat tattcgtgtc agttcttgtg gtaaatccaa  33540
tccacacatt acaaacaggt cccggagggc gccctccacc accattctta aacacaccct  33600
cataatgaca aaatatcttg ctcctgtgtc acctgtagcg aattgagaat ggcaacatca  33660
attgacatgc ccttggctct aagttcttct ttaagttcta gttgtaaaaa ctctctcata  33720
ttatcaccaa actgcttagc cagaagcccc ccgggaacaa gagcagggga cgctacagtg  33780
cagtacaagc gcagacctcc ccaattggct ccagcaaaaa caagattgga ataagcatat  33840
tgggaaccgc cagtaatatc atcgaagttg ctggaaatat aatcaggcag agtttcttgt  33900
aaaaattgaa taaaagaaaa atttgccaaa aaaacattca aaacctctgg gatgcaaatg  33960
caataggtta ccgcgctgcg ctccaacatt gttagttttg aattagtctg caaaaataaa  34020
aaaaaaaaca agcgtcatat catagtagcc tgacgaacag atggataaat cagtctttcc  34080
atcacaagac aagccacagg gtctccagct cgaccctcgt aaaacctgtc atcatgatta  34140
aacaacagca ccgaaagttc ctcgcggtga ccagcatgaa taattcttga tgaagcatac  34200
aatccagaca tgttagcatc agttaacgag aaaaaacagc caacatagcc tttgggtata  34260
attatgctta atcgtaagta tagcaaagcc acccctcgcg gatacaaagt aaaaggcaca  34320
ggagaataaa aaatataatt atttctctgc tgctgttcag gcaacgtcgc ccccggtccc  34380
tctaaataca catacaaagc ctcatcagcc atggcttacc agacaaagta cagcgggcac  34440
acaaagcaca agctctaaag tgactctcca acctctccac aatatatata tacacaagcc  34500
ctaaactgac gtaatgggag taaagtgtaa aaaatcccgc caaacccaac acacaccccg  34560
aaactgcgtc accagggaaa agtacagttt cacttccgca atcccaacag gcgtaacttc  34620
ctctttctca cggtacgtga tatcccacta acttgcaacg tcattttccc acggtcgcac  34680
cgccccttttt agccgttaac cccacagcca atcaccacac gatccacact ttttaaaatc  34740
acctcattta catattggca ccattccatc tataaggtat attatataga taga        34794
```

<210> SEQ ID NO 2

<400> SEQUENCE: 2

000

<210> SEQ ID NO 3
<211> LENGTH: 19
<212> TYPE: PRT
<213> ORGANISM: Artificial Sequence
<220> FEATURE:
<223> OTHER INFORMATION: Heavy chain leader sequence

<400> SEQUENCE: 3

```
Met Asp Trp Thr Trp Arg Ile Leu Phe Leu Val Ala Ala Ala Thr Gly
1               5                   10                  15

Ala His Ser
```

<210> SEQ ID NO 4
<211> LENGTH: 126
<212> TYPE: PRT
<213> ORGANISM: Artificial Sequence
<220> FEATURE:
<223> OTHER INFORMATION: anti-CD40 VH chain amino acid sequence

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125
```

<210> SEQ ID NO 5
<211> LENGTH: 326
<212> TYPE: PRT
<213> ORGANISM: Artificial Sequence
<220> FEATURE:
<223> OTHER INFORMATION: antibody constant heavy chain amino acid
      sequence

<400> SEQUENCE: 5

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
```

```
                    85                  90                  95
Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 6

<400> SEQUENCE: 6

000

<210> SEQ ID NO 7
<211> LENGTH: 19
<212> TYPE: PRT
<213> ORGANISM: Artificial Sequence
<220> FEATURE:
<223> OTHER INFORMATION: Light chain leader sequence

<400> SEQUENCE: 7

Arg Leu Pro Ala Gln Leu Leu Gly Leu Leu Leu Leu Trp Phe Pro Gly
1               5                   10                  15

Ser Arg Cys

<210> SEQ ID NO 8
<211> LENGTH: 107
<212> TYPE: PRT
<213> ORGANISM: Artificial Sequence
<220> FEATURE:
<223> OTHER INFORMATION: anti-CD40 VL chain amino acid sequence

<400> SEQUENCE: 8
```

-continued

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys
            100                 105
```

<210> SEQ ID NO 9
<211> LENGTH: 107
<212> TYPE: PRT
<213> ORGANISM: Artificial Sequence
<220> FEATURE:
<223> OTHER INFORMATION: constant light chain amino acid sequence

<400> SEQUENCE: 9

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 10
<211> LENGTH: 192
<212> TYPE: DNA
<213> ORGANISM: Artificial Sequence
<220> FEATURE:
<223> OTHER INFORMATION: Poly Adenylation sequence

<400> SEQUENCE: 10

```
cagacatgat aagatacatt gatgagtttg gacaaaccac aactagaatg cagtgaaaaa      60
aatgctttat ttgtgaaatt tgtgatgcta ttgctttatt tgtaaccatt ataagctgca     120
ataaacaagt taacaacaac aattgcattc attttatgtt tcaggttcag gggaggtgt      180 gggaggtttt tt                                                         192
```

<210> SEQ ID NO 11
<211> LENGTH: 2468
<212> TYPE: DNA
<213> ORGANISM: Artificial Sequence
<220> FEATURE:
<223> OTHER INFORMATION: NG-350 transgene cassette nucleic acid sequence

<400> SEQUENCE: 11

```
gcgatcgcca ggcccaccat ggactggacc tggaggatcc tcttcttggt ggcagcagcc    60
acaggagccc actcccaggt gcagctggtg cagtctgggg ctgaggtgaa gaagcctggg   120
gcctcagtga aggtctcctg caaggcttct ggatacacct tcaccggcta ctatatgcac   180
tgggtgcgac aggcccctgg acaagggctt gagtggatgg gatggatcaa ccctgacagt   240
ggtggcacaa actatgcaca gaagtttcag gcagggtca ccatgaccag gacacgtcc    300 atcagcacag cctacatgga gctgaacagg ctgagatctg acgacacggc cgtgtattac   360
tgtgcgagag atcagcccct aggatattgt actaatggtg tatgctccta ctttgactac   420
tggggccagg gaaccctggt caccgtctcc tcagcctcca ccaagggccc atcggtcttc   480
cccctggcgc cctgctccag gagcacctcc gagagcacag cggccctggg ctgcctggtc   540
aaggactact cccccgaacc ggtgacggtg tcgtggaact caggcgctct gaccagcggc   600
gtgcacacct tcccagctgt cctacagtcc tcaggactct actccctcag cagcgtggtg   660
accgtgccct ccagcaactt cggcacccag acctacacct gcaacgtaga tcacaagccc   720
agcaacacca aggtggacaa gacagttgag cgcaaatgtt gtgtcgagtg cccaccgtgc   780
ccagcaccac ctgtgcagg accgtcagtc ttcctcttcc ccccaaaacc caaggacacc   840
ctcatgatct cccggacccc tgaggtcacg tgcgtggtgg tggacgtgag ccacgaagac   900
cccgaggtcc agttcaactg gtacgtggac ggcgtggagg tgcataatgc caagacaaag   960
ccacgggagg agcagttcaa cagcacgttc cgtgtggtca gcgtcctcac cgttgtgcac  1020
caggactggc tgaacggcaa ggagtacaag tgcaaggtct ccaacaaagg cctcccagcc  1080
cccatcgaga aaaccatctc caaaaccaaa gggcagcccc gagaaccaca ggtgtacacc  1140
ctgcccccat cccgggagga gatgaccaag aaccaggtca gcctgacctg cctggtcaaa  1200
ggcttctacc ccagcgacat cgccgtggag tgggagagca atgggcagcc ggagaacaac  1260
tacaagacca cacctcccat gctggactcc gacggctcct tcttcctcta cagcaagctc  1320
accgtggaca agagcaggtg gcagcagggg aacgtcttct catgctccgt gatgcatgag  1380
gctctgcaca accactacac gcagaagagc ctctccctgt ctccgggtaa aggaagcgga  1440
gctactaact tcagcctgct gaagcaggct ggagacgtgg aggagaaccc tggacctagg  1500
ctccctgctc agctcctggg gctcctgctg ctctggttcc caggttccag atgcgacatc  1560
cagatgaccc agtctccatc ttccgtgtct gcatctgtag gagacagagt caccatcact  1620
tgtcgggcga gtcagggtat ttacagctgg ttagcctggt atcagcagaa accagggaaa  1680
gcccctaacc tcctgatcta tactgcatcc actttacaaa gtggggtccc atcaaggttc  1740
agcggcagtg gatctgggac agatttcact ctcaccatca gcagcctgca acctgaagat  1800
tttgcaactt actattgtca acaggctaac atttttcccgc tcactttcgg cggagggacc  1860
aaggtggaga tcaaacgaac tgtggctgca ccatctgtct tcatcttccc gccatctgat  1920
gagcagttga aatctggaac tgcctctgtt gtgtgcctgc tgaataactt ctatcccaga  1980
gaggccaaag tacagtggaa ggtggataac gccctccaat cgggtaactc ccaggagagt  2040
gtcacagagc aggacagcaa ggacagcacc tacagcctca gcagcaccct gacgctgagc  2100
aaagcagact acgagaaaca caaagtctac gcctgcgaag tcacccatca gggcctgagc  2160
tcgcccgtca caaagagctt caacaggggga gagtgttagg ctagcttgac tgactgagat  2220
acagcgtacc ttcagctcac agacatgata agatacattg atgagtttgg acaaaccaca  2280
actagaatgc agtgaaaaaa atgctttatt tgtgaaattt gtgatgctat tgctttattt  2340
```

-continued

| | |
|---|---|
| gtaaccatta taagctgcaa taaacaagtt aacaacaaca attgcattca ttttatgttt | 2400 |
| caggttcagg gggaggtgtg ggaggttttt taaagcaagt aaaacctcta caaatgtggt | 2460 |
| cctgcagg | 2468 |

<210> SEQ ID NO 12
<211> LENGTH: 2468
<212> TYPE: DNA
<213> ORGANISM: Artificial Sequence
<220> FEATURE:
<223> OTHER INFORMATION: NG-350A transgene cassette nucleic acid
      sequence

<400> SEQUENCE: 12

| | |
|---|---|
| gcgatcgcca ggcccaccat ggactggacc tggcgcatcc tgttcttggt ggcagctgct | 60 |
| acgggagctc attcccaggt gcagctggtg caatccggcg ctgaggtgaa gaaacccggg | 120 |
| gcttcagtca aagtcagctg caaggctagc ggctacacct ttactggcta ttacatgcac | 180 |
| tgggtgaggc aggctccggg acagggtctg aatggatgg gatggatcaa tccggacagc | 240 |
| ggcgggacca attacgcaca aaagttccaa ggccgcgtga cgatgacccg ggacacttcg | 300 |
| atctcaaccg cctacatgga gctgaaccgc tgaggtcgg atgacaccgc tgtgtactac | 360 |
| tgcgctcgcg accaacccct ggggtactgc accaacggag tgtgttcata cttcgactac | 420 |
| tggggccaag gcacgctggt cactgtgtca tcggcgtcca ctaagggccc gtcggtcttc | 480 |
| ccactagctc cgtgctcgcg gtcgacttcg gaatcaactg cggcactcgg atgccttgtc | 540 |
| aaggactact cccagaaccc cgtgaccgtc tcgtggaact caggcgccct gacgagcggt | 600 |
| gtccacactt tcccggcggt gctgcagtca tcggggctat acagcctgag cagcgtggtt | 660 |
| actgtgccgt catcaaactt cgggacccag acttacactt gcaatgtgga ccacaagccg | 720 |
| tcaaatacca aagtggacaa gactgtggaa cgcaaatgtt gcgtggaatg ccctccgtgc | 780 |
| ccggccccc cagtcgctgg cccatccgtg ttcctcttcc ctccgaagcc aaaagacact | 840 |
| ctgatgattt cgagaactcc ggaggtcact tgcgtggtgg tcgacgtgtc gcacgaggat | 900 |
| ccagaggtgc agttcaactg gtacgtggat ggagtggagg tgcacaatgc caagaccaag | 960 |
| ccgcgcgaag aacaattcaa ctccaccttt cgggtcgtgt ccgtgctgac cgtggtacac | 1020 |
| caagactggc tgaacggaaa ggagtacaaa tgcaaggtga gcaacaaggg gctgccggct | 1080 |
| ccaatcgaaa agaccatctc aaagactaag ggcaacctc gcgagccaca ggtgtatacc | 1140 |
| ctgcctccaa gcagggagga aatgaccaaa aaccaggtga gcctgacctg tctggtgaag | 1200 |
| ggcttttacc ccagcgacat cgccgtcgag tgggaaagca acggacaacc cgagaacaac | 1260 |
| tacaagacca ctccgcccat gctggactcc gacgggtcat ttttcctgta ctcaaagctg | 1320 |
| actgtggaca gtcccggtg cagcaaggt aacgtgttct cctgctcggt gatgcacgaa | 1380 |
| gctttgcaca accactacac tcaaaagtca ctttccttgt caccgggcaa ggggtcgggc | 1440 |
| gccactaact tttccttgct caagcaggcg ggcgatgtgg aggagaatcc gggcccgcgc | 1500 |
| ctcccggcgc aactgctggg cctcctcctc ctctggtttc ccggctcccg ctgtgacatc | 1560 |
| cagatgactc agtcgcccag ctccgtgtcc gcatcggtgg gggacagagt caccatcacc | 1620 |
| tgcagagctt cacaagggat ctattcctgg ctggcgtggt atcagcagaa gcctggaaag | 1680 |
| gcccccaacc tcctgattta caccgcatcg actctccagt caggcgtgcc atcccggttc | 1740 |
| tcagggtccg gctccggaac cgacttcact ctgactatca gctccctgca accagaagat | 1800 |
| ttcgctacct actactgcca gcaggcaaac atctttccgc taactttcgg cggaggcacg | 1860 |

| | |
|---|---:|
| aaggtggaga tcaagagaac cgtggcggcc ccttccgtct tcatcttccc accgtcagac | 1920 |
| gaacaactca aatccggtac cgcctccgtc gtgtgcctgc tcaataactt ctatccacgc | 1980 |
| gaggccaagg tccagtggaa agtggataac gccctgcagt ccggaaacag ccaggagtca | 2040 |
| gtgaccgaac aggattccaa ggacagcact tactcgctct caagcaccct cacccctgtcg | 2100 |
| aaggcggatt acgagaagca caaagtctac gcctgcgaag tgactcatca aggactctca | 2160 |
| tcaccggtaa ctaagagctt caatcgcgga gaatgctagg ctagcttgac tgactgagat | 2220 |
| acagcgtacc ttcagctcac agacatgata agatacattg atgagtttgg acaaaccaca | 2280 |
| actagaatgc agtgaaaaaa atgctttatt tgtgaaattt gtgatgctat tgctttattt | 2340 |
| gtaaccatta taagctgcaa taaacaagtt aacaacaaca attgcattca ttttatgttt | 2400 |
| caggttcagg gggaggtgtg ggaggttttt taaagcaagt aaaacctcta caaatgtggt | 2460 |
| cctgcagg | 2468 |

<210> SEQ ID NO 13
<211> LENGTH: 34794
<212> TYPE: DNA
<213> ORGANISM: Artificial Sequence
<220> FEATURE:
<223> OTHER INFORMATION: NG-350 Virus Genome

<400> SEQUENCE: 13

| | |
|---|---:|
| tctatctata taatatacct tatagatgga atggtgccaa tatgtaaatg aggtgatttt | 60 |
| aaaaagtgtg gatcgtgtgg tgattggctg tggggttaac ggctaaaagg ggcggtgcga | 120 |
| ccgtgggaaa atgacgtttt gtgggggtgg agttttttttg caagttgtcg cgggaaatgt | 180 |
| gacgcataaa aaggcttttt tctcacggaa ctacttagtt ttcccacggt atttaacagg | 240 |
| aaatgaggta gttttgaccg gatgcaagtg aaaattgttg attttcgcgc gaaaactgaa | 300 |
| tgaggaagtg ttttttctgaa taatgtggta tttatggcag ggtggagtat tgttcaggg | 360 |
| ccaggtagac tttgacccat tacgtggagg tttcgattac cgtgtttttt acctgaatttt | 420 |
| ccgcgtaccg tgtcaaagtc ttctgttttt acgtaggtgt cagctgatcg ctagggtatt | 480 |
| tatacctcag ggtttgtgtc aagaggccac tcttgagtgc cagcgagaag agttttctcc | 540 |
| tctgcgccgg cagtttaata taaaaaaat gagagatttg cgatttctgc ctcaggaaat | 600 |
| aatctctgct gagactggaa atgaaatatt ggagcttgtg gtgcacgccc tgatgggaga | 660 |
| cgatccggag ccacctgtgc agcttttttga gcctcctacg cttcaggaac tgtatgattt | 720 |
| agaggtagag ggatcggagg attctaatga ggaagctgta aatggctttt ttaccgattc | 780 |
| tatgcttttta gctgctaatg aagggttaga attagatccg cctttggaca cttttgatac | 840 |
| tccaggggta attgtggaaa gcggtacagg tgtaagaaaa ttacctgatt tgagttccgt | 900 |
| ggactgtgat ttgcactgct atgaagacgg gtttcctccg agtgatgagg aggaccatga | 960 |
| aaaggagcag tccatgcaga ctgcagcggg tgagggagtg aaggctgcca atgttggttt | 1020 |
| tcagttggat tgcccggagc ttcctggaca tggctgtaag tcttgtgaat ttcacaggaa | 1080 |
| aaatactgga gtaaaggaac tgttatgttc gctttgttat atgagaacgc actgccactt | 1140 |
| tatttacagt aagtgtgttt aagttaaaat ttaaaggaat atgctgtttt tcacatgtat | 1200 |
| attgagtgtg agttttgtgc ttcttattat aggtcctgtg tctgatgctg atgaatcacc | 1260 |
| atctcctgat tctactacct cacctcctga gattcaagca cctgttcctg tggacgtgcg | 1320 |
| caagcccatt cctgtgaagc ttaagcctgg gaaacgtcca gcagtggaaa aacttgagga | 1380 |
| cttgttacag ggtgggacg gacctttgga cttgagtaca cggaaacgtc caagacaata | 1440 |

```
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga cttttgaag    1800 ctcttaattt gggccatcag gttcacttta agaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg aagggatga   2340 agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta atgttaagt ttaggggaga    2640 tggttataat ggaatagtgt ttatggccaa taccaaactt atattgcatg gttgtagctt   2700
ttttggtttc aacaataccct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgcctttc    3180 cagaatgagc ctaacaggaa ttttgacat gaacatgcaa atctggaaga tcctgaggta    3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480 gtcatgagtg gaaacgcttc ttttaagggg ggagtcttca gcccttatct gacagggcgt   3540
ctcccatcct gggcaggagt tcgtcagaat gttatggat ctactgtgga tggaagaccc    3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
```

```
aagttacttg tccttttggc ccagctggag gctttgaccc aacgtctggg tgaactttct    3840
cagcaggtgg tcgagttgcg agtacaaact gagtctgctg tcggcacggc aaagtctaaa    3900
taaaaaaatc ccagaatcaa tgaataaata acaagcttg ttgttgattt aaaatcaagt     3960
gttttatt  cattttcgc gcacggtatg ccctagacca ccgatctcta tcattgagaa      4020
ctcggtggat ttttttccagg atcctataga ggtgggattg aatgtttaga tacatgggca   4080
ttaggccgtc tttggggtgg agatagctcc attgaaggga ttcatgctcc ggggtagtgt    4140
tgtaaatcac ccagtcataa caaggtcgca gtgcatggtg ttgcacaata tcttttagaa    4200
gtaggctgat tgccacagat aagcccttgg tgtaggtgtt tacaaaccgg ttgagctggg    4260
atgggtgcat tcggggtgaa attatgtgca ttttggattg gattttttaag ttggcaatat   4320
tgccgccaag atcccgtctt gggttcatgt tatgaaggac caccaagacg gtgtatccgg    4380
tacatttagg aaatttatcg tgcagcttgg atggaaaagc gtggaaaaat ttggagacac    4440
ccttgtgtcc tccaagattt tccatgcact catccatgat aatagcaatg gggccgtggg    4500
cagcggcgcg ggcaaacacg ttccgtgggt ctgacacatc atagttatgt tcctgagtta    4560
aatcatcata agccatttta atgaatttgg ggcggagagt accagattgg ggtatgaatg   4620
ttccttcggg ccccggagca tagttcccct cacagatttg catttcccaa gctttcagtt    4680
ccgagggtgg aatcatgtcc acctgggggg ctatgaaaaa caccgtttct ggggcggggg    4740
tgattaattg tgatgatagc aaattctga  gcaattgaga tttgccacat ccggtggggc    4800
cataaatgat tccgattacg ggttgcaggt ggtagtttag ggaacggcaa ctgccgtctt    4860
ctcgaagcaa gggggccacc tcgttcatca tttcccttac atgcatattt cccgcacca    4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
gtctgttcca cagttcagtg atgtgttcta tggcatctcg atccagcaga cctcctcgtt    5100
tcgcgggttt ggacggctcc tggaataggg tatgagacga tgggcgtcca gcgctgccag    5160
ggttcggtcc ttccagggtc tcagtgttcg agtcagggtt gtttccgtca cagtgaaggg    5220
gtgtgcgcct gcttgggcgc ttgccagggt gcgcttcaga ctcatcctgc tggtcgaaaa    5280
cttctgtcgc ttggcgccct gtatgtcggc caagtagcag tttaccatga gttcgtagtt    5340
gagcgcctcg gctgcgtggc cttggcgcg  gagcttacct ttggaagttt tcttgcatac    5400
cgggcagtat aggcatttca gcgcatacaa cttgggcgca aggaaaacgg attctgggga    5460
gtatgcatct gcgccgcagg aggcgcaaac agtttcacat tccaccagcc aggttaaatc    5520
cggttcattg gggtcaaaaa caagttttcc gccatatttt ttgatgcgtt tcttaccttt    5580
ggtctccatg agttcgtgtc ctcgttgagt gacaaacagg ctgtccgtgt ccccgtagac    5640
tgattttaca ggcctcttct ccagtggagt gcctcggtct tcttcgtaca ggaactctga    5700
ccactctgat acaaaggcgc gcgtccaggc cagcacaaag gaggctatgt gggagggta    5760
gcgatcgttg tcaaccaggg ggtccacctt ttccaaagta tgcaaacaca tgtcaccctc    5820
ttcaacatcc aggaatgtga ttggcttgta ggtgtatttc acgtgacctg ggtccccgc    5880
tgggggggta taaaagggg  cggttctttg ctcttcctca ctgtcttccg gatcgctgtc    5940
caggaacgtc agctgttggg gtaggtattc cctctcgaag gcgggcatga cctctgcact    6000
caggttgtca gtttctaaga acgaggagga tttgatattg acagtgccgg ttgagatgcc    6060
tttcatgagg ttttcgtcca tctggtcaga aaacacaatt ttttattgt  caagtttggt    6120
ggcaaatgat ccatacaggg cgttggataa aagtttggca atggatcgca tggtttggtt    6180
```

```
cttttccttg tccgcgcgct ctttggcggc gatgttgagt tggacatact cgcgtgccag    6240
gcacttccat tcggggaaga tagttgttaa ttcatctggc acgattctca cttgccaccc    6300
tcgattatgc aaggtaatta aatccacact ggtggccacc tcgcctcgaa ggggttcatt    6360
ggtccaacag agcctacctc ctttcctaga acagaaaggg ggaagtgggt ctagcataag    6420
ttcatcggga gggtctgcat ccatggtaaa gattcccgga agtaaatcct tatcaaaata    6480
gctgatggga gtggggtcat ctaaggccat ttgccattct cgagctgcca gtgcgcgctc    6540
atatgggtta aggggactgc cccatggcat gggatgggtg agtgcagagg catacatgcc    6600
acagatgtca tagacgtaga tgggatcctc aaagatgcct atgtaggttg atagcatcg    6660 ccccccctctg atacttgctc gcacatagtc atatagttca tgtgatggcg ctagcagccc    6720
cggacccaag ttggtgcgat tgggtttttc tgttctgtag acgatctggc gaaagatggc    6780
gtgagaattg aagagatggt gggtctttg aaaaatgttg aaatgggcat gaggtagacc    6840
tacagagtct ctgacaaagt gggcataaga ttcttgaagc ttggttacca gttcggcggt    6900
gacaagtacg tctagggcgc agtagtcaag tgtttcttga atgatgtcat aacctggttg    6960
gttttctttt tcccacagtt cgcggttgag aaggtattct tcgcgatcct tccagtactc    7020
ttctagcgga aacccgtctt tgtctgcacg gtaagatcct agcatgtaga actgattaac    7080
tgccttgtaa gggcagcagc ccttctctac gggtagagag tatgcttgag cagcttttcg    7140
tagcgaagcg tgagtaaggg caaaggtgtc tctgaccatg actttgagga attggtattt    7200
gaagtcgatg tcgtcacagg ctccctgttc ccagagttgg aagtctaccc gtttcttgta    7260
ggcggggttg ggcaaagcga agtaacatc attgaagaga atcttgccgg ccctgggcat    7320
gaaattgcga gtgatgcgaa aaggctgtgg tacttccgct cggttattga taacctgggc    7380
agctaggacg atctcgtcga aaccgttgat gttgtgtcct acgatgtata attctatgaa    7440
acgcggcgtg cctctgacgt gaggtagctt actgagctca tcaaaggtta ggtctgtggg    7500
gtcagataag gcgtagtgtt cgagagccca ttcgtgcagg tgaggattcg ctttaaggaa    7560
ggaggaccag aggtccactg ccagtgctgt ttgtaactgg tcccggtact gacgaaaatg    7620
ccgtccgact gccatttttt ctggggtgac gcaatagaag gtttggggt cctgccgcca    7680 gcgatcccac ttgagtttta tggcgaggtc ataggcgatg ttgacgagcc gctggtctcc    7740
agagagtttc atgaccagca tgaagggat tagctgcttg ccaaaggacc ccatccaggt    7800
gtaggtttcc acatcgtagg tgagaaagag cctttctgtg cgaggatgag agccaatcgg    7860
gaagaactgg atctcctgcc accagttgga ggaatggctg ttgatgtgat ggaagtagaa    7920
ctccctgcga cgcgccgagc attcatgctt gtgcttgtac agacggccgc agtagtcgca    7980
gcgttgcacg ggttgtatct cgtgaatgag ttgtacctgg cttcccttga cgagaaattt    8040
cagtgggaag ccgaggcctg gcgattgtat ctcgtgcttt actatgttgt ctgcatcggc    8100
ctgttcatct tctgtctcga tggtggtcat gctgacgagc cctcgcggga ggcaagtcca    8160
gacctcggcg cggcaggggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
cattttggac ggcggtggct ctgttgcttc ttgcatgttt agaagcggtg tcagggcgcg    8460
gcaccgggcg gcaggggcgg ctcgggaccc ggcggcatgg ctggcagtgg tacgtcggcg    8520
```

```
ccgcgcgcgg gtaggttctg gtactgcgcc ctgagaagac tcgcatgcgc gacgacgcgg    8580
cggttgacat cctggatctg acgcctctgg gtgaaagcta ccggcccgt gagcttgaac     8640 ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacgtgg ccgcgaggtc gttggagatg     8820
cgcccaatga gttgagagaa tgcattcatg cccgcctcgt tccagacgcg gctgtagacc    8880
acggccccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgg caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tctcttcttc ttccactaac    9240
atctcttcct cttcaggtgg ggctgcagga ggaggggaa cgcggcgacg ccggcggcgc     9300
acgggcagac ggtcgatgaa tctttcaatg acctctccgc ggcggcgcg catggtttca     9360 gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcgggaa    9660
ggtgagacga tgctgctggt gatgaaatta aagtaggcag ttctaagacg gcggatggtg    9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt tcggcgagga tggcttgctg tacttgggta    9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccagggc gaggtcttcc aacataaggc ggtgatagcc gtagatgtac     10260
ctggacatcc aggtgattcc tgcggcggta gtagaagccc gaggaaactc gcgtacgcgg   10320
ttccaaatgt tgcgtagcgg catgaagtag ttcattgtag gcacggtttg accagtgagg   10380
cgcgcgcagt cattgatgct ctatagacac ggagaaaatg aaagcgttca gcgactcgac   10440
tccgtagcct ggaggaacgt gaacgggttg ggtcgcggtg taccccggtt cgagacttgt   10500
actcgagccg gccggagccg cggctaacgt ggtattggca ctcccgtctc gacccagcct   10560
acaaaaatcc aggatacgga atcgagtcgt tttgctggtt ccgaatggc agggaagtga    10620 gtcctatttt tttttttgc cgctcagatg catcccgtgc tgcgacagat gcgccccaa     10680 caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt tcaactgaaa   10860
aaagattctc gcgaggcgta tgtgccccaa cagaacctat ttagagacag aagcggcgag   10920
```

```
gagccggagg agatgcgagc ttcccgcttt aacgcgggtc gtgagctgcg tcacggtttg   10980
gaccgaagac gagtgttgcg ggacgaggat ttcgaagttg atgaaatgac agggatcagt   11040
cctgccaggg cacacgtggc tgcagccaac cttgtatcgg cttacgagca gacagtaaag   11100
gaagagcgta acttccaaaa gtcttttaat aatcatgtgc gaaccctgat tgcccgcgaa   11160
gaagttaccc ttggtttgat gcatttgtgg gatttgatgg aagctatcat tcagaaccct   11220
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg ggaaaatatt acgctcgcaa aatctacaag   11460
actccatacg ttcccataga caaggagtg aagatagatg ggttctacat gcgcatgacg   11520
ctcaaggtct tgaccctgag cgatgatctt ggggtgtatc gcaatgacag aatgcatcgc   11580
gcggttagcg ccagcaggag gcgcgagtta agcgacaggg aactgatgca cagtttgcaa   11640
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940
catggcgttg acgactcgca accccgaagc ctttagacag caaccccagg ccaaccgtct   12000
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt tccagcgtga   12240
tgccaacctg ggttcgctgg tggcgttaaa tgctttcttg agtactcagc ctgctaatgt   12300
gccgcgtggt caacaggatt atactaactt tttaagtgct ttgagactga tggtatcaga   12360
agtacctcag agcgaagtgt atcagtccgg tcctgattac ttctttcaga ctagcagaca   12420
gggcttgcag acggtaaatc tgagccaagc ttttaaaaac cttaaaggtt tgtggggagt   12480
gcatgccccg gtaggagaaa gagcaaccgt gtctagcttg ttaactccga actcccgcct   12540
attattactg ttggtagctc cttttcaccga cagcggtagc atcgaccgta attcctattt   12600
gggttaccta ctaaacctgt atcgcgaagc catagggcaa agtcaggtgg acgagcagac   12660
ctatcaagaa attcccaag tcagtcgcgc tttgggacag aagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac cttttcattaa caaactgctg gactacttgc acagagctgc   12960
cgctatgaac tctgattatt tcaccaatgc catcttaaac ccgcactggc tgccccacc   13020
tggtttctac acgggcgaat atgacatgcc cgacccctaat gacggatttc tgtgggacga   13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca agtcctttc ctagtctacc cttttctcta cacagtgtac gtagcagcga   13260
```

```
agtgggtaga ataagtcgcc cgagtttaat gggcgaagag gagtatctaa acgattcctt   13320
gctcagaccg gcaagagaaa aaaatttccc aaacaatgga atagaaagtt tggtggataa   13380
aatgagtaga tggaagactt atgctcagga tcacagagac gagcctggga tcatggggat   13440
tacaagtaga gcgagccgta gacgccagcg ccatgacaga cagaggggtc ttgtgtggga   13500
cgatgaggat tcggccgatg atagcagcgt gctggacttg ggtgggagag aaggggcaa    13560 cccgtttgct catttgcgcc ctcgcttggg tggtatgttg taaaaaaaaa taaaaaaaaa   13620
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
cctttgtgcc tccgcgatac ctggcaccta cggagggcag aaacagcatt cgttattcgg   13860
aactggcacc tcagtacgat accaccaggt tgtatctggt ggacaacaag tcggcggaca   13920
ttgcttctct gaactatcag aatgaccaca gcaacttctt gaccacggtg gtgcaaaaca   13980
atgactttac ccctacggaa gccagcaccc agaccattaa ctttgatgaa cgatcgcggt   14040
ggggcggtca gctaaagacc atcatgcata ctaacatgcc aaacgtgaac gagtatatgt   14100
ttagtaacaa gttcaaagcg cgtgtgatgg tgtccagaaa acctcccgac ggtgctgcag   14160
ttggggatac ttatgatcac aagcaggata ttttgaaata tgagtggttc gagtttactt   14220
tgccagaagg caacttttca gttactatga ctattgattt tgatgaacaat gccatcatag   14280 ataattactt gaaagtgggt agacagaatg gagtgcttga aagtgacatt ggtgttaagt   14340
tcgacaccag gaacttcaag ctgggatggg atcccgaaac caagttgatc atgcctggag   14400
tgtatacgta tgaagccttc catcctgaca ttgtcttact gcctggctgc ggagtggatt   14460
ttaccgagag tcgtttgagc aaccttcttg gtatcagaaa aaaacagcca tttcaagagg   14520
gttttaagat tttgtatgaa gatttagaag gtggtaatat tccggccctc ttggatgtag   14580
atgcctatga gaacagtaag aaagaacaaa agccaaaat agaagctgct acagctgctg    14640
cagaagctaa ggcaaacata gttgccagcg actctacaag ggttgctaac gctggagagg   14700
tcagaggaga caattttgcg ccaacacctg ttccgactgc agaatcatta ttggccgatg   14760
tgtctgaagg aacggacgtg aaactcacta ttcaacctgt agaaaaagat agtaagaata   14820
gaagctataa tgtgttggaa gacaaaatca acacagccta tcgcagttgg tatctttcgt   14880
acaattatgg cgatcccgaa aaaggagtgc gttcctggac attgctcacc acctcagatg   14940
tcacctgcgg agcagagcag gtctactggt cgcttccaga catgatgaag gatcctgtca   15000
ctttccgctc cactagacaa gtcagtaact accctgtggt gggtgcagag cttatgcccg   15060
tcttctcaaa gagcttctac aacgaacaag ctgtgtactc ccagcagctc cgccagtcca   15120
cctcgcttac gcacgtcttc aaccgctttc ctgagaacca gatttttaatc cgtccgccgg   15180 cgcccaccat taccaccgtc agtgaaaacg ttcctgctct cacagatcac gggaccctgc   15240
cgttgcgcag cagtatccgg ggagtccaac gtgtgaccgt tactgacgcc agacgccgca   15300
cctgtcccta cgtgtacaag gcactgggca tagtcgcacc gcgcgtcctt tcaagccgca   15360
ctttctaaaa aaaaaaaaaa tgtccattct tatctcgccc agtaataaca ccggttgggg   15420
tctgcgcgct ccaagcaaga tgtacggagg cgcacgcaaa cgttctaccc aacatcctgt   15480
ccgtgttcgc ggacattttc gcgctccatg gggcgccctc aagggccgca ctcgcgttcg   15540
aaccaccgtc gatgatgtaa tcgatcaggt ggttgccgac gcccgtaatt atactcctac   15600
tgcgcctaca tctactgtgg atgcagttat tgacagtgta gtggctgacg ctcgcaacta   15660
```

```
tgctcgacgt aagagccggc gaaggcgcat tgccagacgc caccgagcta ccactgccat   15720
gcgagccgca agagctctgc tacgaagagc tagacgcgtg gggcgaagag ccatgcttag   15780
ggcggccaga cgtgcagctt cgggcgccag cgccggcagg tcccgcaggc aagcagccgc   15840
tgtcgcagcg gcgactattg ccgacatggc ccaatcgcga agaggcaatg tatactgggt   15900
gcgtgacgct gccaccggtc aacgtgtacc cgtgcgcacc cgtcccccctc gcacttagaa   15960
gatactgagc agtctccgat gttgtgtccc agcggcgagg atgtccaagc gcaaatacaa   16020
ggaagaaatg ctgcaggtta tcgcacctga agtctacggc caaccgttga aggatgaaaa   16080
aaaaccccgc aaaatcaagc gggttaaaaa ggacaaaaaa gaagaggaag atggcgatga   16140
tgggctggcg gagtttgtgc gcgagtttgc cccacggcga cgcgtgcaat ggcgtgggcg   16200
caaagttcga catgtgttga gacctggaac ttcggtggtc tttacacccg gcgagcgttc   16260
aagcgctact tttaagcgtt cctatgatga ggtgtacggg gatgatgata ttcttgagca   16320
ggcggctgac cgattaggcg agtttgctta tggcaagcgt agtagaataa cttccaagga   16380
tgagacagtg tcgataccct tggatcatgg aaatcccacc cctagtctta aaccggtcac   16440
tttgcagcaa gtgttacccg taactccgcg aacaggtgtt aaacgcgaag gtgaagattt   16500
gtatcccact atgcaactga tggtacccaa acgccagaag ttggaggacg ttttggagaa   16560
agtaaaagtg gatccagata ttcaacctga ggttaaagtg agacccatta agcaggtagc   16620
gcctggtctg ggggtacaaa ctgtagacat taagattccc actgaaagta tggaagtgca   16680
aactgaaccc gcaaagccta ctgccacctc cactgaagtg caaacggatc catggatgcc   16740
catgcctatt acaactgacg ccgccggtcc cactcgaaga tcccgacgaa agtacggtcc   16800
agcaagtctg ttgatgccca attatgttgt cacaccatct attattccta ctcctggtta   16860
ccgaggcact cgctactatc gcagccgaaa cagtacctcc cgccgtcgcc gcaagacacc   16920
tgcaaatcgc agtcgtcgcc gtagacgcac aagcaaaccg actcccggcg ccctggtgcg   16980
gcaagtgtac cgcaatggta gtgcggaacc tttgacactg ccgcgtgcgc gttaccatcc   17040
gagtatcatc acttaatcaa tgttgccgct gcctccttgc agatatggcc ctcacttgtc   17100
gccttcgcgt tcccatcact ggttaccgag gaagaaactc cgcgccgtaga agagggatgt   17160
tgggacgcgg aatgcgacgc tacaggcgac ggcgtgctat ccgcaagcaa ttgcggggtg   17220
gttttttacc agccttaatt ccaattatcg ctgctgcaat tggcgcgata ccaggcatag   17280
cttccgtggc ggttcaggcc tcgcaacgac attgacattg gaaaaaaacg tataaataaa   17340
aaaaaaaaaa tacaatggac tctgacactc ctggtcctgt gactatgttt tcttagagat   17400
ggaagacatc aattttttcat ccttggctcc gcgacacggc acgaagccgt acatgggcac   17460
ctggagcgac atcggcacga gccaactgaa cgggggcgcc ttcaattgga gcagtatctg   17520
gagcgggctt aaaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaacccca ggtgaaatgc aagtggagga   17760
agaaattcct ccgccagaaa aacgaggcga caagcgtccg cgtccgatt tggaagagac   17820
gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttggatttgc cccctccccc tgctgctact gctgtacccg cttctaagcc   18000
```

```
tgtcgctgcc ccgaaaccag tcgccgtagc caggtcacgt cccgggggcg ctcctcgtcc   18060
aaatgcgcac tggcaaaata ctctgaacag catcgtgggt ctaggcgtgc aaagtgtaaa   18120
acgccgtcgc tgcttttaat taaatatgga gtagcgctta acttgcctat ctgtgtatat   18180
gtgtcattac acgccgtcac agcagcagag gaaaaaagga agaggtcgtg cgtcgacgct   18240
gagttacttt caagatggcc accccatcga tgctgcccca atgggcatac atgcacatcg   18300
ccggacagga tgcttcggag tacctgagtc cgggtctggt gcagttcgcc cgcgccacag   18360
acacctactt caatctggga aataagttta gaaatcccac cgtagcgccg acccacgatg   18420
tgaccaccga ccgtagccag cggctcatgt tgcgcttcgt gcccgttgac cgggaggaca   18480
atacatactc ttacaaagtg cggtacaccc tggccgtggg cgacaacaga gtgctggata   18540
tggccagcac gttctttgac attaggggtg tgttggacag aggtcccagt ttcaaaccct   18600
attctggtac ggcttacaac tccctggctc ctaaaggcgc tccaaataca tctcagtgga   18660
ttgcagaagg tgtaaaaaat acaactggtg aggaacacgt aacagaagag gaaaccaata   18720
ctactactta cacttttggc aatgctcctg taaaagctga agctgaaatt acaaaagaag   18780
gactcccagt aggtttggaa gtttcagatg aagaaagtaa accgatttat gctgataaaa   18840
catatcagcc agaacctcag ctgggagatg aaacttggac tgaccttgat ggaaaaaccg   18900
aaaagtatgg aggcagggct ctcaaacccg atactaagat gaaaccatgc tacgggtcct   18960
ttgccaaacc tactaatgtg aaaggcggtc aggcaaaaca aaaaacaacg gagcagccaa   19020
atcagaaagt cgaatatgat atcgacatgg agttttttga tgcggcatcg cagaaaacaa   19080
acttaagtcc taaaattgtc atgtatgcag aaaatgtaaa tttggaaact ccagacactc   19140
atgtagtgta caaacctgga acagaagaca aagttccgag agctaatttg ggacaacaat   19200
ctatgcccaa cagacccaac tacattggct tcagagataa ctttattgga cttatgtact   19260
ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atacttagc atgtggaatc aggctgtgga cagttatgat cctgatgtac   19440
gtgttattga aaatcatggt gtggaagatg aacttcccaa ctactgtttt ccactggacg   19500
gcataggtgt tccaacaacc agttacaaat caatagttcc aaatggagac aatgcgccta   19560
attggaagga acctgaagta aatggaacaa gtgagatcgg acagggtaat ttgtttgcca   19620
tggaaattaa ccttcaagcc aatctatggc gaagtttcct ttattccaat gtggctctat   19680
atctcccaga ctcgtacaaa tacacccccgt ccaatgtcac tcttccagaa acaaaaaaca   19740
cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg gaactttagg aaggatgtga acatggttct acagagttcc ctcggtaacg   20040
acctgcgggt agatggcgcc agcatcagtt tcacgagcat caacctctat gctacttttt   20100
tccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccatttcc attccttctc gcaactgggc ggcttcaga ggctggtcat   20280
ttaccagact gaaaaccaaa gaactccct cttggggtc tggatttgac ccctactttg   20340
tctattctgg ttctattccc tacctggatg gtaccttcta cctgaaccac actttaaga   20400
```

| | |
|---|---|
| aggtttccat catgtttgac tcttcagtga gctggcctgg aaatgacagg ttactatctc | 20460 |
| ctaacgaatt tgaaataaag cgcactgtgg atggcgaagg ctacaacgta gcccaatgca | 20520 |
| acatgaccaa agactggttc ttggtacaga tgctcgccaa ctacaacatc ggctatcagg | 20580 |
| gcttctacat tccagaagga tacaaagatc gcatgtattc attttttcaga aacttccagc | 20640 |
| ccatgagcag gcaggtggtt gatgaggtca attacaaaga cttcaaggcc gtcgccatac | 20700 |
| cctaccaaca caacaactct ggctttgtgg gttacatggc tccgaccatg cgccaaggtc | 20760 |
| aaccctatcc cgctaactat ccctatccac tcattggaac aactgccgta aatagtgtta | 20820 |
| cgcagaaaaa gttcttgtgt gacagaacca tgtggcgcat accgttctcg agcaacttca | 20880 |
| tgtctatggg ggcccttaca gacttgggac agaatatgct ctatgccaac tcagctcatg | 20940 |
| ctctggacat gacctttgag gtggatccca tggatgagcc caccctgctt tatcttctct | 21000 |
| tcgaagtttt cgacgtggtc agagtgcatc agccacaccg cggcatcatc gaggcagtct | 21060 |
| acctgcgtac accgttctcg gccggtaacg ctaccacgta agaagcttct tgcttcttgc | 21120 |
| aaatagcagc tgcaaccatg gcctgcggat cccaaaacgg ctccagcgag caagagctca | 21180 |
| gagccattgt ccaagacctg ggttgcggac cctatttttt gggaacctac gataagcgct | 21240 |
| tcccggggtt catggccccc gataagctcg cctgtgccat tgtaaatacg gccggacgtg | 21300 |
| agacgggggg agagcactgg ttggcttttcg gttggaaccc acgttctaac acctgctacc | 21360 |
| tttttgatcc tttttggattc tcggatgatc gtctcaaaca gatttaccag tttgaatatg | 21420 |
| agggtctcct gcgccgcagc gctcttgcta ccaaggaccg ctgtattacg ctggaaaaat | 21480 |
| ctacccagac cgtgcagggt cccgttctg ccgcctgcgg acttttctgc tgcatgttcc | 21540 |
| ttcacgcctt tgtgcactgg cctgaccgtc ccatggacgg aaaccccacc atgaaattgc | 21600 |
| taactggagt gccaaacaac atgcttcatt ctcctaaagt ccagcccacc ctgtgtgaca | 21660 |
| atcaaaaagc actctaccat tttcttaata cccattcgcc ttattttcgc tcccatcgta | 21720 |
| cacacatcga aagggccact gcgttcgacc gtatggatgt tcaataatga ctcatgtaaa | 21780 |
| caacgtgttc aataaacatc actttatttt tttacatgta tcaaggctct gcattactta | 21840 |
| tttatttaca agtcgaatgg gttctgacga gaatcagaat gacccgcagg cagtgatacg | 21900 |
| ttgcggaact gatacttggg ttgccacttg aattcgggaa tcaccaactt gggaaccggt | 21960 |
| atatcgggca ggatgtcact ccacagcttt ctggtcagct gcaaagctcc aagcaggtca | 22020 |
| ggagccgaaa tcttgaaatc acaattagga ccagtgcttt gagcgcgaga gttgcggtac | 22080 |
| accggattgc agcactgaaa caccatcagc gacggatgtc tcacgcttgc cagcacggtg | 22140 |
| ggatctgcaa tcatgcccac atccagatct tcagcattgg caatgctgaa cggggtcatc | 22200 |
| ttgcaggtct gcctacccat ggcgggcacc caattaggct tgtggttgca atcgcagtgc | 22260 |
| aggggggatca gtatcatctt ggcctgatcc tgtctgattc ctggatacac ggctctcatg | 22320 |
| aaagcatcat attgcttgaa agcctgctgg gcttttactac cctcggtata aacatcccg | 22380 |
| caggacctgc tcgaaaactg gttagctgca cagccggcat cattcacaca gcagcgggcg | 22440 |
| tcattgttag ctatttgcac cacacttctg ccccagcggt tttgggtgat tttggttcgc | 22500 |
| tcgggattct cctttaaggc tcgttgtccg ttctcgctgg ccacatccat ctcgataatc | 22560 |
| tgctccttct gaatcataat attgccatgc aggcacttca gcttgccctc ataatcattg | 22620 |
| cagccatgag gccacaacgc acagcctgta cattcccaat tatggtgggc gatctgagaa | 22680 |
| aaagaatgta tcattccctg cagaaatctt cccatcatcg tgctcagtgt cttgtgacta | 22740 |

-continued

```
gtgaaagtta actggatgcc tcggtgctcc tcgtttacgt actggtgaca gatgcgcttg    22800
tattgttcgt gttgctcagg cattagttta aaagaggttc taagttcgtt atccagcctg    22860
tacttctcca tcagcagaca catcacttcc atgcctttct cccaagcaga caccaggggc    22920
aagctaatcg gattcttaac agtgcaggca gcagctcctt tagccagagg gtcatcttta    22980
gcgatcttct caatgcttct tttgccatcc ttctcaacga tgcgcacggg cgggtagctg    23040
aaacccactg ctacaagttg cgcctcttct ctttcttctt cgctgtcttg actgatgtct    23100
tgcatgggga tatgtttggt cttccttggc ttcttttttgg ggggtatcgg aggaggagga    23160
ctgtcgctcc gttccggaga cagggaggat tgtgacgttt cgctcaccat taccaactga    23220
ctgtcggtag aagaacctga ccccacacgg cgacaggtgt ttctcttcgg gggcagaggt    23280
ggaggcgatt gcgaagggct gcggtccgac ctggaaggcg gatgactggc agaacccctt    23340
ccgcgttcgg gggtgtgctc cctgtggcgg tcgcttaact gatttccttc gcggctggcc    23400
attgtgttct cctaggcaga gaaacaacag acatggaaac tcagccattg ctgtcaacat    23460
cgccacgagt gccatcacat ctcgtcctca gcgacgagga aaaggagcag agcttaagca    23520
ttccaccgcc cagtcctgcc accacctcta ccctagaaga taaggaggtc gacgcatctc    23580
atgacatgca gaataaaaaa gcgaaagagt ctgagacaga catcgagcaa gacccgggct    23640
atgtgacacc ggtggaacac gaggaagagt tgaaacgctt tctagagaga gaggatgaaa    23700
actgcccaaa acaacgagca gataactatc accaagatgc tggaaatagg gatcagaaca    23760
ccgactacct catagggctt gacggggaag acgcgctcct taaacatcta gcaagacagt    23820
cgctcatagt caaggatgca ttattggaca gaactgaagt gcccatcagt gtggaagagc    23880
tcagccgcgc ctacgagctt aacctcttt cacctcgtac tccccccaaa cgtcagccaa    23940
acggcacctg cgagccaaat cctcgcttaa acttttatcc agcttttgct gtgccagaag    24000
tactggctac ctatcacatc ttttttaaaa atcaaaaaat tccagtctcc tgccgcgcta    24060
atcgcacccg cgccgatgcc ctactcaatc tgggacctgg ttcacgctta cctgatatag    24120
cttccttgga agaggttcca aagatcttcg agggtctggg caataatgag actcgggccg    24180
caaatgctct gcaaaaggga gaaaatggca tggatgagca tcacagcgtt ctggtggaat    24240
tggaaggcga taatgccaga ctcgcagtac tcaagcgaag catcgaggtc acacacttcg    24300
catatcccgc tgtcaacctg cccccctaaag tcatgacggc ggtcatggac cagttactca    24360
ttaagcgcgc aagtccccett tcagaagaca tgcatgaccc agatgcctgt gatgagggta    24420
aaccagtggt cagtgatgag cagctaaccc gatggctggg caccgactct cccagggatt    24480
tggaagagcg tcgcaagctt atgatggccg tggtgctggt taccgtagaa ctagagtgtc    24540
tccgacgttt ctttaccgat tcagaaacct tgcgcaaact cgaagagaat ctgcactaca    24600
cttttagaca cggctttgtg cggcaggcat gcaagatatc taacgtggaa ctcaccaacc    24660
tggtttccta catgggtatt ctgcatgaga atcgcctagg acaaagcgtg ctgcacagca    24720
ccctgaaggg ggaagcccgc cgtgattaca tccgcgattg tgtctatctg tacctgtgcc    24780
acacgtggca aaccggcatg ggtgtatggc agcaatgttt agaagaacag aacttgaaag    24840
agcttgacaa gctcttacag aaatctctta aggttctgtg gacagggttc gacgagcgca    24900
ccgtcgcttc cgacctggca gacctcatct tcccagagcg tctcagggtt actttgcgaa    24960
acggattgcc tgactttatg agccagagca tgcttaacaa ttttcgctct ttcatcctgg    25020
aacgctccgg tatcctgccc gccacctgct gcgcactgcc ctccgacttt gtgcctctca    25080
cctaccgcga gtgccccccg ccgctatgga gtcactgcta cctgttccgt ctggccaact    25140
```

```
atctctccta ccactcggat gtgatcgagg atgtgagcgg agacggcttg ctggagtgtc   25200
actgccgctg caatctgtgc acgccccacc ggtccctagc ttgcaacccc cagttgatga   25260
gcgaaaccca gataataggc acctttgaat tgcaaggccc cagcagccaa ggcgatgggt   25320
cttctcctgg gcaaagttta aaactgaccc cgggactgtg gacctccgcc tacttgcgca   25380
agtttgctcc ggaagattac caccCctatg aaatcaagtt ctatgaggac caatcacagc   25440
ctccaaaggc cgaactttcg gcctgcgtca tcacccaggg ggcaattctg cccaattgc   25500 aagccatcca aaatcccgc caagaatttc tactgaaaaa gggtaagggg gtctaccttg   25560 accccccagac cggcgaggaa ctcaacacaa ggttccctca ggatgtccca acgacgagaa   25620
aacaagaagt tgaaggtgca gccgccgccc ccagaagata tggaggaaga ttgggacagt   25680
caggcagagg aggcggagga ggacagtctg gaggacagtc tggaggaaga cagtttggag   25740
gaggaaaacg aggaggcaga ggaggtggaa gaagtaaccg ccgacaaaca gttatcctcg   25800
gctgcgagga caagcaacag cgctaccatc tccgctccga gtcgaggaac ccggcggcgt   25860
cccagcagta gatgggacga gaccggacgc ttcccgaacc caaccagcgc ttccaagacc   25920
ggtaagaagg atcggcaggg atacaagtcc tggcgggggc ataagaatgc catcatctcc   25980
tgcttgcatg agtgcggggg caacatatcc ttcacgcggc gctacttgct attccaccat   26040
ggggtgaact ttccgcgcaa tgttttgcat tactaccgtc acctcacag cccctactat   26100 agccagcaaa tcccggcagt ctcgacagat aaagacagcg gcggcgacct ccaacagaaa   26160
accagcagcg gcagttagaa aatacacaac aagtgcagca acaggaggat taaagattac   26220
agccaacgag ccagcgcaaa cccgagagtt aagaaatcgg atctttccaa ccctgtatgc   26280
catcttccag cagagtcggg gtcaagagca ggaactgaaa ataaaaaacc gatctctgcg   26340
ttcgctcacc agaagttgtt tgtatcacaa gagcgaagat caacttcagc gcactctcga   26400
ggacgccgag gctctcttca acaagtactg cgcgctgact cttaaagagt aggcagcgac   26460
cgcgcttatt caaaaaaggc gggaattaca tcatcctcga catgagtaaa gaaattccca   26520
cgccttacat gtggagttat caaccccaaa tgggattggc ggcaggcgcc tcccaggact   26580
actccacccg catgaattgg ctcagcgccg ggccttctat gatttctcga gttaatgata   26640
tacgcgccta ccgaaaccaa atacttttgg aacagtcagc tcttaccacc acgccccgcc   26700
aacaccttaa tccccagaaat tggcccgccg ccctagtgta ccaggaaagt cccgctccca   26760
ccactgtatt acttcctcga gacgcccagg ccgaagtcca aatgactaat gcaggtgcgc   26820
agttagctgg cggctccacc ctatgtcgtc acaggcctcg gcataatata aaacgcctga   26880
tgatcagagg ccgaggtatc cagctcaacg acgagtcggt gagctctccg cttggtctac   26940
gaccagacgc aatctttcag attgccggct gcgggagatc ttccttcacc cctcgtcagg   27000
ctgttctgac tttggaaagt tcgtcttcgc aaccccgctc gggcggaatc gggaccgttc   27060
aatttgtgga ggagtttact ccctctgtct acttcaaccc cttctccgga tctcctgggc   27120
attacccgga cgagttcata ccgaacttcg acgcgattag cgagtcagtg gacggctacg   27180
attgatgtct ggtgacgcgg ctgagctatc tcggctgcga catctagacc actgccgccg   27240
ctttcgctgc tttgcccggg aactcattga gttcatctac ttcgaactcc ccaaggatca   27300
ccctcaaggt ccggcccacg gagtgcggat ttctatcgaa ggcaaaatag actctcgcct   27360
gcaacgaatt ttctcccagc ggcccgtgct gatcgagcga gaccagggaa acaccacggt   27420
ttccatctac tgcatttgta atcaccccgg attgcatgaa agcctttgct gtcttatgtg   27480
```

```
tactgagttt aataaaaact gaattaagac tctcctacgg actgccgctt cttcaacccg    27540
gattttacaa ccagaagaac gaaactttc ctgtcgtcca ggactctgtt aacttcacct     27600
ttcctactca caaactagaa gctcaacgac tacaccgctt ttccagaagc attttcccta    27660
ctaatactac tttcaaaacc ggaggtgagc tccaaggtct tcctacagaa aacccttggg    27720
tggaagcggg ccttgtagtg ctaggaattc ttgcgggtgg gcttgtgatt attctttgct    27780
acctatacac accttgcttc actttcttag tggtgttgtg gtattggttt aaaaaatggg    27840
gcccatacta gtcttgcttg ttttactttc gcttttggaa ccgggttctg ccaattacga    27900
tccatgtcta gacttcgacc cagaaaactg cacacttact tttgcacccg acacaagccg    27960
catctgtgga gttcatcgcc tctcttacga acttggcccc caacgacaaa aatttacctg    28020
catggtggga atcaacccca tagttatcac ccagcaaagt ggagatacta agggttgcat    28080
tcactgctcc tgcgattcca tcgagtgcac ctacaccctg ctgaagaccc tatgcggcct    28140
aagagacctg ctaccaatga attaaaaaat gattaataaa aaatcactta cttgaaatca    28200
gcaataaggt ctctgttgaa attttctccc agcagcacct cacttccctc ttcccaactc    28260
tggtattcta aaccccgttc agcggcatac tttctccata cttaaaggg gatgtcaaat     28320 tttagctcct ctcctgtacc cacaatcttc atgtctttct tcccagatga ccaagagagt    28380
ccggctcagt gactccttca accctgtcta cccctatgaa gatgaaagca cctcccaaca    28440 ccccttata aacccagggt ttatttcccc aaatggcttc acacaaagcc caaacggagt     28500
tcttacttta aaatgtttaa ccccactaac aaccacaggc ggatctctac agctaaaagt    28560
gggaggggga cttacagtgg atgacaccaa cggttttttg aaagaaaaca taagtgccac    28620
cacaccactc gttaagactg gtcactctat aggtttacca ctaggagccg gattgggaac    28680
gaatgaaaat aaaactttgta tcaaattagg acaaggactt acattcaatt caaacaacat    28740
ttgcattgat gacaatatta acaccttatg gacaggagtc aaccccaccg aagccaactg    28800
tcaaatcatg aactccagtg aatctaatga ttgcaaatta attctaacac tagttaaaac    28860
tggagcacta gtcactgcat ttgtttatgt tataggagta tctaacaatt ttaatatgct    28920
aactacacac agaaatataa attttactgc agagctgttt ttcgattcta ctggtaattt    28980
actaactaga ctctcatccc tcaaaactcc acttaatcat aaatcaggac aaaacatggc    29040
tactggtgcc attactaatg ctaaaggttt catgcccagc acgactgcct atccttttcaa   29100 tgataattct agagaaaaag aaaactacat ttacggaact tgttactaca cagctagtga    29160
tcgcactgct tttcccattg acatatctgt catgcttaac cgaagagcaa taaatgacga    29220
gacatcatat tgtattcgta aacttggtc ctggaacaca ggagatgccc cagaggtgca     29280
aacctctgct acaacccctag tcacctcccc atttaccttt tactacatca gagaagacga    29340
ctgacaaata aagtttgcga tcgccaggcc caccatggac tggacctgga ggatcctctt    29400
cttggtggca gcagccacag gagcccactc ccaggtgcag ctggtgcagt ctggggctga    29460
ggtgaagaag cctgggcct cagtgaaggt ctcctgcaag gcttctggat acaccttcac      29520
cggctactat atgcactggg tgcgacaggc ccctggacaa gggcttgagt ggatgggatg    29580
gatcaaccct gacagtggtg gcacaaaacta tgcacagaag tttcagggca gggtcaccat    29640
gaccagggac acgtccatca gcacagccta catggagctg aacaggctga gatctgacga    29700
cacggccgtg tattactgtg cgagagatca gcccctagga tattgtacta atggtgtatg    29760
ctcctacttt gactactggg gccagggaac cctggtcacc gtctcctcag cctccaccaa    29820
gggcccatcg gtcttccccc tggcgccctg ctccaggagc acctccgaga gcacagcggc    29880
```

```
cctgggctgc ctggtcaagg actacttccc cgaaccggtg acggtgtcgt ggaactcagg   29940
cgctctgacc agcggcgtgc acaccttccc agctgtccta cagtcctcag gactctactc   30000
cctcagcagc gtggtgaccg tgccctccag caacttcggc acccagacct acacctgcaa   30060
cgtagatcac aagcccagca acaccaaggt ggacaagaca gttgagcgca aatgttgtgt   30120
cgagtgccca ccgtgcccag caccacctgt ggcaggaccg tcagtcttcc tcttccccc    30180
aaaacccaag gacaccctca tgatctcccg gacccctgag gtcacgtgcg tggtggtgga   30240
cgtgagccac gaagacccccg aggtccagtt caactggtac gtggacggcg tggaggtgca  30300
taatgccaag acaaagccac gggaggagca gttcaacagc acgttccgtg tggtcagcgt   30360
cctcaccgtt gtgcaccagg actggctgaa cggcaaggag tacaagtgca aggtctccaa   30420
caaaggcctc ccagccccca tcgagaaaac catctccaaa accaaagggc agccccgaga   30480
accacaggtg tacaccctgc ccccatcccg ggaggagatg accaagaacc aggtcagcct   30540
gacctgcctg gtcaaaggct tctaccccag cgacatcgcc gtggagtggg agagcaatgg   30600
gcagccggag aacaactaca agaccacacc tcccatgctg gactccgacg gctccttctt   30660
cctctacagc aagctcaccg tggacaagag caggtggcag caggggaacg tcttctcatg   30720
ctccgtgatg catgaggctc tgcacaacca ctacacgcag aagagcctct ccctgtctcc   30780
gggtaaagga agcggagcta ctaacttcag cctgctgaag caggctggag acgtggagga   30840
gaaccctgga cctaggctcc ctgctcagct cctggggctc ctgctgctct ggttcccagg   30900
ttccagatgc gacatccaga tgacccagtc tccatcttcc gtgtctgcat ctgtaggaga   30960
cagagtcacc atcacttgtc gggcgagtca gggtatttac agctggttag cctggtatca   31020
gcagaaacca gggaaagccc ctaacctcct gatctatact gcatccactt tacaaagtgg   31080
ggtcccatca aggttcagcg gcagtggatc tgggacagat ttcactctca ccatcagcag   31140
cctgcaacct gaagattttg caacttacta ttgtcaacag gctaacattt cccgctcac    31200
tttcggcgga gggaccaagg tggagatcaa acgaactgtg gctgcaccat ctgtcttcat   31260
cttcccgcca tctgatgagc agttgaaatc tggaactgcc tctgttgtgt gcctgctgaa   31320
taacttctat cccagagagg ccaaagtaca gtggaaggtg gataacgccc tccaatcggg   31380
taactcccag gagagtgtca cagagcagga cagcaaggac agcacctaca gcctcagcag   31440
caccctgacg ctgagcaaag cagactacga gaaacacaaa gtctacgcct gcgaagtcac   31500
ccatcagggc ctgagctcgc ccgtcacaaa gagcttcaac aggggagagt gttaggctag   31560
cttgactgac tgagatacag cgtaccttca gctcacagac atgataagat acattgatga   31620
gtttggacaa accacaacta gaatgcagtg aaaaaaatgc tttatttgtg aaatttgtga   31680
tgctattgct ttatttgtaa ccattataag ctgcaataaa caagttaaca acaacaattg   31740
cattcatttt atgtttcagg ttcaggggga ggtgtgggag gttttttaaa gcaagtaaaa   31800
cctctacaaa tgtggtcctg caggaacttg tttatttgaa aatcaattca caaaatccga   31860
gtagttattt tgcctccccc ttcccattta acagaataca ccaatctctc cccacgcaca   31920
gctttaaaca tttggatacc attagatata gacatggttt tagattccac attccaaaca   31980
gtttcagagc gagccaatct ggggtcagtg atagataaaa atccatcggg atagtctttt   32040
aaagcgcttt cacagtccaa ctgctgcgga tgcgactccg gagtctggat cacggtcatc   32100
tggaagaaga acgatgggaa tcataatccg aaaacggtat cggacgattg tgtctcatca   32160
aacccacaag cagccgctgt ctgcgtcgct ccgtgcgact gctgtttatg ggatcagggt   32220
```

```
ccacagtgtc ctgaagcatg attttaatag cccttaacat caactttctg gtgcgatgcg   32280
cgcagcaacg cattctgatt tcactcaaat ctttgcagta ggtacaacac attattacaa   32340
tattgtttaa taaaccataa ttaaaagcgc tccagccaaa actcatatct gatataatcg   32400
cccctgcatg accatcatac caaagtttaa tataaattaa atgacgttcc ctcaaaaaca   32460
cactacccac atacatgatc tcttttggca tgtgcatatt aacaatctgt ctgtaccatg   32520
gacaacgttg gttaatcatg caacccaata taaccttccg gaaccacact gccaacaccg   32580
ctcccccagc catgcattga agtgaaccct gctgattaca atgacaatga agaacccaat   32640
tctctcgacc gtgaatcact tgagaatgaa aaatatctat agtggcacaa catagacata   32700
aatgcatgca tcttctcata atttttaact cctcaggatt tagaaacata tcccagggaa   32760
taggaagctc ttgcagaaca gtaaagctgg cagaacaagg aagaccacga acacaactta   32820
cactatgcat agtcatagta tcacaatctg gcaacagcgg gtggtcttca gtcatagaag   32880
ctcgggtttc attttcctca caacgtggta actgggctct ggtgtaaggg tgatgtctgg   32940
cgcatgatgt cgagcgtgcg cgcaaccttg tcataatgga gttgcttcct gacattctcg   33000
tattttgtat agcaaaacgc ggccctggca gaacacactc ttcttcgcct tctatcctgc   33060
cgcttagcgt gttccgtgtg atagttcaag tacaaccaca ctcttaagtt ggtcaaaaga   33120
atgctggctt cagttgtaat caaaactcca tcgcatctaa tcgttctgag gaaatcatcc   33180
aagcaatgca actggattgt gtttcaagca ggagaggaga gggaagagac ggaagaacca   33240
tgttaatttt tattccaaac gatctcgcag tacttcaaat tgtagatcgc gcagatggca   33300
tctctcgccc ccactgtgtt ggtgaaaaag cacagctaga tcaaaagaaa tgcgattttc   33360
aaggtgctca acggtggctt ccagcaaagc ctccacgcgc acatccaaga acaaaagaat   33420
accaaaagaa ggagcatttt ctaactcctc aatcatcata ttacattcct gcaccattcc   33480
cagataattt tcagctttcc agccttgaat tattcgtgtc agttcttgtg gtaaatccaa   33540
tccacacatt acaaacaggt cccggagggc gccctccacc accattctta aacacacccct  33600 cataatgaca aaatatcttg ctcctgtgtc acctgtagcg aattgagaat ggcaacatca   33660
attgacatgc ccttggctct aagttcttct ttaagttcta gttgtaaaaa ctctctcata   33720
ttatcaccaa actgcttagc cagaagcccc ccgggaacaa gagcagggga cgctacagtg   33780
cagtacaagc gcagacctcc ccaattggct ccagcaaaaa caagattgga ataagcatat   33840
tgggaaccgc cagtaatatc atcgaagttg ctggaaatat aatcaggcag agtttcttgt   33900
aaaaattgaa taaagaaaa  atttgccaaa aaacattca aaacctctgg gatgcaaatg    33960
caataggtta ccgcgctgcg ctccaacatt gttagttttg aattagtctg caaaaataaa   34020
aaaaaaaaca agcgtcatat catagtagcc tgacgaacag atggataaat cagtctttcc   34080
atcacaagac aagccacagg gtctccagct cgaccctcgt aaaacctgtc atcatgatta   34140
aacaacagca ccgaaagttc ctcgcggtga ccagcatgaa taattcttga tgaagcatac   34200
aatccagaca tgttagcatc agttaacgag aaaaaacagc caacatagcc tttgggtata   34260
attatgctta atcgtaagta tagcaaagcc acccctcgcg gatacaaagt aaaaggcaca   34320
ggagaataaa aatataatt atttctctgc tgctgttcag gcaacgtcgc ccccggtccc    34380
tctaaataca catacaaagc ctcatcagcc atggcttacc agacaaagta cagcgggcac   34440
acaaagcaca agctctaaag tgactctcca acctctccac aatatatata tacacaagcc   34500
ctaaactgac gtaatgggag taaagtgtaa aaaatcccgc caaacccaac acacacccccg  34560 aaactgcgtc accagggaaa agtacagttt cacttccgca atcccaacag gcgtaacttc   34620
```

```
ctctttctca cggtacgtga tatcccacta acttgcaacg tcattttccc acggtcgcac    34680
cgcccctttt agccgttaac cccacagcca atcaccacac gatccacact ttttaaaatc    34740
acctcattta catattggca ccattccatc tataaggtat attatataga taga           34794
```

<210> SEQ ID NO 14
<211> LENGTH: 13
<212> TYPE: RNA
<213> ORGANISM: Artificial Sequence
<220> FEATURE:
<223> OTHER INFORMATION: Kozak sequence
<220> FEATURE:
<221> NAME/KEY: misc_feature
<222> LOCATION: (7)..(7)
<223> OTHER INFORMATION: R is purine, adenine or guanine
<400> SEQUENCE: 14

```
gccgccrcca ugg                                                        13
```

<210> SEQ ID NO 15
<211> LENGTH: 26
<212> TYPE: DNA
<213> ORGANISM: Artificial Sequence
<220> FEATURE:
<223> OTHER INFORMATION: splice acceptor sequence
<400> SEQUENCE: 15

```
tgctaatctt cctttctctc ttcagg                                          26
```

<210> SEQ ID NO 16
<211> LENGTH: 14
<212> TYPE: DNA
<213> ORGANISM: Artificial Sequence
<220> FEATURE:
<223> OTHER INFORMATION: splice acceptor sequence
<400> SEQUENCE: 16

```
tttctctctt cagg                                                       14
```

<210> SEQ ID NO 17
<211> LENGTH: 22
<212> TYPE: DNA
<213> ORGANISM: Artificial Sequence
<220> FEATURE:
<223> OTHER INFORMATION: Forward Primer
<400> SEQUENCE: 17

```
acggaacttg ttactacaca gc                                              22
```

<210> SEQ ID NO 18
<211> LENGTH: 21
<212> TYPE: DNA
<213> ORGANISM: Artificial Sequence
<220> FEATURE:
<223> OTHER INFORMATION: Reverse Primer
<400> SEQUENCE: 18

```
ctttcacagt ccaactgctg c                                               21
```

<210> SEQ ID NO 19
<211> LENGTH: 22
<212> TYPE: DNA
<213> ORGANISM: Artificial Sequence
<220> FEATURE:
<223> OTHER INFORMATION: Forward Primer

```
<400> SEQUENCE: 19
agccggagaa caactacaag ac                                              22

<210> SEQ ID NO 20
<211> LENGTH: 21
<212> TYPE: DNA
<213> ORGANISM: Artificial Sequence
<220> FEATURE:
<223> OTHER INFORMATION: Forward Primer

<400> SEQUENCE: 20
catccagatg acccagtctc c                                               21

<210> SEQ ID NO 21
<211> LENGTH: 24
<212> TYPE: DNA
<213> ORGANISM: Artificial Sequence
<220> FEATURE:
<223> OTHER INFORMATION: Reverse Primer

<400> SEQUENCE: 21 ggacaaaacca caactagaat gcag                                           24

<210> SEQ ID NO 22
<211> LENGTH: 20
<212> TYPE: DNA
<213> ORGANISM: Artificial Sequence
<220> FEATURE:
<223> OTHER INFORMATION: Forward primer

<400> SEQUENCE: 22
cctcagtgaa ggtctcctgc                                                 20

<210> SEQ ID NO 23
<211> LENGTH: 24
<212> TYPE: DNA
<213> ORGANISM: Artificial Sequence
<220> FEATURE:
<223> OTHER INFORMATION: Reverse Primer

<400> SEQUENCE: 23 ggacaaaacca caactagaat gcag                                           24

<210> SEQ ID NO 24
<211> LENGTH: 22
<212> TYPE: PRT
<213> ORGANISM: Artificial Sequence
<220> FEATURE:
<223> OTHER INFORMATION: High efficiency self-cleavable P2A peptide
      sequence

<400> SEQUENCE: 24

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 25
<211> LENGTH: 21
<212> TYPE: PRT
<213> ORGANISM: Artificial Sequence
<220> FEATURE:
<223> OTHER INFORMATION: High efficiency self-cleavable F2A peptide
      sequence

<400> SEQUENCE: 25
```

```
Gly Ser Gly Glu Gly Arg Gly Ser Leu Leu Thr Cys Gly Asp Val Glu
1               5                   10                  15

Glu Asn Pro Gly Pro
            20

<210> SEQ ID NO 26
<211> LENGTH: 23
<212> TYPE: PRT
<213> ORGANISM: Artificial Sequence
<220> FEATURE:
<223> OTHER INFORMATION: High efficiency self-cleavable E2A peptide
      sequence

<400> SEQUENCE: 26

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 27
<211> LENGTH: 25
<212> TYPE: PRT
<213> ORGANISM: Artificial Sequence
<220> FEATURE:
<223> OTHER INFORMATION: High efficiency self-cleavable T2A peptide
      sequence

<400> SEQUENCE: 27

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```